(12) United States Patent
Lieber et al.

(10) Patent No.: US 7,301,199 B2
(45) Date of Patent: Nov. 27, 2007

(54) NANOSCALE WIRES AND RELATED DEVICES

(75) Inventors: Charles M. Lieber, Lexington, MA (US); Xiangfeng Duan, Somerville, MA (US); Yi Cui, Union City, CA (US); Yu Huang, Cambridge, MA (US); Mark Gudiksen, Watertown, MA (US); Lincoln J. Lauhon, Boston, MA (US); Jianfang Wang, Goleta, CA (US); Hongkun Park, Lexington, MA (US); Qingqiao Wei, Corvallis, OR (US); Wenjie Liang, Somerville, MA (US); David C. Smith, Reading (GB); Deli Wang, Cambridge, MA (US); Zhaohui Zhong, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 10/196,337

(22) Filed: Jul. 16, 2002

(65) Prior Publication Data
US 2003/0089899 A1    May 15, 2003

Related U.S. Application Data

(63) Continuation-in-part of application No. 10/152,490, filed on May 20, 2002, now abandoned, application No. 10/196,337, which is a continuation-in-part of application No. 09/935,776, filed on Aug. 22, 2001, now abandoned, said application No. 10/152,490 is a continuation-in-part of application No. 10/020,004, filed on Dec. 11, 2001, now Pat. No. 7,129,554.

(60) Provisional application No. 60/354,642, filed on Feb. 6, 2002, provisional application No. 60/348,313, filed on Nov. 9, 2001, provisional application No. 60/292,045, filed on May 18, 2001, provisional application No. 60/291,896, filed on May 18, 2001, provisional application No. 60/292,121, filed on May 18, 2001, provisional application No. 60/292,035, filed on May 18, 2001, provisional application No. 60/254,745, filed on Dec. 11, 2000, provisional application No. 60/226,835, filed on Aug. 22, 2000.

(51) Int. Cl.
*H01L 29/76* (2006.01)
*H01L 29/94* (2006.01)
*H01L 29/06* (2006.01)

(52) U.S. Cl. .......................... 257/327; 257/9; 977/938; 977/936; 977/958

(58) Field of Classification Search .............. 257/9–30, 257/368, 327; 977/DIG. 1, 762, 813, 938, 977/936, 958
See application file for complete search history.

(56) References Cited

U.S. PATENT DOCUMENTS

| | | |
|---|---|---|
| 3,873,359 A | 3/1975 | Lando |
| 3,873,360 A | 3/1975 | Lando |
| 3,900,614 A | 8/1975 | Lando |
| 4,673,474 A | 6/1987 | Ogawa |
| 4,939,556 A | 7/1990 | Eguchi et al. |
| 5,023,139 A | 6/1991 | Birnboim et al. |
| 5,089,545 A | 2/1992 | Pol |
| 5,252,835 A | 10/1993 | Lieber et al. |
| 5,274,602 A | 12/1993 | Glenn |
| 5,453,970 A | 9/1995 | Rust et al. |
| 5,475,341 A | 12/1995 | Reed |
| 5,512,131 A | 4/1996 | Kumar et al. |
| 5,537,075 A | 7/1996 | Miyazaki |
| 5,539,214 A | 7/1996 | Lynch et al. |
| 5,581,091 A | 12/1996 | Moskovits et al. |
| 5,589,692 A | 12/1996 | Reed |
| 5,607,876 A | 3/1997 | Biegelsen et al. |
| 5,620,850 A | 4/1997 | Bamdad et al. |
| 5,640,343 A | 6/1997 | Gallagher et al. |
| 5,726,524 A | 3/1998 | Debe |
| 5,739,057 A | 4/1998 | Tiwari et al. |
| 5,747,180 A | 5/1998 | Miller et al. |
| 5,751,156 A | 5/1998 | Muller et al. |
| 5,776,748 A | 7/1998 | Singhvi et al. |
| 5,824,470 A | 10/1998 | Baldeschwieler et al. |

| | | | | | |
|---|---|---|---|---|---|
| 5,830,538 A | 11/1998 | Gates et al. | 2002/0040805 A1 | 4/2002 | Swager |
| 5,840,435 A | 11/1998 | Lieber et al. | 2002/0055239 A1 | 5/2002 | Tuominen et al. |
| 5,847,565 A | 12/1998 | Narayanan | 2002/0084502 A1 | 7/2002 | Jang et al. |
| 5,858,862 A | 1/1999 | Westwater et al. | 2002/0086335 A1 | 7/2002 | Massey et al. |
| 5,864,823 A | 1/1999 | Levitan | 2002/0117659 A1 | 8/2002 | Lieber et al. |
| 5,897,945 A | 4/1999 | Lieber et al. | 2002/0122766 A1 | 9/2002 | Lieber et al. |
| 5,900,160 A | 5/1999 | Whitesides et al. | 2002/0130311 A1 | 9/2002 | Lieber et al. |
| 5,903,010 A | 5/1999 | Flory et al. | 2002/0130353 A1 | 9/2002 | Lieber et al. |
| 5,908,692 A | 6/1999 | Hamers et al. | 2002/0146714 A1 | 10/2002 | Lieber et al. |
| 5,916,642 A | 6/1999 | Chang | 2002/0158342 A1 | 10/2002 | Tuominen et al. |
| 5,942,443 A | 8/1999 | Parce et al. | 2002/0172820 A1 | 11/2002 | Majumdar et al. |
| 5,997,832 A * | 12/1999 | Lieber et al. ............... 423/249 | 2002/0175408 A1 | 11/2002 | Majumdar et al. |
| 6,036,774 A | 3/2000 | Lieber et al. | 2002/0179434 A1* | 12/2002 | Dai et al. ................... 204/242 |
| 6,038,060 A | 3/2000 | Crowley | 2002/0187504 A1 | 12/2002 | Reich et al. |
| 6,060,121 A | 5/2000 | Hidber et al. | 2003/0001091 A1 | 1/2003 | Nakayama et al. |
| 6,060,724 A | 5/2000 | Flory et al. | 2003/0003300 A1 | 1/2003 | Korgel et al. |
| 6,069,380 A | 5/2000 | Chou et al. | 2003/0032892 A1 | 2/2003 | Erlach et al. |
| 6,123,819 A * | 9/2000 | Peeters ........................ 204/452 | 2003/0048619 A1 | 3/2003 | Kaler et al. |
| 6,128,214 A | 10/2000 | Kuekes et al. | 2003/0073071 A1 | 4/2003 | Fritz et al. |
| 6,143,184 A | 11/2000 | Martin et al. | 2003/0089899 A1 | 5/2003 | Lieber et al. |
| 6,149,819 A | 11/2000 | Martin et al. | 2003/0098488 A1 | 5/2003 | O'Keeffe et al. |
| 6,159,742 A | 12/2000 | Lieber et al. | 2003/0113713 A1 | 6/2003 | Glezer et al. |
| 6,180,239 B1 | 1/2001 | Whitesides et al. | 2003/0113940 A1 | 6/2003 | Erlanger et al. |
| 6,187,165 B1 | 2/2001 | Chien et al. | 2003/0121764 A1 | 7/2003 | Yang et al. |
| 6,190,634 B1 | 2/2001 | Lieber et al. | 2003/0124509 A1 | 7/2003 | Kenis et al. |
| 6,203,864 B1 | 3/2001 | Zhang et al. | 2003/0124717 A1 | 7/2003 | Awano et al. |
| 6,207,392 B1 | 3/2001 | Weiss et al. | 2003/0134267 A1 | 7/2003 | Kang et al. |
| 6,231,744 B1 | 5/2001 | Ying et al. | 2003/0134433 A1 | 7/2003 | Gabriel et al. |
| 6,256,767 B1 | 7/2001 | Kuekes et al. | 2003/0135971 A1 | 7/2003 | Liberman et al. |
| 6,270,074 B1 | 8/2001 | Rasmussen et al. | 2003/0156992 A1 | 8/2003 | Anderson et al. |
| 6,278,231 B1 | 8/2001 | Iwasaki et al. | 2003/0186522 A1 | 10/2003 | Duan et al. |
| 6,286,226 B1 | 9/2001 | Jin | 2003/0186544 A1 | 10/2003 | Yoshitaka et al. |
| 6,287,765 B1 | 9/2001 | Cubicciotti | 2003/0189202 A1 | 10/2003 | Li et al. |
| 6,314,019 B1 | 11/2001 | Kuekes et al. | 2003/0197456 A1 | 10/2003 | Den et al. |
| 6,325,904 B1 | 12/2001 | Peeters | 2003/0200521 A1 | 10/2003 | DeHon et al. |
| 6,340,822 B1 | 1/2002 | Brown et al. | 2004/0005723 A1 | 1/2004 | Empedocles et al. |
| 6,346,189 B1* | 2/2002 | Dai et al. ................... 205/766 | 2004/0026684 A1 | 2/2004 | Empedocles |
| 6,355,198 B1 | 3/2002 | Kim et al. | 2004/0067530 A1 | 4/2004 | Gruner |
| 6,359,288 B1 | 3/2002 | Ying et al. | 2004/0095658 A1 | 5/2004 | Bureta et al. |
| 6,437,329 B1 | 8/2002 | Yedur et al. | 2004/0112814 A1 | 6/2004 | Takamatsu et al. |
| 6,459,095 B1 | 10/2002 | Heath et al. | 2004/0112964 A1 | 6/2004 | Empedocles et al. |
| 6,465,132 B1 | 10/2002 | Jin | 2004/0113138 A1 | 6/2004 | DeHon et al. |
| 6,468,657 B1 | 10/2002 | Hou et al. | 2004/0113139 A1 | 6/2004 | DeHon et al. |
| 6,503,375 B1 | 1/2003 | Maydan et al. | 2004/0118448 A1 | 6/2004 | Scher et al. |
| 6,528,020 B1 | 3/2003 | Dai et al. | 2004/0136866 A1 | 7/2004 | Pontis et al. |
| 6,538,367 B1 | 3/2003 | Choi et al. | 2004/0146560 A1 | 7/2004 | Whiteford et al. |
| 6,559,468 B1 | 5/2003 | Kuekes et al. | 2004/0157414 A1 | 8/2004 | Gole et al. |
| 6,586,095 B2 | 7/2003 | Wang et al. | 2004/0213307 A1 | 10/2004 | Lieber et al. |
| 6,628,053 B1 | 9/2003 | Den et al. | 2005/0037374 A1 | 2/2005 | Melker et al. |
| 6,716,409 B2 | 4/2004 | Hafner et al. | 2005/0064185 A1 | 3/2005 | Buretea et al. |
| 6,741,019 B1 | 5/2004 | Filas et al. | 2005/0064731 A1 | 3/2005 | Park et al. |
| 6,743,408 B2 | 6/2004 | Lieber | 2005/0066883 A1 | 3/2005 | Dubrow et al. |
| 6,756,025 B2 | 6/2004 | Colbert et al. | 2005/0072213 A1 | 4/2005 | Besnard et al. |
| 6,756,795 B2 | 6/2004 | Hunt et al. | 2005/0079533 A1 | 4/2005 | Samuelson et al. |
| 6,762,056 B1 | 7/2004 | Imamiya | 2005/0079659 A1 | 4/2005 | Duan et al. |
| 6,781,166 B2 | 8/2004 | Lieber et al. | 2005/0100960 A1 | 5/2005 | Dai et al. |
| 6,803,840 B2 | 10/2004 | Hunt et al. | 2005/0101026 A1 | 5/2005 | Sailor et al. |
| 6,808,746 B1 | 10/2004 | Dai et al. | 2005/0109989 A1 | 5/2005 | Whiteford, et al. |
| 6,815,706 B2 | 11/2004 | Li et al. | 2005/0110064 A1 | 5/2005 | Duan et al. |
| 6,846,565 B2 | 1/2005 | Korgel et al. | 2004/0106203 A1 | 6/2004 | Stasiak et al. |
| 6,872,645 B2 | 3/2005 | Duan et al. | 2005/0161662 A1 | 7/2005 | Majumdar et al. |
| 6,882,051 B2 | 4/2005 | Majumdar et al. | 2005/0181587 A1 | 8/2005 | Duan et al. |
| 6,882,767 B2 | 4/2005 | Yang et al. | 2005/0201149 A1 | 9/2005 | Duan et al. |
| 6,902,720 B2 | 6/2005 | McGimpsey | 2005/0202615 A1 | 9/2005 | Duan et al. |
| 6,946,197 B2 | 9/2005 | Yadav et al. | 2005/0212079 A1 | 9/2005 | Stumbo et al. |
| 6,958,216 B2 | 10/2005 | Kelley et al. | 2005/0214967 A1 | 9/2005 | Scher et al. |
| 6,962,823 B2 | 11/2005 | Empedocles et al. | 2005/0219788 A1 | 10/2005 | Chow et al. |
| 6,974,706 B1 | 12/2005 | Melker et al. | 2005/0230356 A1 | 10/2005 | Empedocles |
| 6,996,147 B2 | 2/2006 | Majumdar et al. | 2005/0253137 A1 | 11/2005 | Whang et al. |
| 7,048,903 B2 | 5/2006 | Colbert et al. | 2005/0287717 A1 | 12/2005 | Heald et al. |
| 7,129,554 B2 | 10/2006 | Lieber et al. | 2006/0008942 A1 | 1/2006 | Romano et al. |
| 2001/0054709 A1* | 12/2001 | Heath et al. ................... 257/25 | 2006/0009003 A1 | 1/2006 | Romano et al. |
| 2002/0013031 A1 | 1/2002 | Chen et al. | | | |

2006/0019472 A1  1/2006  Pan et al.

FOREIGN PATENT DOCUMENTS

| EP | 1 087 413 A2 | 3/2001 |
|---|---|---|
| JP | 11-11917 A2 | 1/1999 |
| JP | 2000-31462 A | 1/2000 |
| WO | WO 91/06036 A1 | 5/1991 |
| WO | WO 95/02709 A2 | 1/1995 |
| WO | WO 96/29629 A2 | 9/1996 |
| WO | WO 97/33737 A1 | 9/1997 |
| WO | WO 97/34025 A1 | 9/1997 |
| WO | WO 98/39250 A1 | 9/1998 |
| WO | WO 98/48456 A1 | 10/1998 |
| WO | WO 98/42620 A1 | 10/1999 |
| WO | WO 99/63347 A2 | 12/1999 |
| WO | WO 00/09443 A1 | 2/2000 |
| WO | WO 00/17101 A1 | 3/2000 |
| WO | WO 00/19494 A1 | 4/2000 |
| WO | WO 00/51186 * | 8/2000 |
| WO | WO 00/51189 | 8/2000 |
| WO | WO 01/03208 A1 | 1/2001 |
| WO | WO 01/44796 A1 | 6/2001 |
| WO | WO 02/17362 A2 | 2/2002 |
| WO | WO 02/31183 A1 | 4/2002 |
| WO | WO 02/48701 A2 | 6/2002 |
| WO | WO 02/080280 A1 | 10/2002 |
| WO | WO 02/086480 A1 | 10/2002 |
| WO | WO 03/005450 A2 | 1/2003 |
| WO | WO 03/016901 A1 | 2/2003 |
| WO | WO 03/053851 A2 | 7/2003 |
| WO | WO 03/054931 A1 | 7/2003 |
| WO | WO 03/063208 A2 | 7/2003 |
| WO | WO 2004/003535 | 1/2004 |
| WO | WO 2004/010552 A1 | 1/2004 |
| WO | WO 2004/032190 A2 | 4/2004 |
| WO | WO 2004/032193 A2 | 4/2004 |
| WO | WO 2004/034025 A2 | 4/2004 |
| WO | WO 2005/089165 | 9/2005 |
| WO | WO 2005/093831 A1 | 10/2005 |
| WO | WO 2005/094440 | 10/2005 |
| WO | WO 2005/114282 A2 | 12/2005 |
| WO | WO 2006/107312 A1 | 10/2006 |

OTHER PUBLICATIONS

Chung et al., Applied Physics Letters, V76, N15, 2000, p. 2069-2070.*
Wolf et al., Silicon Processing for the VLSI Era, Lattice Press, V1, 2000, pp. 12-13.*
Morales et al., Science, V279, 1998, pp. 208-211.*
Tans et al., Nature, V393, 1998, p. 49-52.*
Haraguchi et al., Applied Physics Letters, V60, 1992, p. 745-747.*
Yu et al., Applied Physics Letters, V72, 1998, p. 3458-3460.*
Esfarjani et al., Applied Physics Letters, V74, 1999, p. 79-81.*
Yamada, Applied Physisc Letters, V76, 2000, p. 628-630.*
Martel et a., Applied Physics Letters, V73, N17, Oct. 26, 1998, pp. 2447-2449.*
(Morales et al, Science, V279, 1998, pp. 208-211.*
Cui, Yi, et al. "Doping and Electrical Transport in Silicon Nanowires", *The Journal of Physical Chemistry*, vol. 104, No. 22, Jun. 8, 2000, pp. 5213-5216.
Gudiksen, Mark S., et al. "Diameter-Selective Synthesis of Semiconductor Nanowires", *J. Am. Chem. Soc. 2000*, 122, Jun. 6, 2000, pp. 8801-8802.
Duan, Xiangfeng, et al., "General Synthesis of Compound Semiconductor Nanowires", *Adv. Materials. 2000*, 12, No. 4, pp. 298-302, published on Web Feb. 17, 2000.
Duan, Xiangfeng, et al., "Laser-Assisted Catalytic Growth of Single Crystal GaN Nanowires", *J. Am. Chem. Soc. 2000*, 122, Oct. 18, 1999, pp. 188-189; published on Web Dec. 18, 1999.
Huang, Yu, et al., "Directed Assembly of One-dimensional Nanostructures into Functional Networks", *SCIENCE*, vol. 291, Jan. 26, 2001, pp. 630-633.

Duan, Xiangfeng, et al., "Indium phosphide nanowires as building blocks for nanoscale electronic and optoelectronic devices", *Nature*, vol. 409, Jan. 4, 2001, pp. 66-69.
Collier, C.P., et al., "Electronically Configurable Molecular-Based Logic Gates", *SCIENCE*, vol. 285, Jul. 16, 1999, pp. 391-394.
J. Chen et al, "Large On-Off Ratios and Negative Differential Resistance in a Molecular Electronic Device," *Science*, vol. 286, Nov. 19, 1999, pp. 1550-1551.
Office Action mailed Sep. 2, 2003 in co-pending U.S. Appl. No. 09/935,776, filed Aug. 22, 2001.
Office Action mailed Jan. 15, 2003 in co-pending U.S. Appl. No. 10/020,004, filed Dec. 11, 2001.
Yamada, Applied Physics Letters, V76, 2000, p. 628-630.
Chen et al, "Large on-off ratios and negative differential resistance in a molecular electronic device", *Science*, Nov. 19, 1999, vol. 286, , pp. 1550-1551.
Collier et al., "Electronically configurable molecular-based logic gates", *Science*, Jul. 16, 1999, vol. 285, pp. 391-394.
Cui et al., "Nanowire nanosensors for highly sensitive and selective detection of biological and chemical species", *Science*, Aug. 17, 2001, vol. 293, pp. 1289-1292.
Cui et al, "Diameter-controlled synthesis of single-crystal silicon nanowires", *Applied Physics Letters*, Apr. 9, 2001, vol. 78, No. 15, pp. 2214-2216.
Cui et al. "Doping and electrical transport in silicon nanowires", *The Journal of Physical Chemistry*, Jun. 8, 2000, vol. 104, No. 22, , pp. 5213-5216.
Cui et al., "Functional nanoscale electronic devices assembled using silicon nanowire building blocks", *Science*, Feb. 2, 2001, vol. 291, pp. 851-853.
Duan et al., "Indium phosphide nanowires as building blocks for nanoscale electronic and optoelectronic devices", Jan. 4, 2001, *Nature*, vol. 409, pp. 66-69.
Duan et al., "General synthesis of compound semiconductor nanowires", *Adv. Materials. 2000*, vol. 12, No. 4, pp. 298-302, published on Web Feb. 17, 2000.
Duan et al., "Laser-assisted catalytic growth of single GaN nanowires", *J. Am. Chem. Soc. 2000*, Oct. 18, 1999, vol. 122, pp. 188-189; published on Web Dec. 18, 1999.
Duan et al. "Nanoscale electronic and optoelectronic devices assembled from indium phosphide nanowire building blocks", supplementary article, *Nature*, 2001, vol. 409, pp. 66-69.
Givargizov, "Fundamental aspects of VSL growth", *Journal of Crystal Growth*, 1975, vol. 31, pp. 20-30.
Gudiksen et al. "Diameter-selective synthesis of semiconductor nanowires", *J. Am. Chem. Soc. 2000*, Jun. 6, 2000, vol. 122, pp. 8801-8802.
Gudiksen et al., "Growth of nanowire superlattice structures for nanoscale photonics and electronics", *Nature*, 2002, vol. 415, pp. 617-620.
Haraguchi et al. "Polarization dependence of light emitted from GaAs p-n junctions in a quantum wire crystals", *Journal of Applied Physics*, Apr. 1994, vol. 75, No. 8, pp. 4220-4225.
Hiruma et al., "Self-organized growth of GaAs/InAs heterostructure nanocylinders by organometalic vapor phase epitaxy", *Journal of Crystal Growth*, 1996, vol. 163, pp. 226-231.
Huang et al., "Directed assembly of one-dimensional nanostructures into functional networks", *Science*, Jan. 26, 2001, vol. 291, pp. 630-633.
Huang et al., "Logic gates and computation from assembled nanowire building blocks", *Science*,2000, vol. 287, pp. 624-625.
Kanjanachuchai et al., "Coulomb blockade in strained-Si nanowires on leaky virtual substrates", *Semiconductor Science and Technology*, 2001, vol. 16, pp. 72-76.
Kong et al. "Nanotube molecular wires as chemical sensors", *Science*, Jan. 28, 2000, vol. 287, pp. 622-625.
Lahoun et al., "Epitaxial core-shell and core-multishell nanowire heterostructures", *Nature*, 2002, vol. 420, pp. 57-61.
Star et al., "Preparation and properties of polymer-wrapped single-walled carbon nanotubes", *Angew. Chem. Int.*, 2001, vol. 40, No. 9, pp. 1721-1725.

Wang et al., "Highly polarized photoluminescence and photodetection from single indium phosphide nanowires", Science, 2001, vol. 293, pp. 1455-1457.
Wu et al., "Block-by-block growth of single-crystalline Si/SiGe superlattice nanowires", web release date, Jan. 19, 2002, http://pubs.acs.org/hotartcl/nalefd/2002/nl0156888_rev.html.
"IBM creates highest performing nanotube transistors", IBM News, 2002.
Cheung, C.L., et al., "Diameter Controlled Synthesis of Carbon Nanotubes," *J. Phys. Chem B*, 106, (2002), pp. 2429-2433.
Duan, X., et al., "Nonvolatile Memory and Programmable Logic from Molecule-Gated Nanowires," *Nano Letters*, 2(5), (2002), pp. 487-490.
Duan, X., et al., "Single-nanowire electrically driven lasers," Nature, 421, (2003), pp. 241-245.
Gudiksen, M.S., et al., "Synthetic Control of the Diameter and Length of Single Crystal Semiconductor Nanowires," *J. Phys. Chem. B*, 105, (2001), pp. 4062-4064.
Gudiksen, M.S., et al., "Size-Dependent Photoluminescence from Single Indium Phosphide Nanowires," *J. Phys. Chem. B*, 106, (2002), pp. 4036-4039.
Holmes, et al., "Control of Thickness and Orientation of Solution-Grown Silicon Nanowires," Science, 287, (2000), pp. 1471-1473.
Hu, J., et al., "Chemistry and Physics in One Dimension: Synthesis and Properties of Nanowires and Nanotubes," Acc. Chem. Res., 32. (1999), pp. 435-445.
Hu, J., et al., "Controlled growth and electrical properties of heterojunctions of carbon nanotubes and silicon nanowires," *Nature*, 399, (1999), pp. 48-51.
Hu, S.-Y., Serpentine Superlattice Nanowire-Array Lasers, *J. Quant. Electron.*, 31(8), (1995), pp. 1380-1388.
Huang, M., et al., "Room-Temperature Ultraviolet Nanowire Nanolasers," *Science*292, (2001), pp. 1897-1898.
Huang, Y., et al., "Gallium Nitride Nanowire Nanodevices," *Nano Letters*, 2(2), (2002), pp. 101-104.
Huang, Y., et al., "Logic Gates and Computation from Assembled Nanowire Building Blocks," *Science*, 294, (2001), pp. 1313-137.
Johnson, J.C., et al., "Single Nanowire Lasers," *J. Phys. Chem.*, 105(46), (2001), pp. 11387-11390.
Johnson, J.C., et al., "Single gallium nitride nanowire lasers," *Nature*, 1, (2002), pp. 106-110.
Joselevich, E., et al., "Vectorial Growth of Metallic and Semiconducting Single-Wall Carbon Nanotubes," *Nano Letters*, 2(10), (2002), pp. 1137-1141.
Kong, J. et al., "Synthesis of individual single-walled carbon nanotubes on patterned silicon wafers," *Nature*, 395, (1998), pp. 878-881.
Kong, J. et al., "Chemical vapor deposition of methane for single-walled carbon nanotubes," Chem. Physics Letters, 292, (1998) pp. 567-574.
Rueckes, T., et al., "Carbon Nanotube-Based Nonvolatile Random Access Memory for Molecular Computing," *Science*, 298, (2000), pp. 94-97.
Thess, A. et al., "Crystalling Ropes of Metallic Carbon Nanotubes," *Science*, 273, (1996), pp. 483-487.
Wang, N., et al., "$SiO_2$-enhanced synthesis of Si nanowires by laser ablation," *App. Physics Letters*, 73(26); (1998), pp. 3902-3904.
Wei, Q., et al., "Synthesis of Single Crystal Bismuth-Telluride and Lead-Telluride Nanowires for New Thermoelectric Materials," *Mat. Res. Soc. Symp. Proc.*, 581, (2000), pp. 219-223.
Wong, et al., "Covalently functionalized nanotubes as nanometre-sized probes in chemistry and biology," Nature, 394, (1998), pp. 52-55.
Wu, Y., et al., "Block-by-Block Growth of Single-Crystalline Si/SiGe Superlattice Nanowires," *Nano Letters*, 2(2), (2002), pp. 83-86.
Yang, P. et al., "Controlled Growth of ZnO Nanowires and Their Optical Properties," *Adv. Funct. Mater*, 12(5), (2002), pp. 323-331.
Zhou, G., et al., "Growth morphology and micro-structural aspects of Si nanowires synthesized by laser ablation," *J. of Crystal Growth*, 197, (1999), pp. 129-135.
Office Action mailed Sep. 15, 2004 in U.S. Appl. No. 09/935,776, filed Aug. 22, 2001.
Office Action mailed Jun. 25, 2004 in U.S. Appl. No. 10/020,004, filed Dec. 11, 2001.
PCT International Search Report for PCT/US03/22061, dated Jun. 22, 2004, International Filing Date Jul. 16, 2003.
Haraguchi, et al., "Polarization dependence of light emitted from GaAs p-n junctions in quantum wire cyrstals," *J.Appl.Phys.*, 1994 75(8): 4220-4225.
Jin, et al., "Scalable Interconnection and Integration of Nanowire Devices without Registration," *NanoLetters*, 2004, 4(5):915-919.
Lauhon, et al., "Semiconductor nanowire heterostructures", *Phil. Trans. R. Soc. Lond. A* (2004) 362:1247-1260.
Lieber, "Nanoscale Science and Technology: Building a Big Future from Small Things," *MRS Bulletin*, 2003, 486-491.
Lu, et al., "One-dimensional hole gas in germanium/silicon nanowire heterostructures," *PNAS*, 2005, 102(29):10046-10051.
Zhong, et al., "Nanowire Crossbar Arrays as Address Decoders for Integrated Nanosystems," *Science*, 2003, 302:1377-1379.
Office Action mailed Aug. 30, 2005 in U.S. Appl. No. 09/935,776, filed Aug. 22, 2001.
Office action mailed Aug. 30, 2005 in U.S. Appl. No. 10/020,004, filed Dec. 11, 2001.
Search Report in PCT/US01/48230 filed Dec. 11, 2001.
Agarwal, R. et al., "Lasing in Single Cadmium Sulfide Nanowire Optical Cavities," *Nano Letters*, 2005, 5(5):917-920.
Chen, R.J. et al., "Noncovalent functionalization of carbon nanotubes for highly specific electronic biosensors," *PNAS*, Apr. 2003, 100(9):4984-4989.
Choi, K.J. et al., "Enhancement of Ferroelectricity in Strained $BaTiO_3$ Thin Films," *Science*, Nov. 2004, 306:1005-1009.
Duan, X. et al., "Synthesis and optical properties of gallium arsenide nanowires," *Applied Physics Letters*, Feb. 2000, 76(9):1116-1118.
Friedman, R.S. et al., "High-speed integrated nanowire circuits," *Nature*, Apr. 2005, 434:1085.
Gradecak, S. et al., "GaN nanowire lasers with now lasing thresholds," *Applied Physics Letters*, 2005, 87:173111-1-173111-3.
Hahm, J. et al., "Direct Ultrasensitive Electrical Detection of DNA and DNA Sequence Variations Using Nanowire Nanosensors," *Nano Letters*, 2004, 4(1):51-54.
Heath, J.R. et al., "A liquid solution synthesis of single crystal germanium quantum wires," *Chemical Physics Letters*, Jun. 1993, 208(3,4):263-268.
Hiruma, K. et al., "GaAs fr e-standing quantum-siz wires," J. Appl. Phys., 1993, 74(5):3162-3171.
Hu, S.Y. et al., "Serpentine Superlattice Nanowire-Array Lasers," *IEEE Journal of Quantum Electronics*, Aug. 1995, 31(8):1380-1388.
Law, M. et al., "Nanoribbon Waveguides for Subwavelength Photonics Integration," *Science*, Aug. 2004, 305:1269-1273.
Leff, D.V. et al., "Thermodynamic Control of Gold Nanocrystal Size: Experiment and Theory," *J. Phys. Chem.*, 1995, 99:7036-7041.
Lei, B. et al., "Nanowire transistors with ferroelectric gate dielectrics: Enhanced performance and memory effects," *Applied Physics Letters*, May 2004, 84(22):4553-4555.
Lieber, C., "Nanowire Superlattices," *Nano Letters*, Feb. 2002, 2(2):81-82.
McAlpine, M.C. et al., "High-Performance Nanowire Electronics and Photonics and Nanoscale Patterning on Flexible Plastic Substrates," Proceedings of the IEEE, Jul. 2005, 93(7):1357-1363.
Menon, V.P. et al., "Fabrication and Evaluation of Nanoelectrode Ensembles," Anal. Chem., Jul. 1995, 67(13):1920-1928.
Patolsky, F. et al., "Nanowire nanosensors," Materials Today, Apr. 2005, 8:20-28.
Patolsky, F. et al., "Electrical detection of single viruses," PNAS, Sep. 2004, 101(39):14017-14022.
Pavesi, L., et al., "Optical gain in silicon nanocrystals," *Nature*, vol. 408, pp. 440-444 (2000).
Qi, P. et al., "Toward Large Arrays of Multiplex Functionalized Carbon Nanotube Sensors for Highly Sensitive and Selective Molecular Detection," *Nano Letters*, 2003, 3(3):347-351.
Tong, L. et al., "Subwavelength-diameter silica wires for low-loss optical wave guiding," *Nature*, Dec. 2003, 426:816-819.

Urban, J. et al., "Single-Crystalline Barium Titanate Nanowires," Adv. Mater., 2003, 15(5):423-426.

Vossmeyer, T. et al., "Combinatorial approaches toward patterning nanocrystals," Journal of Applied Physics, 1998, 84(7):3664-3670.

Wang, W.U., "Label-free detection of small-molecule-protein interactions by using nanowire nanosensors," PNAS, 2005, 102(9):3208-3212.

Whang, D. et al., "Large-Scale Hierarchical Organization of Nanowire Arrays for Integrated Nanosystems," Nano Letters, 2003, 3(9) 1255-1259.

Whang, D. et al., "Nanolithography Using Hierarchically Assembled Nanowire Masks," Nano Letters, 2003, 3(7):951-954.

Wu, Y. et al., "Controlled Growth and Structures of Molecular-Scale Silicon Nanowires," Nano Letters, 2004, 4(3):433-436.

Wu, Y. et al. "Single-Crystal metallic nanowires and metal/semiconductor nanowire heterostructures," Nature, 2004, 430:61-65.

Xiang, J., et al., "Ge/Si Nanowire Heterostructures as High-Performance Field-Effect Transistors," Nature, 2006, 441, 489-493.

Yang, P., "Wires on water," Nature, 2003, 425-243-244.

Zheng, G. et al., "Synthesis and Fabrication of High-Performance n-Type Silicon Nanowire Transistors," Advanced Materials, 2004, 16(21):1890-1893.

Zheng, G. et al., "Multiplexed electrical detection of cancer markers with nanowire sensor arrays," Nature Biotechnology, 2005, 23(10):1294-1301.

Zhong, Z. et al., "Synthesis of p-Type Gallium Nitride Nanowires for Electronic and Photonic Nanodevices," Nano Letters, 2003, 3(3):343-346.

Zhong, Z. et al., "Coherent Single Charge Transport in Molecular-Scale Silicon Nanowires," Nano Letters, 2005, 5(6):1143-1146.

Office Action dated Nov. 29, 2005 in U.S. Appl. No. 10/995,075.

Office Action dated Apr. 7, 2006 in U.S. Appl. No. 10/734,086.

Office Action dated May 16, 2006 in U.S. Appl. No. 09/935,776.

International Search Report from Int. Apl. No. PCT/US03/22753, filed Jul. 21, 2003.

International Search Report from Int. Apl. No. PCT/US2005/004459, filed Feb. 14, 2005.

Internatioanl Search Report from Int. Apl. No. PCT/US2005/026759, filed Jul. 28, 2005.

Written Opinion from Int. Apl. No. PCT/US2005/004459, filed Feb. 14, 2005.

Written Opinion from Int. Apl. No. PCT/US2005/026759, filed Jul. 28, 2005.

Written Opinion from PCT/US2005/020974, filed Jun. 15, 2005.

Search Report from PCT/US2005/020974, filed Jun. 15, 2005.

Javey, A., et al., "Ballistic carbon nanotube filed-effect transistors," *Nature*, vol. 424, pp. 654 (2003).

Mizutani, T., et al., "Fabrication and characterization of carbon nanotube FETs," *Proceedings of SPIE*, vol. 5732, pp. 28-36 (2005).

Musin, R.N., et al., "Structural and electronic properties of epitaxial core-shell nanowire heterostructures," *Physical Review*, vol. 71, pp. 155318-1155381-4 (2005).

Nosho, Y., et al., "*n*-type carbon nanotube field-effect transistors fabricated by using Ca contact electrodes," *Applied Physics Letters*, vol. 86, pp. 073105 (2005).

Office Action mailed Oct. 27, 2006 in U.S. Appl. No. 10/734,086 filed Dec. 11, 2003.

Office Action mailed Nov. 2, 2006 in U.S. Appl. No. 10/196,337 filed Jul. 16, 2002.

Office Action mailed Dec. 20, 2006 in U.S. Appl. No. 11/012,549 filed Dec. 15, 2004.

International Search Report from PCT/US2005/034345, filed Sep. 21, 2005.

Written Opinion from PCT/US2005/034345, filed Sep. 21, 2005.

Office Action mailed Mar. 11, 2005 in U.S. Appl. No. 09/935,776 filed Aug. 22, 2001.

Office Action mailed Mar. 14, 2005 in U.S. Appl. No. 10/020,004 filed Dec. 11, 2001.

Duan, X., et al., "High-performance thin-film transistors using semiconductor nanowires and nanoribbons", 2003, Nature, vol. 425, pp. 274-278.

Guo, L. et al., "Nanoscale silicon field effect transistors fabricated using imprint Lithography", 871(13):1881; 1997.

Guo, L. et al., "A Silicon Single-Electron Transitor Memory Operating at Room Temperature", 275:649; 1997.

Huang, et al., "Logic Gates and Computation from Assembled Nanowire Building Blocks", 2001, Science, vol. 294, pp. 1313-1317.

McAlpine, M., "Nanoimprint ithography for Hybrid Plastic Electronics ", Nano-Letters, 2003, vol. 3, No. 4, pp. 443-445.

McAlpine, M. "High-Performance Nanowire Electronics and Photonics on Glass and Plastic Substrates", Nano Letters, 2003, pp. 1531.

Padeste, et al., "Modular amperometric immunosensor devices", 1995, 8th International Conference on Solid-State Sensors an Actuators and Eurosensors, pp. 487-490.

Takayama, S., et al., "Patterning cells and their enviroments using multiple laminar fluid flows in capillary networks", Proc. Natl. Acad. Sci., 1999, vol. 96, pp. 5545-5548.

Tiefenauer, et al., "Towards Amperometric Immunosensor Devices", 1997, Biosensors and Bioelectronics, pp. 213-223.

"IBM creates highest performing nanotube transistors", IBM News, 2002.

International Search Report in PCT Application No. PCT/US01/48230, Int'l Filing Date, Dec. 11, 2001.

Written Opinion in PCT Application No. PCT/US01/48230, Int'l Filing Date, Dec. 11, 2001.

\* cited by examiner

*Primary Examiner*—Shouxiang Hu

(74) *Attorney, Agent, or Firm*—Wolf, Greenfield & Sacks, PC

(57) ABSTRACT

The present invention relates generally to sub-microelectronic circuitry, and more particularly to nanometer-scale articles, including nanoscale wires which can be selectively doped at various locations and at various levels. In some cases, the articles may be single crystals. The nanoscale wires can be doped, for example, differentially along their length, or radially, and either in terms of identity of dopant, concentration of dopant, or both. This may be used to provide both n-type and p-type conductivity in a single item, or in different items in close proximity to each other, such as in a crossbar array. The fabrication and growth of such articles is described, and the arrangement of such articles to fabricate electronic, optoelectronic, or spintronic devices and components. For example, semiconductor materials can be doped to form n-type and p-type semiconductor regions for making a variety of devices such as field effect transistors, bipolar transistors, complementary inverters, tunnel diodes, light emitting diodes, sensors, and the like.

23 Claims, 94 Drawing Sheets

First layer

Second layer

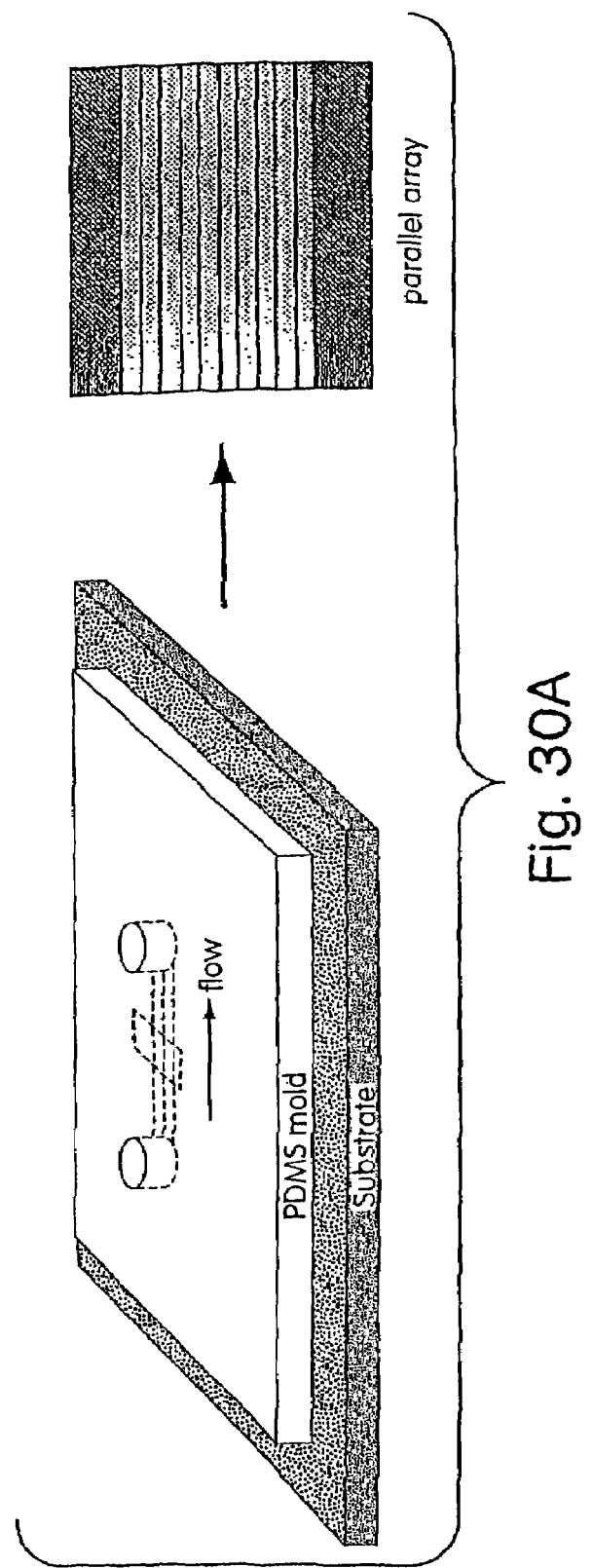

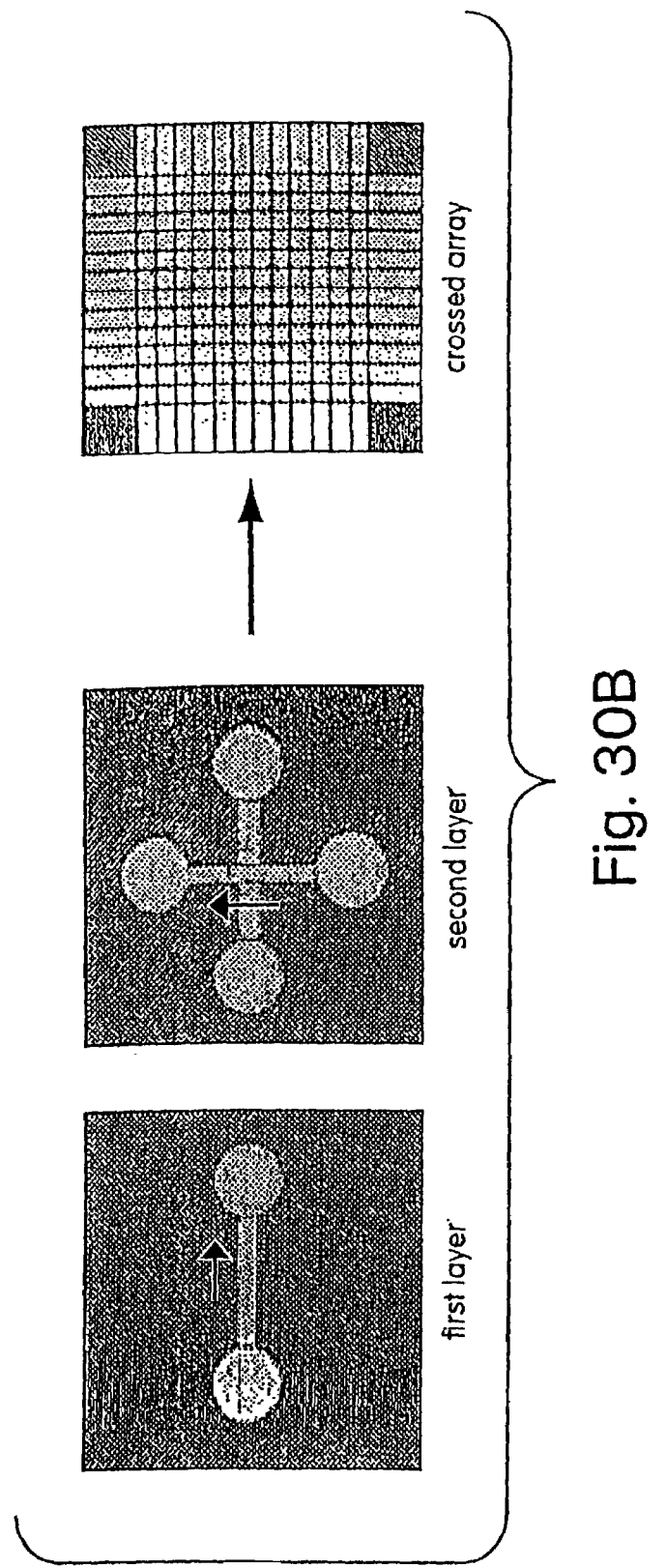

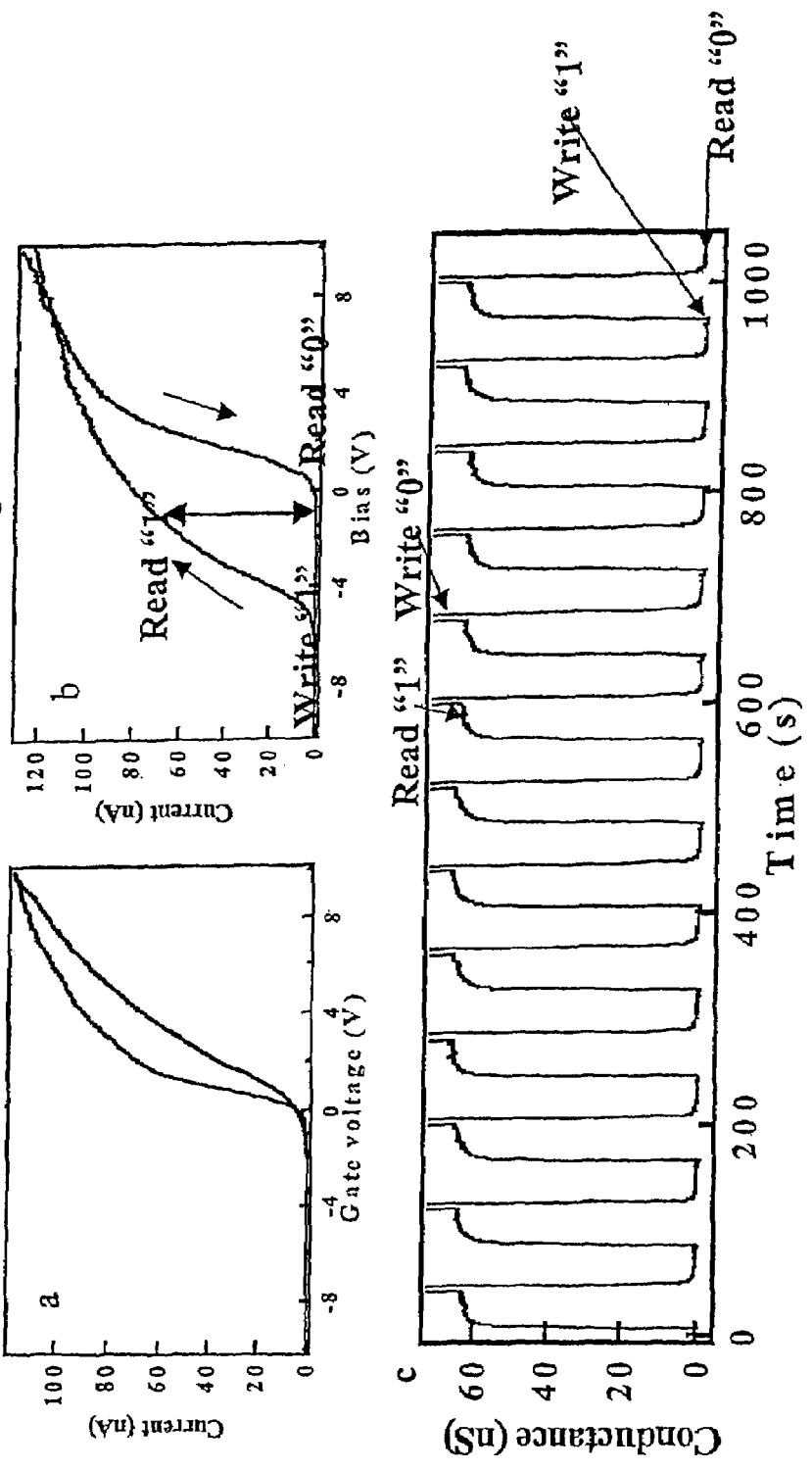

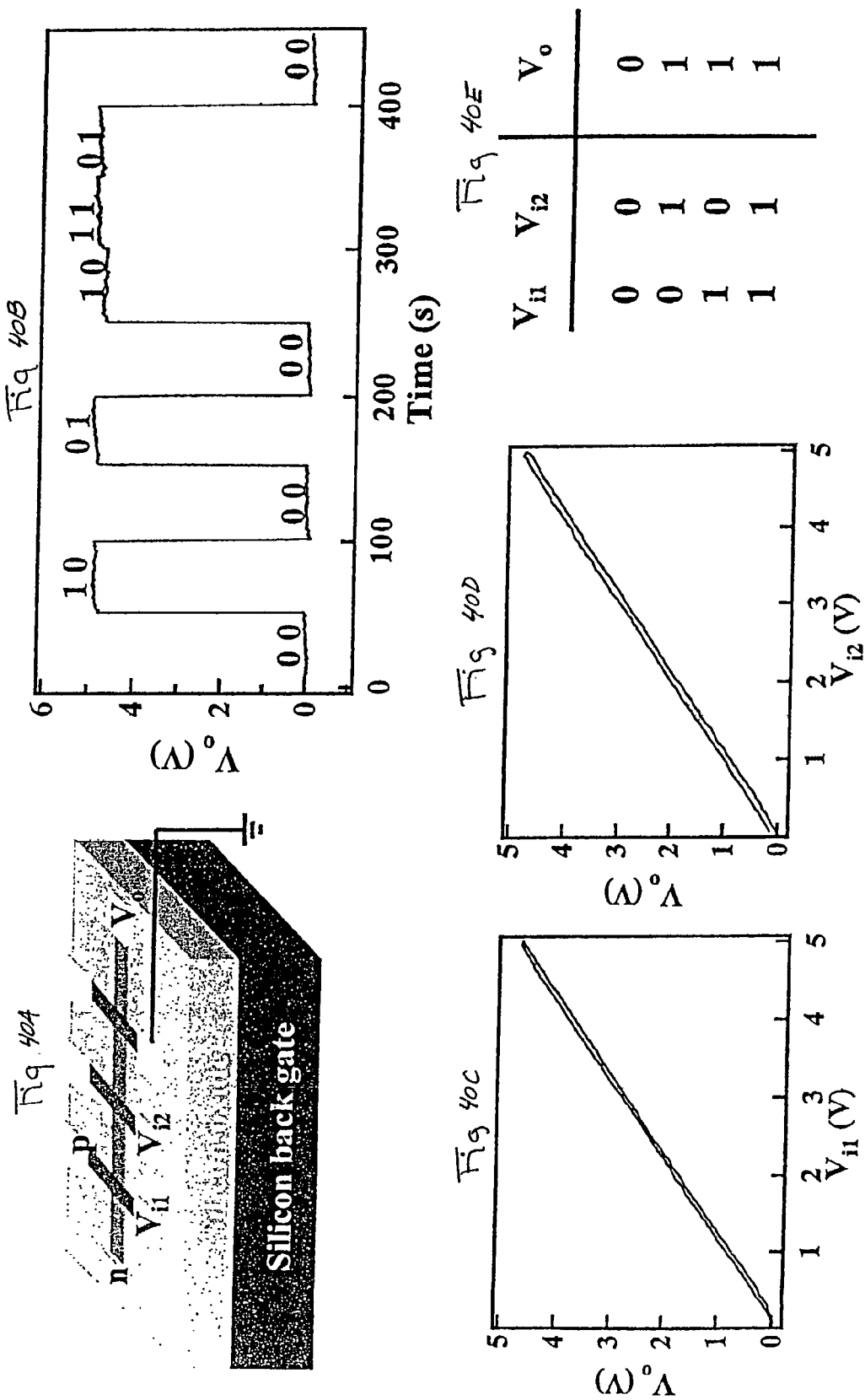

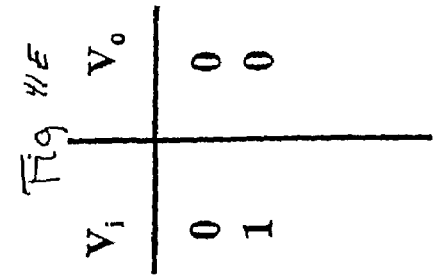
Fig. 4/E
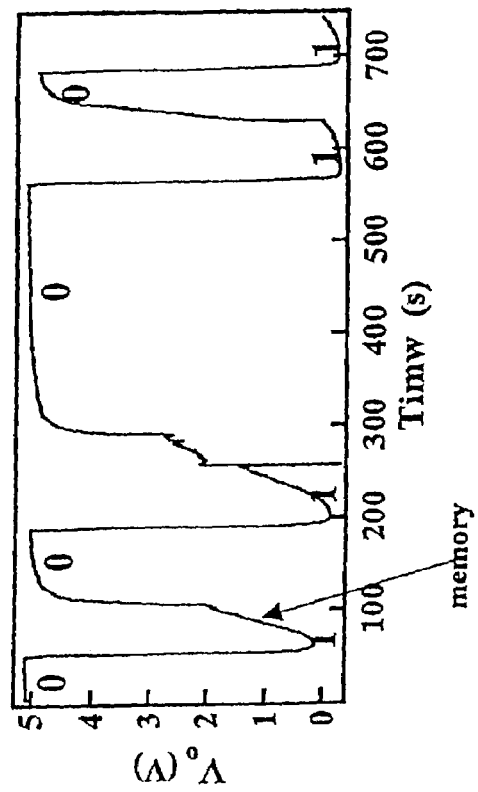
Fig. 4/B
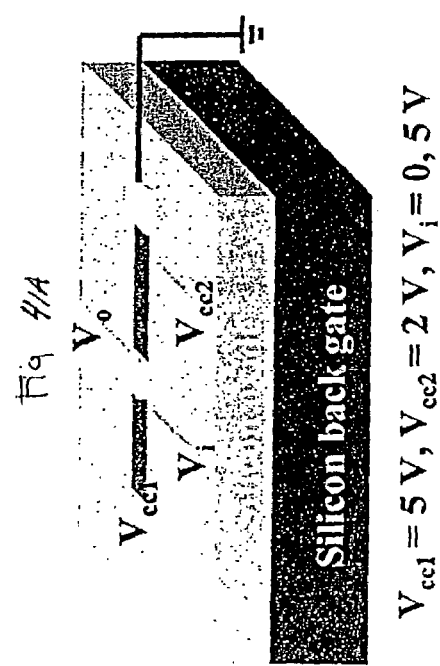
Fig. 4/A
$V_{cc1} = 5V, V_{cc2} = 2V, V_i = 0, 5V$
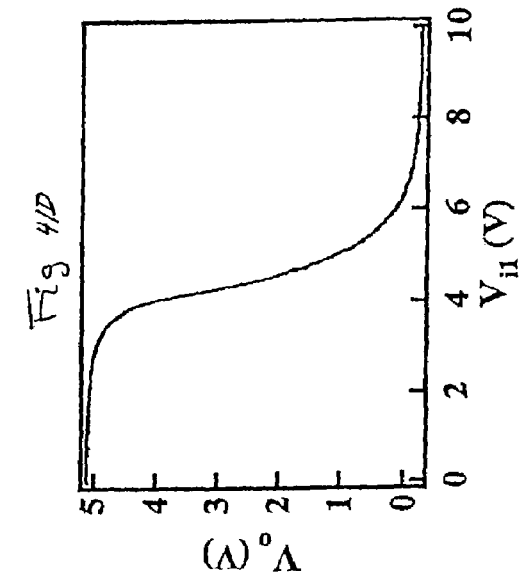
Fig. 4/D
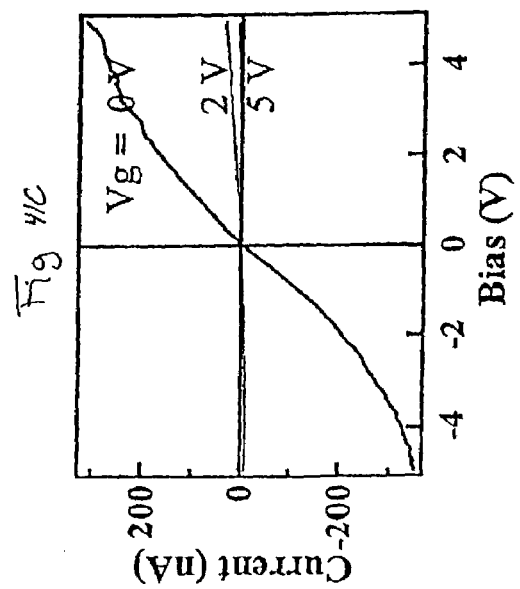
Fig. 4/C

| $V_{i1}$ | $V_{i2}$ | $V_o$ |
|---|---|---|
| 0 | 0 | 1 |
| 0 | 1 | 0 |
| 1 | 0 | 0 |
| 1 | 1 | 0 |

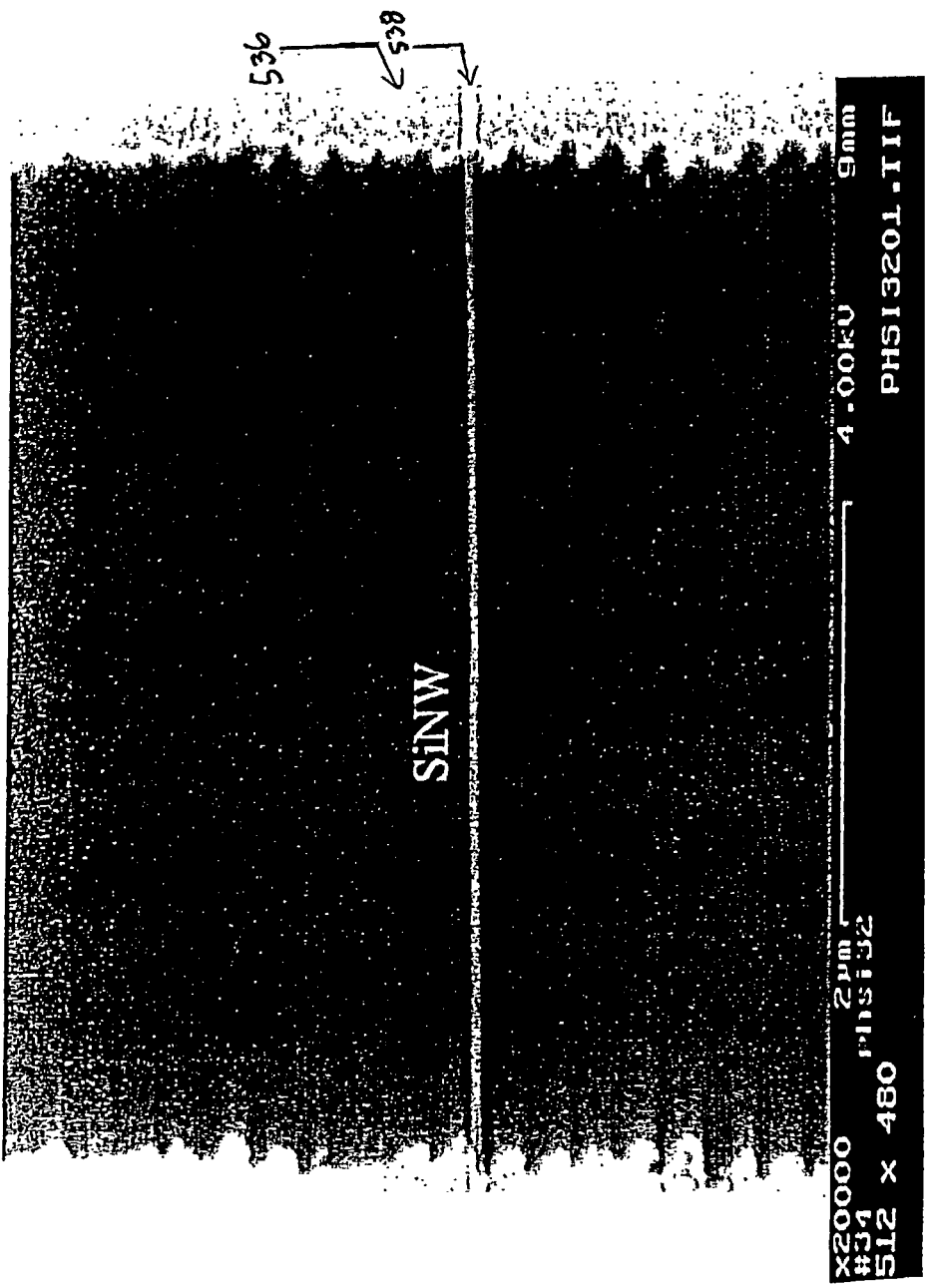

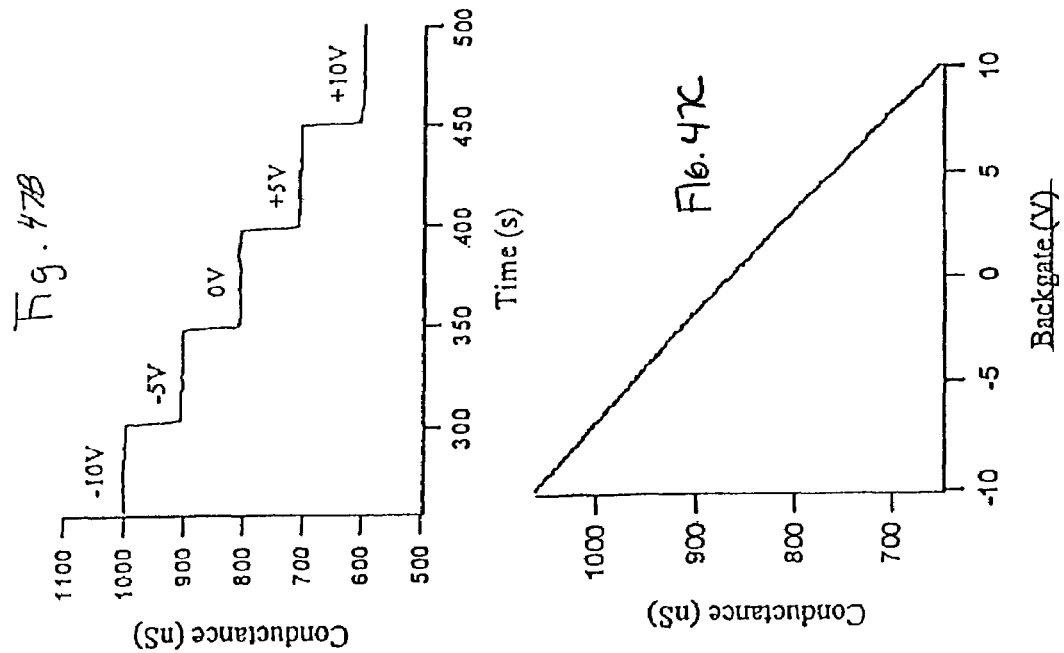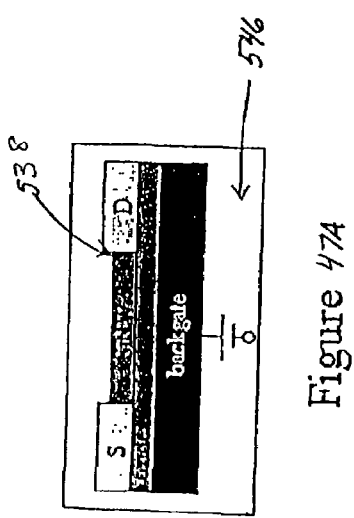
Figure 47A

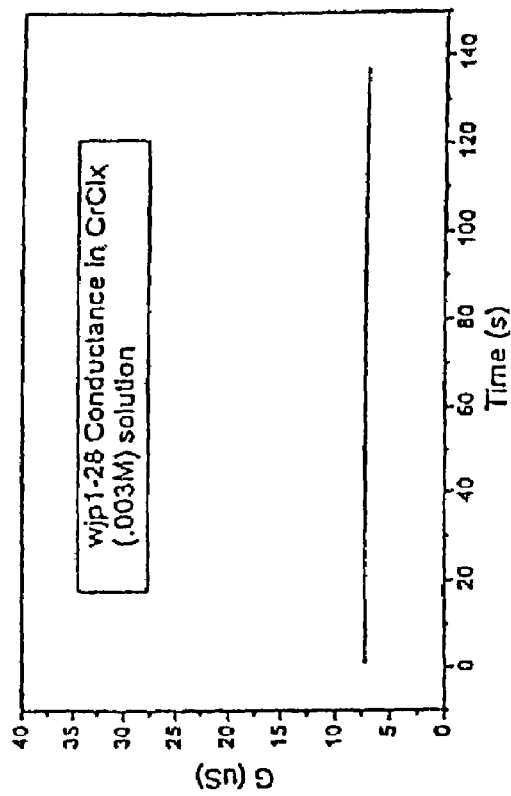
FIG. 5/C
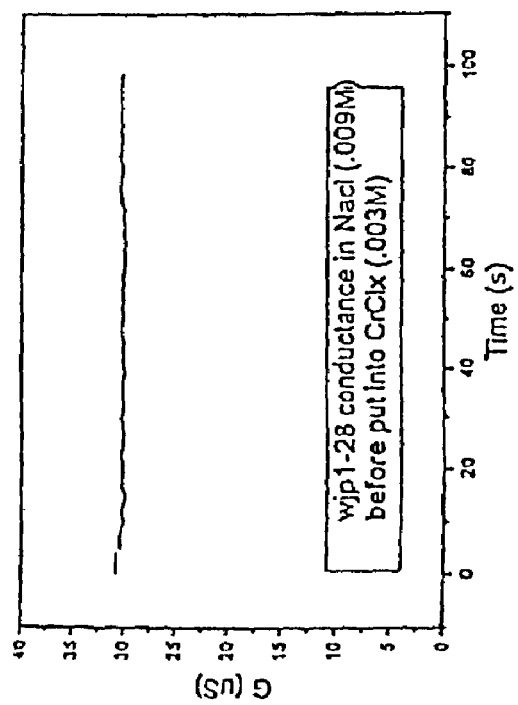
FIG. 5/B

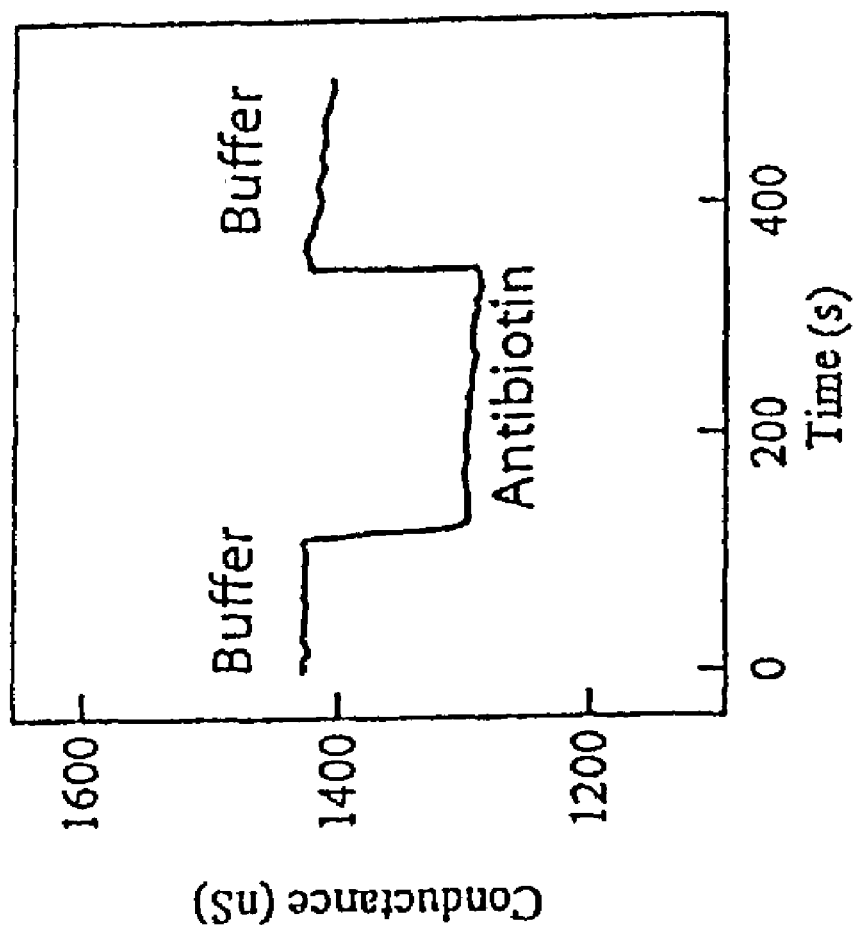

FIG. 56A
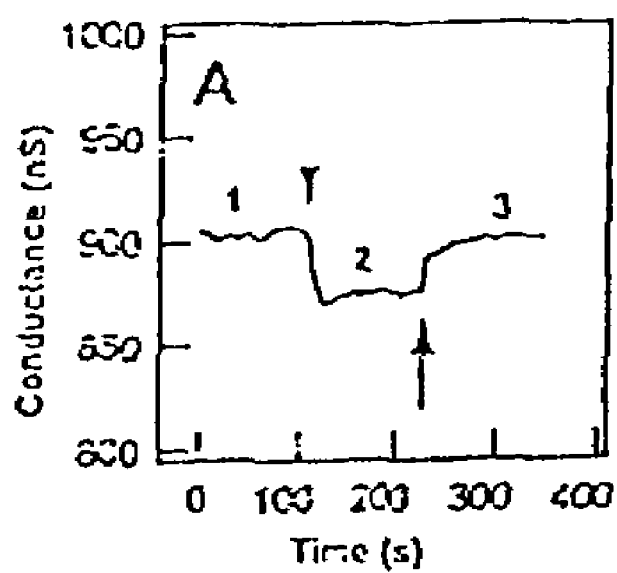
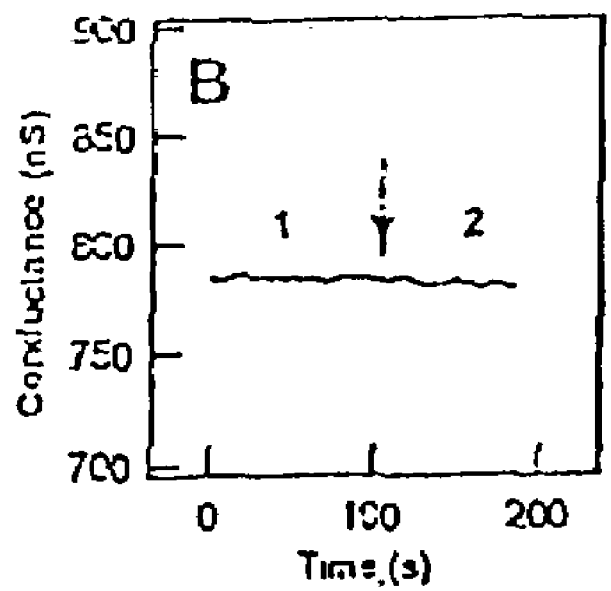
Fig 56B

InP pH Sensor

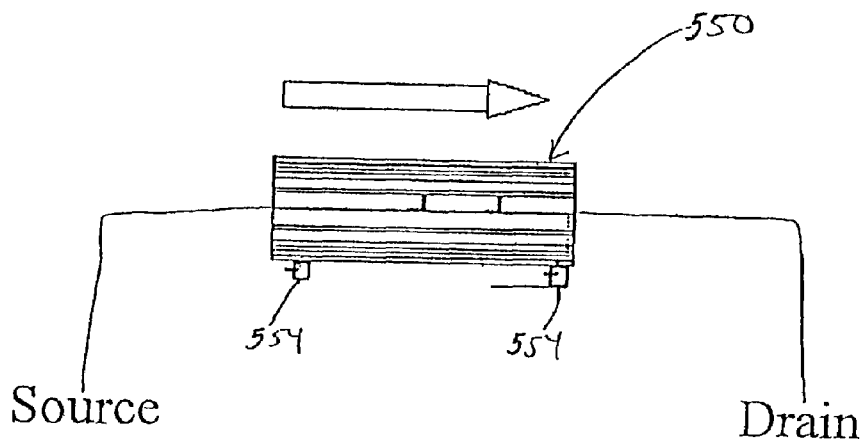
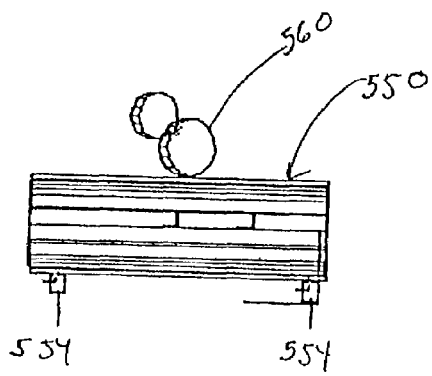
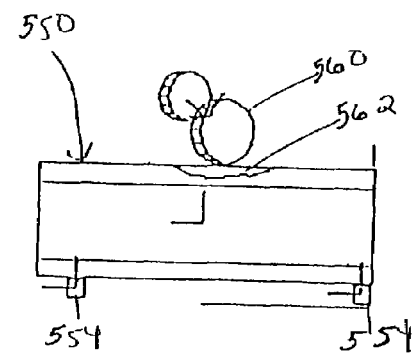

FIG. 69
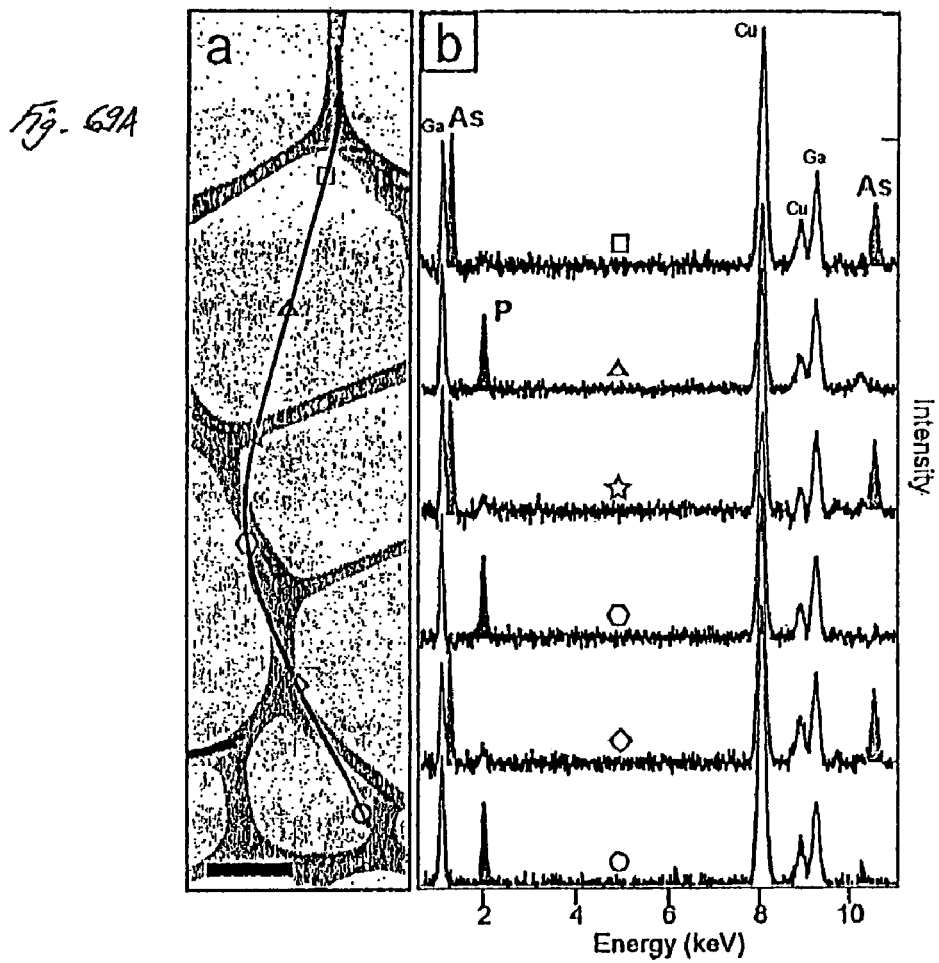
Fig. 69A
Fig. 69B
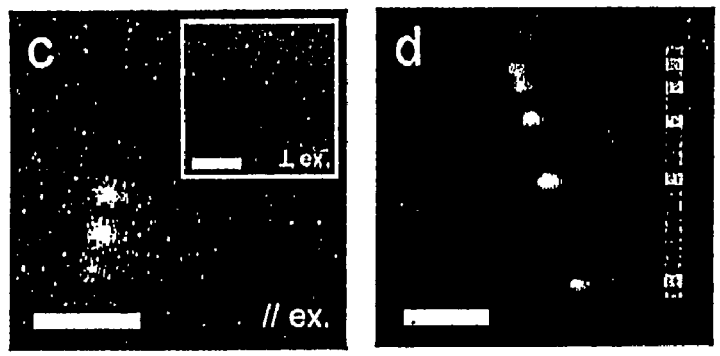
Fig. 69C
Fig. 69D
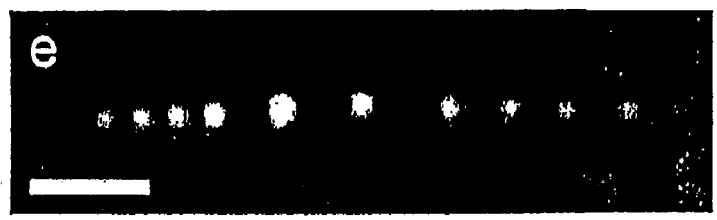
Fig. 69E FIG. 70
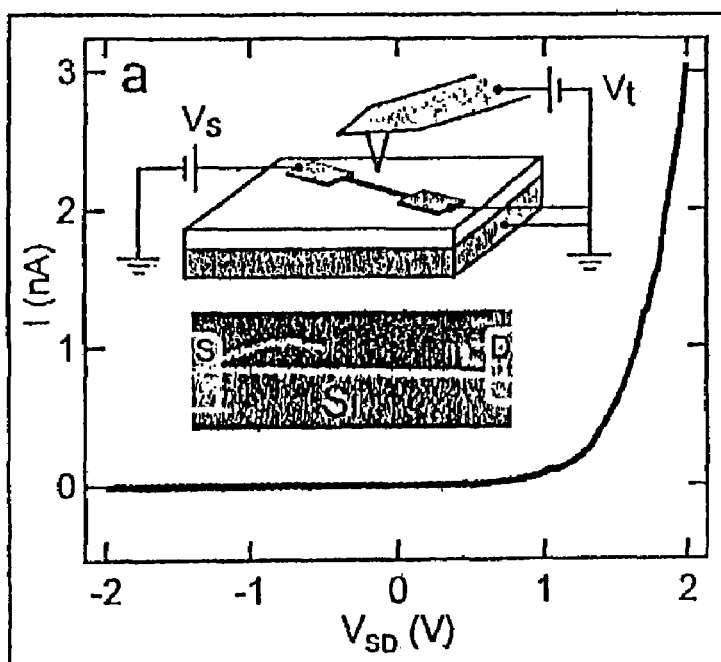
Fig. 70A
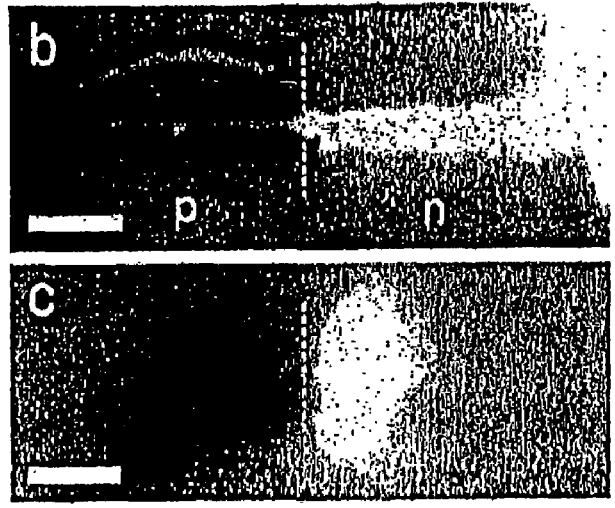
Fig. 70B
Fig. 70C
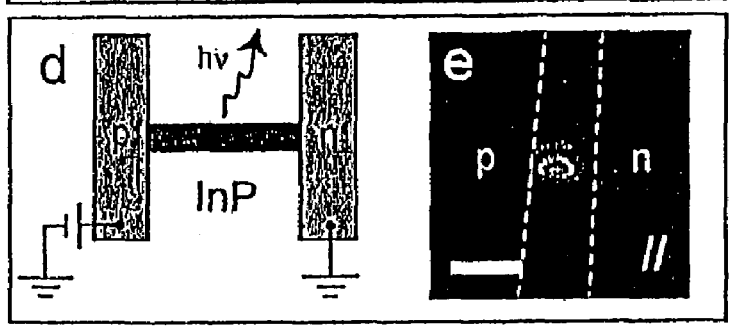
Fig. 70D
Fig. 70E Single nanowire light emitting diode created by introduction of dopants from contacts
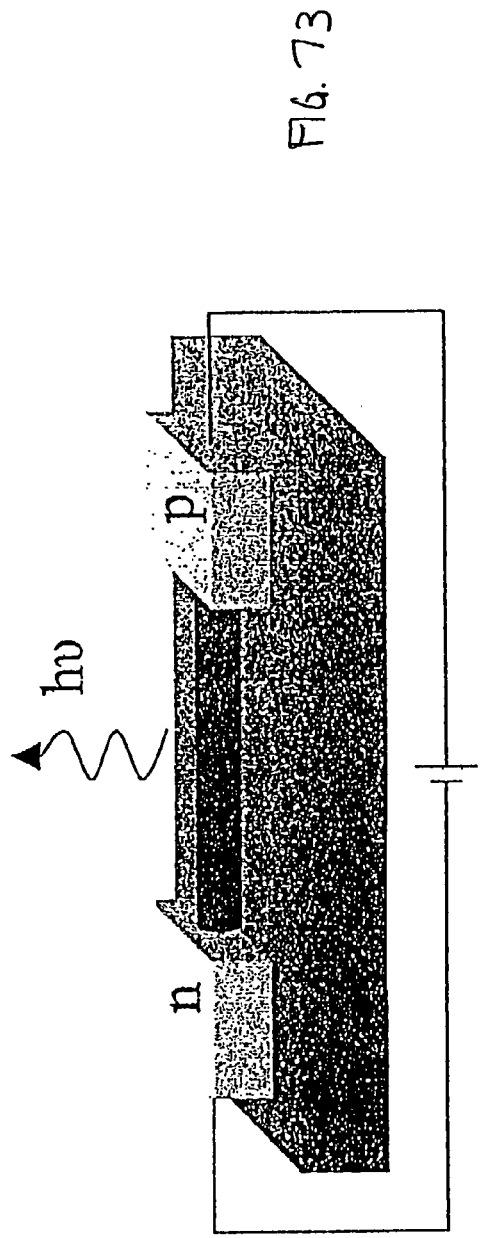
FIG. 73
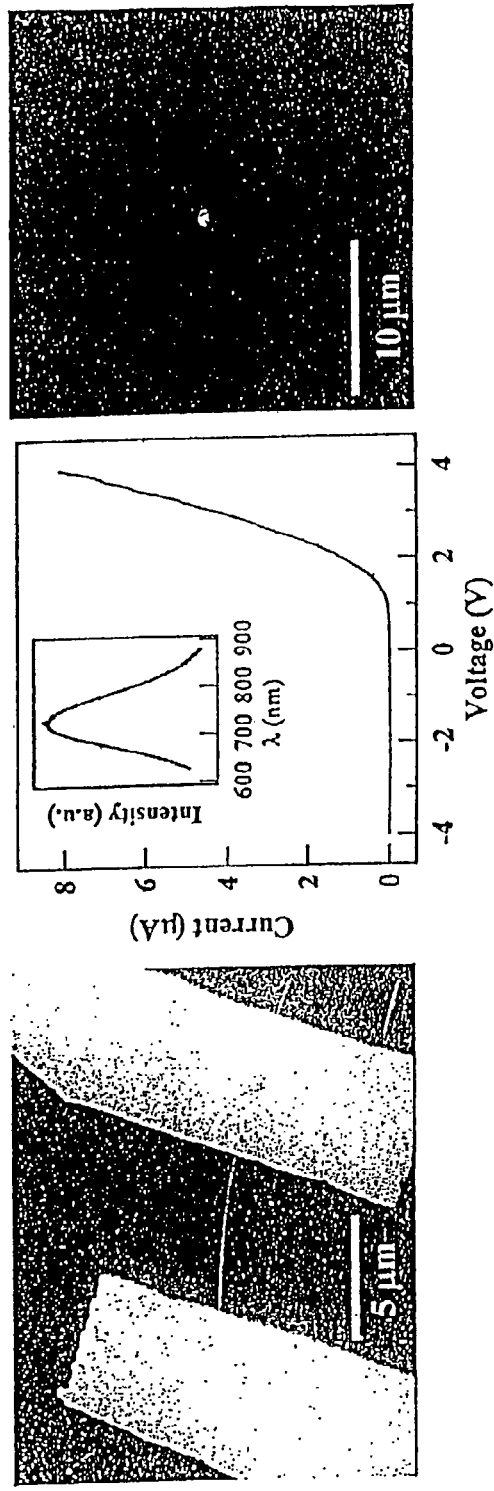

NANOSCALE WIRES AND RELATED DEVICES

This application is a continuation-in-part of U.S. Ser. No. 10/152,490, filed May 20, 2002 now abandoned, which claims priority to U.S. Ser. No. 60/292,045, filed May 18, 2001, and to U.S. Ser. No. 60/291,896, filed May 18, 2001, and to U.S. Ser. No. 60/354,642, filed Feb. 6, 2002, and to U.S. Ser. No. 60/348,313, filed Nov. 9, 2001; which U.S. Ser. No. 10/152,490 also is a continuation-in-part of U.S. Ser. No. 09/935,776, filed Aug. 22, 2001 now abandoned, which claims priority to U.S. Ser. No. 60/226,835, filed Aug. 22, 2000, and to U.S.S.N. 60/292,121, filed May 18, 2001; and which U.S. Ser. No. 10/152,490 also is a continuation-in-part of U.S. Ser. No. 10/020,004, filed Dec. 11, 2001 now U.S. Pat. No. 7,129,554, which claims priority to U.S. Ser. No. 60/292,035, filed May 18, 2001 and to U.S. Ser. No. 60/254,745, filed Dec. 11, 2000.

PRIORITY APPLICATIONS

This application claims the benefit of priority under 35 U.S.C. §120 of U.S. patent application Ser. No. 10/152,490, filed May 20, 2002, of Lieber, et al., entitled "Nanoscale Wires and Related Devices," which claims the benefit of priority under 35 U.S.C. §119(e) to provisional patent application Ser. No. 60/292,045, filed May 18, 2001, of Lieber, et al., entitled, "Nanowire Electronic Devices Including Memory and Switching Devices," and of No. 60/291,896, filed May 18, 2001, of Lieber, et al., entitled "Nanowire Devices Including Emissive Elements and Sensors," and of No. 60/354,642, filed Feb. 06, 2002 of Lieber, et al., entitled "Nanowire Devices Including Emissive Elements and Sensors," each of which is hereby incorporated by reference in its entirety for all purposes.

FEDERALLY SPONSORED RESEARCH

This invention was sponsored by the Office of Naval Research Contract Nos. N00014-01-1-0651, N00014-99-1-0495, and N00014-00-1-0476. The government has certain rights in the invention.

FIELD OF THE INVENTION

The present invention relates generally to nanotechnology, and more particularly to nanoelectronics, i.e., nanoscale semiconductors and other articles, and associated methods and devices. Articles and devices of size greater than the nanoscale are also included.

BACKGROUND OF THE INVENTION

Interest in nanotechnology, in particular sub-microelectronic technologies such as semiconductor quantum dots and nanowires, has been motivated by the challenges of chemistry and physics at the nanoscale, and by the prospect of utilizing these structures in electronic and related devices. While nanoscopic articles might be well-suited for transport of charge carriers and excitons (e.g. electrons, electron pairs, etc.) and thus may be useful as building blocks in nanoscale electronics applications, other than standard small-scale lithographic techniques, nanoelectronics is not a well-developed field. Thus there is a need in the art for new and improved articles and techniques involving nanoelectronics.

SUMMARY OF THE INVENTION

The present invention relates to articles and devices, methods of making and using them, and related systems. Most aspects and embodiments of the invention involve nanometer-scale articles and devices, but larger articles and devices are provided as well.

In one aspect, the invention comprises methods of growing, assembling, and otherwise making articles and devices. In one embodiment, a method of the invention involves doping a semiconductor during growth of the semiconductor. In another embodiment, the method includes the step of growing a nanoscale semiconductor having a plurality of regions able to produce light.

In another embodiment, a series of methods are provided that involve assembling one or articles that are elongated structures, or semiconductors (which can be elongated structures) on a surface, where at least one of the articles is at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers. One method involves contacting one or more of the articles to a surface. Another method involves conditioning the surface with one or more functionalities that attract the one or more of the articles to particular positions on the surface, and aligning the one or more articles by attracting the one or more articles to the particular positions using the one or more functionalities. Another method involves depositing the plurality of the articles onto the surface, and electrically charging the surface to produce electrostatic forces between two or more of the articles. Another method involves dispersing the one or more of the articles on a surface of a liquid phase to form a Langmuir-Blodgett film compressing the Langmuir-Blodgett film, and transferring the compressed Langmuir-Blodgett film onto a surface. Another method involves dispersing the one or more of the articles in a flexible matrix, stretching the flexible matrix in a direction to produce a shear force on the articles that causes at least one article to align in the direction, removing the flexible matrix, and transferring the at least one aligned elongated structure to a surface.

In another set of embodiments, the invention comprises systems for growing, assembling, or otherwise making articles and/or devices. One system of the invention for growing a doped semiconductor includes means for providing a molecules of the semiconductor and molecules of a dopant, and means for doping the molecules of the semiconductor with the molecules of the dopant during growth of the semiconductor to produce the doped semiconductor.

Another set of systems are provided for assembling one or more elongated structures on a surface. In one embodiment, the system comprises means for flowing a fluid that comprises the one or more elongated structures onto the surface, and means for aligning the one or more elongated structures on the surface to form an array of the elongated structures. In several embodiments, one or more of the elongated structures are at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers. In one of these embodiments, the system includes means for conditioning the surface with one or more functionalities that attract the one or more elongated structures to particular positions on the surface, and means for aligning the one or more elongated structures by attracting the one or more elongated structures to the particular positions using the one or more functionalities. In another of these embodiments, the system comprises means for depositing the plurality of elongated structures onto the surface, and means for electrically charging the surface to produce electrostatic forces between two or more of the plurality of the elongated structures. In another of these embodiments, the system comprises means for dispersing the one or more elongated structures on a surface of a liquid phase to form a Langmuir-Blodgett film, means for compressing the Langmuir-Blodgett film, and means for transferring the compressed Langmuir-Blodgett film onto a surface. In another of these embodiments, the system includes means for dispersing the one or more elongated structures in a flexible matrix, means for stretching the flexible matrix in a direction to produce a shear force on the one or more elongated structures that causes the at least one elongated structure to align in the direction, means for removing the flexible matrix, and means for transferring the at least one aligned elongated structure to a surface.

In another aspect, the invention comprises a series of devices. In one embodiment, a device includes a semiconductor having a longitudinal axis, at least two regions differing in composition along the longitudinal axis, and a boundary between the regions. The semiconductor has a maximum dimension at the boundary of no more than about 100 nm.

In another embodiment, a device of the invention includes a free-standing wire including a first region, and a second region having a composition different from that of the first region. The first region has a smallest dimension that is less than about 100 nm and the second region has a smallest dimension that is less than about 100 nm.

In another embodiment, a device of the invention includes a free-standing bulk-doped nanoscopic material having a first region having a composition and a second region having a composition different from the composition of the first region. At least one of the first region and the second region has an aspect ratio of at least about 100:1.

In another embodiment, a device of the invention includes a free-standing bulk-doped semiconductor comprising a first region having a composition and a second region having a composition different from the composition of the first region. At least one of the first and second region has a maximum dimension of less than about 100 nm.

In one set of embodiments, the invention provides a series of devices each including a free-standing wire. In each embodiment, the free-standing wire can be a nanoscopic wire, but need not be. In one embodiment, the free-standing wire includes a first region having a dopant and a second region having a dopant different from the dopant of the first region. The first region and the second region overlap to form an overlap region having a composition that is a mixture of the dopants of the first and second regions. The composition of the overlap region comprises between about 10 vol % and about 90 vol % of the dopant of the first region with a complementary amount of the dopant of the second region. The overlap region has a maximum dimension of less than about 100 nm. In another embodiment, the free-standing wire is nanoscopic and includes a first region comprising a dopant at a first concentration and a second region comprising the dopant at a second concentration. The second concentration is different from the first concentration. In another embodiment, the free-standing wire is nanoscopic and includes a first semiconductor and a second semiconductor. At least one of the first semiconductor and the second semiconductor is a doped semiconductor. The composition of the first semiconductor and the composition of the second semiconductor are different. In another embodiment, free-standing wire is nanoscopic and comprises a first region having a first concentration of a semiconductor material and a second region having a second concentration of the semiconductor material. The first concentration and the second concentration are different. In another embodiment, the free-standing nanoscopic wire comprises a first region having a first resistivity and a second region having a second resistivity different from the first resistivity. In another embodiment, the free-standing nanoscopic wire comprises a first region having a first band gap and a second region having a second band gap different from the first band gap.

In another embodiment, the device includes a free-standing photoluminescent nanoscopic wire. In another embodiment, the device includes a free-standing nanoscopic wire able to produce polarized light. In another embodiment, the device includes a free-standing nanoscopic wire comprising a plurality of light-emitting regions. In another embodiment, the device includes a nanoscopic wire able to produce light having a polarization ratio of at least about 0.60.

In another embodiment, the device includes a photodetector having a responsivity of at least about 3000 A/W. In another embodiment, the device includes a photodetector having a detection speed of less than about 100 fs.

In another embodiment, the device includes a nanoscopic wire having a first region and a second region having a composition different from that of the first region. The first region and the second region overlap to form an overlap region having a composition that is a mixture of the compositions of the first and second regions. The composition of the overlap region comprises between about 10 vol % and about 90 vol % of the composition of the first region with a complementary amount of the composition of the second region. The overlap region is able to emit light.

In another embodiment, the device includes a light-emitting diode comprising a nanoscale wire comprising a first region having a dopant and a second region having a dopant different from the dopant of the first region. The first region and the second region overlap to form an overlap region having a composition that is a mixture of the dopants of the first and second regions. The composition of the overlap region comprises between about 10 vol % and about 90 vol % of the dopant of the first region with a complementary amount of the dopant of the second region. The light-emitting diode has an emission wavelength determined by a dimension of the overlap region.

In another embodiment, the device includes a nanoscale wire comprising a first region having a dopant and a second region having a dopant different from the dopant of the first region. The first region and the second region overlap to form an overlap region having a composition that is a mixture of the dopants of the first and second regions. The composition of the overlap region comprises between about 10 vol % and about 90 vol % of the dopant of the first region with a complementary amount of the dopant of the second region.

In another embodiment, the device includes a wire comprising a semiconductor, where the wire is able to emit light at a higher frequency than the semiconductor in a bulk state. In another embodiment, the device includes a uniformly photoluminescent nanoscopic wire.

In another embodiment, the device includes a semiconductor disposed proximate to an inductive material capable of establishing a field in the semiconductor. The inductive material has at least two different electronic or mechanical states which able to differentially affect a property of the semiconductor. In another embodiment, the device includes a semiconductor disposed proximate to an inductive material capable of establishing a field in the semiconductor. The inductive material having at least two different states able to differentially affect a property of the semiconductor.

In another embodiment, the device includes a doped channel, and an inductive material having at least two different electronic or mechanical states and being disposed proximate to the doped channel for inducing a field within the doped channel for effecting a flow of carriers. In another embodiment, the device includes a doped semiconductor, and an inductive material having at least two different states, the inductive material being disposed proximate to the doped semiconductor.

In another embodiment, the device includes an article formed of a bulk-doped semiconductor material. The article is able to emit light at a frequency lower than the frequency of light emission inherent to the bulk-doped semiconductor material.

In another embodiment, the device includes a memory element comprising a memory active element having a volume of less than 314 $\mu m^3$. The active element is switchable electronically between a first readable state and a second readable state electronically distinguishable from the first readable state.

In another embodiment, the device includes a transistor having a smallest dimension that is less than about 100 nm.

In another embodiment, the device includes at least one doped semiconductor, where at least one doped semiconductor is at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers.

In another embodiment, the device is a semiconductor device including a doped channel, and an inductive material having at least two different electronic or mechanical states and being disposed proximate to the doped channel for inducing a field within the doped channel for affecting a flow of carriers.

In another embodiment, a device of the invention includes a doped semiconductor, and an inductive material having at least two different states, the inductive material being positioned so as to be able to affect a flow of carriers within the doped semiconductor.

In another set of embodiments, the invention comprises a sensor. In one embodiment, the sensor includes at least one nanoscale wire, and means for measuring a change in a property of the at least one nanoscale wire. In another embodiment, a nanosensor is provided that includes a semiconductor having a first end in electrical contact with a conductor to form a source electrode, a second end in electrical contact with a conductor to form a drain electrode, and an exterior surface having an oxide formed thereon to form a gate electrode, and a binding agent having specificity for a selected moiety and being bound to the exterior surface, whereby a voltage at the gate electrode varies in response to the binding of the moiety to the binding agent to provide a chemically gated field effect sensor device.

In another aspect, the invention comprises a series of articles. In one embodiment, an article of the invention comprises a free-standing and bulk-doped semiconductor including at least one portion with a smallest width of less than 500 nanometers. In another embodiment, the article comprises an elongated and bulk-doped semiconductor that, at any point along its longitudinal axis, has a largest cross-sectional dimension less than 500 nanometers.

In another embodiment, an article of the invention comprises a nanoscopic wire and a functional moiety positioned relative to the nanoscopic wire such that an interaction involving the moiety causes a detectable change in a property of the nanoscopic wire. In another embodiment, the article comprises a sample exposure region, and a nanoscopic wire, at least a portion of which is addressable by a sample in the sample exposure region.

In another embodiment, an article of the invention comprises a doped semiconductor. At least a portion of the semiconductor is made by the method of doping the semiconductor during growth of the semiconductor.

In another embodiment, an article of the invention includes a sample cassette comprising a sample exposure region and a nanoscale wire, at least a portion of which is addressable by a sample in the sample exposure region. The sample cassette is operatively connectable to a detector apparatus able to determine a property associated with the nanoscale wire.

In another embodiment, the invention comprises an analyte-gated field effect transistor having a predetermined current-voltage characteristic and adapted for use as a chemical or biological sensor. The transistor includes a substrate formed of a first insulating material, a source electrode disposed on the substrate, a drain electrode disposed on the substrate, a semiconductor disposed between the source and drain electrodes to form a field effect transistor having a predetermined current-voltage characteristic, and an analyte-specific binding agent disposed on a surface of the semiconductor, where a binding event occurring between a target analyte and the binding agent causes a detectable change in the current-voltage characteristic of said field effect transistor.

In another embodiment, the invention comprises a field effect transistor. The transistor includes a conducting channel comprising a doped semiconductor having at least one portion having a smallest width of less then 500 nanometers, and a gate electrode comprising an elongated material having at least one portion having a smallest width of less then 500 nanometers.

In another embodiment, the invention comprises a logic gate. The logic gate comprises a doped semiconductor having a smallest width of less than 500 nanometers.

In another embodiment, the invention comprises a bulk-doped semiconductor that is at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers. A phenomena produced by a section of the bulk-doped semiconductor exhibits a quantum confinement caused by a dimension of the section.

In another embodiment, the invention comprises a bulk-doped semiconductor that exhibits coherent transport. In another embodiment, the invention comprises a bulk-doped semiconductor that exhibits ballistic transport. In another embodiment, the invention comprises a bulk-doped semiconductor that exhibits Luttinger liquid behavior. In another embodiment, the invention comprises a doped semiconductor comprising a single crystal.

In another embodiment, the invention comprises a solution comprising one or more doped semiconductors, where at least one of the semiconductors is at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers.

In another embodiment, the invention comprises a collection of reagents for growing a doped semiconductor that will be at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers that comprises at least one portion having a smallest width of less than 500 nanometers. The collection comprises a semiconductor reagent and a dopant reagent.

In another aspect, the invention comprises methods of using articles and devices. One series of embodiments involve use of conductors and/or semiconductors. One method involves providing a free-standing nanoscale semiconductor, which can be a doped semiconductor, having a first region and a second region having a composition different from that of the first region, and allowing an electrical current to flow through the semiconductor.

In another embodiment, the invention comprises a method involving exposing a conductor to a source of electromagnetic radiation, and changing the electrical conductivity of the conductor by altering polarity of the electromagnetic radiation in the absence of a grating between the source and the conductor.

In another embodiment, a method of the invention involves causing the emission of light from a semiconductor wire at a frequency lower than 700 nm. In another embodiment, the invention comprises a method of generating light involving applying energy to one or more semiconductors causing the one or more semiconductors to emit light. At least one of the semiconductors is at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers.

In another set of embodiments, the invention provides methods of detection or determination of species. One embodiment involves a method of detecting an analyte, involving contacting a nanoscopic wire with a sample, and determining a property associated with the nanoscopic wire where a change in the property, when the nanoscopic wire is contacted with the sample, indicates the presence and/or quantity of the analyte in the sample. In another embodiment, the method involves contacting an electrical conductor, or a nanoscopic wire, with a sample, and determining the presence and/or quantity of an analyte in the sample by measuring a change in a property of the conductor resultant from the contact, where less than ten molecules of the analyte contribute to the a change in said property.

In another embodiment, a method of the invention includes contacting a nanoscopic wire with a sample suspected of containing an analyte, and determining a change in a property of the nanoscopic wire. In another embodiment, the method involves contacting a nanoscopic wire with a sample having a volume of less than about 10 microliters, and measuring a change in a property of the nanoscopic resultant from the contact.

Other advantages, novel features, and objects of the invention will become apparent from the following detailed description of the invention, including descriptions of non-limiting embodiments, when considered in conjunction with the accompanying drawings, which are schematic and which are not intended to be drawn to scale. In the figures, each identical, or substantially similar component that is illustrated in various figures is represented by a single numeral or notation. For purposes of clarity, not every component is labeled in every figure, nor is every component of each embodiment of the invention shown where illustration is not necessary to allow those of ordinary skill in the art to understand the invention.

BRIEF DESCRIPTION OF THE DRAWINGS

FIGS. 30A and 30B are schematics of fluidic channel structures for flow assembly;

FIGS. 35A-35C illustrates hysteresis;

FIGS. 40A-40E illustrate an OR logic gate;

FIGS. 41A-41E illustrate a NOT logic gate;

FIG. 46B is a high resolution scanning electron micrograph of a single silicon nanoscale wire device connected to two metal electrodes;

FIG. 47A shows schematically another embodiment of a nanoscale sensor having a backgate;

FIG. 47B shows conductance vs. time with various backgate voltages;

FIG. 47C shows conductance vs. backgate voltage;

FIG. 51B shows current-voltage (I-V) measurements for the single-walled carbon nanotube device of FIG. 8a in NaCl;

FIG. 51C shows current-voltage (I-V) measurements for a single-walled carbon nanotube device of FIG. 51B in $CrCl_x$;

FIG. 54A shows the conductance of a BSA-biotin modified SiNW as it is exposed first to a blank buffer solution, then to a solution containing antibiotin;

FIG. 56A shows the conductance of a calmodulin-modified silicon nanoscale wire exposed to a buffer solution and then to a solution containing calcium ions;

FIG. 56B shows the conductance of a bare silicon nanoscale wire exposed to a buffer solution and then to a solution containing calcium ions;

FIG. 59B show another view of the nanoscale wire of FIG. 59A;

FIG. 59C illustrates the nanoscale wire of FIG. 59A with moieties at the surface;

FIG. 59D illustrates the nanoscale wire of FIG. 59C with a depletion region;

FIGS. 69A-69E illustrate data from one embodiment of the invention;

FIGS. 70A-70E illustrate data from one embodiment of the invention;

FIG. 73 illustrate data from one embodiment of the invention;

DETAILED DESCRIPTION

Figure 1:
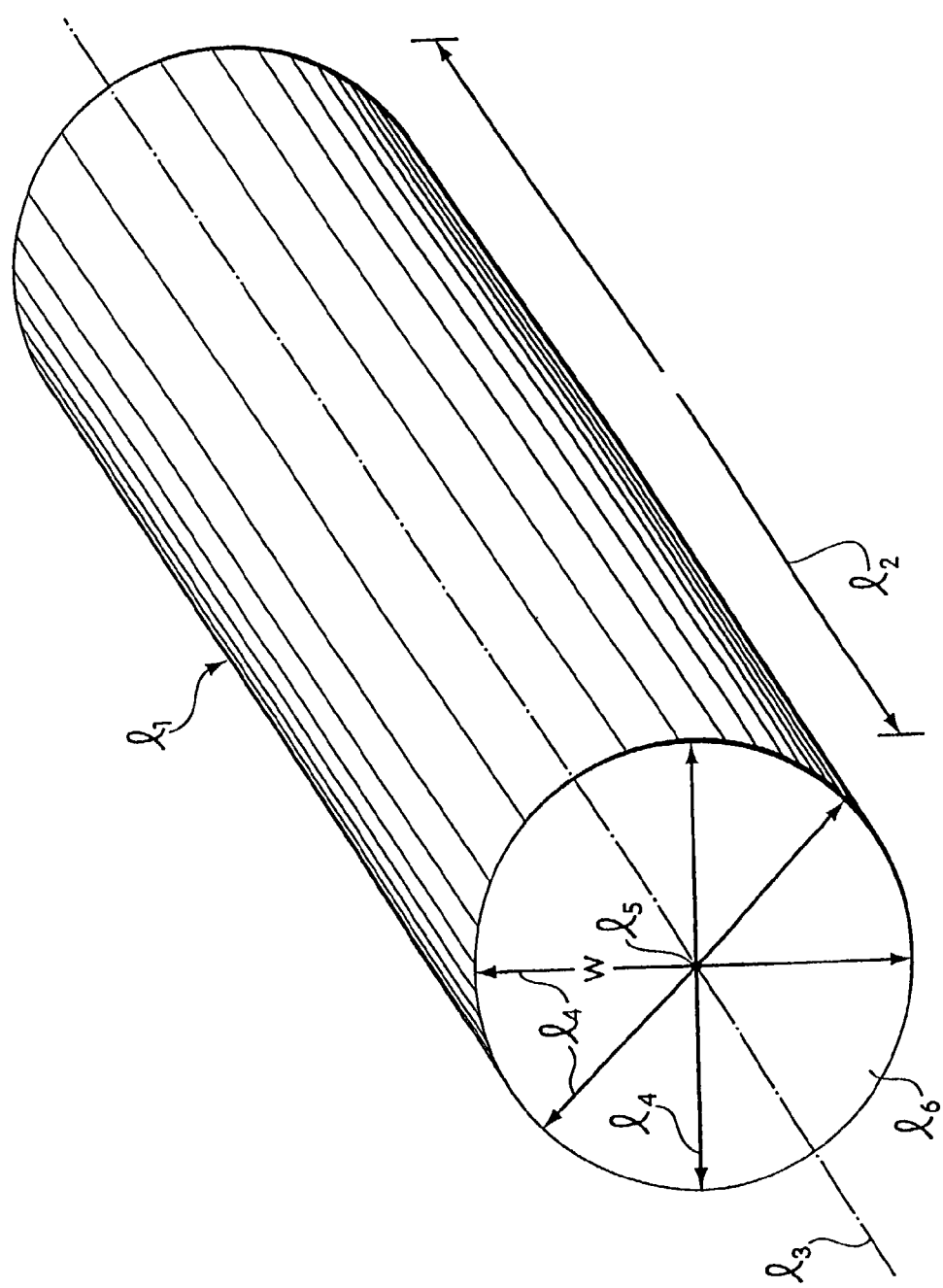
FIG. 1 is a perspective view of an example of a semiconductor article in accordance with an embodiment of the invention.

The following U.S. provisional and utility patent application documents are incorporated herein by reference in their entirety for all purposes: Ser. No. 60/226,835, entitled, "Semiconductor Nanowires," filed Aug. 22, 2000; Ser. No. 60/254,745, entitled, "Nanowire and Nanotube Nanosensors," filed Dec. 11, 2000 Ser. No. 60/292,035, entitled "Nanowire and Nanotube Nanosensors," filed May 18, 2001 Ser. No. 60/292,121, entitled, "Semiconductor Nanowires," filed May 18, 2001 Ser. No. 60/292,045, entitled "Nanowire Electronic Devices Including Memory and Switching Devices," filed May 18, 2001; Ser. No. 60/291,896, entitled "Nanowire Devices Including Emissive Elements and Sensors," filed May 18, 2001; Ser. No. 09/935,776, entitled "Doped Elongated Semiconductors, Growing Such Semiconductors, Devices Including Such Semiconductors, and Fabricating Such Devices," filed Aug. 22, 2001; Ser. No. 10/020,004, entitled "Nanosensors," filed Dec. 11, 2001; Ser. No. 60/348,313, entitled "Transistors, Diodes, Logic Gates and Other Devices Assembled from Nanowire Building Blocks," filed Nov. 9, 2001; Ser. No. 60/354,642, entitled "Nanowire Devices Including Emissive Elements and Sensors," filed Feb. 6, 2002; Ser. No. 10/152,490, entitled "Nanoscale wires and Related Devices," filed May 20, 2002. The following International Patent Publication is incorporated herein by reference in their entirety for all purposes: International Patent Publication No. WO 02/17362, published Feb. 28, 2002, entitled "Doped Elongated Semiconductors, Growing Such Semiconductors, Devices Including Such Semiconductors, and Fabricating Such Devices."

The present invention relates generally to sub-microelectronic circuitry and devices, and more particularly to nanometer-scale articles, including nanoscale wires which can be selectively doped at various locations. In some cases, the articles are single crystals. The nanoscale wires can be doped, for example, differentially along their length, or radially, and either in terms of identity of dopant, concentration of dopant, or both. This may be used to provide both n-type and p-type conductivity in a single item, or in different items in close proximity to each other, such as in a crossbar array. The fabrication and growth of such articles is described herein, and the arrangement of such articles to fabricate electronic, optoelectronic, or spintronic devices and components. For example, semiconductor materials can be doped to form n-type and p-type semiconductor regions for making a variety of devices such as field effect transistors, bipolar transistors, complementary inverters, tunnel diodes, light emitting diodes, sensors, and the like.

In preferred embodiments, devices of the invention may include wires or other components of scale commensurate with nanometer-scale wires, which includes nanotubes and nanowires. In certain embodiments, however, the invention comprises articles that may be greater than nanometer size (e.g., micrometer-sized).

All definitions as used herein are solely for the purposes of this application. These definitions should not necessarily be imputed to other commonly-owned applications, whether related or unrelated to this application.

As used herein, the term "Group" is given its usual definition as understood by one of ordinary skill in the art. For instance, Group II elements include Zn, Cd and Hg; Group III elements include B, Al, Ga, In and Tl; Group IV elements include C, Si, Ge, Sn and Pb; Group V elements include N, P, As, Sb and Bi; and Group VI elements include O, S, Se, Te and Po. Combinations involving more than one element from each group are also possible. For example, a Group II-VI material may include at least one member from Group II and at least one member from Group VI, for example, ZnS, ZnSe, ZnSSe, ZnCdS, CdS, or CdSe. Similarly, a Group III-V material may comprise at least one member from Group III and at least one member from Group V, for example GaAs, GaP, GaAsP, InAs, InP, AlGaAs, or InAsP. Other dopants may also be included with these materials and combinations thereof, for example, transition metals such as Fe, Co, Te, Au, and the like.

As used herein, "nanoscopic-scale," "nanoscopic," "nanometer-scale," "nanoscale," the "nano-" prefix, and the like generally refers to elements or articles having widths or diameters of less than about 1 µm, preferably less than about 100 nm in some cases. In all embodiments, specified widths can be smallest width (i.e. a width as specified where, at that location, the article can have a larger width in a different dimension), or largest width (i.e. where, at that location, the article's width is no wider than as specified, but can have a length that is greater).

A "wire" generally refers to any material having a conductivity of any semiconductor or any metal, and in some embodiments may be used to connect two electronic components such that they are in electronic communication with each other. For example, the term "electrically conductive" or a "conductor" or an "electrical conductor" when used with reference to a "conducting" wire or a nanoscale wire, refers to the ability of that wire to pass charge. Preferred electrically conductive materials have a resistivity lower than about $10^{-3}$, more preferably lower than about $10^{-4}$, and most preferably lower than about $10^{-6}$ or $10^{-7}$ Ωm.

A "nanoscopic wire" (also known herein as a "nanoscopic-scale wire" or "nanoscale wire") generally is a wire, that at any point along its length, has at least one cross-sectional dimension and, in some embodiments, two orthogonal cross-sectional dimensions less than 1 µm, preferably less than about 500 nm, preferably less than about 200 nm, more preferably less than about 150 nm, still more preferably less than about 100 nm, even more preferably less than about 70, still more preferably less than about 50 nm, even more preferably less than about 20 nm, still more preferably less than about 10 nm, and even less than about 5 nm. In other embodiments, the cross-sectional dimension can be less than 2 nm or 1 nm. In one set of embodiments, the nanoscale wire has at least one cross-sectional dimension ranging from 0.5 nm to 200 nm. Where nanoscale wires are described having, for example, a core and an outer region, the above dimensions generally relate to those of the core. The cross-section of the elongated semiconductor may have any arbitrary shape, including, but not limited to, circular, square, rectangular, tubular, or elliptical, and may a regular or an irregular shape. The nanoscale wire may be solid or hollow. Any nanoscale wire can be used, including carbon nanotubes, nanorods, nanowires, organic and inorganic conductive and semiconducting polymers, and the like, unless otherwise specified. Other conductive or semiconducting elements that may not be molecular wires, but are of various small nanoscopic-scale dimension, also can be used in some instances, e.g. inorganic structures such as main group and metal atom-based wire-like silicon, transition metal-containing wires, gallium arsenide, gallium nitride, indium phosphide, germanium, cadmium selenide structures. A wide variety of these and other nanoscale wires can be grown on and/or applied to surfaces in patterns useful for electronic devices in a manner similar to technique described herein involving nanoscale wires, without undue experimentation. The nanoscale wires should be able to be formed of at least 1 µm, preferably at least 3 µm, more preferably at least 5 µm, and more preferably still at least 10 or 20 µm in length, and preferably are less than about 100 nm, more preferably less than about 75 nm, and more preferably less than about 50 nm, and more preferably still less than about 25 nm in thickness (height and width). The wires should have an aspect ratio (length to thickness) of at least about 2:1, preferably greater than about 10:1, and more preferably greater than about 1000:1.

As used herein, a "nanotube" (e.g. a carbon nanotube) is generally nanoscopic wire that is hollow, or that has a hollowed-out core, including those nanotubes known to those of ordinary skill in the art. "Nanotube" is abbreviated herein as "NT." Nanotubes are used as one example of small wires for use in the invention and, in preferred embodiments, devices of the invention include wires of scale commensurate with nanotubes.

A "nanowire" (e.g. comprising silicon or an other semiconductor material) is a nanoscopic wire that is generally a solid wire, and may be elongated in some cases. Preferably, a nanowire (which is abbreviated herein as "NW") is an elongated semiconductor, i.e., a nanoscale semiconductor. A "non-nanotube nanowire" is any nanowire that is not a nanotube. In one set of embodiments of the invention, a non-nanotube nanowire having an unmodified surface is used in any arrangement of the invention described herein in which a nanowire or nanotube can be used.

Many nanoscopic wires as used in accordance with the present invention are individual nanoscopic wires. As used herein, "individual nanoscopic wires" means a nanoscopic wire free of contact with another nanoscopic wire (but not excluding contact of a type that may be desired between individual nanoscopic wires in a crossbar array). For example, an "individual" or a "free-standing" article may at some point in its life, not be attached to another article, for example, with another nanoscopic wire, or the free-standing article maybe in solution. As one example, typical individual nanotubes can have a thickness as small as about 0.5 nm. This is in contrast to nanotubes produced primarily by laser vaporization techniques that produce high-quality materials, but materials formed as ropes having diameters of about 2 to about 50 nm or more and containing many individual nanotubes (see, for example, Thess, et al., "Crystalline Ropes of Metallic Carbon Nanotubes" *Science* 273:483-486 (1996), incorporated herein by reference in its entirety for all purposes).

As used herein, an "elongated" article (e.g. a semiconductor or a section thereof) is an article for which, at any point along the longitudinal axis of the article, the ratio of the length of the article to the largest width at that point is greater than 2:1. This ratio is termed the "aspect ratio."

In some embodiments, at least a portion of a nanoscopic wire may be a bulk-doped semiconductor. As used herein, a "bulk-doped" article (e.g. an article or a section or region of an article) is an article for which a dopant is incorporated substantially throughout the crystalline lattice of the article, as opposed to an article in which a dopant is only incorporated in particular regions of the crystal lattice at the atomic scale, for example, only on the surface or exterior. For example, some articles such as carbon nanotubes are typically doped after the base material is grown, and thus the dopant only extends a finite distance from the surface or exterior into the interior of the crystal line lattice. It should be understood that "bulk-doped" does not define or reflect a concentration or amount of doping in a semiconductor, nor does it indicate that the doping is necessarily uniform. In particular, in some embodiments, a bulk-doped semiconductor may comprise two or more bulk-doped regions. Thus, as used herein to describe nanoscopic wires, "doped" refers to bulk-doped nanoscopic wires, and, accordingly, a "doped nanoscopic (or nanoscale) wire" is a bulk-doped nanoscopic wire. "Heavily doped" and "lightly doped" are terms the meaning of which is clearly understood by those of ordinary skill in the art.

As used herein, a "width" of an article is the distance of a straight line from a point on a perimeter of the article, through the center of the article, to another point on the perimeter of the article. As used herein, a "width" or a "cross-sectional dimension" at a point along a longitudinal axis of an article is the distance along a straight line that passes through the center of a cross-section of the article at that point and connects two points on the perimeter of the cross-section. The "cross-section" at a point along the longitudinal axis of the article is a plane at that point that crosses the article and is orthogonal to the longitudinal axis of the article. The "longitudinal axis" of an article is the axis along the largest dimension of the article. Similarly, a "longitudinal section" of an article is a portion of the article along the longitudinal axis of the article that can have any length greater than zero and less than or equal to the length of the article. Additionally, the "length" of an elongated article is a distance along the longitudinal axis from end to end of the article. FIG. 1 is a perspective diagram illustrating an example of a cylindrical semiconductor L1, for example, a wire-like semiconductor such as a nanowire. The cylindrical semiconductor L1 has a length L2 and a longitudinal axis L3. At a point L5 along the longitudinal axis L3, the cylindrical semiconductor L1 has a plurality of widths L4 across cross-section L6, where one of the widths L4 is a smallest width at the point L5.

As used herein, a "cylindrical" article is an article having an exterior shaped like a cylinder, but does not define or reflect any properties regarding the interior of the article. In other words, a cylindrical article may have a solid interior or may have a hollowed-out interior. Generally, a cross-section of a cylindrical article appears to be circular or approximately circular, but other cross-sectional shapes are also possible, such as a hexagonal shape. The cross-section may have any arbitrary shape, including, but not limited to, square, rectangular, or elliptical. Regular and irregular shapes are also included.

As used herein, a first article (e.g., a nanoscopic wire or larger-sized structure) "coupled" to a second article is disposed such that the first article either physically contacts the second article or is proximate enough to the second article to influence a property (e.g., an electrical property, an optical property, or a magnetic property) of the second article. The term "electrically coupled" when used with reference to a nanoscopic wire and an analyte or another moiety such as a reaction entity, refers to an association between any of the analyte, other moiety, and the nanoscopic wire such that electrons can move from one to the other, or in which a change in an electrical characteristic of one can be determined by the other. This may include electron flow between these entities, or a change in a state of charge, oxidation state, redox potential, and the like. As examples, electrical coupling can include direct covalent linkage between the analyte or other moiety and the nanoscopic wire, indirect covalent coupling (e.g. via a linking entity), direct or indirect ionic bonding, or other types of bonding (e.g. hydrophobic bonding). In some cases, no actual bonding may be required and the analyte or other moiety may simply be contacted with the nanoscopic wire surface. There also need not necessarily be any contact between the nanoscopic wire and the analyte or other moiety, in embodiments where the nanoscopic wire is sufficiently close to the analyte to permit electron tunneling or other field effects between the analyte and the nanoscopic wire.

As used herein, an "array" of articles (e.g., nanoscopic wires) comprises a plurality of the articles. As used herein, a "crossed array" is an array where at least one of the articles contacts either another of the articles or a signal node (e.g., an electrode).

As used herein, a "single crystal" item (e.g., a semiconductor) is an item that has covalent bonding, ionic bonding, or a combination thereof throughout the item. Such a single crystal item may include defects in the crystal, but is distinguished from an item that includes one or more crystals, not ionically or covalently bonded, but merely in close proximity to one another.

In some embodiments, the invention may be part of a system constructed and arranged to determine an analyte in a sample to which the nanoscopic wire is exposed. "Determine," and similar terms in this context, means to determine the quantity and/or presence of the an entity such as an analyte in a sample. Determining steps may include, for example, electronic measurements, piezoelectric measurements, electrochemical measurements, electromagnetic measurements, photodetections, mechanical measurements, acoustic measurements, gravimetric measurements and the like. The presence of an analyte can be determined by determining a change in a characteristic in a nanoscopic wire, for example, an electrical characteristic or an optical characteristic, and this change may be detectable. "Determining" may refer to detecting or quantifying interaction between species, e.g., detection of binding between two species.

The term "reaction entity" refers to any entity that can interact with aanother entity such as analyte (which can be a chemical or biological species, e.g.) in such a manner to cause a detectable change in a property of a nanoscopic wire. The reaction entity may enhance the interaction between the nanoscopic wire and the analyte, or generate a new chemical species that has a higher or lower affinity to the nanoscopic wire, or to enrich the analyte around the nanoscopic wire. The reaction entity can comprise a binding partner to which the analyte binds. The reaction entity, when it comprises a binding partner, can comprise a specific binding partner of the analyte. For example, the reaction entity may be a nucleic acid, an antibody, a sugar, a carbohydrate, or a protein. In other embodiments, the reaction entity may be a polymer, a catalyst, or a quantum dot. A reaction entity that includes a catalyst may catalyze a reaction involving the analyte, resulting in a product that causes a detectable change in the nanoscopic wire, for example, via binding to an auxiliary binding partner of the product electrically coupled to the nanoscopic wire. Another examplary reaction entity is a reactant that reacts with the analyte, producing a product that can cause a detectable change in the nanoscopic wire. The reaction entity may define at least a portion of a shell or a coating on or surrounding at least a part of the nanoscopic wire. As one example, the shell may include a polymer that recognizes molecules in, for example, a gaseous or liquid sample, causing a change in the conductivity of the polymer which, in turn, causes a detectable change in the nanoscopic wire. In some cases, the reaction entity may comprise a nanoparticle, for example, a nanoparticle having binding partners immobilized thereto.

The term "quantum dot" is given its ordinary meaning in the art, and generally refers to semiconductor or metal nanoparticles (for example, a cadmium selenide nanoparticle) that absorb light and re-emit light in a different color. The wavelength of the emitted light may depend on the size of the quantum dot. For example, a 2 nm quantum dot may be able to emit green light, while a 5 nm quantum dot may be able to emit red light.

As used herein, "attached to," in the context of a species relative to another species or to a surface of an article, means that the species is chemically or biochemically linked via covalent attachment, attachment via specific biological binding (e.g., biotin/streptavidin), coordinative bonding such as chelate/metal binding, or the like. For example, "attached" in this context includes multiple chemical linkages, multiple chemical/biological linkages, etc.

The term "binding partner" refers to a chemical or biological species, such as a protein, antigen, antibody, small molecule, etc., that can undergo binding with another entity, e.g. an analyte, or its respective "binding partner." The term includes specific, semi-specific, and non-specific binding partners, as known to those of ordinary skill in the art. As one example, Protein A is usually regarded as a "non-specific" or semi-specific binder. The term "specifically binds," when referring to a binding partner (e.g., a protein, a nucleic acid, an antibody, or the like.), may refer to a reaction that is determinative of the presence and/or identity of one or more other members of the binding pair in a mixture of heterogeneous molecules (e.g., including proteins and other biologics). Thus, for example, in the case of a receptor/ligand binding pair, the ligand would specifically and/or preferentially select its receptor from a complex mixture of molecules, or vice versa. Other examples include an enzyme that would specifically bind to its substrate, a nucleic acid that would specifically bind to its complement, or an antibody that would specifically bind to its antigen. Other examples include nucleic acids that specifically bind or hybridize to their complements, antibodies that specifically bind to their antigens, and the like. The binding may be by one or more of a variety of mechanisms including, but not limited to, ionic interactions, covalent interactions, hydrophobic interactions, van der Waals interactions, or the like.

The term "fluid" generally refers to a substance that tends to flow and to conform to the outline of its container. Typically, fluids are materials that are unable to withstand a static shear stress. When a shear stress is applied to a fluid, it experiences a continuing and permanent distortion. Typical fluids include liquids and gasses, but may also include free flowing solid particles, viscoelastic fluids, and the like.

The term "sample" can be any cell, tissue, or fluid that can be derived from or originates from a biological source (a "biological sample"), or other similar media, biological or non-biological, and that can be evaluated in accordance with the invention, such as a bodily fluid, enviromental matter, water, or the like. A sample can include, but is not limited to, a biological sample drawn from an organism (e.g. a human, a non-human mammal, an invertebrate, a plant, a fungus, an algae, a bacteria, a virus, etc.); a sample drawn from food designed for human consumption, a sample including food designed for animal consumption such as livestock feed, milk; an organ donation sample, a sample of blood destined for a blood supply; a sample from a water supply, and the like. One example of a sample is a sample drawn from a human or animal to determine the presence or absence of a specific nucleic acid sequence.

A "sample suspected of containing" a particular component means a sample with respect to which the content of the component is unknown. For example, a fluid sample from a human suspected of having a disease, such as a neurodegenerative disease or a non-neurodegenerative disease, but not known to have the disease, defines a sample suspected of containing neurodegenerative disease. "Sample," in this context, includes naturally-occurring samples, such as physiological samples from humans or other animals, samples from food, livestock feed, and the like. Typical samples taken from humans or other animals include tissue biopsies, cells, whole blood, serum or other blood fractions, urine, ocular fluid, saliva, cerebro-spinal fluid, fluid or other samples from tonsils, lymph nodes, needle biopsies, etc.

The terms "polypeptide," "peptide," and "protein," may be used interchangeably herein to refer to a polymer of amino acid residues. The terms generally apply to amino acid polymers in which one or more amino acid residues is a naturally occurring or artificially created amino acid. The term also includes variants on the traditional peptide linkage joining the amino acids making up the polypeptide, such as an ester linkage.

The terms "nucleic acid," "oligonucleotide," and their grammatical equivalents herein generally refer to at least two nucleotides covalently linked together. A nucleic acid of the present invention is preferably single-stranded or double stranded, and may generally contain phosphodiester bonds, although in some cases, as outlined below, nucleic acid analogs are included that may have alternate backbones, comprising, for example, phosphoramide (Beaucage et al. (1993) *Tetrahedron* 49(10): 1925 and references therein); Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 1419), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111 :2321, O-methylphophoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature,* 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research," Ed. Y. S. Sanghui and P. Dan Cook; Mesmacker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem.*

Soc. Rev. pp. 169-176). Several nucleic acid analogs are described in Rawls, *C & E News* Jun. 2, 1997 page 35. These modifications of the ribose-phosphate backbone may be performed, for example, to facilitate the addition of additional moieties such as labels, or to increase the stability and half-life of such molecules in physiological environments. Similarly, "polynucleotides" or "oligonucleotides" may generally refer to a polymer of nucleotides, which may include natural nucleosides (for example, adenosine, thymidine, guanosine, cytidine, uridine, deoxyadenosine, deoxythymidine, deoxyguanosine and deoxycytidine), nucleoside analogs (for example, 2-aminoadenosine, 2-thiothymidine, inosine, pyrrolopyrimidine, 3-methyladenosine, C5-bromouridine, C5-fluorouridine, C5-iodouridine, C5-propynyluridine, C5-propynylcytidine, C5-methylcytidine, 7-deazaadenosine, 7-deazaguanosine, 8-oxoadenosine, 8-oxoguanosine, 06-methylguanosine or 2-thiocytidine), chemically or biologically modified bases (for example, methylated bases), intercalated bases, modified sugars (2'-fluororibose, arabinose, or hexose), or modified phosphate groups (for example, phosphorothioates or 5'-N-phosphoramidite likages).

As used herein, an "antibody" refers to a protein or glycoprotein consisting of one or more polypeptides substantially encoded by immunoglobulin genes or fragments of immunoglobulin genes. The recognized immunoglobulin genes include, for example, the kappa, lambda, alpha, gamma, delta, epsilon and mu constant region genes, as well as other immunoglobulin variable region genes. Light chains may be classified as either kappa or lambda. Heavy chains may be classified as gamma, mu, alpha, delta, or epsilon, which in turn may define the immunoglobulin classes, for example, IgG, IgM, IgA, IgD and IgE, respectively. A typical immunoglobulin (antibody) structural unit may be a tetramer. Each tetramer may be composed of two identical or similar pairs of polypeptide chains, each pair having one "light" (about 25 kD) and one "heavy" chain (about 50-70 kD). The N-terminus of each chain may define a variable region of about 100 to 110 or more amino acids primarily responsible for antigen recognition. The terms variable light chain (VL) and variable heavy chain (VH) refer to these light and heavy chains, respectively, and are well-known to those of ordinary skill in the art.

Antibodies may exist as intact immunoglobulins or as a number of well characterized fragments produced by digestion with various peptidases. Thus, as one example that would be understood by one of ordinary skill in the art, pepsin may digest an antibody below (i.e. toward the Fc domain) the disulfide linkages in the hinge region to produce F(ab)'2, a dimer of Fab which itself is a light chain joined to $V_H-C_H1$ by a disulfide bond. The F(ab)'2 may be reduced under mild conditions to break the disulfide linkage in the hinge region thereby converting the (Fab')2 dimer into an Fab' monomer. The Fab' monomer may be a Fab with part of the hinge region (see, Paul (1993) *Fundamental Immunology*, Raven Press, N.Y. for a more detailed description of other antibody fragments). While various antibody fragments may be defined in terms of the digestion of an intact antibody, one of skill will appreciate that such fragments may be synthesized de novo either chemically, by utilizing recombinant DNA methodology, by "phage display" methods (see, e.g., Vaughan et al. (1996) *Nature Biotechnology*, 14(3): 309-314, and PCT/US96/10287) or other similar techniques. Antibodies may also include single chain antibodies, e.g., single chain Fv (scFv) antibodies in which a variable heavy and a variable light chain are joined together (directly or through a peptide linker) to form a continuous polypeptide.

As used herein, "plurality" means two or more.

As used herein, a "set" of items may include one or more of such items.

As used herein, the terms "comprising," "including," "carrying," "having," "containing," "involving," and the like are to be understood to be open-ended, i.e., to mean including but not limited to.

The present invention, in many embodiments, includes nanoscopic wires, each of which can be any nanoscopic wire, including nanorods, nanowires, organic and inorganic conductive and semiconducting polymers, nanotubes, semiconductor components or pathways and the like. Other nanoscopic-scale conductive or semiconducting elements that may be used in some instances include, for example, inorganic structures such as Group IV, Group III/Group V, Group II/Group VI elements, transition group elements, or the like, as described below. For example, the nanoscale wires may be made of semiconducting materials such as silicon, indium phosphide, gallium nitride and others. The nanoscale wires may also include, for example, any organic, inorganic molecules that are polarizable or have multiple charge states. For example, nanoscopic-scale structures may include main group and metal atom-based wire-like silicon, transition metal-containing wires, gallium arsenide, gallium nitride, indium phosphide, germanium, or cadmium selenide structures.

The nanoscale wires may include various combinations of materials, including semiconductors and dopants. The following are non-comprehensive examples of materials that may be used as dopants. For example, the dopant may be an elemental semiconductor, for example, silicon, germanium, tin, selenium, tellurium, boron, diamond, or phosphorous. The dopant may also be a solid solution of various elemental semiconductors. Examples include a mixture of boron and carbon, a mixture of boron and $P(BP_6)$, a mixture of boron and silicon, a mixture of silicon and carbon, a mixture of silicon and germanium, a mixture of silicon and tin, or a mixture of germanium and tin.

In some embodiments, the dopant or the semiconductor may include mixtures of Group IV elements, for example, a mixture of silicon and carbon, or a mixture of silicon and germanium. In other embodiments, the dopant or the semiconductor may include a mixture of a Group III and a Group V element, for example, BN, BP, BAs, AlN, AlP, AlAs, AlSb, GaN, GaP, GaAs, GaSb, InN, InP, InAs, or InSb. Mixtures of these may also be used, for example, a mixture of BN/BP/BAs, or BN/AlP. In other embodiments, the dopants may include alloys of Group III and Group V elements. For example, the alloys may include a mixture of AlGaN, GaPAs, InPAs, GaInN, AlGaInN, GaInAsP, or the like. In other embodiments, the dopants may also include a mixture of Group II and Group VI semiconductors. For example, the semiconductor may include ZnO, ZnS, ZnSe, ZnTe, CdS, CdSe, CdTe, HgS, HgSe, HgTe, BeS, BeSe, BeTe, MgS, MgSe, or the like. Alloys or mixtures of these dopants are also be possible, for example, (ZnCd)Se, or Zn(SSe), or the like. Additionally, alloys of different groups of semiconductors may also be possible, for example, a combination of a Group II-Group VI and a Group III-Group V semiconductor, for example, $(GaAs)_x(ZnS)_{1-x}$. Other examples of dopants may include combinations of Group IV and Group VI elemnts, such as GeS, GeSe, GeTe, SnS, SnSe, SnTe, PbO, PbS, PbSe, or PbTe. Other semiconductor mixtures may include a combination of a Group I and a Group VII, such as CuF, CuCl, CuBr, CuI, AgF, AgCl, AgBr, AgI, or the like. Other dopant compounds may include different mixtures of these elements, such as $BeSiN_2$, $CaCN_2$, $ZnGeP_2$, $CdSnAs_2$, $ZnSnSb_2$, $CuGeP_3$, $CuSi_2P_3$, $Si_3N_4$, $Ge_3N_4$, $Al_2O_3$, $(Al,Ga,In)_2(S,Se,Te)_3$, $Al_2CO$, $(Cu,Ag)(Al,Ga,In,Tl,Fe)(S,Se,Te)_2$ and the like.

For Group IV dopant materials, a p-type dopant may be selected from Group III, and an n-type dopant may be selected from Group V, for example. For silicon semiconductor materials, a p-type dopant may be selected from the group consisting of B, Al and In, and an n-type dopant may be selected from the group consisting of P, As and Sb. For Group III-Group V semiconductor materials, a p-type dopant may be selected from Group II, including Mg, Zn, Cd and Hg, or Group IV, including C and Si. An n-type dopant may be selected from the group consisting of Si, Ge, Sn, S, Se and Te. It will be understood that the invention is not limited to these dopants, but may include other elements, alloys, or materials as well.

Controlled doping of nanoscale wires can be carried out to form, e.g., n-type or p-type semiconductors. One set of embodiments involves use of at least one semiconductor, controllably-doped with a dopant (e.g., boron, aluminum, phosphorous, arsenic, etc.) selected according to whether an n-type or p-type semiconductor is desired. A bulk-doped semiconductor may include various combinations of materials, including other semiconductors and dopants. For instance, the nanoscopic wire may be a semiconductor that is doped with an appropriate dopant to create an n-type or p-type semiconductor, as desired. As one example, silicon may be doped with boron, aluminum, phosphorous, or arsenic. In various embodiments, this invention involves controlled doping of semiconductors selected from among indium phosphide, gallium arsenide, gallium nitride, cadmium selenide. Dopants including, but not limited to, zinc, cadmium, or magnesium can be used to form p-type semiconductors in this set of embodiments, and dopants including, but not limited to, tellurium, sulfur, selenium, or germanium can be used as dopants to form n-type semiconductors from these materials. These materials may define direct band gap semiconductor materials and these and doped silicon are well known to those of ordinary skill in the art. The present invention contemplates use of any doped silicon or direct band gap semiconductor materials for a variety of uses.

Nanotubes that may be used in the present invention include single-walled nanotubes (SWNTs) that exhibit unique electronic, and chemical properties that may be particularly suitable for molecular electronics. Structurally, SWNTs may be formed of a single graphene sheet rolled into a seamless tube with a diameter that may be, for example, on the order of about 0.5 nm to about 5 nm, and a length that can exceed about 10 µm, about 20 µm, or more in some cases. Depending on diameter and helicity, SWNTs may behave as a one-dimensional metal or a semiconductor material, and may also be formed as a mixture of metallic and semiconducting regions. Methods of manufacture of nanotubes, including SWNTs, and characterization are known. Methods of selective functionalization on the ends and/or sides of nanotubes also are known, and the present invention makes use of these capabilities for use in molecular electronics. The basic structural and electronic properties of nanotubes can be used to create connections or input/output signals, and nanotubes have a size consistent with molecular or nanoscopic-scale architecture.

The present invention contemplates, in one aspect, a nanoscale wire, for example, with a smallest width of less than 500 nm, having two or more regions having different compositions. The regions may be positioned radially, as in a core/shell arrangement, or longitudinally from each other. Combinations of these arrangements are also possible. Each regions may have any shape or dimension, as long as at least one of the regions is nanoscopically-sized. For example, the region may have a smallest dimension of less than 1 µm, less than 100 nm, less than 10 nm, or less than 1 nm. In some cases, one or more regions may comprise a single monolayer of atoms ("delta-doping"). In certain cases, the region may be less than a single monolayer thick (for example, if some of the atoms within the monolayer are absent).

As used herein, regions differing in composition may comprise different materials or elements, or may comprise the same materials or elements, but at different ratios or concentrations. Each region may be of any size or shape within the wire, for example, the regions may be adjacently positioned along the longitudinal axis of the nanoscale wire. The junctions may be, for example, a p/n junction, a p/p junction, an n/n junction, a p/i junction (where i refers to an intrinsic semiconductor), an n/i junction, an i/i junction, or the like. The junction may also be a Schottky junction. The junction may also be a semiconductor/semiconductor junction, a semiconductor/metal junction, a semiconductor/insulator junction, a metal/metal junction, a metal/insulator junction, an insulator/insulator junction, or the like. The junction may also be a junction of two materials, a doped semiconductor to a doped or an undoped semiconductor, or a junction between regions having different dopant concentrations. The junction may also be a defected region to a perfect single crystal, an amorphous region to a crystal, a crystal to another crystal, an amorphous region to another amorphous region, a defected region to another defected region, an amorphous region to a defected region, or the like.

More than two regions may be present, and these regions may have unique compositions or may comprise the same compositions. As one example, a wire may have a first region having a first composition, a second region having a second composition, and a third region having a third composition or the same composition as the first composition. Specific non-limiting examples include gallium arsenide/gallium phosphide compositionally modulated superlattices containing from 2 to 21 layers, or n-silicon/p-silicon and n-indium phosphide/p-indium phosphide modulation doped nanoscale wires.

Figure 78:
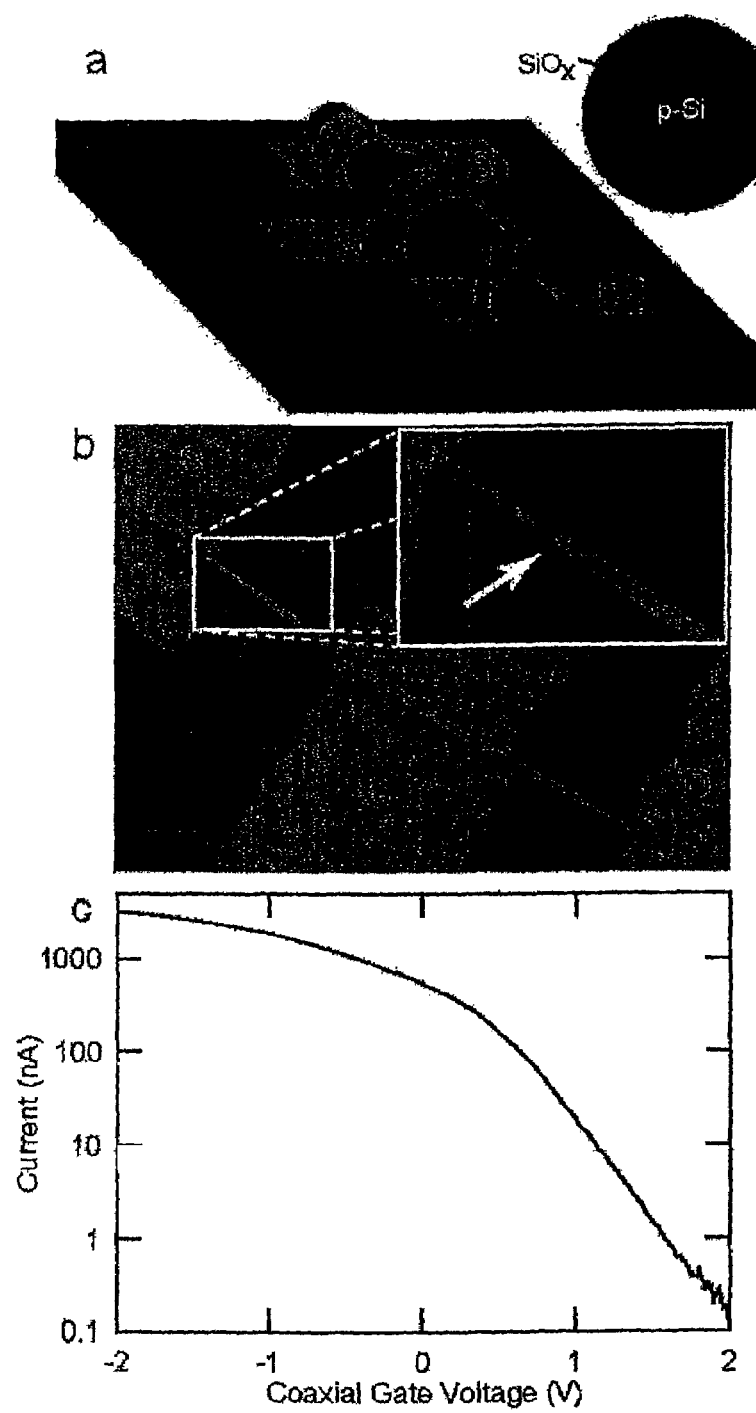
FIGS. 78A-78C illustrates certain nanoscale transistors of the invention.

The regions of the nanoscale wire may be distinct from each other with minimal cross-contamination, or the composition of the nanoscale wire may vary gradually from one region to the next. The regions may be both longitudinally arranged relative to each other, or radially arranged (e.g., as in a core/shell arrangement) on the nanoscale wire. As one example, the nanoscale wire may have multiple regions of alternating semiconductor materials arranged longitudinally, each having a segment length of about 500 nm. In another example, a nanoscale wire may have two regions having different compositions arranged longitudinally, surrounded by a third region or more having a composition different from that of the other regions. As a specific example, the regions may be arranged in a layered structure within the nanoscale wire, and one or more of the regions may be delta-doped or partially delta-doped. One example of a nanoscale wire having a series of regions positioned both longitudinally and radially relative to each other is shown in FIG. 78a. FIG. 78 illustrates one specific embodiment in which a nanowire arrangement includes at least one portion (at least the core, as illustrated), that is constant in composition along its length, and includes at least two shell portions, arranged longitudinally relative to each other, each of which is radially arranged relative to the core, each differing from the other in composition. The arrangement can include a core that differs in composition along its length (changes in composition or concentration longitudinally). The shell portions can be adjacent each other (contacting each other, or defining a change in composition or concentration of a unitary shell structure longitudinally), or can be separated from each other by, for example, air (as illustrated), an insulator, a fluid, or an auxiliary, non-nanowire component. The shell portions can be positioned directly on the core, or can be separated from the core by one or more intermediate shells portions that can themselves be consistent in composition longitudinally, or varying in composition longitudinally. That is, the invention allows the provision of any combination of a nanowire core and any number of radially-positioned shells (e.g., concentric shells), where the core and/or any shells can vary in composition and/or concentration longitudinally, any shell sections can be spaced from any other shell sections longitudinally, and different numbers of shells can be provided at different locations longitudinally along the structure.

In some embodiments, the junction between two differing regions (e.g., between different longitudinal regions of a core or shell, or between a core and shell, or between two different shells) may be "atomically-abrupt," where there is a sharp transition at the atomic scale between two adjacent regions that differ in composition. However, in other embodiments, the junction between two differing regions may be more gradual. For example, the "overlap region" between the adjacent regions may be a few nanometers wide, for example, less than about 10 nm, less than about 20 nm, less than about 40 nm, less than about 50 nm, less than about 100 nm, or less than about 500 nm. In certain embodiments, the overlap region between a first region having a composition and a second region having a composition different from the first region (i.e., different concentrations or different species) can be defined as the distance between where the composition of the overlap region ranges between about 10 vol % and about 90 vol % of the composition of the first region, with the remainder having a complementary amount of the composition of the second region. In certain embodiments of the invention, nanoscale wires having more than one junction between two regions having different compositions are also contemplated. For example, a nanoscale wire may have 2, 3, 4, or more overlap regions. The number of periods and the repeat spacing may be constant or varied during growth.

In some embodiments, a gradual change in composition between two adjacent regions may relieve strain and may enable the defect free junctions and superlattices. However, in other embodiments, atomically-abrupt interfaces may be desirable, for example, in certain photonic and electronic applications. The nature of the interface between the two adjacent regions may be controlled by any suitable method, for example, by using different nanocluster catalysts or varying the growth temperature when reactants are switched during synthesis. Nanoscale wires having atomically abrupt regions may be fabricated, for example, by reducing the diameter of the nanoscale wire, for example, by reducing the size of the starting nanocluster, or by controlling exposure of the growing wire to dopant gases, for example, by selectively purging or evacuating the region surrounding the wire between different gas exposures or reaction conditions. All of these embodiments can be provided with one, or multiple shells. These shells can be of the same or different composition relative to each other, and any of the shells can be of the same composition of a segment of the core, or of a different composition, or can contain the same or different concentration of a dopant as is provided in a section of the core. The shells may be grown using any suitable growth technique, for example, including the techniques described herein, such as CVD or LCG.

Certain devices of the invention make particular use of adjacent regions having different compositions within a nanoscale wire, for example, p-type and n-type semiconductor regions. A p/n junction may be defined by at least one n-type semiconductor and at least one p-type semiconductor positioned adjacent to each other within the nanoscale wire, where at least one portion of each region contacts at least one portion of the other region, and each semiconductor including portions that do not contact the other component.

In various embodiments, this invention also involves controlling and altering the doping of semiconductors in a nanoscale wire. In certain embodiments, the nanoscale wires may be produced using techniques that allow for direct and controlled growth of the nanoscale wires. The direct growth of doped nanoscale wires may eliminate the need to use lithographic steps during production of the nanoscale wire, thus facilitating the "bottom-up" assembly of complex functional structures.

Figure 71:
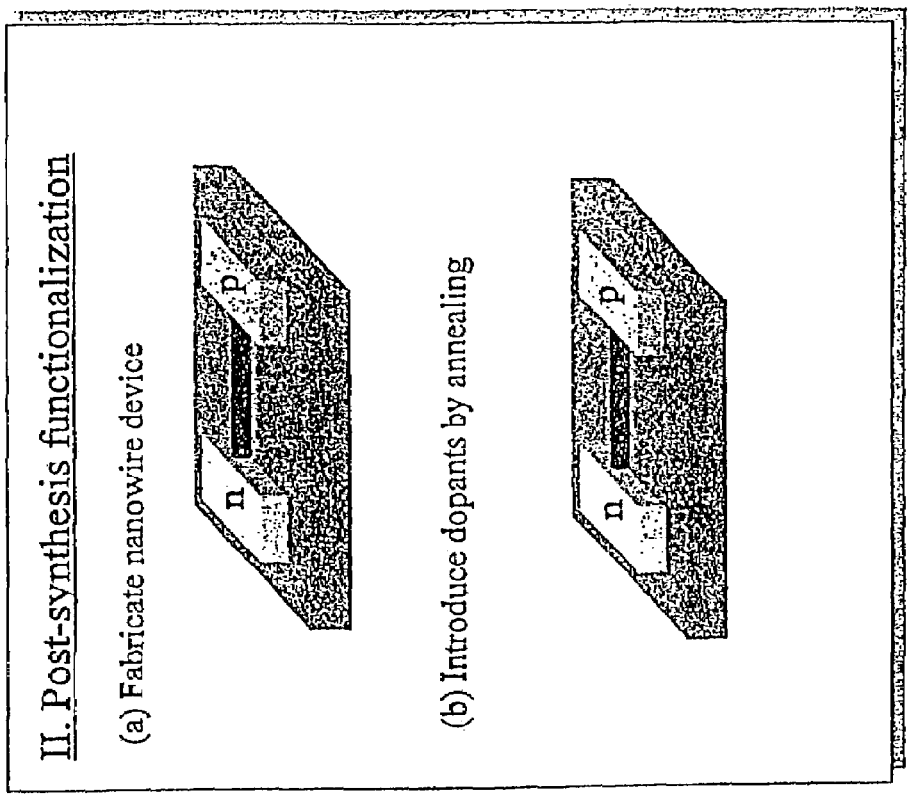
FIG. 71 illustrates fabrication techniques.

As illustrated in FIG. 71, fabrication paradigms for single nanoscale wire devices that are contemplated in the present invention include, but are not limited to, direct fabrication of nanoscale wire junctions during synthesis, or doping of nanoscale wires via post-synthesis techniques (e.g., annealing of dopants from contacts or solution-processing techniques). The dopants may be changed at any point during the growth of the nanoscale wire.

In one set of embodiments, a region of a nanoscopic wire (e.g. a shell of a nanoscopic wire) can comprise molecules where one end has an alkyoxysilane group (e.g. —Si(OCH$_3$)) that may be able to react with the surface of another region such as an inner core region, the other end of which may comprise —CH$_3$, —COOH, —NH$_2$, —SH, —OH, a hydrazide, or an aldehyde group. In another embodiment, the end may comprise a light activatable moiety, such as an aryl azide, a fluorinated aryl azide, a benzophenone or the like. External substrates and electrodes may also be modified with certain functional groups to allow the nanoscopic wires to specifically bind or not bind onto the substrate/electrodes surface, based on the interaction of the surface with the nanoscopic wire.

Surface-functionalized nanoscopic wires (e.g. wires having shells comprising functional moieties) may also be coupled to the substrate surface with functional cross-linkers, such as homobifunctional cross-linkers, comprising homobifunctional NHS esters, homobifunctional imidoesters, homobifunctional sulfhydryl-reactive linkers, difluorobenzene derivatives, homobifunctional photoactive linkers, homobifunctional aldehyde, bis-epoxides, homobifunctional hydarzide etc.; heterobifuntional cross-linkers; or trifuntional cross-linkers. In another embodiment, a region may include amorphous oxide, which may allow other molecules to be attached to the surface of the region. This may facilitate attachment or modification, in certain instances.

The functional moieties may also include simple functional groups, for example, but not limited to, —OH, —CHO, —COOH, —SO$_3$H, —CN, —NH$_2$, —SH, —COSH, COOR, or a halide; biomolecular entities including, but not limited to, amino acids, proteins, sugars, DNA, antibodies, antigens, and enzymes; grafted polymer chains with chain length less than the diameter of the nanoscale wire core, including, but not limited to, polyamide, polyester, polyimide, polyacrylic; a thin coating (e.g., shell), covering the surface of the nanoscale wire core, including, but not limited to, the following groups of materials: metals, semiconductors, and insulators, which may be a metallic element, an oxide, a sulfide, a nitride, a selenide, a polymer and a polymer gel. In another embodiment, the invention provides a nanoscale wire and a reaction entity with which the analyte interacts, positioned in relation to the nanoscale wire such that the analyte can be determined by determining a change in a characteristic of the nanoscale wire.

Light-emission sources are provided in accordance with the invention as well, in which electrons and holes may combine to emit light. One embodiment of a light-emission source of the invention includes at least one p/n junction, in particular, a p/n junction within a single, free-standing nanoscale wire. When forward-biased (i.e., positive charge applied to the p-type region and a negative charge applied to the n-type region), electrons flow toward the junction in the n-type region and holes flow toward the junction in the p-type region. At the p/n junction, holes and electrons may combine, emitting light. Other techniques may be used to cause one or more nanoscale wires, or other semiconductors to emit light, as described below in more detail.

At the size scale of the invention (nanoscale) the wavelength of light emission may be controlled by controlling the size of the p/n junction, for example, the overlap region between the p-type region and the n-type region, the diameter of the nanoscale wire or by controlling the size of at least one, and preferably both components in embodiments having configurations involving crossed wires. Where nanowires are used, a nanowire with a larger smallest dimension will provide emission at a lower frequency. For example, in the case of a doped indium phosphide wire, at size scales associated with typical fabrication processes, the material may emit at 920 nm, depending on the dopant. At the size scales of the present invention, the wavelength of emission may be controlled to emit at wavelengths shorter than 920 nm, for example between 920 and 580 nm. Wavelengths can be selected within this range, such as 900, 850, 800, 750, 700 nm, etc., depending upon the wire size.

Thus, one aspect of the invention involves a doped semiconductor light-emission source that emits electromagnetic radiation at a frequency higher than that emitted by the doped semiconductor in its bulk state, such that the increase of the frequency of the emission of light may be referred to herein as quantum confinement. "Bulk state," in this context, generally refers to a state in which it is present as a component, or a portion of a component having a smallest dimension of greater than 500 nm or more. "Bulk state" also may be defined as that state causing a material's inherent wavelength or frequency of emission, i.e. a state at which growth in mass of the material no longer causes a change in frequency of emission of electromagnetic radiation. The present invention provides for such control over emission frequency of essentially any semiconducting or doped semiconducting material.

In certain embodiments, the nanoscale wires may be photoluminescent, for example, in nanoscale wires comprising indium phosphide. In these embodiments, the emission maxima may systematically blue shift with decreasing nanoscale wire diameter due to radial quantum confinement. The excitations may remain delocalized down to low experimental temperatures due to the quantum effects. The nanoscopic wires of the present invention have a size such that the optical and electronic properties of the nanoscopic wires are strongly size-dependent due to quantum confinement effects.

The photoluminescence of the nanoscale wire may exhibit uniform emission intensities over the entire length of the nanoscopic wire. In addition, the luminescence spectra of different positions along the nanoscopic wire axis may have nearly identical line shapes or emission energies. The uniformity in the photoluminescence of the nanoscopic wires may be due to the regularity in the structure of the nanoscopic wire. Due to this uniformity, multiple nanoscopic wires, each having the same diameter and composition but differing lengths may all exhibit nearly the same luminescence maxima and line shape. The line widths may be broadened due to delocalization from the Heisenburg Uncertainty Principle. Additionally, the photoluminescence spectra may exhibit a systematic shift to higher energies as the nanoscopic wire diameter is reduced, as expected for quantum confinement.

The nanoscale wires may also exhibit polarization anisotropy in some embodiments. The polarization anisotropy may arise from the large dielectric contrast inherent to the nanoscale wires having two or more regions having different compositions. In contrast, mixing of valence bands due to quantum confinement yields smaller polarization ratios (i.e., less than about 0.60) in single-region nanoscale wires. Thus, polarization-sensitive nanoscale photodetectors may be constructed using the nanoscale wires of the present invention, which may be used in integrated photonic circuits, near-field imaging, or other high-resolution or high-speed detectors.

The excitation and emission spectra for the nanoscale wires may show strong linearized polarization, parallel to the wire axis, essentially turning "on" and "off" as the polarization angle is rotated. The ratio of parallel to perpendicular emission may be over an order-of-magnitude in some embodiments. Quantitatively, the measured excitation and emission polarization ratios, $\rho=(I_{\parallel}-I_{\perp})/(I_{\parallel}+I_{\perp})$, of the intensities parallel ($I_{\parallel}$) and perpendicular ($I_{\perp}$) to the wire axis may be between 0.91±0.07, with some nanoscopic wires exhibiting the theoretical maximum polarization of 0.96 in the case of certain indium phosphide wires of the present invention.

The conductance (G) of an individual nanoscale wire may increase by about 2 to 3 orders of magnitude with increasing excitation power density in some cases. In some embodiments, polarization-sensitive photodetectors in which an individual nanoscale wire serves as the detection element may be constructed. These photodetectors may have a reproducible photoconductivity with a nearly instantaneous response time (i.e., with a response time of less than about 1 s, preferably less than about 1 ms, more preferably less than about 1 µs, still more preferably less than about 1 ns, and even more preferably less than about 1 ps, and even more preferably still less than about 1 fs. Preferably, the photoconductivity may also exhibit polarization anisotropy, where the parallel excitation is over an order of magnitude larger than the perpendicular excitation. Quantitatively, the photoconductivity anisotropy ratio, $\sigma=(G_{\parallel}-G_{\perp})/(G_{\parallel}+G_{\perp})$, where $G_{\parallel}$ is the conductance with parallel excitation and $G_{\perp}$ is the conductance with perpendicular excitation, may be between 0.91±0.07, with some nanodetectors exhibiting the theoretical maximum polarization of 0.96 in the case of certain indium phosphide wires. The active device nanoscale wire element of the present invention may also be sensitive to multiple wavelengths of light.

The present invention also provides information-recording devices based on semiconducting nanoscale wires. In certain embodiments, switching memory may be achieved based on the observation that the conductance of these semiconducting nanoscale wires can change significantly upon either a gate or bias voltage pulse when the surface of the nanoscale wires are appropriately modified, for example, with molecules, functional groups, or nanocrystals. Other properties of the nanoscale wire may also be used to record memory, for example, but not limited to, the redox state of the nanoscale wire, mechanical changes, magnetic changes, induction from a nearby field source, and the like.

Specifically, with respect to changes in conductance, subjection to positive or negative gate or bias voltage pulses may cause the change of charge states in the molecules or nanocrystals, and induces the device to make a fully reversible transition between low and high resistance states. The different states may hysterically persist in the set state, even after the voltage source is deactivated. This feature (change in electrical properties upon voltage pulse) may enable the fabrication of electrically erasable and rewritable memory switching devices in which the reversible states are indicated by the conductance of the nanoscale wires. In addition, the memory switching devices may be assembled specifically from nanoscale material building blocks, and may not be created in planar materials by lithography.

Figure 34:
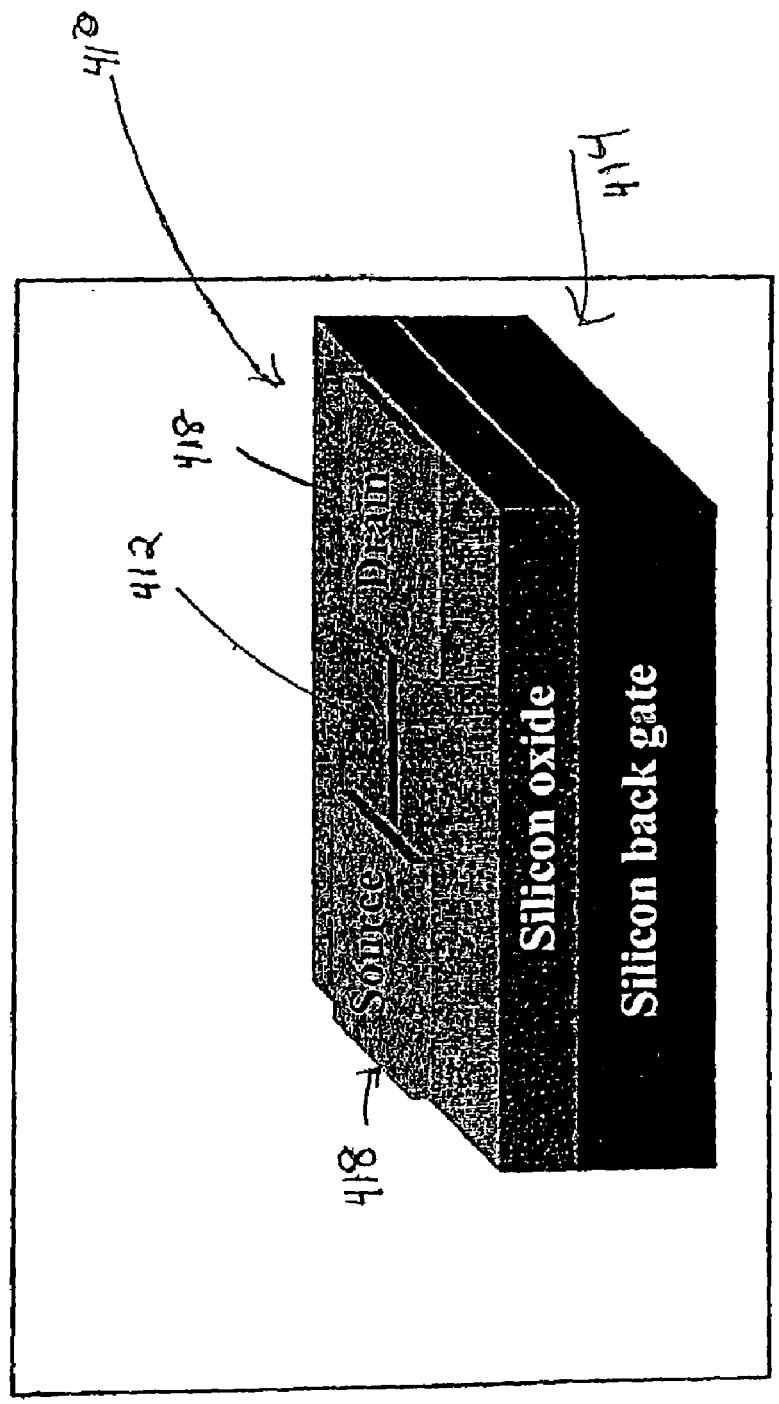
FIG. 34 is a schematic view of a memory cell of an embodiment of the invention.

FIG. 34 is a schematic view of a memory cell comprising a single semiconductor nanoscale wire. Memory device 410 may comprise a single n-InP nanoscale wire 412 on silicon substrate 414 with silicon oxide 416 with the gate dielectrics. Two metal electrodes 418 are deposited onto the two ends of the nanoscale wire to electrically address the nanoscale wires. The silicon substrate may act as the gate electrode. Measuring the conductance of the nanoscale wire vs. gate voltage shows a small hysteresis in the source drain current with respect to gate voltage at constant bias of one volt. (FIG. 35a). This hysteresis may be greatly enhanced when certain organic molecules are added to the surface of the nanoscale wire. (FIG. 35b), for example, organic molecules such as cobalt (II) phthalocyanine, cobalt (II) 2,3-naphthalocyanine and cobalt (II) 1,2,3,4,8,9,10,11,15,16,17,18,22,23,24,25-hexadecafluoro-29H,31H-phthalocyanine. Without being bound to any particular theory or mechanism, it is believed that the positive gate voltage may charge the absorbed molecules, which in turn may change the conductance of the nanoscale wires, and that the negative gate voltage may discharge the absorbed molecules. This large hysteresis may enable fabrication of particular memory switching devices. In particular, with reference to FIG. 35b, writing "1" or "0" may be done with either a negative or positive 10 V gate pulse, and reading "1" or "0" may be done by measuring the conductance of the nanoscale wire around the zero gate voltage region. This memory device may be reversibly written and read over thousands of times in certain embodiments. Further, the nanoscale memory device may be stable in air at room temperature up to several weeks (FIG. 35c). Retention times on the order of hours are possible. In some embodiments, the device may be able to memorize the state even after the device is powered off. On-off ratios up to 2 to 4 orders of magnitude may also be possible. Similar devices fabricated of p-Si n-GaN nanoscale wires have also shown similar behavior.

Figure 72:
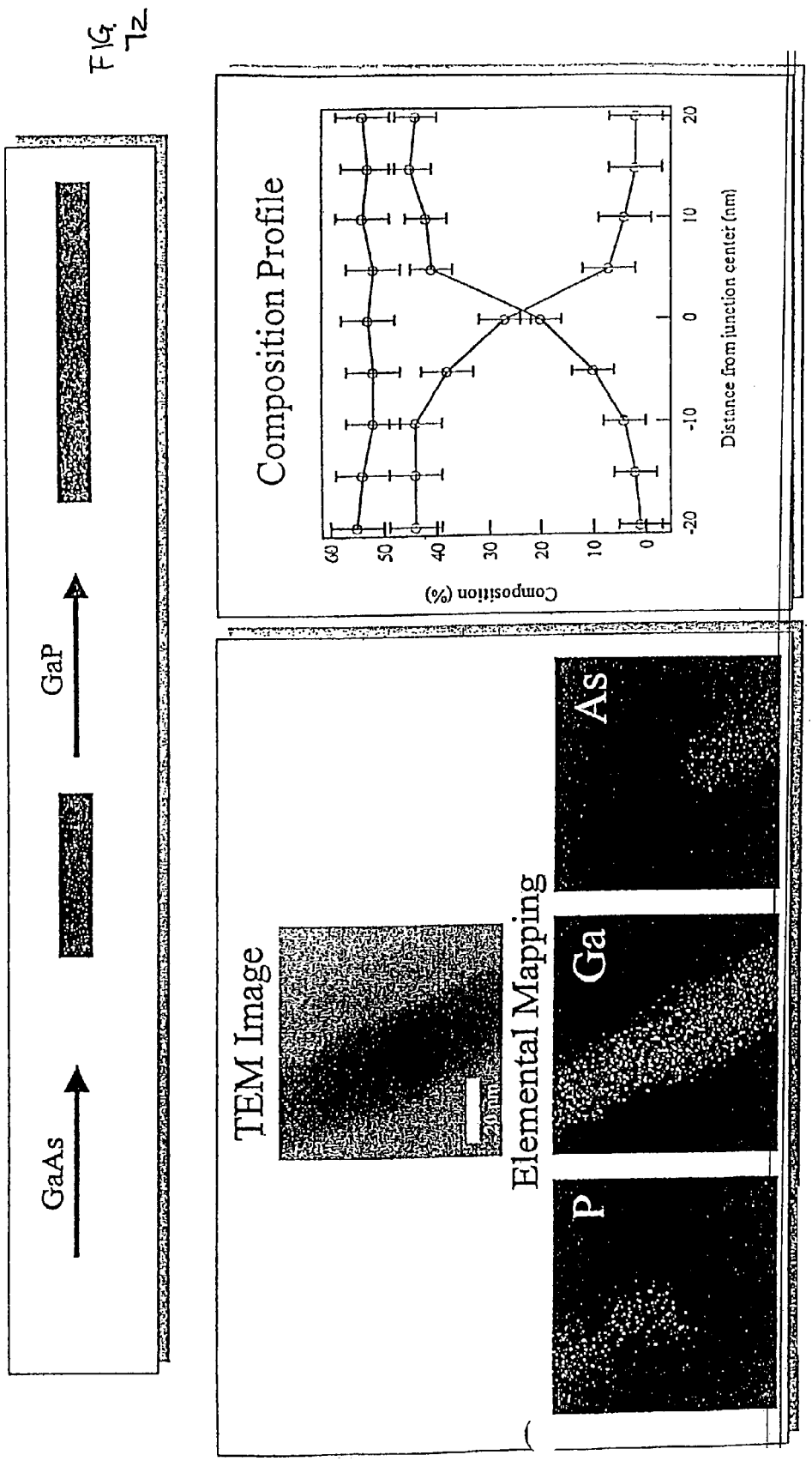
FIG. 72 illustrate data from one embodiment of the invention.

One technique for direct fabrication of nanoscale wire junctions during synthesis is generally referred to as laser catalytic growth ("LCG"). This methodology allows the direct formation of adjacent regions having different compositions within a nanoscale wire, such as a p/n junction, and/or adjacent regions differing in concentration of a particular element or composition. LCG also allows the creation of semiconductor superlattices, in which multiple layers of different composition are grown, which may give rise to a one-dimensional analog of multiple quantum states that are well known from thin-film studies. In LCG, a nanoparticle catalyst is used during growth of the nanoscale wire, which may be further subjected to different semiconductor reagents during growth. Alteration of the semiconductor reagents may allow for the formation of abrupt or gradual changes in the composition of the growing semiconductor material, allowing heterostructured materials to be synthesized. One example of an LCG-grown semiconductor is depicted in FIG. 72, where a GaP/GaAs heterojunction within a single 20 nm nanowire is shown. An initial growth of GaAs, followed by subsequent GaP growth, gives an abrupt junction within a single nanowire, as is shown from transmission electron microscopy ("TEM") elemental mapping.

A technique of post-synthetic doping of nanoscale wires is illustrated in FIG. 73. In this figure, a nanoscale wire having a substantially homogeneous composition is first synthesized, then is doped post-synthetically with various dopants as is discussed below. For example, in FIG. 73, a p/n junction was created by introducing p-type and an n-type dopants down on a single nanoscale wire. The p/n junction was then further annealed to allow the dopants to migrate further into the nanoscale wire to form a bulk-doped nanoscale wire.

As one example, the nanoscale wire may be doped during growth of the nanoscale wire. Doping the nanoscale wire during growth may result in the property that the doped nanoscale wire is bulk-doped. Furthermore, such doped nanoscale wires may be controllably doped, such that a concentration of a dopant within the doped nanoscale wire can be controlled and therefore reproduced consistently, making possible the commercial production of such nanoscale wires. Additionally, the dopant may be systematically altered during the growth of the nanoscale wire, for example, so that the final nanoscale wire has a first doped region comprising a first dopant and a second doped region differing in composition from the first region, for example, by comprising a second dopant, comprising the first dopant at a different concentration, or omitting the first dopant.

Figure 2:
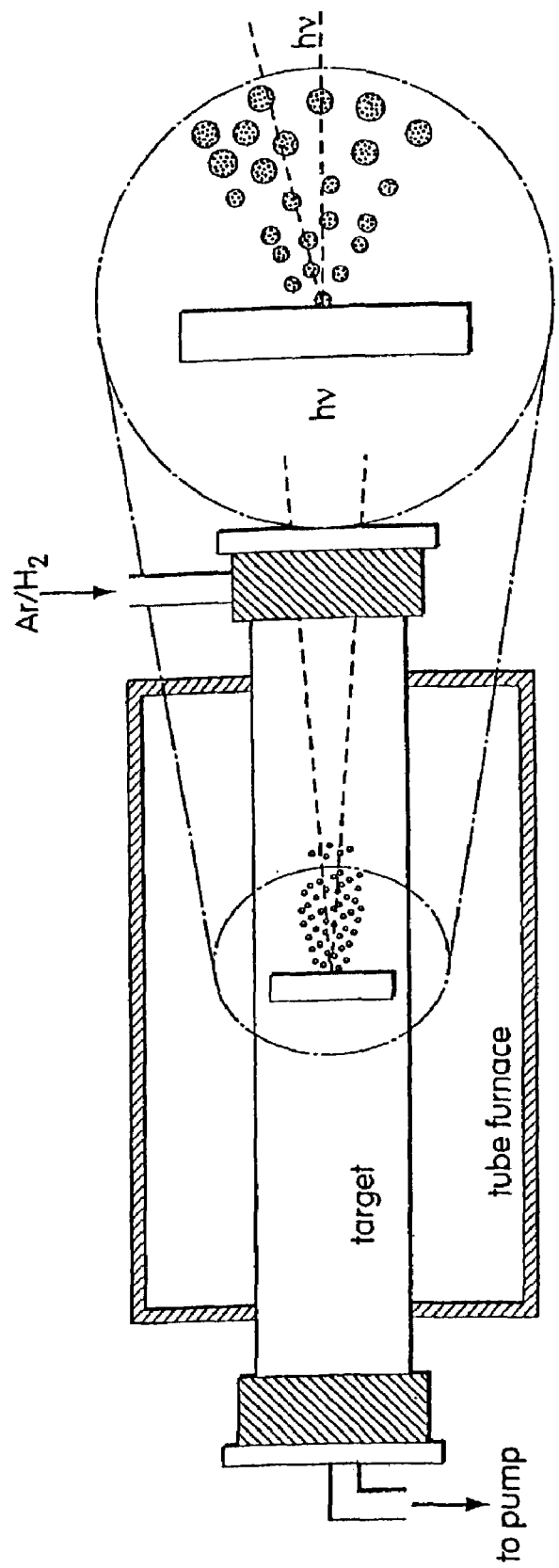
FIG. 2 is a simplified schematic diagram of an example of a laser assisted catalytic growth process for fabrication of semiconductors.
Figure 3:
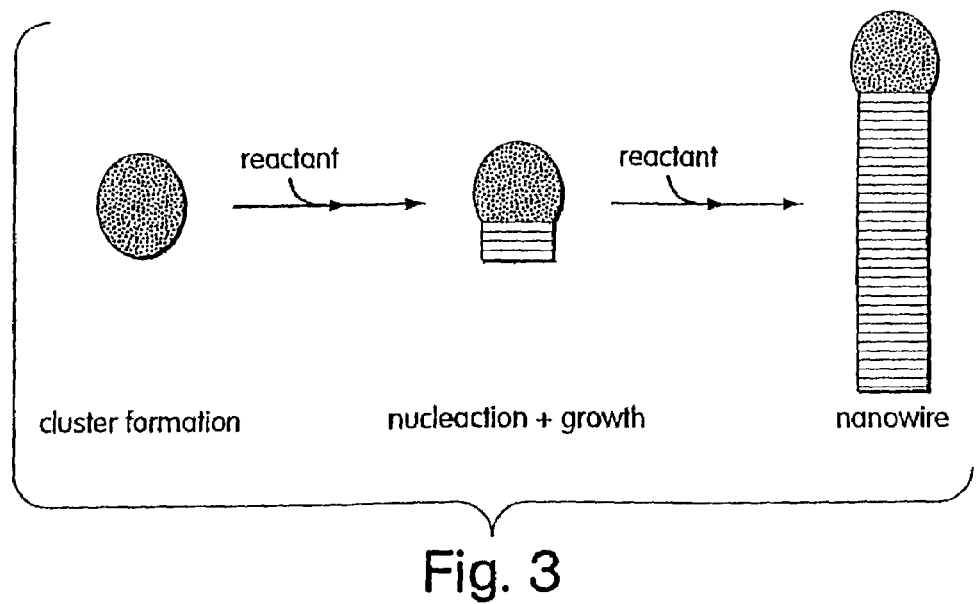
FIG. 3 is a schematic diagram that illustrates nanoscopic wire growth.

In some embodiments, laser catalytic growth techniques ("LCG") may be used to controllably introduce dopants during vapor phase growth of nanoscale wires. As shown in FIGS. 2 and 3, laser vaporization of a composite target composed of a desired material (e.g. silicon or indium phosphide) and a catalytic material (e.g. gold) may create a hot, dense vapor. The vapor may condenses into liquid nanoclusters through collision with a buffer gas. Growth may begin when the liquid nanoclusters become supersaturated with the desired phase and can continue as long as reactant is available. Growth may terminate when the nanoscale wire passes out of the hot reaction zone or when the temperature is decreased.

In LCG, vapor phase semiconductor reactants required for nanoscale wire growth may be produced by laser ablation of solid targets, vapor-phase molecular species, or the like. To create a single junction within a nanoscale wire, the addition of the first reactant may be stopped during growth, and then a second reactant may be introduced for the remainder of the synthesis. Repeated modulation of the reactants during growth is also contemplated, which may produce nanoscale wire superlattices. LCG also may require a nanocluster catalyst suitable for growth of the different superlattice components, for example, a gold nanocluster catalyst can be used in a wide-range of III-V and IV materials. Nearly monodisperse metal nanoclusters may be used to control the diameter, and, through growth time, the length various semiconductor nanoscale wires.

Figure 74:
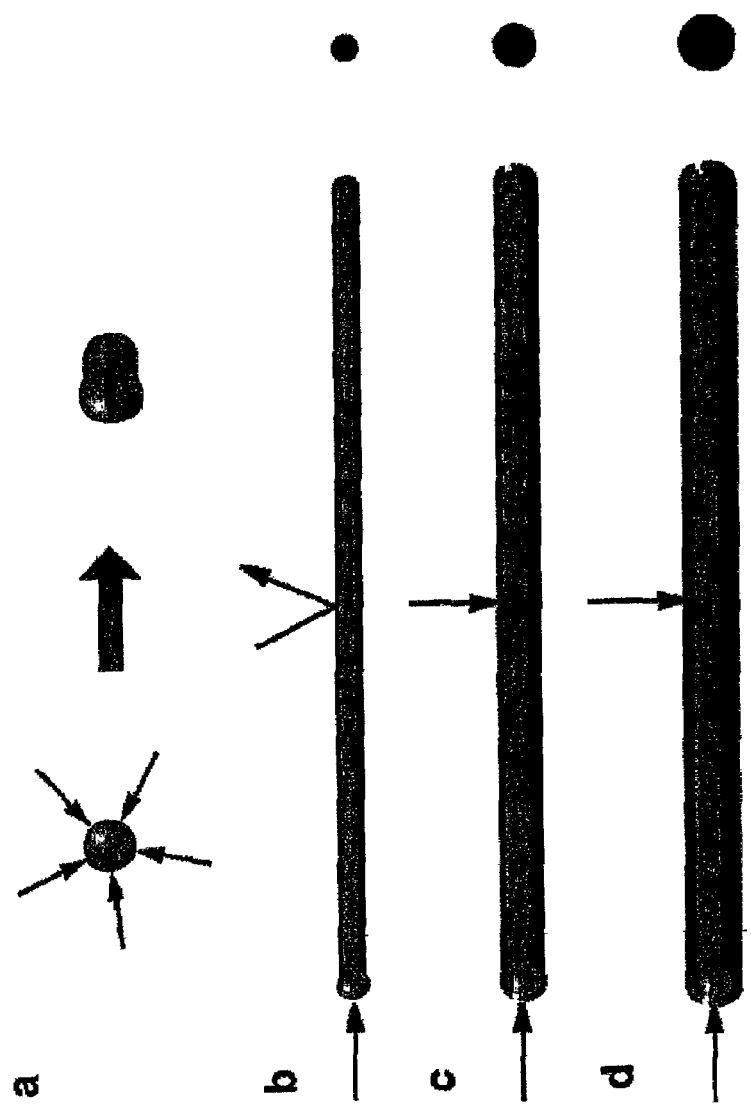
FIGS. 74A-74D is a schematic diagram of certain core-shell nanoscale wires of the invention.
Figure 75:
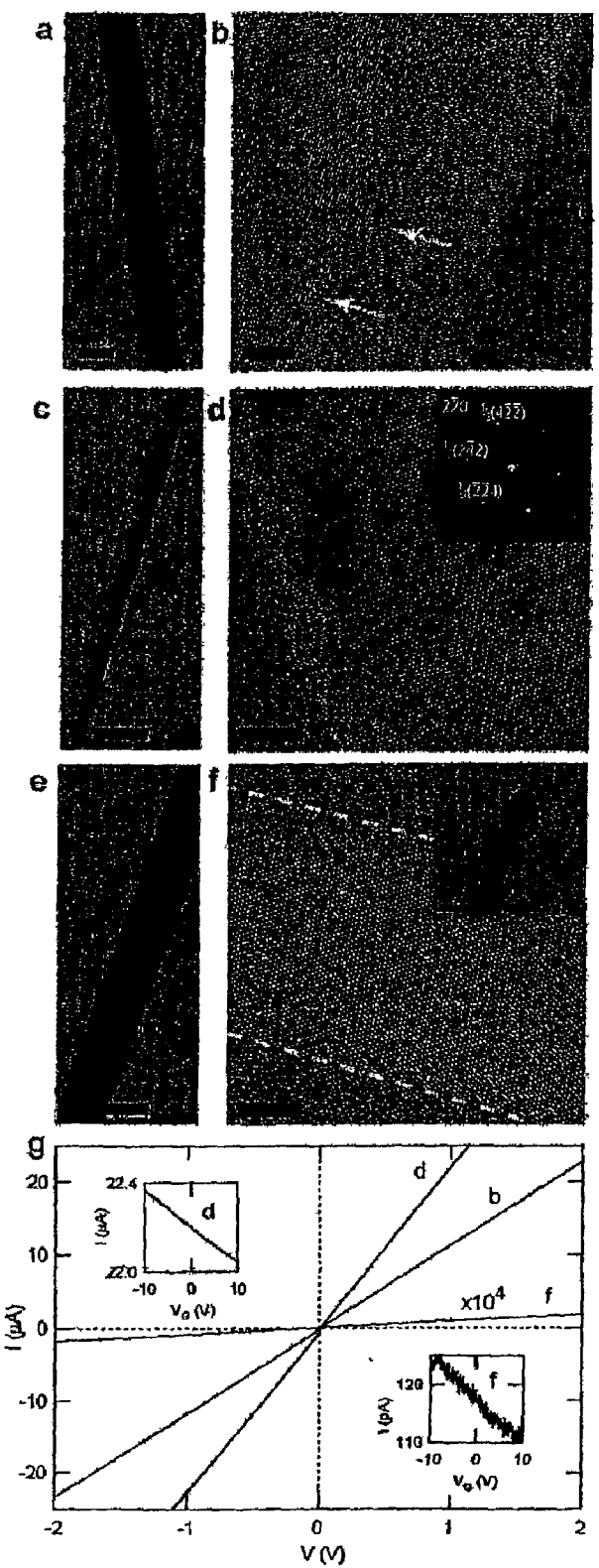
FIGS. 75A-75G illustrates certain core-shell nanoscale wires of the invention.
Figure 76:
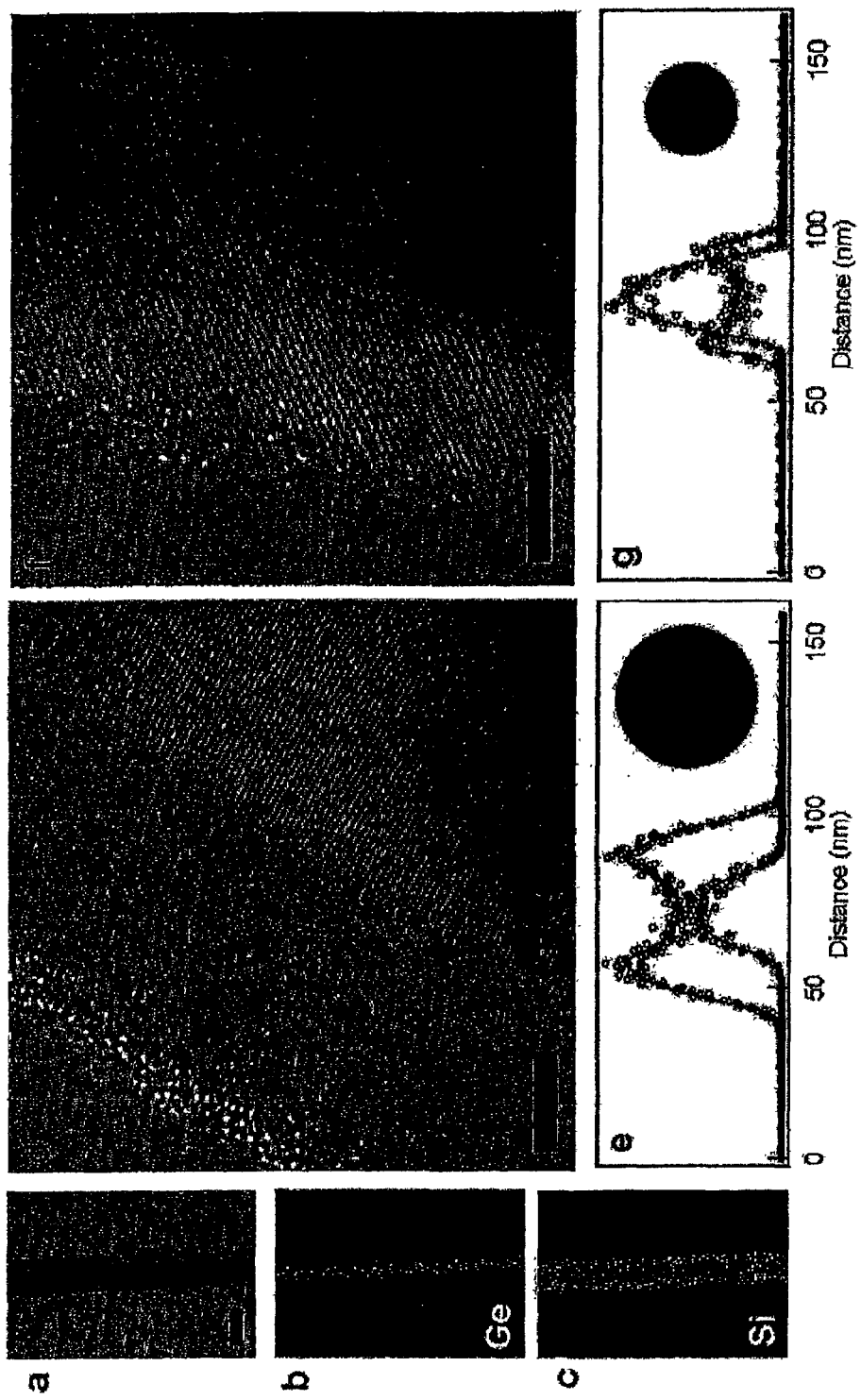
FIGS. 76A-76G illustrates certain nanoscale wires of the invention, comprising germanium or silicon.

As another example, LCG methods may be used to create nanoscale wires having a multishell configuration, for example, as illustrated in FIG. 75e or FIG. 76a. For example, by altering the synthetic conditions during laser catalytic growth, homogeneous reactant decomposition may occur on the surface of the nanoscale wire, as is illustrated in FIG. 74. Control of the synthetic conditions may lead to a shell forming on the surface of the nanoscale wire, and in some embodiments, the synthetic reaction conditions may be controlled to cause the formation of a thin, uniform shell, a shell having a thickness of one atomic layer, or less in some cases. In other embodiments, by modulating or altering the reactants within the laser catalytic growth system, more than one shell may be built up on the outer surface of the nanoscale wire, as is shown in FIG. 74d. As one example, a silicon nanoscale wire core may be grown, and additional semiconductor materials may be deposited onto the surface, for example, a germanium shell, or a silicon shell doped with a dopant such as boron, or other dopants as described elsewhere in this application. The boundaries between the shells may be atomically abrupt, or may be graduated in some fashion, depending on how reactants such as, for example, silane, germane, or diborane are introduced into the laser catalytic growth system. Arbitrary sequences of Si, Ge, and alloy overlayers on both Si and Ge nanowire cores may also be prepared. Other factors may also contribute to the growing nanoscale wire, such as, for example, the reaction temperature, or the sample position within the furnace. By varying these parameters, the ratio of axial growth to radio growth may be controlled as desired.

Any catalyst able to catalyze the production of nanoscale wires may be used. Gold may be preferred in certain embodiments. A wide range of other materials may also be contemplated, for example, a transition metal such as silver, copper, zinc, cadmium, iron, nickel, cobalt, and the like. Generally, any metal able to form an alloy with the desired semiconductor material, but does not form a more stable compound than with the elements of the desired semiconductor material may be used as the catalyst.

The buffer gas may be any inert gas, for example, $N_2$ or a noble gas such as argon. In some embodiments, a mixture of $H_2$ and a buffer gas may be used to reduce undesired oxidation by residual oxygen gas.

A reactive gas used during the synthesis of the nanoscale wire may also be introduced when desired, for example, ammonia for semiconductors containing nitrogen, such as gallium nitride. Nanoscale wires may also be flexibly doped by introducing one or more dopants into the composite target, for example, a germanium alloy during n-type doping of InP. The doping concentration may be controlled by controlling the relative amount of doping element, for example, between 0 and about 10% or about 20%, introduced in the composite target.

Laser ablation may generate liquid nanoclusters that subsequently define the size and direct the growth direction of the nanoscale wires. The diameters of the resulting nanoscale wires are determined by the size of the catalyst cluster, which may be varied by controlling the growth conditions, such as the pressure, the temperature, the flow rate and the like. For example, lower pressure may produce nanoscale wires with smaller diameters in certain cases. Further diameter control may be performed by using uniform diameter catalytic clusters.

Figure 4:
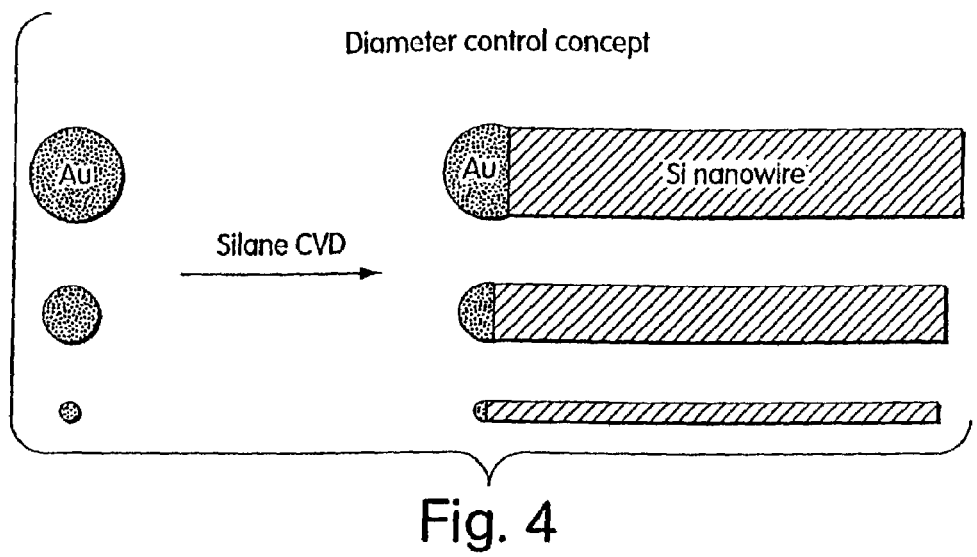
FIG. 4 is a schematic diagram that illustrates an example of a method for controlling nanoscopic wire diameter.

With same basic principle as LCG, if uniform diameter nanoclusters (less than 10-20% variation depending on how uniform the nanoclusters are) are used as the catalytic cluster, nanoscale wires with uniform size (diameter) distribution can be produced, where the diameter of the nanoscale wires is determined by the size of the catalytic clusters, as illustrated in FIG. 4. By controlling the growth time or the position of the sample within the reactor, nanoscale wires with different lengths or different shell thicknesses may be grown.

Nanoscale wires having uniform diameters or size distributions may be produced in embodiments where the diameter of the nanoscale wire is determined by the size of the catalytic cluster. For example, uniform diameter nanoclusters (for example, having a variation of less than about 10% to about 20% in the average diameter) may be used as the starting catalytic clusters. By controlling the growth time, nanoscale wires having different lengths may be grown.

The catalytic clusters or the vapor phase reactants may be produced by any suitable technique. For example, laser ablation techniques may be used to generate catalytic clusters or vapor phase reactant that may be used during LCG. Other techniques may also be contemplated, such as thermal evaporation techniques.

The laser ablation technique may generate liquid nanoclusters that may subsequently define the size and direct the growth direction of the nanoscopic wires. The diameters of the resulting nanoscale wires may be determined by the size of the catalyst cluster, which in turn may be determined using routine experiments that vary the growth conditions, such as background pressure, temperature, flow rate of reactants, and the like. For example, lower pressure generally produces nanoscale wires with smaller diameters. Further diameter control may be achieved by using uniform diameter catalytic clusters.

Certain aspects of the invention may utilize metal-catalyzed CVD techniques ("chemical vapor deposition") to synthesize individual nanoscopic-scale wires, such as nanotubes for molecular electronics. CVD synthetic procedures needed to prepare individual wires directly on surfaces and in bulk form are generally known, and can readily be carried out by those of ordinary skill in the art. See, for example, Kong, et al., "Synthesis of Individual Single-Walled Carbon Nanotubes on Patterned Silicon Wafers," *Nature*, 395:878-881 (1998); or Kong, et al., "Chemical Vapor Deposition of Methane for Single-Walled Carbon Nanotubes," *Chem. Phys. Lett.*, 292:567-574 (1998), both incorporated herein by reference their entirety for all purposes. Nanoscopic wires may also be grown through laser catalytic growth. See, for example, Morales, et al., "A Laser Ablation Method for the Synthesis of Crystalline Semiconductor Nanowires," *Science*, 279:208-211 (1998), incorporated herein by reference in its entirety for all purposes. With same basic principles as LCG, if uniform diameter nanoclusters (less than 10-20% variation depending on how uniform the nanoclusters are) are used as the catalytic cluster, nanoscale wires with uniform size (diameter) distribution can be produced, where the diameter of the nanoscale wires is determined by the size of the catalytic clusters, as illustrated in FIG. 4. By controlling the growth time, nanoscale wires with different lengths can be grown.

One technique that may be used to grow nanoscale wires is catalytic chemical vapor deposition ("C-CVD"). In the C-CVD method, the reactant molecules (e.g., silane and the dopant) are formed from the vapor phase, as opposed to from laser vaporization. In C-CVD, nanoscale wires may be doped by introducing the doping element into the vapor phase reactant (e.g. diborane and phosphane for p-type and n-type doped regions). The doping concentration may be controlled by controlling the relative amount of the doping compound introduced in the composite target. The final doping concentration or ratios are not necessarily the same as the vapor-phase concentration or ratios. By controlling growth conditions, such as temperature, pressure or the like, nanoscale wires having the same doping concentration may be produced.

To produce a nanoscale wire having adjacent regions having different compositions within a nanoscale wire, the doping concentration may be varied by simply varying the ratio of gas reactant (e.g. from about 1 ppm to about 10%, from about 10 ppm to about 20%, from about 100 ppm to about 50%, or the like), or the types of gas reactants used may be altered during growth of the nanoscale wire. The gas reactant ratio or the type of gas reactants used may be altered several times during growth of the nanoscale wire, which may produce nanoscale wires comprising regions having multiple compositions, all of which may or may not be unique.

Figure 5:
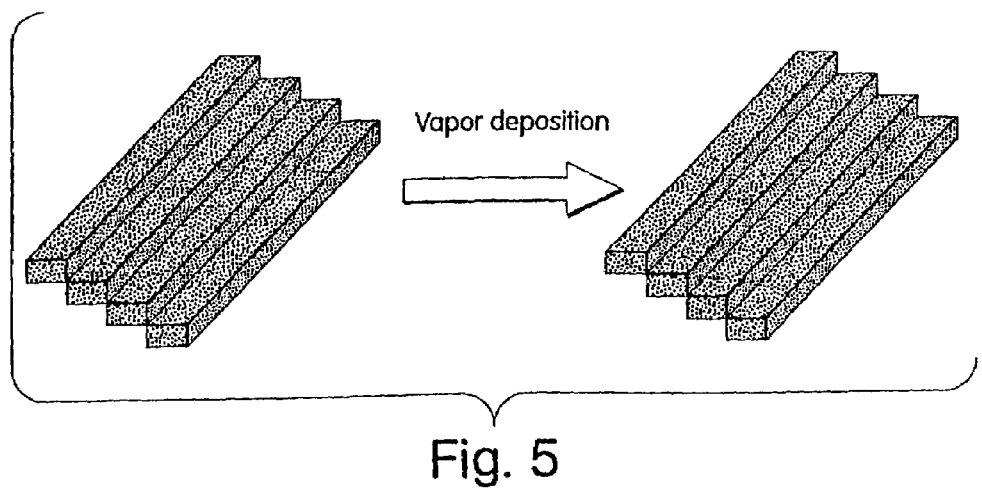
FIG. 5 is a schematic diagram that illustrates nanoscopic wire fabrication by deposition on the edge of surface steps.
Figure 6:
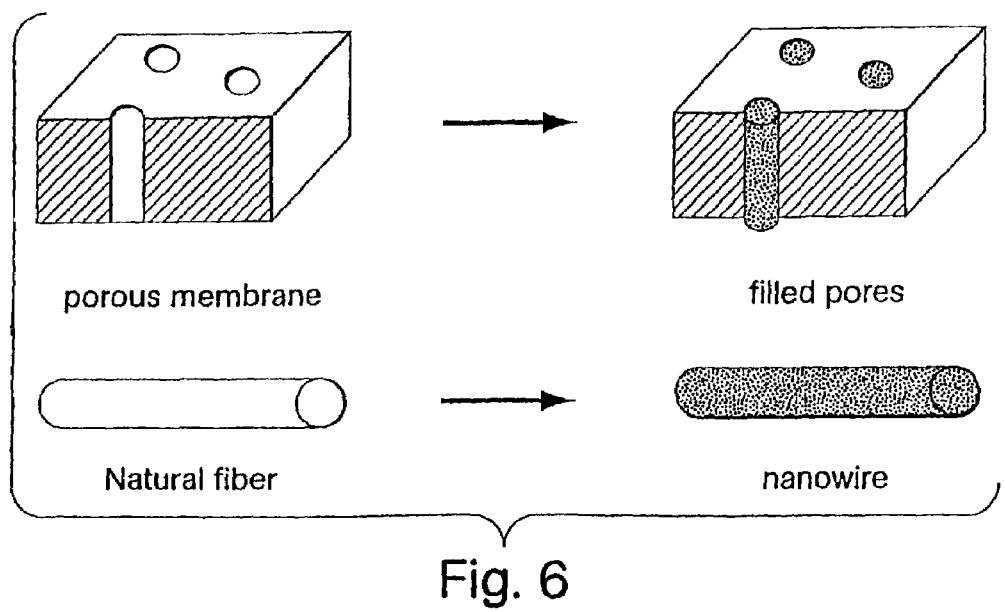
FIG. 6 is a schematic diagram that illustrates nanoscale wire growth by vapor deposition in or on an elongated template.
Figure 7A:
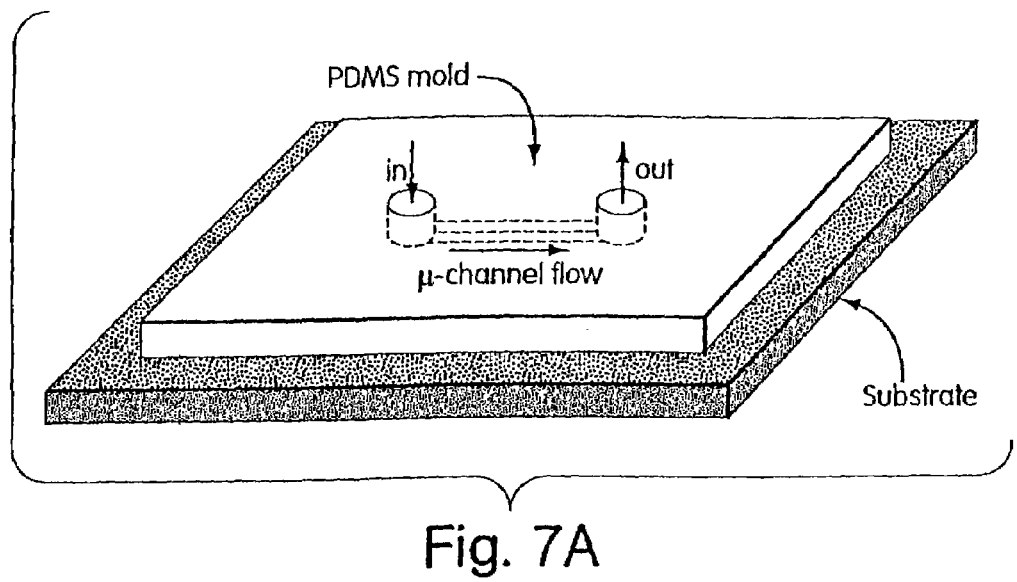
FIGS. 7A-7E illustrate orthogonal assembly of semiconductor nanoscale wires to form devices.
Figure 7B:
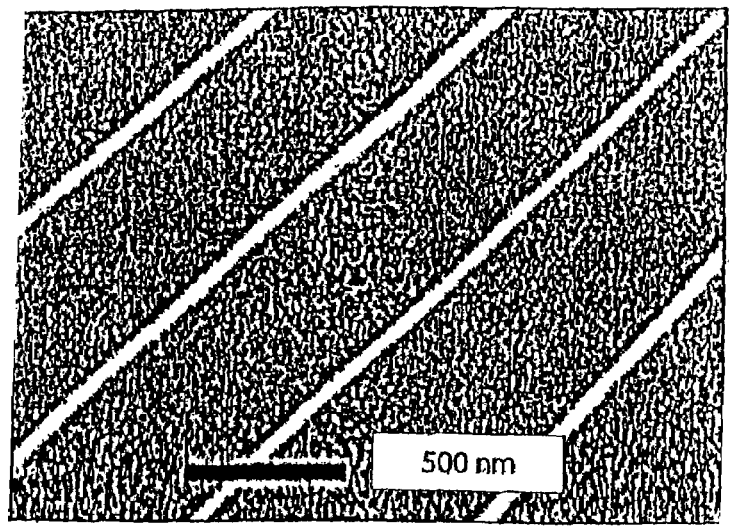
Figure 7C:
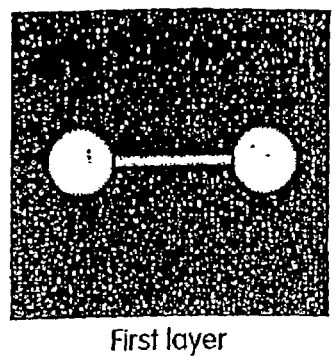
Figure 7D:
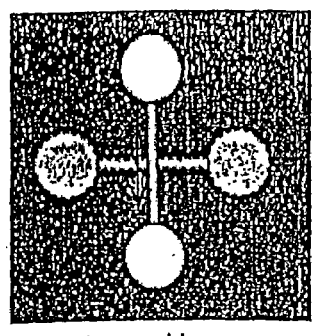
Figure 7E:
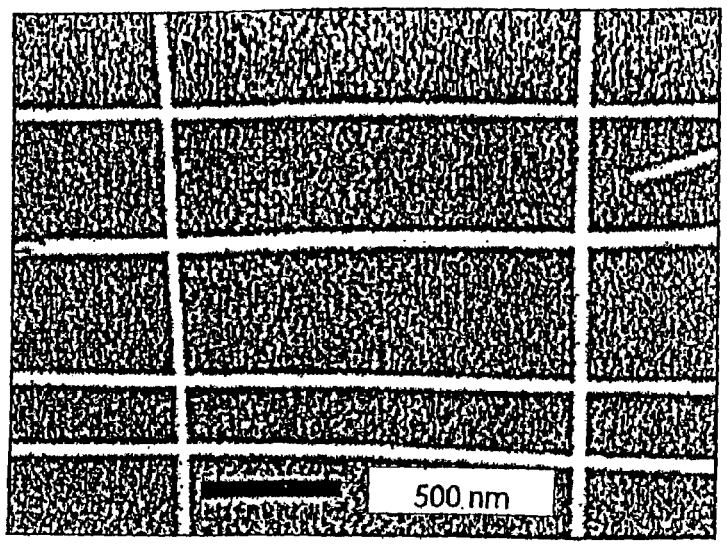

Other techniques to produce nanoscale semiconductors such as nanoscale wires are also within the scope of the present invention. For example, nanoscale wires of any of a variety of materials may be grown directly from vapor phase through a vapor-solid process. Also, nanoscale wires may also be produced by deposition on the edge of surface steps, or other types of patterned surfaces, as shown in FIG. 5. Further, nanoscale wires may be grown by vapor deposition in or on any generally elongated template, for example, as shown in FIG. 6. The porous membrane may be porous silicon, anodic alumnia, a diblock copolymer, or any other similar structure. The natural fiber may be DNA molecules, protein molecules carbon nanotubes, any other elongated structures. For all the above described techniques, the source materials may be a solution or a vapor. In some embodiments, while in solution phase, the template may also include be column micelles formed by surfactant molecules in addition to the templates described above.

For a doped semiconductor, the semiconductor may be doped during growth of the semiconductor. Doping the semiconductor during growth may result in the property that the doped semiconductor is bulk-doped. Further, such doped semiconductors may be controllably doped, such that a concentration of a dopant within the doped semiconductor can be controlled and therefore reproduced consistently, making possible the commercial production of such semiconductors.

The nanoscopic wires may be either grown in place or deposited after growth. Assembly, or controlled placement of nanoscopic wires on surfaces after growth may be performed by aligning nanoscopic wires using an electrical field. An electrical field may be generated between electrodes. The nanoscopic wires may be positioned between the electrodes (optionally flowed into a region between the electrodes in a suspending fluid), and may align in the electrical field, thereby spanning the distance between and contact each of the electrodes.

In another arrangement, individual contact points may be arranged in opposing relation to each other. The individual contact points may be tapered to form points directed towards each other. An electric field may be generated between such points that will attract a single nanoscopic wire to span the distance between the points, forming a pathway for electronic communication between the points. Thus, individual nanoscopic wires may be assembled between individual pairs of electrical contacts. Crossed-wire arrangements, including multiple crossings (multiple parallel wires in a first direction crossed by multiple parallel wires in a perpendicular or approximately perpendicular second direction) can readily be formed by first positioning contact points (electrodes) at locations where opposite ends of the crossed wires desirably will lie. Electrodes, or contact points, may be fabricated via any suitable microfabrication techniques, such as the ones described herein.

These assembly techniques can be substituted by, or complemented with, a positioning arrangement involving positioning a fluid flow directing apparatus to direct a fluid that may contain suspended nanoscopic wires toward and in the direction of alignment with locations at which nanoscale wires are desirably positioned. A nanoscopic wire solution may be prepared as follows. After nanoscopic wires are synthesized, they are transferred into a solvent (e.g., ethanol), and then may be sonicated for several seconds to several minutes to obtain a stable suspension.

Another arrangement involves forming surfaces including regions that selectively attract nanoscale wires surrounded by regions that do not selectively attract them. For example, —NH$_2$ can be presented in a particular pattern at a surface, and that pattern will attract nanoscale wires or nanotubes having surface functionality attractive to amines. Surfaces can be patterned using known techniques such as electron-beam patterning, "soft-lithography" such as that described in International Patent Publication No. WO 96/29629, published Jul. 26, 1996, or U.S. Pat. No. 5,512,131, issued Apr. 30, 1996, each of which is incorporated herein by reference in its entirety for all purposes. Additional techniques are described in U.S. Patent Application Ser. No. 60/142,216, filed Jul. 2, 1999, by Lieber, et al., incorporated herein by reference in its entirety for all purposes. Fluid flow channels can be created at a size scale advantageous for placement of nanoscale wires on surfaces using a variety of techniques such as those described in International Patent Publication No. WO 97/33737, published Sep. 18, 1997, and incorporated herein by reference in its entirety for all purposes. Other techniques include those described in U.S. patent application Ser. No. 09/578,589, filed May 25, 2000, and incorporated herein by reference in its entirety for all purposes.

FIG. 7 show one such technique for creating a fluid flow channel using a polydimethylsiloxane (PDMS) mold. Channels may be created and applied to a surface, and a mold may be removed and re-applied in a different orientation to provide a cross flow arrangement or different arrangement. The flow channel arrangement can include channels having a smallest width of less than about 1 mm, preferably less than about 0.5 mm, more preferably less than about 200 μm or less. Such channels are easily made by fabricating a master by using photolithography and casting PDMS on the master, as described in the above-referenced patent applications and international publications. Larger-scale assembly may be possible as well. The area that can be patterned with nanoscale wire arrays may be defined only by the feature of the channel which can be as large as desired.

The assembly of nanoscale wires onto substrate and electrodes may also be assisted using bimolecular recognition in certain embodiments, for example, by immobilizing one biological binding partner on a nanoscale wire surface and the other one on substrate or electrodes using physical adsorption or covalently linking. Bio-recognition techniques suitable for use in the present invention may include DNA hybridization, antibody-antigen binding, biotin-avidin, biotin-streptavidin binding, and the like.

Another technique which may be used to direct the assembly of a nanoscopic wires into a device is by using "SAMs," or self-assembled monolayers. The SAMs may be chemically patterned in certain embodiments. In one example of patterning SAMs for directed assembly of nanoscopic scale circuitry using nanoscopic wires of the present invention, atomic force microscopy (AFM) may be used to write, at high resolution, a pattern in a SAM, after which the SAM may then be removed. The pattern may be, for example, a linear or a parallel array, or a crossed array of lines.

In another embodiment, microcontact printing may be used to apply patterned SAMs to a substrate. Open areas in the patterned surface (i.e., the SAM-free linear region between linear SAM) may be filled, for example, with an amino-terminated SAM that may interact in a highly specific manner with a nanoscopic wire such as a nanotube. The result may be a patterned SAM, on a substrate, that includes linear SAM portions separated by a line of amino-terminated SAM material. Any desired pattern may be formed where regions of the amino-terminated SAM material corresponds to regions at which wire deposition may be desired. The patterned surface may then be dipped into a suspension of nanoscopic wires, e.g. nanotubes, and may be rinsed to create an array of nanoscale wires. Where nanotubes are used, an organic solvent such as dimethyl formamide may be used to create the suspension of nanotubes. Suspension and deposition of other nanoscopic-scale wires may be achieved with solvents well-known to those of ordinary skill in the art.

Any of a variety of substrates and SAM-forming material can be used along with microcontact printing techniques, such as those described in international patent publication WO 96/29629 of Whitesides, et al., published Jun. 26, 1996 and incorporated herein by reference in its entirety for all purposes. Patterned SAM surfaces may be used to direct a variety of nanoscopic wires or nanoscopic-scale electronic elements. SAM-forming material can be selected, with suitable exposed chemical functionality, to direct assembly of a variety of electronic elements. Electronic elements, including nanotubes, can be chemically tailored to be attracted specifically to specific, predetermined areas of a patterned SAM surface. Suitable functional groups include, but are not limited to SH, $NH_3$, and the like. Nanotubes are particularly suitable for chemical functionalization on their exterior surfaces, as is well known.

Chemically patterned surfaces other than SAM-derivitized surfaces can be used, and many techniques for chemically patterning surfaces are known. Suitable exemplary chemistries and techniques for chemically patterning surfaces are described in, among other places, International Patent Publication Serial No. WO 97/34025 of Hidber, et al., entitled, "Microcontact Printing of Catalytic Colloids," and U.S. Pat. Nos. 3,873,359; 3,873,360; and 3,900,614, each by Lando, all of these documents incorporated herein by reference in their entirety for all purposes. Another example of a chemically patterned surface may be a micro-phase separated block copolymer structure. These structures provide a stack of dense lamellar phases. A cut through these phases reveals a series of "lanes" wherein each lane represents a single layer. The block copolymer may typically be an alternating block and can provide varying domains by which to dictate growth and assembly of a nanoscopic wire. Additional techniques are described in International Patent Application Ser. No. PCT/US00/18138 filed Jun. 30, 2000, by Lieber, et al., incorporated herein by reference in its entirety for all purposes.

The present invention also comprises a wide variety of devices. Such devices may include electrical devices, optical devices, optronic devices, spintronic devices, mechanical devices or any combination thereof, for example, optoelectronic devices and electromechanical devices. Functional devices assembled from the nanoscale wires of the present invention may be used to produce various computer or device architectures. For example, nanoscale wires of the invention may be assembled into nanoscale versions of conventional semiconductor devices, such as diodes, light emitting diodes (LEDs), inverters, sensors, and bipolar transistors. These inventions may include single, free-standing nanoscale wires, crossed nanoscale wires, or combinations of single nanoscale wires combined with other components. Nanoscale wires having different dopants, doping levels, or combinations of dopants may also be used in certain cases to produce these devices. The nanoscale wires, in particular cases, may also have multiple regions, each of which may have different compositions. In some embodiments, a further step may include the fabrication of these structures within the nanoscale wires themselves, wherein a single nanoscale wire may operate as a functional devices. In other embodiments, a nanoscale wire may also be used as an interconnect between two devices, or between a device and an external circuit or system.

One aspect of the present invention includes the ability to fabricate essentially any electronic device from adjacent n-type and p-type semiconducting components. This includes any device that can be made in accordance with this aspect of the invention that one of ordinary skill in the art would desirably make using n-type and p-type semiconductors in combination. Examples of such devices include, but are not limited to, field effect transistors (FETs), bipolar junction transistors (BJTs), tunnel diodes, modulation doped superlattices, complementary inverters, light emitting devices, light sensing devices, biological system imagers, biological and chemical detectors or sensors, thermal or temperature detectors, Josephine junctions, nanoscale light sources, photodetectors such as polarization-sensitive photodetectors, gates, inverters, AND, NAND, NOT, OR, TOR, and NOR gates, latches, flip-flops, registers, switches, clock circuitry, static or dynamic memory devices and arrays, state machines, gate arrays, and any other dynamic or sequential logic or other digital devices including programmable circuits. Also included are analog devices and circuitry, including but not limited to, amplifiers, switches and other analog circuitry using active transistor devices, as well as mixed signal devices and signal processing circuitry. Also included are p/n junction devices with low turn-on voltages; p/n junction devices with high turn-on voltages; and computational devices such as a half-adder. Furthermore, junctions having large dielectric contrasts between the two regions may be used to produce 1D waveguides with built-in photonic band gaps, or cavities for nanoscale wire lasers. In some embodiments, the nanoscale wires of the present invention may be manufactured during the device fabrication process. In other embodiments, the nanoscale wires of the present inventions may first be synthesized, then assembled in a device.

One aspect of the present invention includes any electronic device that may be formed from adjacent n-type and p-type semiconducting components, where the components are pre-fabricated (doped, in individual and separate processes with components separate from each other when doped) and then brought into contact after doping. This is in contrast to typical prior art arrangements in which a single semiconductor is n-doped in one region and p-doped in an adjacent region, but the n-type semiconductor region and p-type semiconducting regions are initially adjacent prior to doping and do not move relative to each other prior to or after doping. That is, n-type and p-type semiconductors, initially in non-contacting arrangement, may be brought into contact with each other to form a useful electronic device. Essentially any device can be made in accordance with this aspect of the invention that one of ordinary skill in the art would desirably make using n-type and p-type semiconductors in combination.

Many devices of the invention make particular use of crossed nanoscopic wires. In some of these cases, the crossed nanoscopic wires may include p/n junctions which are formed at the junctions of crossed n-type and p-type nanoscale wires. Crossed p/n junctions are defined by at least one n-type semiconductor and at least one p-type semiconductor, at least one portion of each material contacting at least one portion of the other material, and each semiconductor including portions that do not contact the other component. They can be arranged by pre-doping the nanoscale wires, then bringing them into proximity with each other using techniques described below.

In one set of embodiments, the invention includes a nanoscale inverter. Any nanoscale inverter may be contemplated that is constructed using adjacent regions having different compositions, for example, a p-type and an n-type semiconductor region. For example, in one embodiment, the invention provides a lightly-doped complementary inverters (complementary metal oxide semiconductors) arranged by contact of an n-type semiconductor region with a p-type semiconductor region. The invention also provides lightly-doped complementary inverters (complementary metal oxide semiconductors) arranged simply by contact of an n-type semiconductor with a p-type semiconductor, for example, by arrangement of crossed n-type and p-type semiconducting nanoscale wires, or by the arrangement of two adjacent regions.

In another set of embodiments, the invention includes a nanoscale diode. Any nanoscale diode may be contemplated that is constructed using adjacent regions having different compositions, for example, a p-type and an n-type semiconductor region, for example, Zener diodes, tunnel diodes, light-emitting diodes, and the like. For example, the diode may be a tunnel diodes heavily-doped with semiconducting components. A tunnel diode may be arranged similarly or exactly the same as a complementary inverter, with the semiconductors being heavily doped rather than lightly doped.

In yet another set of embodiments, the invention comprises a nanoscale transistor, such as a field effect transistor ("FET") or a bipolar junction transistor ("BJT"). Example transistors are illustrated in FIG. 78. The transistor may have a smallest width of less than 500 nm, less than 100 nm, or other widths as described above. Any transistor constructed using adjacent regions having different compositions, for example, a p-type and an n-type semiconductor region may be contemplated, for example, arranged longitudinally within a single wire, arranged radially within the wire, or between adjacent crossed wires. In some embodiments, the transistor may comprise a doped semiconductor, such as a p-type or n-type semiconductor, as is known by those of ordinary skill in the art in transistor fabrication. While FETs are known using nanotubes, to the inventors' knowledge, prior arrangements select nanotubes at random, without control over whether the nanotube is metallic or semiconducting. In such a case a very low percentage of devices are functional, perhaps less than one in twenty, or one in fifty, or perhaps approximately one in one hundred. The present invention contemplates controlled doping of nanoscale wires such that a fabrication process can involve fabricating functional FETs according to a technique in which much greater than one in fifty devices is functional. For example, the technique can involve preparing a doped nanoscale wire and fabricating an FET therefrom.

In one embodiment, a FET comprising a nanoscale wire may serve as a conducting channel, and an elongated material having a smallest width of less than 500 nm (e.g., a nanoscale wire) serving as the gate electrode. For such a FET, the widths of the nanoscale wire and the elongated material may define a width of the FET. The field effect transistor may also comprise a conducting channel comprising a doped semiconductor having at least one portion having a smallest width of less then 500 nanometers, and a gate electrode comprising an elongated material having at least one portion having a smallest width of less then 500 nanometers in another embodiment. Further, the nanoscale wire may comprise a semiconductor, or have a core/shell arrangement, and such shell may function as a gate dielectric for the FET. In another emobidment, the two regions may longitudinally positioned. Also, in another embodiment, the intersection of the nanoscale wire and an elongated material may define a length of the FET. In another embodiment, the transistor may be a coaxially-gated transistor.

Such distinct nanometer-scale metrics may lead to significantly improved device characteristics such as high gain, high speed, and low power dissipation. Further, such FETs may be readily integratable, and the assembly of such FETs may be shrunk in a straightforward manner into nanometers scale. Such a "bottom-up" approach may scale down to sizes far beyond what is predicted for traditional "top-down" techniques typically used in the semiconductor industry today. Further, such bottom-up assembly may prove to be far cheaper than the traditional top-down approach.

Electronic devices incorporating semiconductor nanoscale wires may be controlled, for example, using any input signal, such as an electrical, optical or a magnetic signal. The control may involve switching between two or more discrete states or may involve continuous control of nanoscale wire current, i.e., analog control. In addition to electrical signals, optical signals and magnetic signals, the devices may also be controlled in certain embodiments in response to biological and chemical species, for example, DNA, protein, metal ions. In a more general sense, these species may be charged or have a dipole moment. In other embodiments, the device may be switchable in response to mechanical stimuli, for example, mechanical stretching, vibration and bending. In yet other embodiments, the device may be switchable in response to temperature, pressure, or fluid movement, for example, the movement of an environmental gas or liquid.

As one example, as illustrated in FIG. 71, a nanoscale wire comprising a p/n junction may be used as a nanoscale LED. In forward bias, an individual nanoscale wire device may exhibit light emission from its p/n junction that may be both highly polarized and blue-shifted due to the one-dimensional structure and radial quantum confinement, respectively. The efficiency may be at least about 0.1%, preferably at least about 0.5%, more preferably at least about 1%, and still more preferably about 5% or higher. By defining a quantum dot heterostructure within a p/n junction during nanoscale wire synthesis, an electrically-driven single photon source having a well-defined polarization may be manufactured. Other nanoscale photonics and electronics devices that may be manufactured include, but are not limited to, nanoscale emitters and complementary logic circuits, which may be obtained from series of nanoscale wire p/n junctions. Additionally, the present invention contemplates complex periodic superlattices that may be used in nanoscale wire injection lasers or "engineered" 1D electron waveguides.

Another type of light-emission source of the invention includes at least one crossed p/n junction, in particular, crossed p-type and n-type nanoscale wires. In this and other arrangements of the invention using crossed nanoscale wires, the wires need not be perpendicular, but can be. When forward biased (positive charge applied to the p-type wire and a negative charge applied to the n-type wire) electrons may flow toward the junction in the n-type wire and holes flow toward the junction in the p-type wire. At the junction, holes and electrons may combine, emitting light.

In certain embodiments, nanoscale wires having more than one region able to produce or emit light are contemplated. For example, a nanoscale wire having multiple p-type and n-type regions which may be produced, where each p/n junction is able to emit light. The nanoscale wire may have 2, 3, 4, or more p/n junctions. The number of periods and the repeat spacing between each p/n junction may be constant or varied during growth. Thus, for example, nanoscale wires having multiple light-emitting and non-light-emitting regions may be used as "nano-bar codes," where different sequences, patterns, and/or frequencies of light-emitting and non-light-emitting regions may be used to uniquely "tag" or label an article that the nanoscale wire is used in. As varying the composition of each p/n junction (for example, by using different dopants) may alter the frequency of the emitted light, additional information can be encoded through variations in the color of the emitting region using multi-component superlattices.

In some embodiments, the responsivity of the nanophotodetector may be greater than about 1000 A/W, more preferably greater than about 3000 A/W, more preferably still greater than about 5000 A/W, or even more preferably greater than about 10000 A/W. In certain embodiments, the response time of the semiconductor photodetector may be less than 1 ps, preferably less than about 100 fs, more preferably less than about 10 fs, and more preferably still less than about 1 fs, due to the small capacitances of the nanoscale wires, which may be less than about 100 aF or about 10 aF in some cases.

Electrically erasable and re-writable memory structures and devices with reversible states and good retention time may be constructed from nanoscale building blocks such as nanoscale wires, nanotubes, nanocrystals and molecules. The memory structures may be based on either individual semiconducting nanoscale wires or crossed nanoscale wire p/n junctions. When the surfaces of these devices are appropriately modified with either molecules or nanocrystals, reversible memory switching behavior may be observed when electrical pulses of opposite polarity is applied. Specifically, subjection to positive or negative voltage pulses in either gate or bias voltages may cause the devices to make fully reversible transition between low-resistance and high resistance states. In some cases, the transition between states is performed directly, through the flow of electrons through the device or component. In other cases, the transition between states is accomplished inductively, through the use of field effects, electron tunneling, or the like.

A nanoscale memory switching devices may be assembled from nanoscale building blocks (including nanowires, nanotubes, nanocrystals and molecules which may have, for example, two or more regions having differing compositions). The memory switching device may have multiple states, non-volatile reversible states, or a large on/off ratio. The nanoscale memory switching devices may be highly parallel and scalable with simple chemical assembly process, and can be useful in construction of a chemically assemble computer in some cases.

In one embodiment, the memory switching device is a three terminal devices based on individual nanoscale wires using the gate pulse to induce the switching between two states, such as between high- and low-resistance states. In another embodiment, the memory switching device is a two terminal devices based on individual nanoscale wires using the bias pulse to induce the switching between high- and low-resistance states. In another embodiment, the memory switching device is based on the junction between two regions having different compositions, for example, in a core/shell arrangement, in an arrangement where the two regions are longitudinally positioned relative to each other, or in arrangements having crossed nanoscale wire p-n junctions. A bias pulse or a gate pulse may be used to induce switching between high- and low resistance states, for example, by supplying a charge or a current through the nanoscale wire or a region thereof, such as through a core region. In other embodiments, the memory switching device may 3, 4, 6, 8, or other multiple states or configurations.

Memory systems using these nanomaterials may take the form of novel structures such as two dimensional parallel, crossing, or three dimensional stacked memory arrays to achieve ultra-high density data storage, and non-volatile state switches for computer systems fabricated by chemical assembly.

Figures 36A, 36B, 36C:
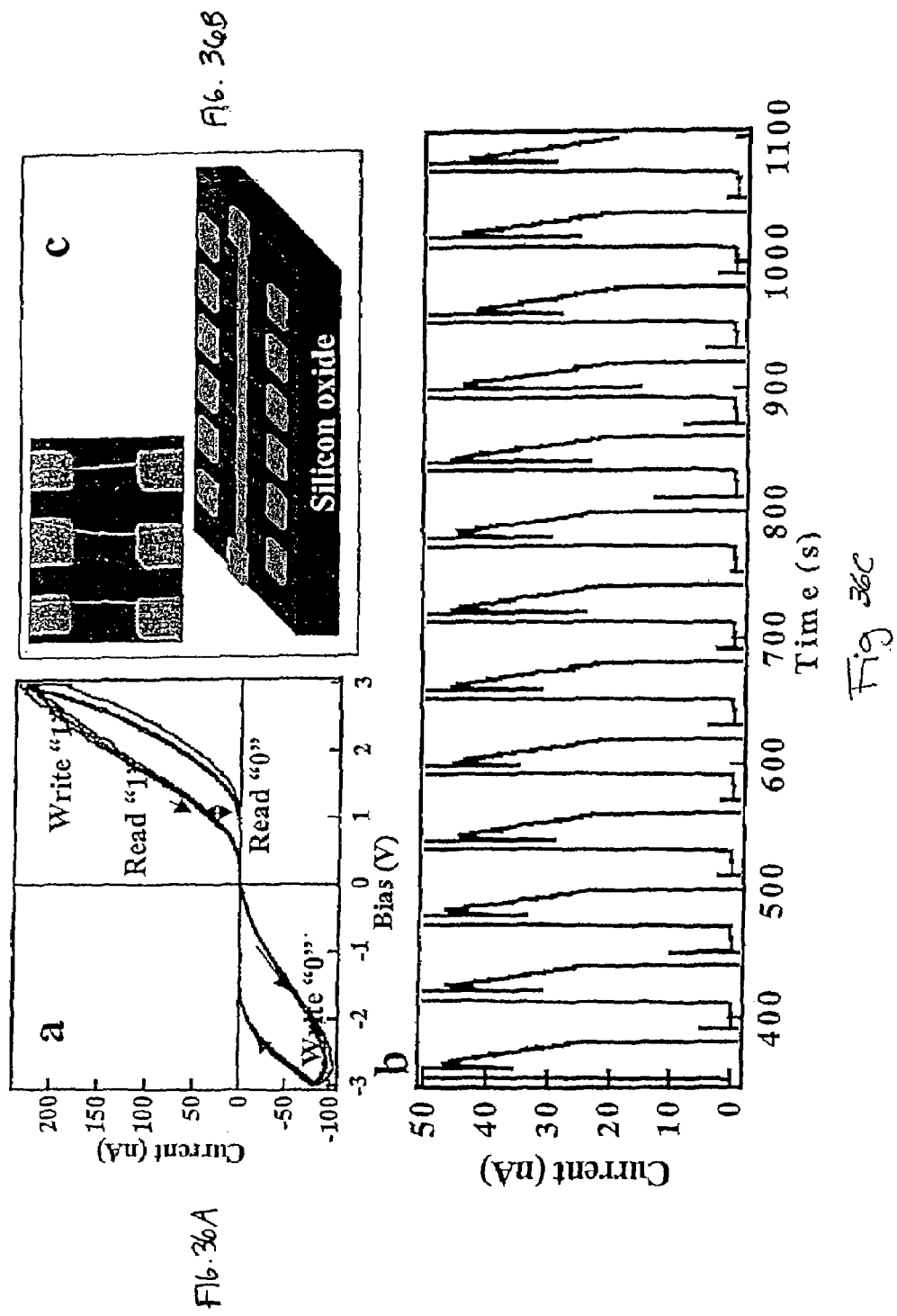
FIGS. 36A-36C illustrate a nanoscale memory switching device.

In another embodiment, the nanoscale memory switching device comprises a two terminal memory cell made of individual semiconductor nanoscale wires. In particular, a large bias voltage may have a similar effect on the conductance of the nanoscale wires. With reference to FIG. 36a, a large hysteresis may be observed in the current-voltage curve of a p-Si nanoscale wire, indicating that a bias pulse may be used to switch the nanoscale wire between high and low conductance states, as could potentially be used in a two terminal memory deices. This nanoscale memory device may be reversibly switched on and off with on-off, ratio up to 2-3 orders of magnitude (FIG. 36b). Similar behavior may be observed with n-InP nanoscale wires. The two-terminal feature of these devices make them highly parallel and may be scaled up to make highly integrated device arrays (FIG. 36c).

Figure 37A:
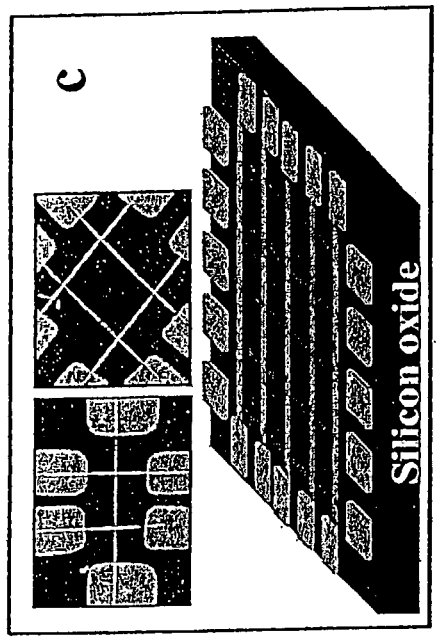
FIGS. 37A-37C illustrate a nanoscale memory cell.
Figure 37B:
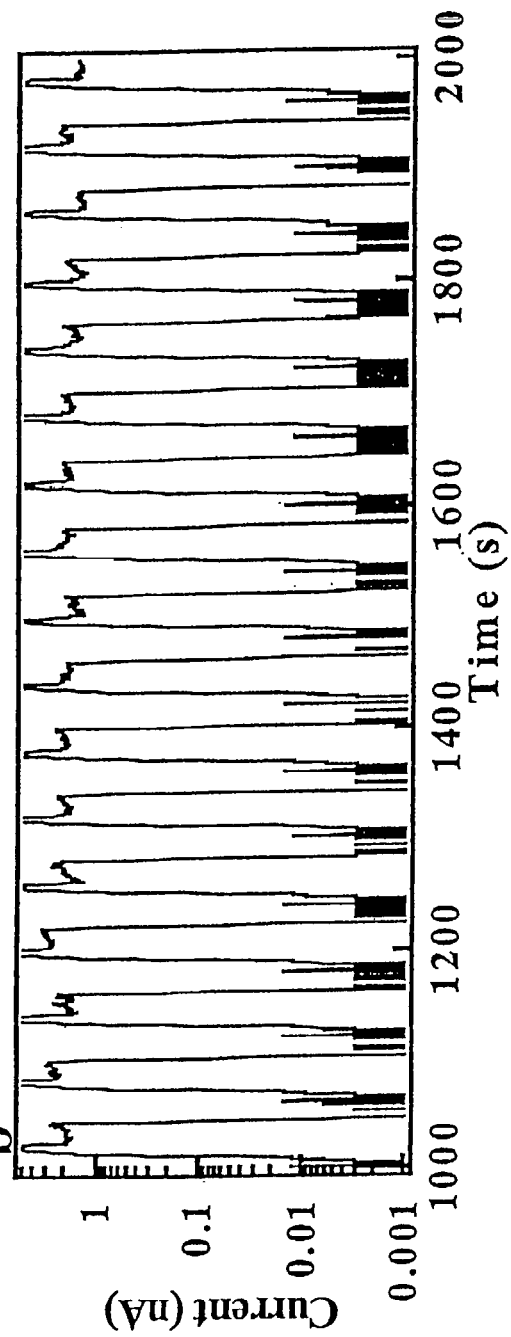
Figure 37C:
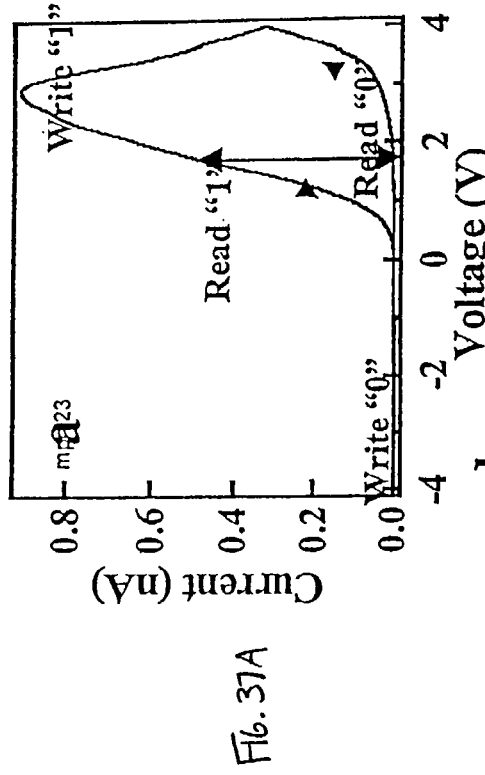

In another embodiment, the nanoscale memory device may comprise memory cells made from crossed p/n junctions. Similarly, these p/n junctions may be switched between a high and low conductance states by either a gate voltage or a bias pulse. With reference to FIG. 37a, a crossed nanoscale wire p/n junction may show clear rectification and large hysteresis in current-voltage behavior. Writing may be done with either a negative to positive voltage pulse depending on the application, and reading may be done around the hysteresis region. In some cases, these nanoscale memory devices may be reversibly switched on and off for hundreds of time at room temperature. The on-off ratio may differ by up to four orders of magnitude (FIG. 37b). Two terminal memory cells made from crossed p-n junctions may enable ultra-high density integration of the memory cells in two dimensions (FIG. 37c) and even in three dimensions.

Thus, it is possible to achieve an active element two-dimensional density of at least $10^{11}$ memory elements/cm$^2$, preferably at least about $10^{12}$ memory elements/cm$^2$. This is facilitated where an array of molecular wires 42 (FIG. 37b) are positioned at 20 nm intervals. Where wires 46 are similarly arranged, this density is achieved. Using nanotubes of 10 μm length, with a memory element every 20 nm along each nanotube, an array can be formed with 500 parallel wires in each direction, each wire containing 500 crossbar array junctions (memory elements). 250,000 memory elements are formed in such an array. Three-dimensional arrays can be created as well. Where a 1 μm spacing is created between two-dimensional array planes, the invention provides a three-dimensional array density of at least about $10^{14}$ memory elements/cm$^3$, preferably at least about $10^{15}$ memory elements/cm$^3$.

Figure 38:
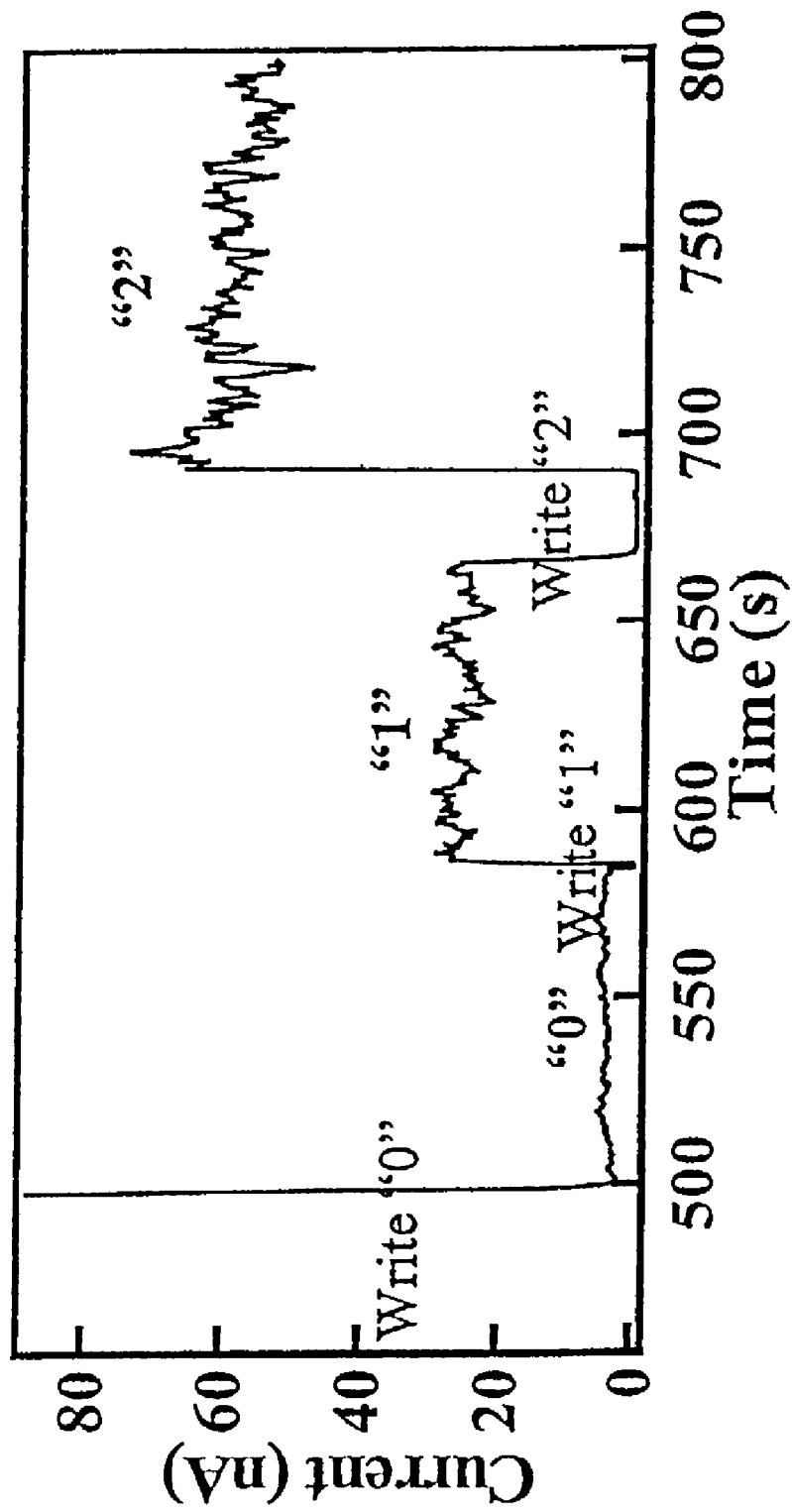
FIG. 38 illustrates a device with multiple states.

In another embodiment, the nanoscale memory device may comprise memory having more than two states. By varying the writing time and voltage, the device can be switched to a designated state with a designated conductance. FIG. 38 shows such a device with multiple states depending on writing time.

Figure 39B:
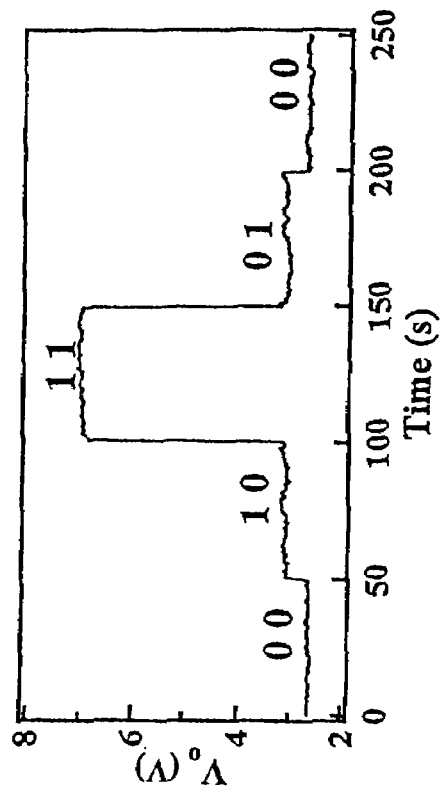
FIGS. 39A-39E illustrate an AND logic gate.
Figure 39E:
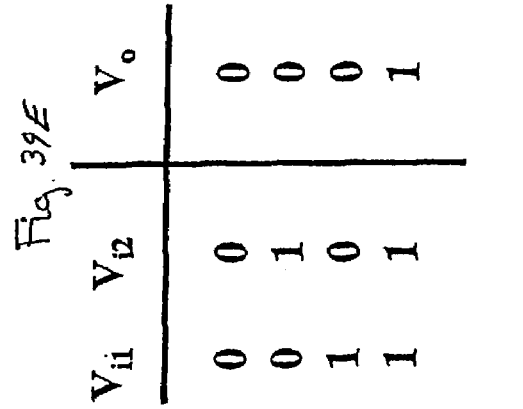
Figure 39A:
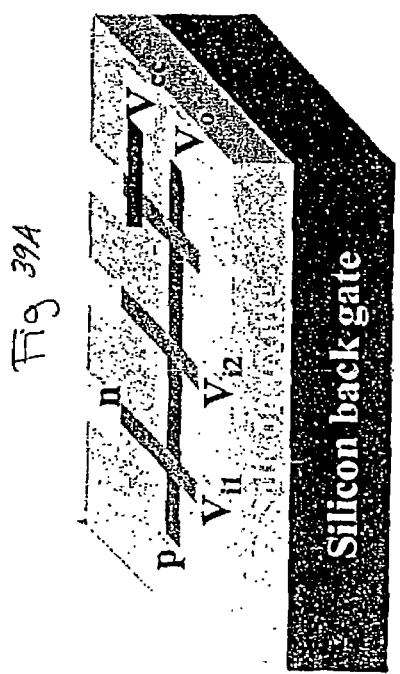
Figure 39D:
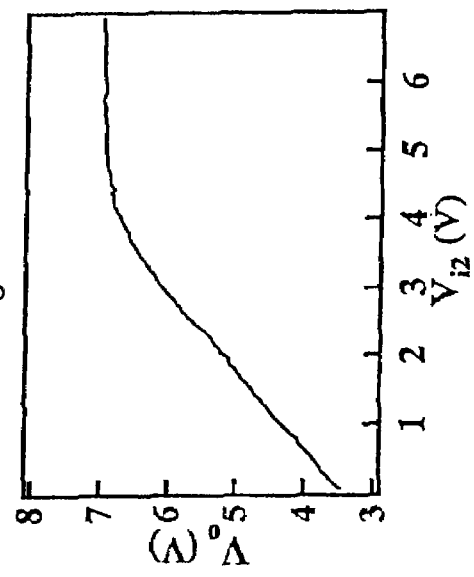
Figure 39C:
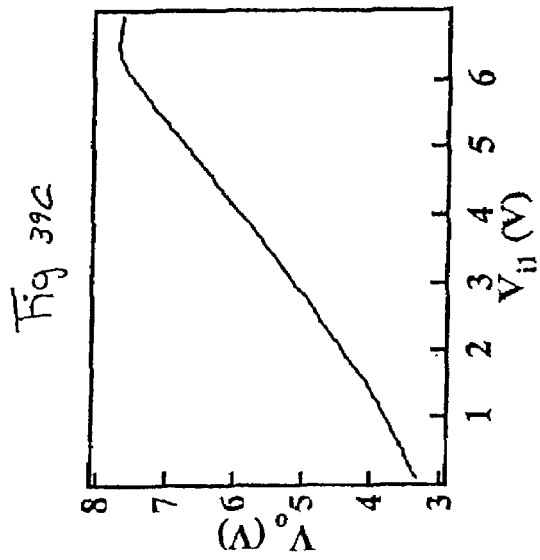
Figure 42B:
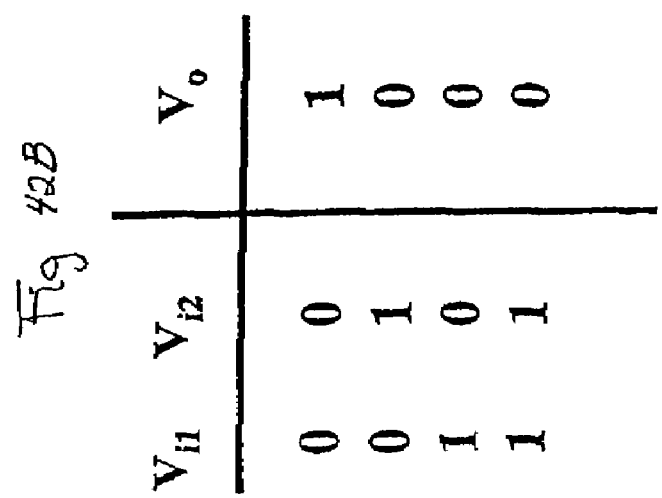
FIGS. 42A and 42B illustrate a NOR logic gate.
Figure 42A:
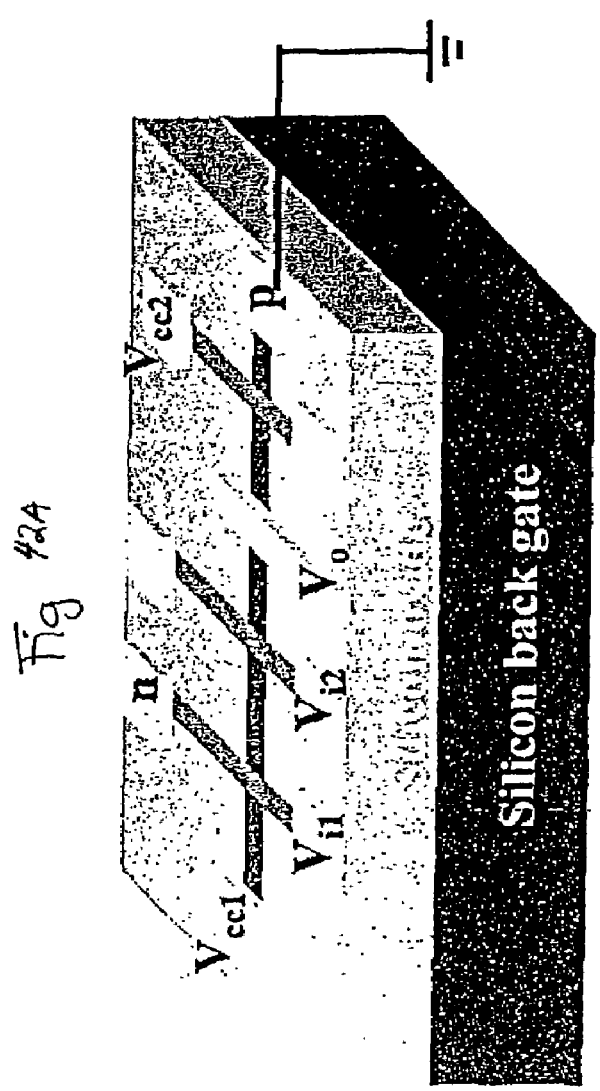
Figures 43A, 43B:
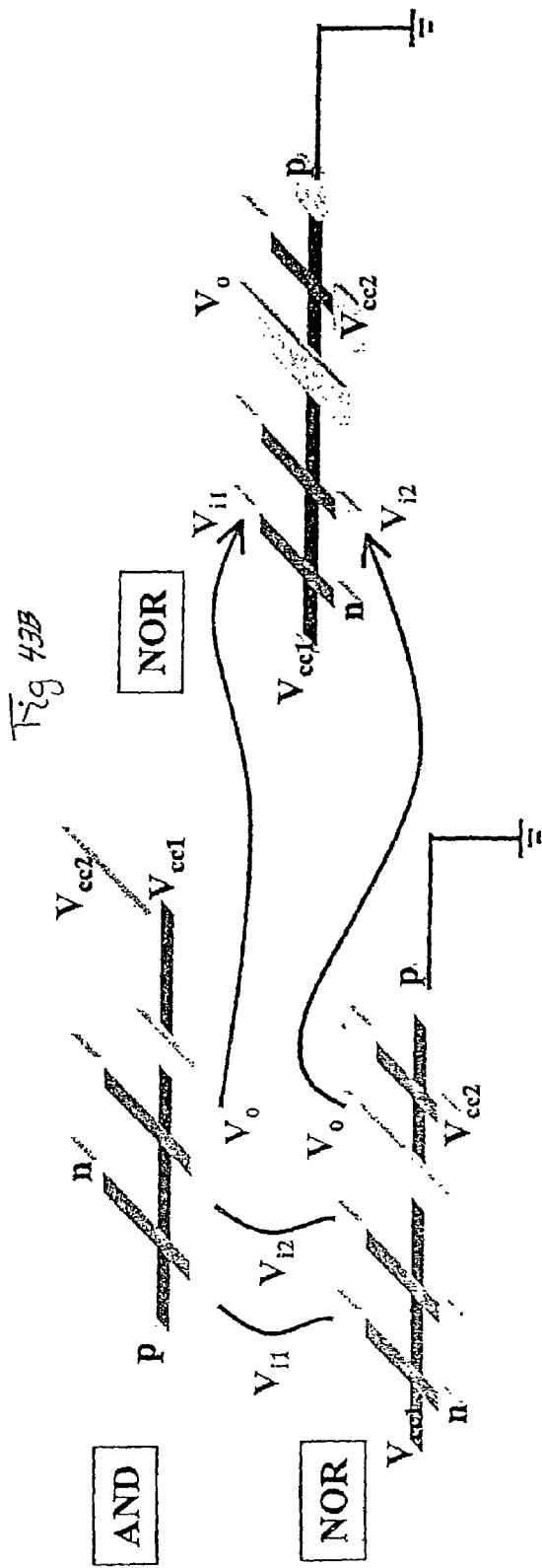
FIGS. 43A and 43B illustrate an XOR logic gate.

FIG. 39a schematically shows an AND logic gate in accordance with the invention. FIG. 39b shows the voltage out as a function of voltages in $(V_{i1}, V_{i2})$ FIG. 39c shows the voltage out vs. voltage in $V_{i1}$. FIG. 39d shows the voltage out vs. voltage in $V_{i2}$. FIG. 39e tabulates the voltage results of FIG. 39b. FIG. 40a schematically shows an OR logic gate. FIG. 40b shows the voltage out as a function of voltages in $(V_{i1}, V_{i2})$ FIG. 40c shows the voltage out vs. voltage in $V_{i1}$. FIG. 40d shows the voltage out vs. voltage in $V_{i2}$. FIG. 40e tabulates the voltage results of FIG. 40b. FIG. 41a shows a NOT logic gate wherein $V_{cc1}$=5V, $V_{cc2}$=2 V, $V_i$=0,5 V. FIG. 41b shows the current as a function of bias voltage. FIG. 41c shows the voltage out vs. voltage in $V_i$. FIG. 8d shows the voltage out vs. voltage in $V_{i2}$. FIG. 41e tabulates the voltage results of FIG. 41b. FIGS. 42a and 42b show a NOR logic gate. FIGS. 43a and 43b show an XOR logic gate.

In another embodiment, control and growth of the nanoscale wire structures, for example a core-multishell structure, may be used to study a variety of fundamental phenomena, for example electron gases in radially symmetric core or shell potentials; or new device concepts.

The invention also provides a sensing element, which may be an electronic sensing element, and a nanoscale wire able to detect the presence, absence, and/or amount (concentration), of a species such as an analyte in a sample (e.g. a fluid sample) containing, or suspected of containing, the species. Nanoscale sensors of the invention may be used, for example, in chemical applications to detect pH or the presence of metal ions; in biological applications to detect a protein, nucleic acid (e.g. DNA, RNA, etc.), a sugar or carbohydrate, and/or metal ions; and in environmental applications to detect pH, metal ions, or other analytes of interest. Also provided is an article comprising a nanoscale wire and a detector constructed and arranged to determine a change in an electrical property of the nanoscale wire. At least a portion of the nanoscale wire is addressable by a sample containing, or suspected of containing, an analyte. The phrase "addressable by a fluid" is defined as the ability of the fluid to be positioned relative to the nanoscale wire so that an analyte suspected of being in the fluid is able to interact with the nanoscale wire. The fluid may be proximate to or in contact with the nanoscale wire.

Whether nanotubes or nanowires are selected, the criteria for selection of nanoscale wires and other conductors or semiconductors for use in the invention are based, in some instances, mainly upon whether the nanoscale wire itself is able to interact with an analyte, or whether the appropriate reaction entity, e.g. binding partner, can be easily attached to the surface of the nanoscale wire, or the appropriate reaction entity, e.g. binding partner, is near the surface of the nanoscale wire. Selection of suitable conductors or semiconductors, including nanotubes or nanoscale wires, will be apparent and readily reproducible by those of ordinary skill in the art with the benefit of the present disclosure.

Chemical changes associated with the nanoscale wires used in the present invention can modulate the properties of the wires and create electronic devices of a variety of types. Presence of the analyte can change the electrical properties of the nanoscale wires through electrocoupling with a binding agent of the nanoscale wire. If desired, the nanoscale wires may be coated with a specific reaction entity, binding partner or specific binding partner, chosen for its chemical or biological specificity to a particular analyte.

The reaction entity is positioned relative to the nanoscale wire to cause a detectable change in the nanoscale wire. The reaction entity may be positioned within 100 nm of the nanoscale wire, preferably with in 50 nm of the nanoscale wire, and more preferably with in 10 nm of the nanoscale wire, and the proximity can be determined by those of ordinary skill in the art. In one embodiment, the reaction entity is positioned less than 5 nm from the nanoscopic wire. In alternative embodiments, the reaction entity is positioned with 4 nm, 3 nm, 2 nm, and 1 nm of the nanoscopic wire. In one embodiment, the reaction entity is attached to the nanoscopic wire through a linker.

The invention also provides an article comprising a sample exposure region and a nanoscale wire able to detect the presence of absence of an analyte. The sample exposure region may be any region in close proximity to the nanoscale wire wherein a sample in the sample exposure region addresses at least a portion of the nanoscale wire. Examples of sample exposure regions include, but are not limited to, a well, a channel, a microchannel, and a gel. In preferred embodiments, the sample exposure region holds a sample proximate the nanoscale wire, or may direct a sample toward the nanoscale wire for determination of an analyte in the sample. The nanoscale wire may be positioned adjacent to or within the sample exposure region. Alternatively, the nanoscale wire may be a probe that is inserted into a fluid or fluid flow path. The nanoscale wire probe may also comprise a microneedle and the sample exposure region may be addressable by a biological sample. In this arrangement, a device that is constructed and arranged for insertion of a microneedle probe into a biological sample will include a region surrounding the microneedle that defines the sample exposure region, and a sample in the sample exposure region is addressable by the nanoscale wire, and viceversa. Fluid flow channels can be created at a size and scale advantageous for use in the invention (microchannels) using a variety of techniques such as those described in International Patent Publication No. WO 97/33737, published Sep. 18, 1997, and incorporated herein by reference in its entirety for all purposes.

In another aspect of the invention, an article may comprise a plurality of nanoscopic wires (2) able to detect the presence or absence of a plurality of one or more analytes. The individual nanoscopic wires may be differentially doped as described above, thereby varying the sensitivity of each nanoscale wire to the analyte. Alternatively, individual nanoscale wires may be selected based on their ability to interact with specific analytes, thereby allowing the detection of a variety of analytes. The plurality of nanoscale wires may be randomly oriented or parallel to one another. Alternatively, the plurality of nanoscale wires may be oriented in an array on a substrate.

Figure 44A:
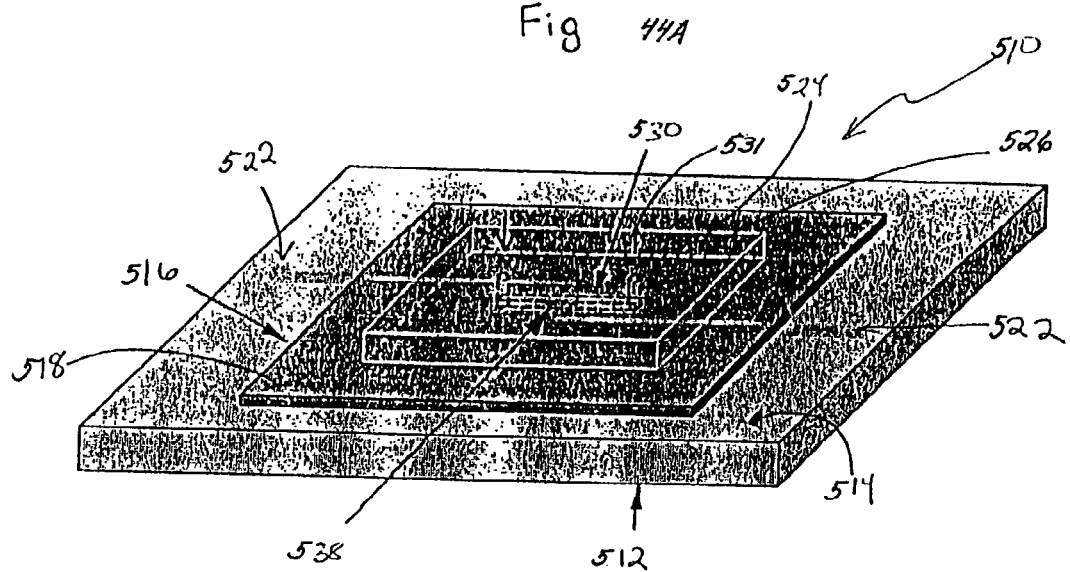
FIG. 44A illustrates, schematically, a nanoscale detector device.

FIG. 44a shows one example of an article of the present invention. In FIG. 44a, nanoscale detector device 510 is comprised of a single nanoscale wire 538 positioned above upper surface 518 of substrate 516. Chip carrier 512 has an upper surface 514 for supporting substrate 516 and electrical connections 522. Chip carrier 512, may be made of any insulating material that allows connection of electrical connections 522 to electrodes 536. In a preferred embodiment, the chip carrier is an epoxy. Upper surface 514 of the chip carrier, may be of any shape including, for example, planar, convex, and concave. In a preferred embodiment, upper surface 514 of the chip carrier is planar.

As shown in FIG. 44a, lower surface of 520 of substrate 516 is positioned adjacent to upper surface 514 of the chip carrier and supports electrical connection 522. Substrate 516 may typically be made of a polymer, silicon, quartz, or glass, for example. In a preferred embodiment, the substrate 516 is made of silicon coated with 600 nm of silicon oxide. Upper surface 518 and lower surface 520 of substrate 516 may be of any shape, such as planar, convex, and concave. In a preferred embodiment, lower surface 520 of substrate 516 contours to upper surface 514 of chip carrier 512. Similarly, mold 524 has an upper surface 526 and a lower surface 528, either of which may be of any shape. In a preferred embodiment, lower surface 526 of mold 524 contours to upper surface 518 of substrate 516.

Figure 46A:
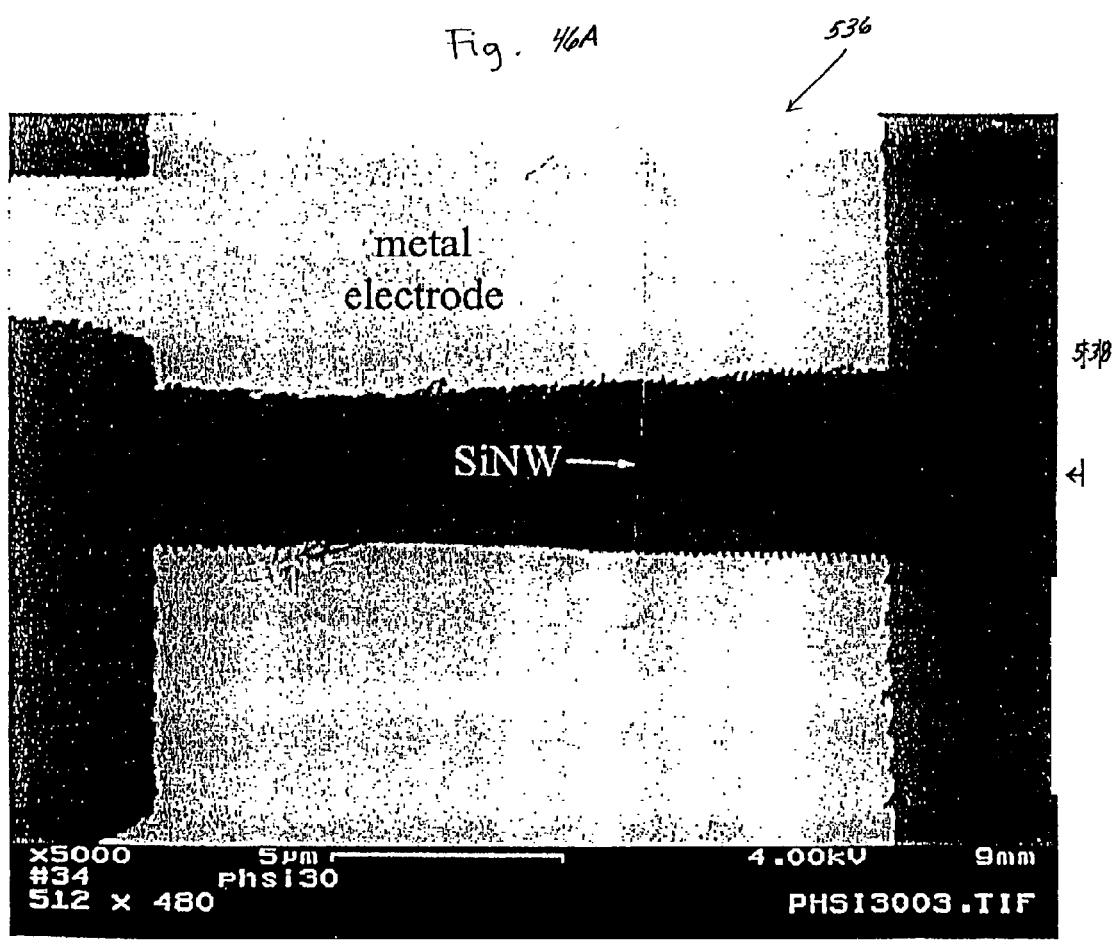
FIG. 46A is a low resolution scanning electron micrograph of a single silicon nanoscale wire connected to two metal electrodes.
Figure 50:
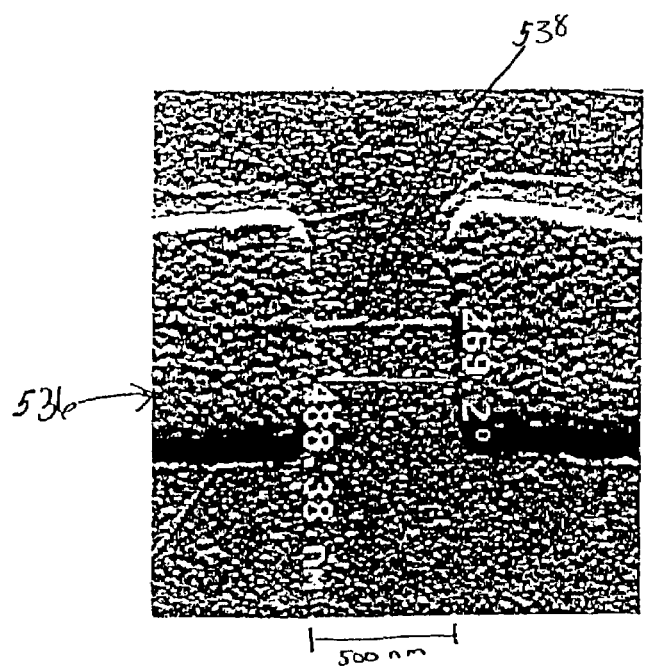
FIG. 50 is an atomic force microscopy image of a typical single wall nanotube detector device.

Mold 524 has a sample exposure region 530, shown here as a microchannel, having a fluid inlet 532 and fluid outlet 534, shown in FIG. 44a on the upper surface 526 of mold 524. Nanoscale wire 538 is positioned such that at least a portion of the nanoscale wire is positioned within sample exposure region 530. Electrodes 536 connect nanoscale wire 538 to electrical connection 522. Electrical connections 522 are, optionally, connected to a detector (not shown) that measures a change in an electrical, or other property of the nanoscale wire. FIGS. 46a and 46b are low and high resolution scanning electron micrographs, respectively, of one embodiment of the present invention. A single silicon nanoscale wire 538 is connected to two metal electrodes 536. FIG. 50 shows an atomic force microscopy image of a typical SWNT positioned with respect to two electrodes. As seen in FIG. 50, the distance between electrodes 536 is about 500 nm. In certain preferred embodiments, electrode distances will range from 50 nm to about 20000 nm, more preferably from about 100 nm to about 10000 nm, and most preferably from about 500 nm to about 5000 nm.

Where a detector is present, any detector capable of determining a property associated with the nanoscale wire can be used. The property can be electronic, optical, or the like. An electronic property of the nanoscale wire can be, for example, its conductivity, resistivity, etc. An optical property associated with the nanoscale wire can include its emission intensity, or emission wavelength where the nanoscale wire is an emissive nanoscale wire where emission occurs at a p/n junction. For example, the detector can be constructed for measuring a change in an electronic or magnetic property (e.g. voltage, current, conductivity, resistance, impedance, inductance, charge, etc.) can be used. The detector typically includes a power source and a voltmeter or amp meter. In one embodiment, a conductance less than 1 nS can be detected. In a preferred embodiment, a conductance in the range of thousandths of a nS can be detected. The concentration of a species, or analyte, may be detected from less than micromolar to molar concentrations and above. By using nanoscale wires with known detectors, sensitivity can be extended to less than 10 molecules or a single molecule. In one embodiment, an article of the invention is capable of delivering a stimulus to the nanoscale wire and the detector is constructed and arranged to determine a signal resulting from the stimulus. For example, a nanoscale wire including a p/n junction can be delivered a stimulus (electronic current), where the detector is constructed and arranged to determine a signal (electromagnetic radiation) resulting from the stimulus. In such an arrangement, interaction of an analyte with the nanoscale wire, or with a reaction entity positioned proximate the nanoscale wire, can affect the signal in a detectable manner. In another example, where the reaction entity is a quantum dot, the quantum dot may be constructed to receive electromagnetic radiation of one wavelength and emit electromagnetic radiation of a different wavelength. Where the stimulus is electromagnetic radiation, it can be affected by interaction with an analyte, and the detector can detect a change in a signal resulting therefrom. Examples of stimuli include a constant current/voltage, an alternating voltage, and electromagnetic radiation such as light.

In one example, a sample, such as a fluid suspected of containing an analyte that is to be detected and/or quantified, e.g. a specific chemical contacts nanoscopic wire having a corresponding reaction entity at or near nanoscopic wire 538 (or, at least the fluid sample contacts the reaction entity). An analyte present in the fluid binds to the corresponding reaction entity and causes a change in at least one property of the nanoscopic wire, e.g. a change in an electrical property of the nanoscale wire that is detected, e.g. using conventional electronics. That is, the interaction of the analyte with the reaction entity induces a change in the nanoscopic wire in that it causes a change, which can be via induction in the electrical sense. If the analyte is not present in the fluid, the electrical properties of the nanoscale wire will remain unchanged, and the detector will measure a zero change. Presence or absence of a specific chemical can be determined by monitoring changes, or lack thereof, in the electrical properties of the nanoscale wire. The term "determining" refers to a quantitative or qualitative analysis of a species via, piezoelectric measurement, electrochemical measurement, electromagnetic measurement, photodetection, mechanical measurement, acoustic measurement, gravimetric measurement and the like. "Determining" also means detecting or quantifying interaction between species, e.g. detection of binding between two species.

Particularly preferred flow channels 530 for use in this invention are "microchannels." The term microchannel is used herein for a channel having dimensions that provide low Reynolds number operation, i.e., for which fluid dynamics are dominated by viscous forces rather than inertial forces. Reynolds number, sometimes referred to the ratio of inertial forces to viscous forces is given as:

$$Re = \rho d^2/\eta\tau + \rho u d/\eta$$

where u is the velocity vector, $\rho$ is the fluid density, $\eta$ is the viscosity of the fluid, d is the characteristic dimension of the channel, and $\tau$ is the time scale over which the velocity is changing (where $u/\tau = \delta u/dt$). The term "characteristic dimension" is used herein for the dimension that determines Reynolds number, as is known in the art. For a cylindrical channel it is the diameter. For a rectangular channel, it depends primarily on the smaller of the width and depth. For a V-shaped channel it depends on the width of the top of the "V," and so forth. Calculation of Re for channels of various morphologies can be found in standard texts on fluid mechanics (e.g. Granger (1995) *Fluid Mechanics*, Dover, N.Y.; Meyer (1982) *Introduction to Mathematical Fluid Dynamics*, Dover, N.Y.).

Fluid flow behavior in the steady state ($\tau \rightarrow$infinity) is characterized by the Reynolds number, Re=$\rho$ud/$\eta$. Because of the small sizes and slow velocities, microfabricated fluid systems are often in the low Reynolds number regime (Re less than about 1). In this regime, inertial effects, that cause turbulence and secondary flows, and therefore mixing within the flow, are negligible and viscous effects dominate the dynamics. Under these conditions, flow through the channel is generally laminar. In particularly preferred embodiments, the channel with a typical analyte-containing fluid provides a Reynolds number less than about 0.001, more preferably less than about 0.0001.

Since the Reynolds number depends not only on channel dimension, but on fluid density, fluid viscosity, fluid velocity and the timescale on which the velocity is changing, the absolute upper limit to the channel diameter is not sharply defined. In fact, with well designed channel geometries, turbulence can be avoided for R<100 and possibly for R<1000, so that high throughput systems with relatively large channel sizes are possible. The preferred channel characteristic dimension range is less than about 1 millimeter, preferably less than about 0.5 mm, and more preferably less than about 200 microns.

In one embodiment, the sample exposure region, such as a fluid flow channel 30 may be formed by using a polydimethyl siloxane (PDMS) mold. Channels can be created and applied to a surface, and a mold can be removed. In certain embodiments, the channels are easily made by fabricating a master by using photolithography and casting PDMS on the master, as described in the above-referenced patent applications and international publications. Larger-scale assembly is possible as well.

Figure 44B:
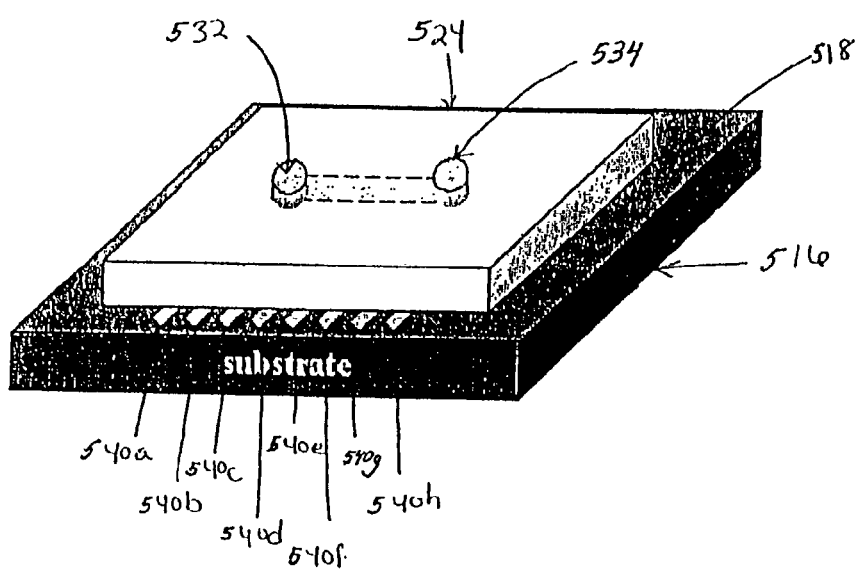
FIG. 44B illustrates, schematically, a nanoscale detector device with a parallel array of nanoscale wires.

FIG. 44b shows an alternative embodiment of the present invention wherein the nanoscale detector device 510 of FIG. 44a further includes multiple nanoscale wires 538a-h (not shown). In FIG. 44b, wire interconnects 540a-h connect corresponding nanoscale wires 538a-h to electrical connections 522a-h, respectively (not shown). In a preferred embodiment, each nanoscale wires 538a-h has a unique reaction entity selected to detect a different analytes in the fluid. In this way, the presence or absence of several analytes may be determined using one sample while performing one test.

Figures 45A, 45B:
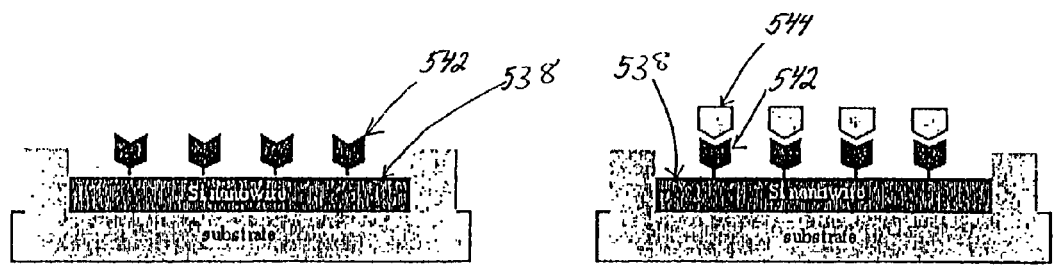
FIG. 45A illustrates, schematically, a nanoscale detector device in which a nanoscale wire has been modified with a binding agent for detection of a complementary binding partner.
FIG. 45B illustrates, schematically, the nanoscale detector device of FIG. 2a, in which a complementary binding partner is fastened to the binding agent.

FIG. 45a schematically shows a portion of a nanoscale detector device in which the nanoscale wire 538 has been modified with a reactive entity that is a binding partner 542 for detecting analyte 544. FIG. 45b schematically shows a portion of the nanoscale detector device of FIG. 45a, in which the analyte 544 is attached to the specific binding partner 542. Selectively functionalizing the surface of nanoscale wires can be done, for example, by functionalizing the nanoscale wire with a siloxane derivative. For example, a nanoscale wire may be modified after construction of the nanoscale detector device by immersing the device in a solution containing the modifying chemicals to be coated. Alternatively, a microfluidic channel may be used to deliver the chemicals to the nanoscale wires. For example, amine groups may be attached by first making the nanoscale detector device hydrophilic by oxygen plasma, or an acid and/or oxidizing agent and the immersing the nanoscale detector device in a solution containing amino silane. By way of example, DNA probes may be attached by first attaching amine groups as described above, and immersing the modified nanoscale detector device in a solution containing bifunctional crosslinkers, if necessary, and immersing the modified nanoscale detector device in a solution containing the DNA probe. The process may be accelerated and promoted by applying a bias voltage to the nanoscale wire, the bias voltage can be either positive or negative depending on the nature of reaction species, for example, a positive bias voltage will help to bring negatively charged DNA probe species close to the nanoscale wire surface and increase its reaction chance with the surface amino groups.

FIG. 47a schematically shows another embodiment of a nanoscale sensor having a backgate 546. FIG. 47b shows conductance vs. time at with a backgate voltage ranging from −10 V to +10 V. FIG. 47c shows conductance vs. backgate voltage. The backgate can be used to inject or withdraw the charge carriers from the nanoscale wire. Therefore, it may be used to control the sensitivity and the dynamic range of the nanoscale wire sensor and to draw analytes to the nanoscale wire.

Figure 48A:
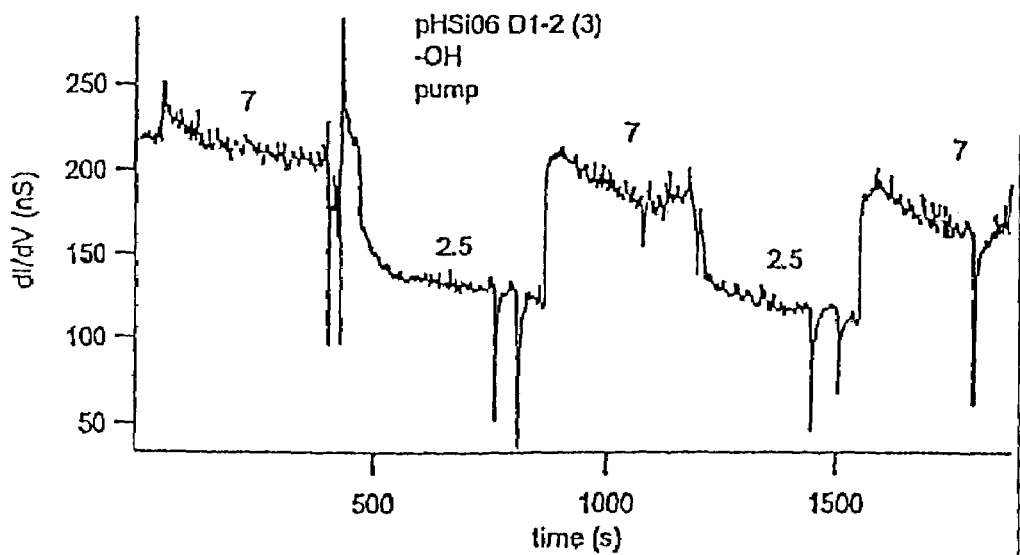
FIG. 48A shows conductance for a single silicon nanoscale wire as a function of pH.
Figure 48B:
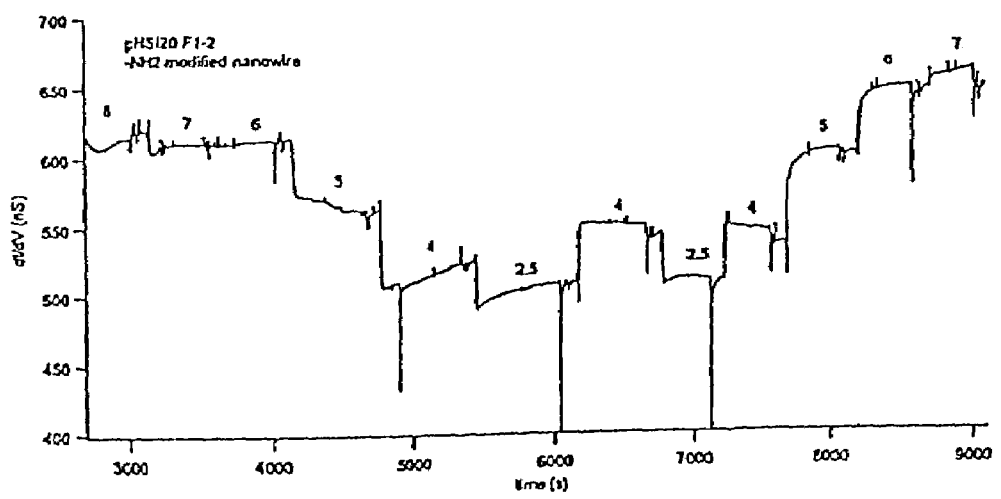
FIG. 48B shows conductance versus pH for a single silicon nanoscale wire that has been modified to expose amine groups at the surface.

FIGS. 48a and 48b show the conductance for a single silicon nanoscale wire, native and coated, respectively, as a function of pH. As seen in FIG. 47, the conductance of the silicon nanoscale wire changes from 7 to 2.5 when the sample is changed. The silicon nanoscale wire of FIG. 48 has been modified to expose amine groups at the surface of the nanoscale wire. FIG. 48 shows a change in response to pH when compared to the response in FIG. 47. The modified nanoscale wire of FIG. 48 shows a response to milder conditions such as, for example, those present in physiological conditions in blood.

Figure 49:
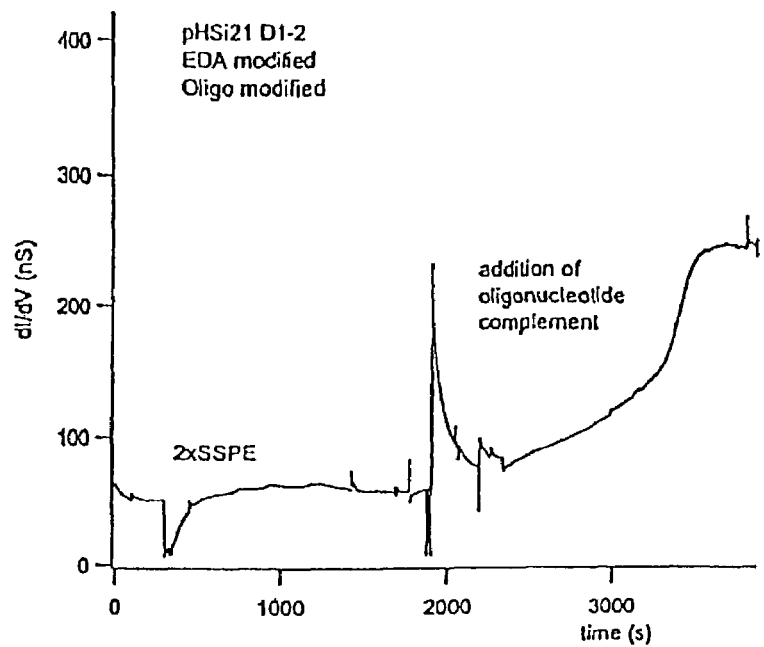
FIG. 49 shows conductance versus time for a silicon nanoscale wire with a surface modified with oligonucleotide agents.

FIG. 49 shows the conductance for a silicon nanoscale wire having a surface modified with an oligonucleotide agent reaction entity. The conductance changes dramatically where the complementary oligonucleotide analyte binds to the attached oligonucleotide agent.

Figure 51A:
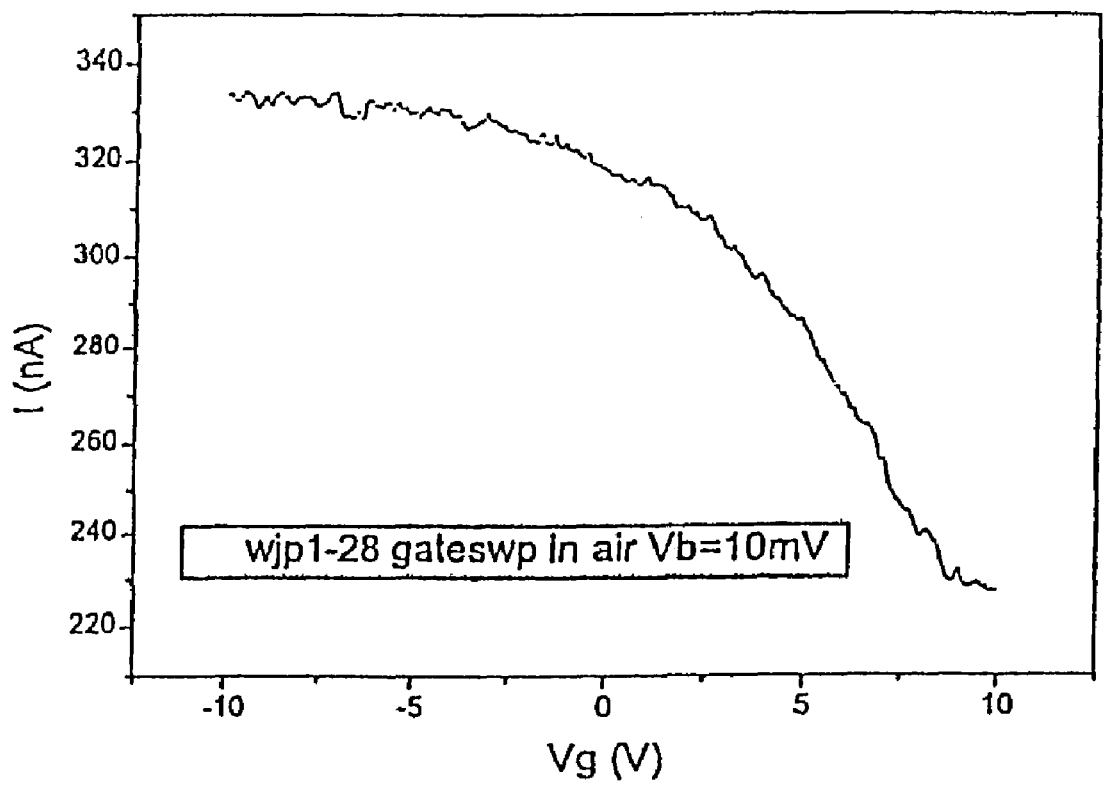
FIG. 51A shows current-voltage (I-V) measurements for a single-walled carbon nanotube device in air.

FIG. 51a shows the change in the electrostatic environment with change in gate voltage for a single-walled nanotube. FIGS. 51b and 51c, show the change in conductance induced by the presence of NaCl and $CrCl_x$ of a single-walled carbon nanotube.

Figure 9A:
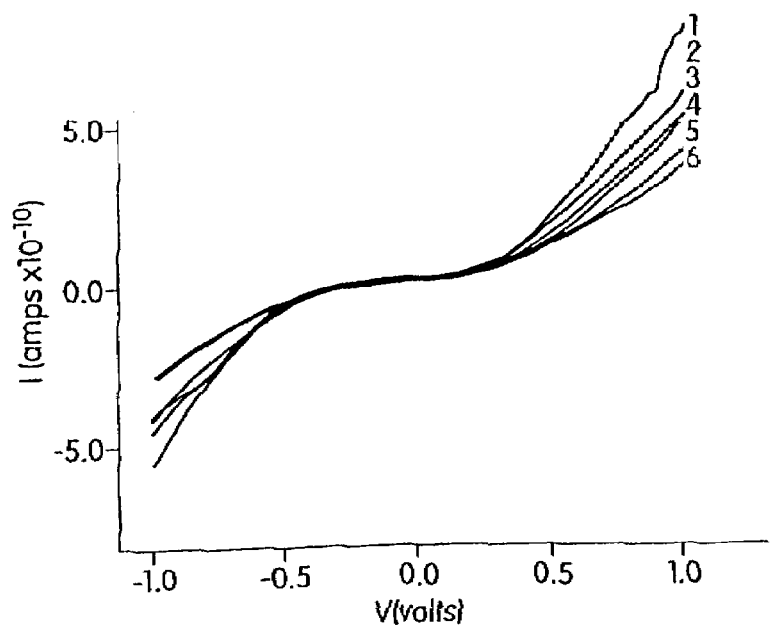
FIGS. 9A and 9B show silicon nanoscale current as a function of bias voltage for different phosphorous doping levels and gate voltages.
Figure 52A:
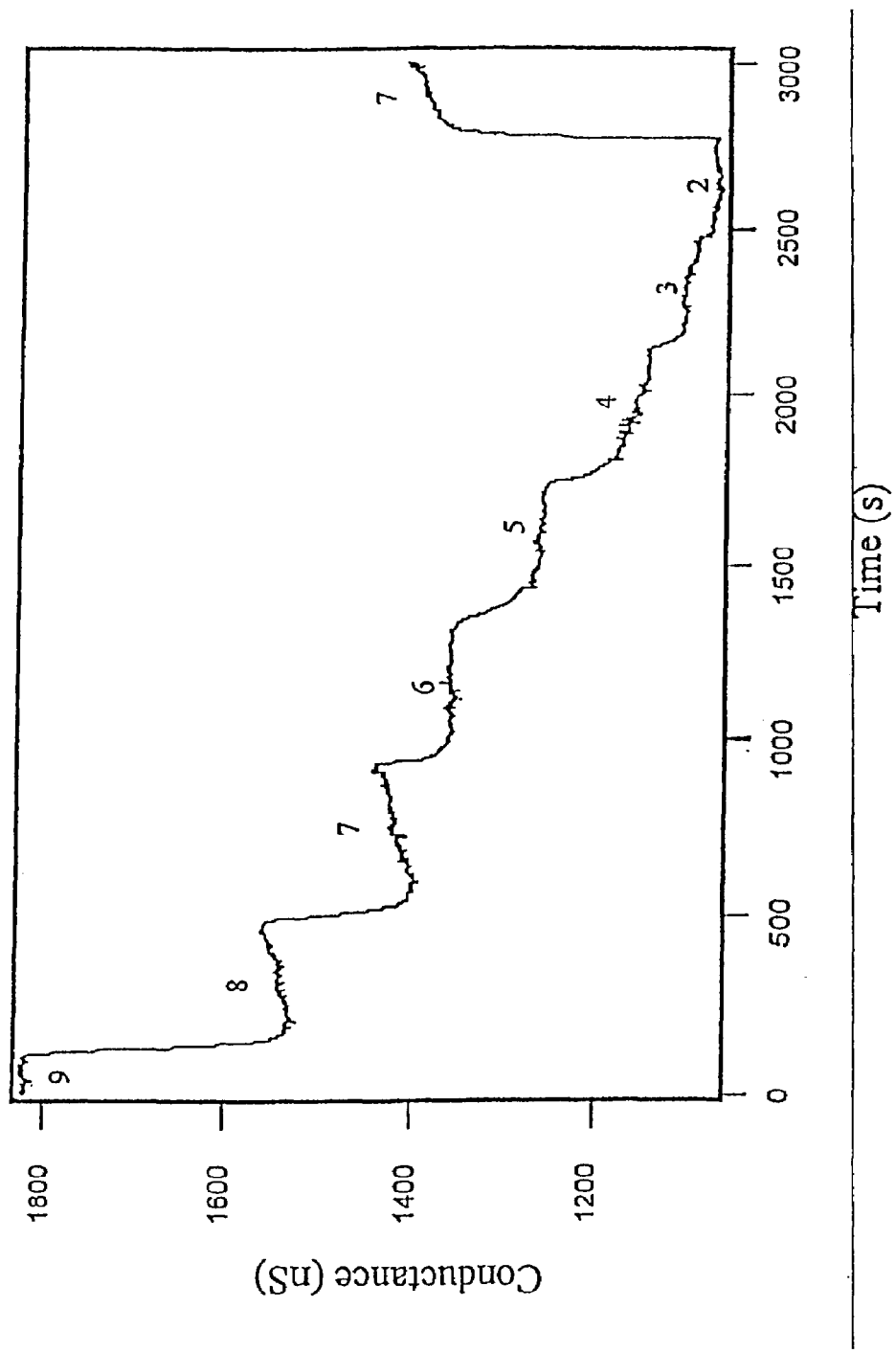
FIG. 52A shows the conductance of nanosensors with hydroxyl surface groups when exposed to pH levels from 2 to 9.
Figure 52B:
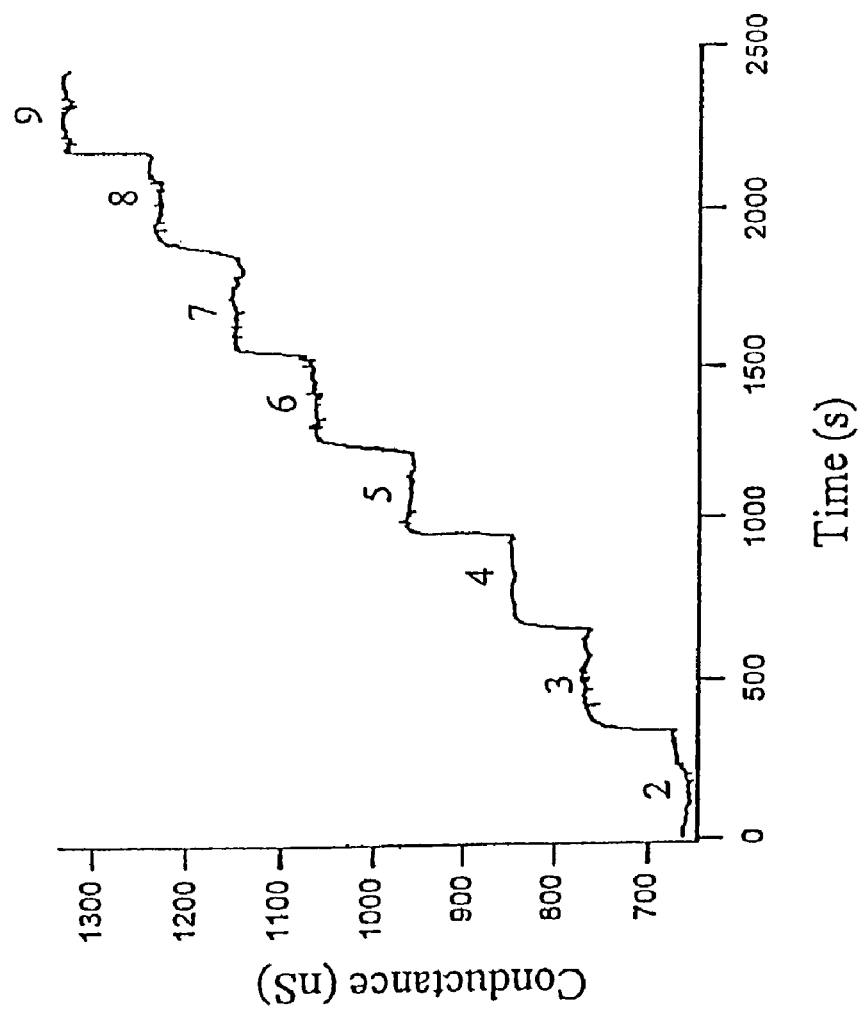
FIG. 52B shows the conductance of nanosensors modified with amine groups when exposed to pH levels from 2 to 9.
Figure 52C:
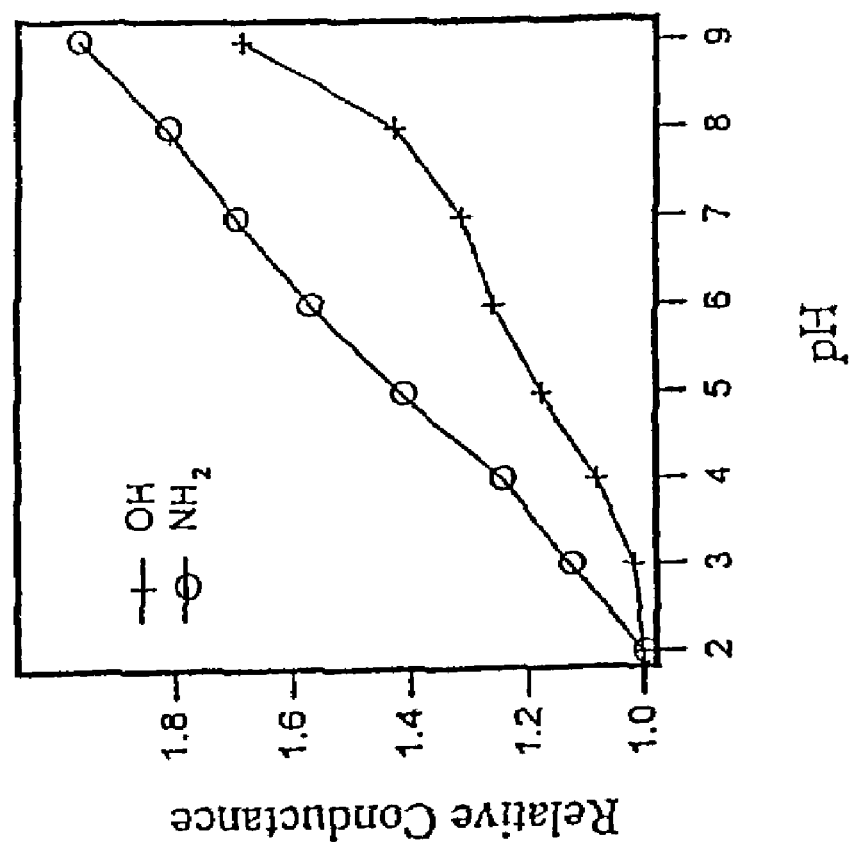
FIG. 52C show the relative conductance of the nanosensors with changes in pH levels.

FIG. 9a shows the change in conductance as nanosensors with hydroxyl surface groups are exposed to pH levels from 2 to 9. FIG. 52b shows the change in conductance as nanosensors modified with amine groups are exposed to pH levels from 2 to 9. FIG. 52c show the relative conductance of the nanosensors with changes in pH levels. The results showed a linear response in a wide range of pH, which clearly demonstrated the device is suitable for measuring or monitoring pH conditions of a physiological fluid.

Figure 53B:
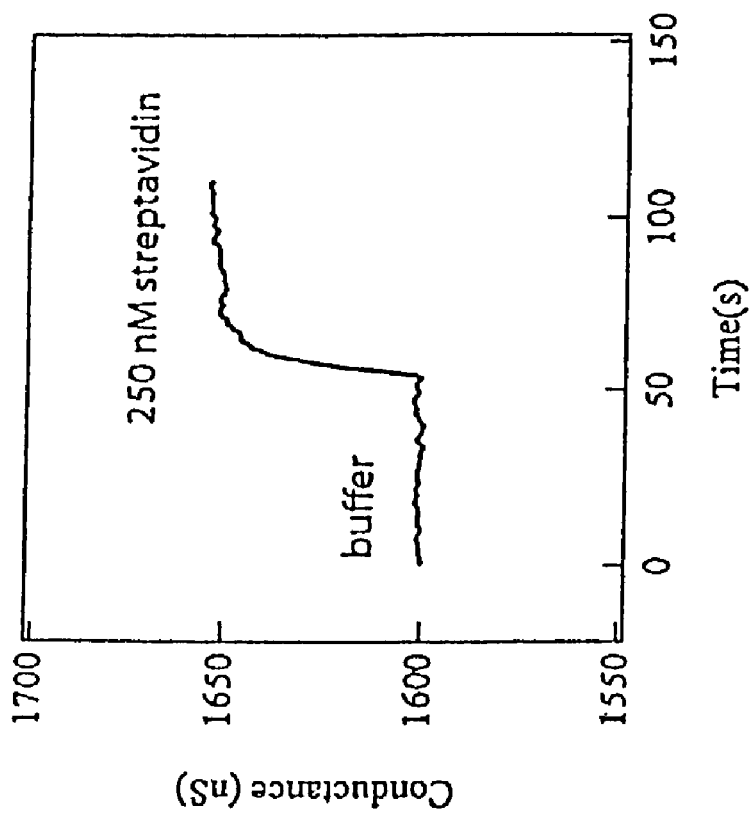
FIG. 53B shows the conductance of a SiNW modified with BSA biotin, as it is exposed first to a blank buffer solution, and then to a solution containing 25 pM streptavidin.
Figure 53A:
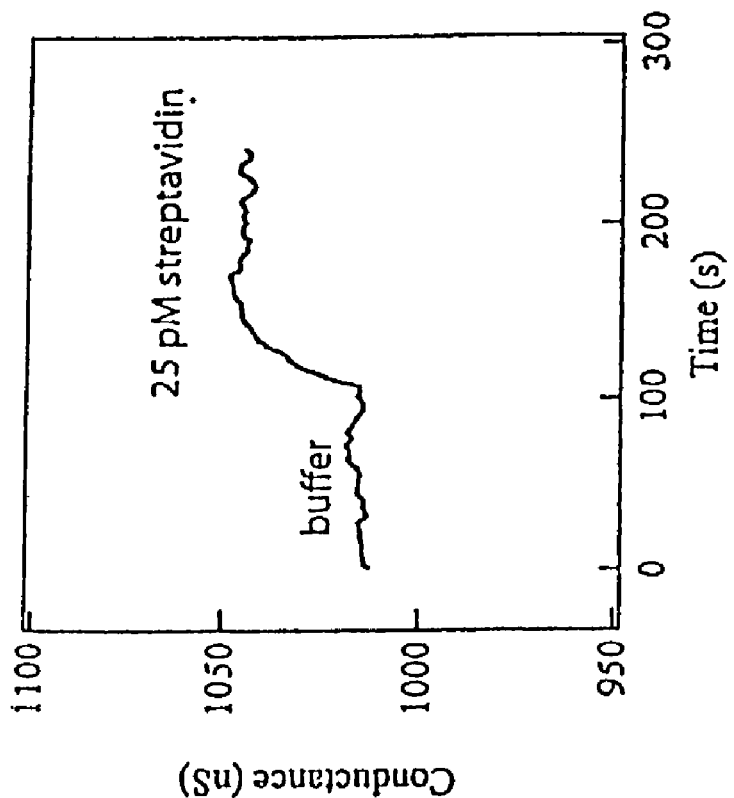
FIG. 53A shows the conductance of a SiNW modified with BSA biotin, as it is exposed first to a blank buffer solution, and then to a solution containing 250 nM streptavidin.
Figure 53D:
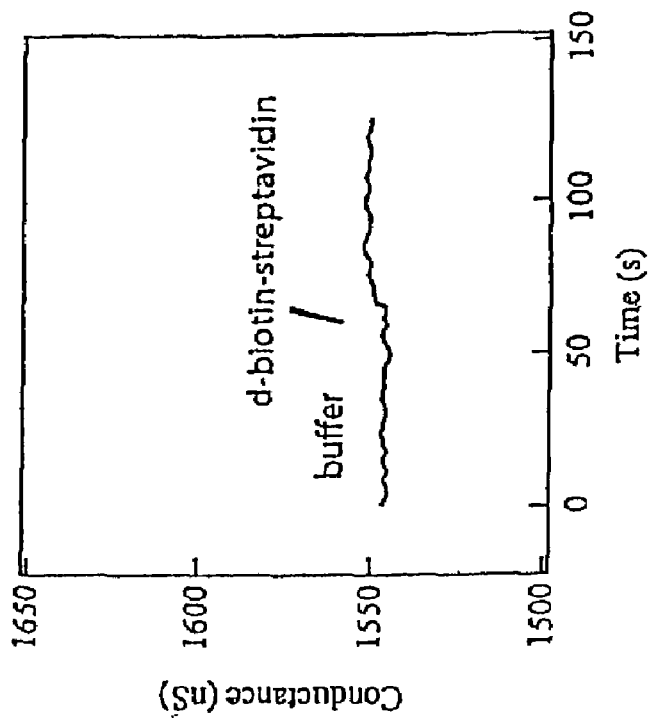
FIG. 53D shows the conductance of a SiNW modified with BSA biotin, as it is exposed to a buffer solution, and then to a solution containing d-biotin streptavidin.
Figure 53C:
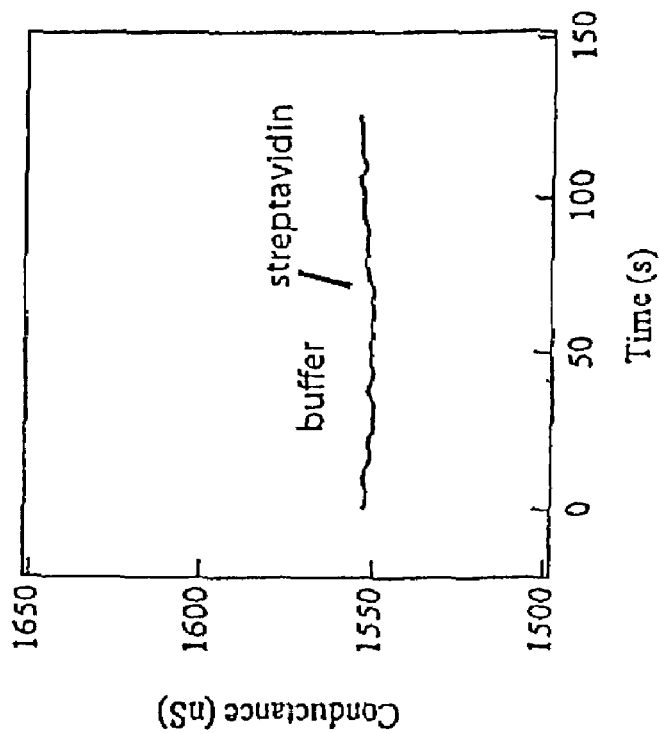
FIG. 53C shows the conductance of a bare SiNW as it is exposed first to a blank buffer solution, and then to a solution containing streptavidin.
Figure 53F:
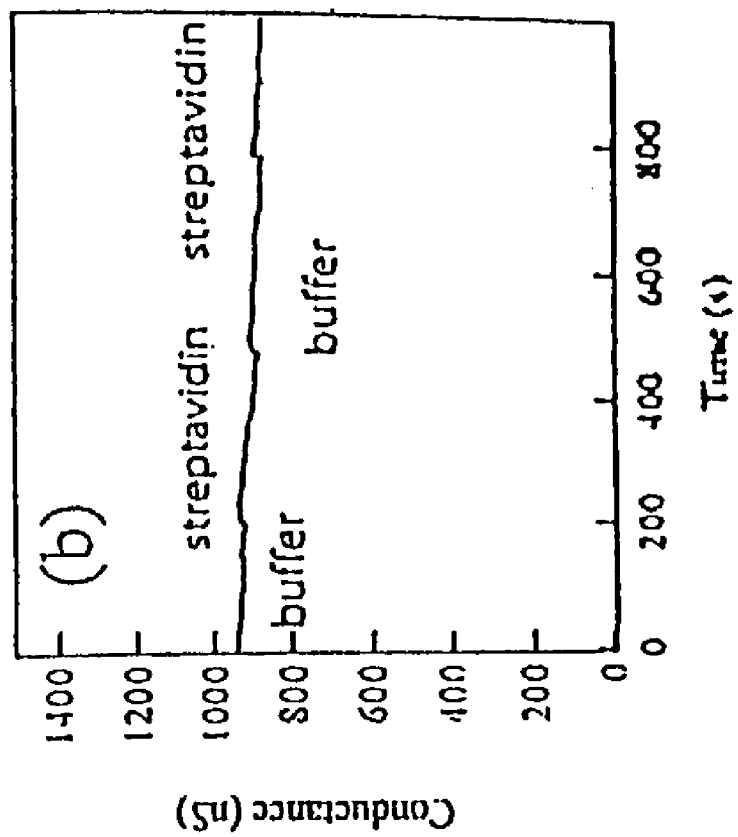
FIG. 53F shows the conductance of a bare SiNW as it is alternately exposed to a buffer solution and a solution containing streptavidin.
Figure 53E:
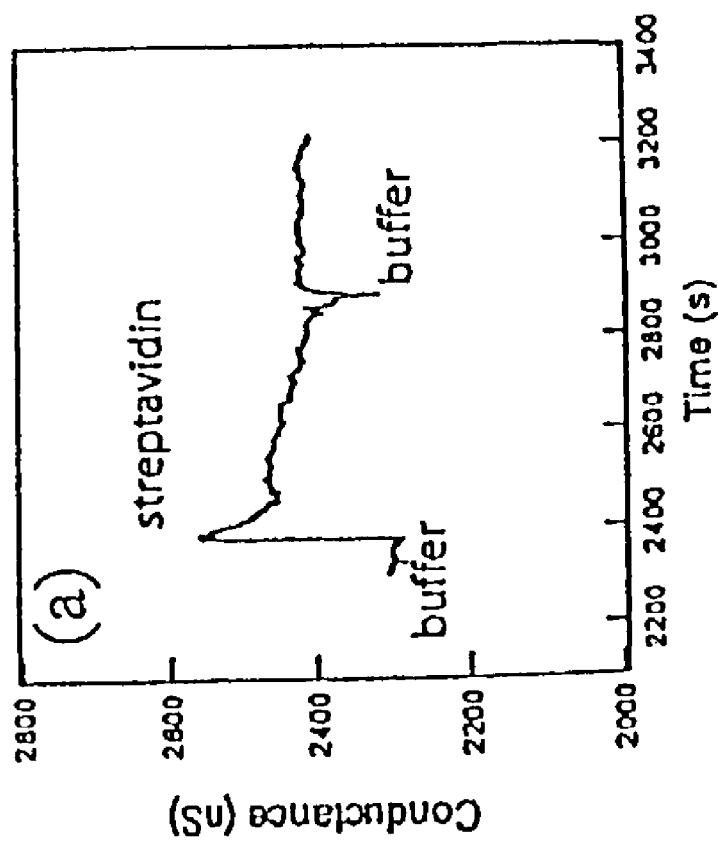
FIG. 53E shows the conductance of a biotin modified nanosensor exposed to a blank buffer solution, then to a solution containing streptavidin, and then again to a blank buffer solution.

FIG. 53a shows an increase in conductance of a silicon nanowire (SiNW) modified with a reaction entity BSA biotin, as it is exposed first to a blank buffer solution, and then to a solution containing an analyte, 250 nM streptavidin. FIG. 53b shows an increase in conductance of a SiNW modified with BSA biotin, as it is exposed first to a blank buffer solution, and then to a solution containing 25 pM streptavidin. FIG. 53c shows no change in conductance of a bare SiNW as it is exposed first to a blank buffer solution, and then to a solution containing streptavidin. FIG. 53d shows the conductance of a SiNW modified with BSA biotin, as it is exposed to a buffer solution, and then to a solution containing d-biotin streptavidin. FIG. 53e shows the change in conductance of a biotin modified nanosensor exposed to a blank buffer solution, then to a solution containing streptavidin, and then again to a blank buffer solution. Replacing streptavidin with the blank buffer does not change the conductance, indicating that the streptavidin has irreversibly bound to the BSA Biotin modified nanosensor. FIG. 53f shows no change in conductance of a bare SiNW as it is alternately exposed to a buffer solution and a solution containing streptavidin. These results demonstrate this nanoscale wire sensor is suitable for specific detection of bio-markers at very high sensitivity.

Figure 54C:
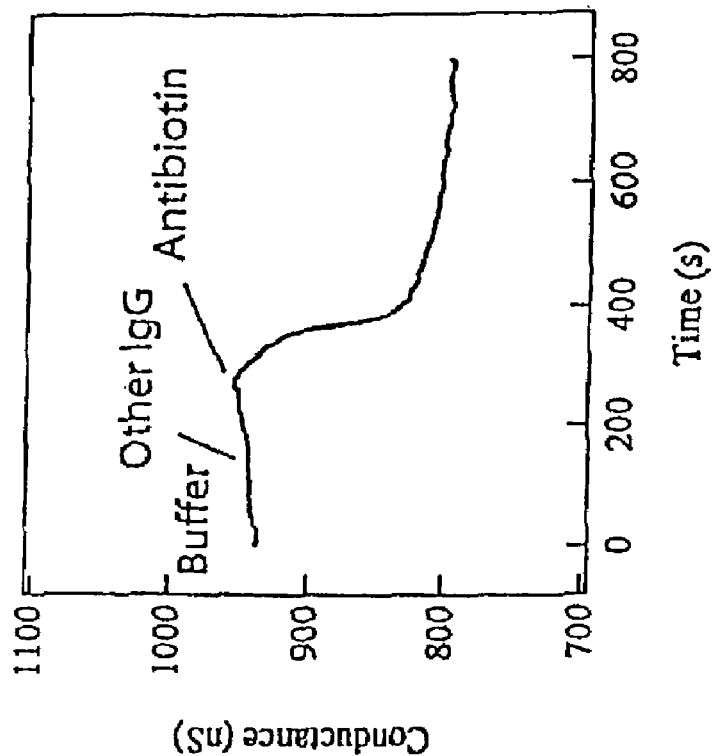
FIG. 54C shows the conductance of a BSA-biotin modified SiNW during exposure to a buffer, other IgG type antibodies, and then antibiotin.
Figure 54B:
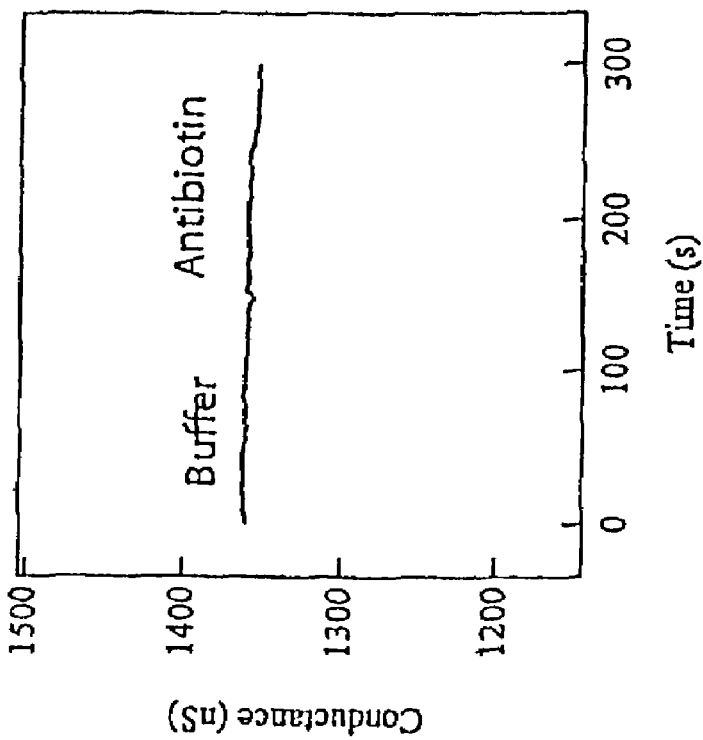
FIG. 54B shows the conductance of a bare SiNW during contact with a buffer solution and then a solution containing antibiotin.

FIG. 54a shows a decrease in conductance of a BSA-biotin modified SiNW as it is exposed first to a blank buffer solution, then to a solution containing antibiotin. The conductance then increases upon replacing the solution containing antibiotin with a blank buffer solution, and then again decreases upon exposing the nanosensor to a solution containing antibiotin. FIG. 54a indicates a reversible binding between biotin and antibiotin. FIG. 54b shows the conductance of a bare SiNW during contact with a buffer solution and then a solution containing antibiotin. FIG. 54c shows the change in conductance of a BSA-biotin modified SiNW during exposure to a buffer, other IgG type antibodies, and then antibiotin, an IgG1 type antibody to biotin. FIG. 54c indicates that the BSA biotin modified SiNW detects the presence of antibiotin, without being hindered by the presence of other IgG type antibodies. These results demonstrate the potential of the nanoscale wire sensor for dynamic bio-marker monitoring under a real physiological condition.

Figure 55A:
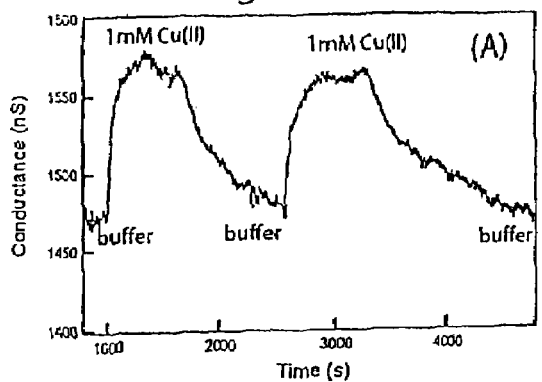
FIG. 55A shows the conductance of an amine modified SiNW when alternately exposed to a blank buffer solution and a solution containing 1 mM Cu(II)
Figure 55B:
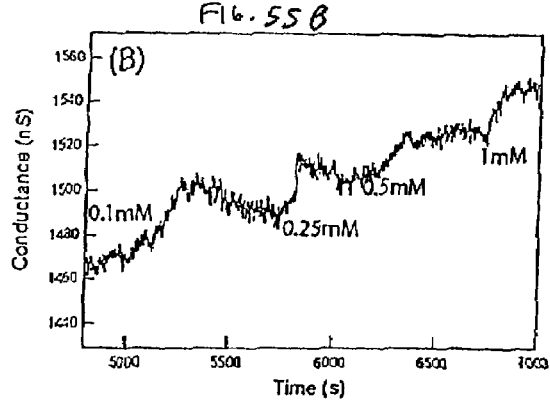
FIG. 55B shows the conductance of the amine modified SiNW is exposed to concentrations of Cu(II) from 0.1 mM to 1 mM.
Figure 55C:
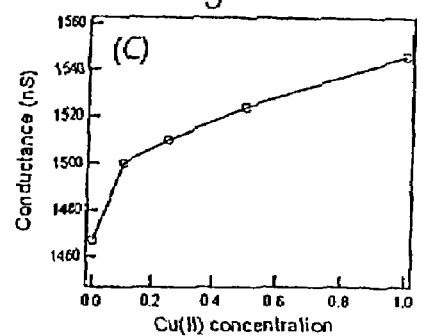
FIG. 55C shows the conductance verses Cu(II) concentration.
Figure 55D:
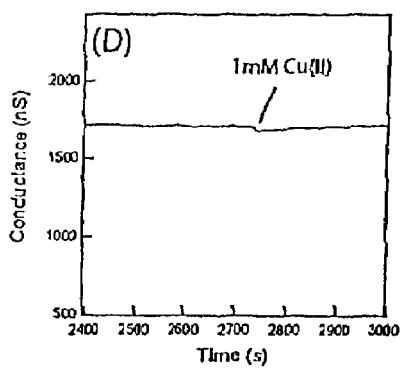
FIG. 55D shows conductance of an unmodified SiNW when exposed first to a blank buffer solution and then to 1 mM Cu(II)
Figure 55E:
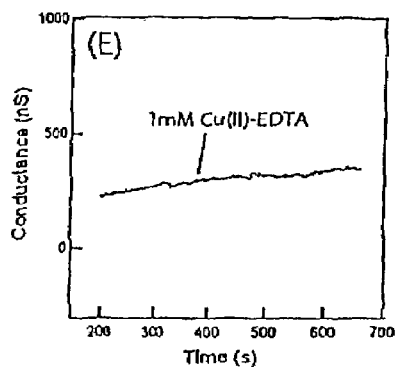
FIG. 55E shows conductance of an amine-modified SiNW when exposed first to a blank buffer solution and then to 1 mM Cu(II)-EDTA.

Amine modified SiNW may also detect the presence of metal ions. FIG. 55a shows the change in conductance of an amine modified SiNW when alternately exposed to a blank buffer solution and a solution containing 1 mM Cu (II). FIG. 55b shows the increases in conductance as the amine modified SiNW is exposed to concentrations of Cu (II) from 0.1 mM to 1 mM. FIG. 55c shows the increase in conductance verses Cu (II) concentration. FIG. 55d shows no change in conductance of an unmodified SiNW when exposed first to a blank buffer solution and then to 1 mM Cu (II). FIG. 55e shows no change in the conductance of an amine modified SiNW when exposed first to a blank buffer solution and then to 1 mM Cu (II)-EDTA, wherein the EDTA interferes with the ability of Cu (II) to bind to the modified SiNW. These results demonstrate the potential of the nanoscale wire sensor for use in inorganic chemical analysis.

FIG. 56a shows the conductance of a silicon nanoscale wire modified with calmodulin, a calcium binding protein. In FIG. 56a, region 1 shows the conductance of the calmodulin modified silicon when exposed to a blank buffer solution. Region 2 shows the drop in conductance of the same nanoscale wire when exposed to a solution containing calcium ions noted in FIG. 46 with a downward arrow. Region 3 shows the increase in conductance of the same nanoscale wire is again contacted with a blank buffer solution, indicated with an upward arrow. The subsequent return of conductance to its original level indicates that the calcium ion is reversible bound to the calmodulin modified nanoscale wire. FIG. 56b shows no change in conductance of an unmodified nanoscale wire when exposed first to a blank buffer solution, and then to a solution containing calcium ions.

As indicated above, in one embodiment, the invention provides a nanoscale electrically based sensor for determining the presence or absence of analytes suspected of being present in a sample. The nanoscale sensor may provide greater sensitivity in detection than that provided by macroscale sensors. Moreover, the sample size used in nanoscale sensors is less than or equal to about 10 microliters, preferably less than or equal to about 1 microliter, and more preferably less than or equal to about 0.1 microliter. The sample size may be as small as about 10 nl or less. The nanoscale sensor may also allow for unique accessibility to biological species and may be used both in vivo and in vitro applications. When used in vivo, the nanoscale sensor and the corresponding method may result in a minimally invasive procedure.

Figure 57B:
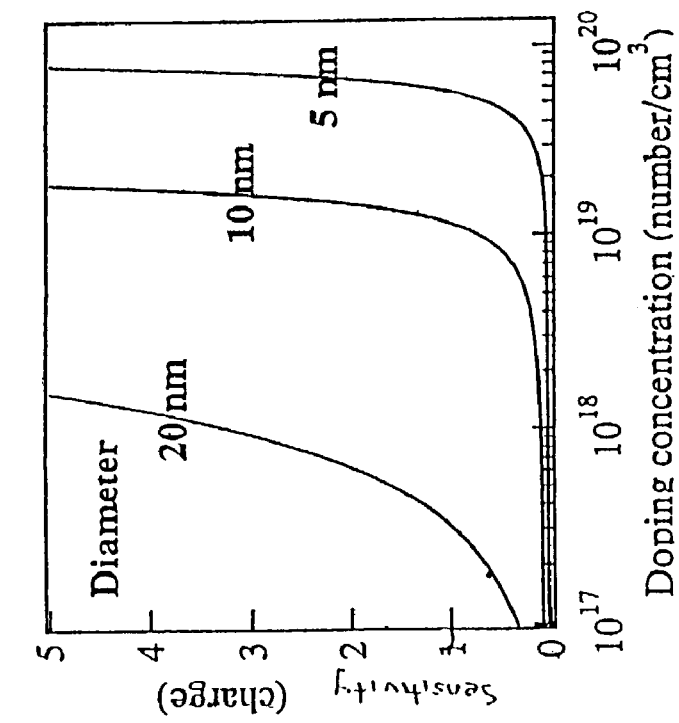
FIG. 57B shows a calculation of the threshold doping density compared to nanoscale wire diameter for detecting a single charge.
Figure 57A:
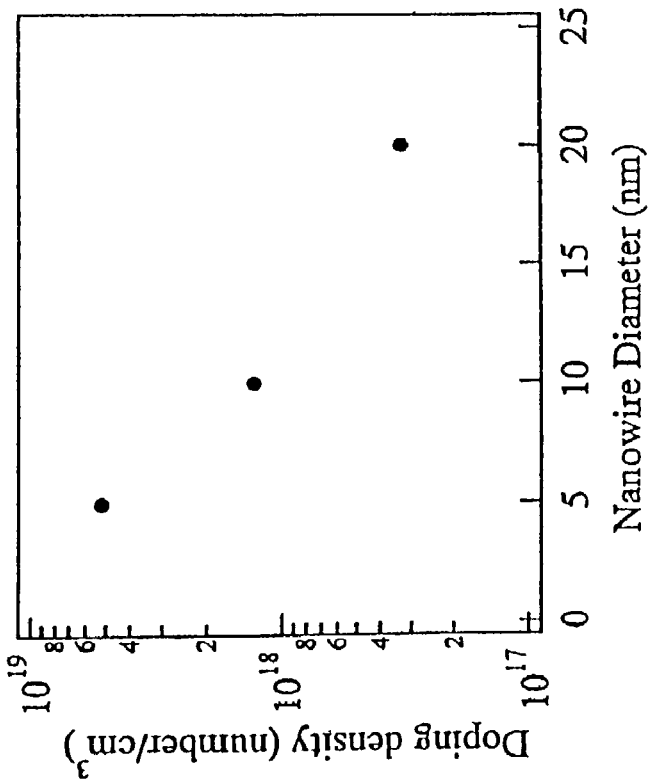
FIG. 57A shows a calculation of sensitivity for detecting up to 5 charges compared with doping concentration and nanoscale wire diameter.

FIG. 57a shows a calculation of sensitivity for detecting up to 5 charges compared to the doping concentration and nanoscale wire diameter. As indicated, the sensitivity of the nanoscale wire may be controlled by changing the doping concentration or by controlling the diameter of the nanoscale wire. For example, increasing the doping concentration of a nanoscale wire may increase the ability of the nanoscale wire to detect more charges. Also, a 20 nm wire may require less doping than a 5 nm nanoscale wire for detecting the same number of charges. FIG. 57b shows a calculation of a threshold doping density for detecting a single charge compared to the diameter of a nanoscale wire. A 20 nm nanoscale wire may require less doping than a 5 nm nanoscale wire to detect a single charge.

Figure 58A:
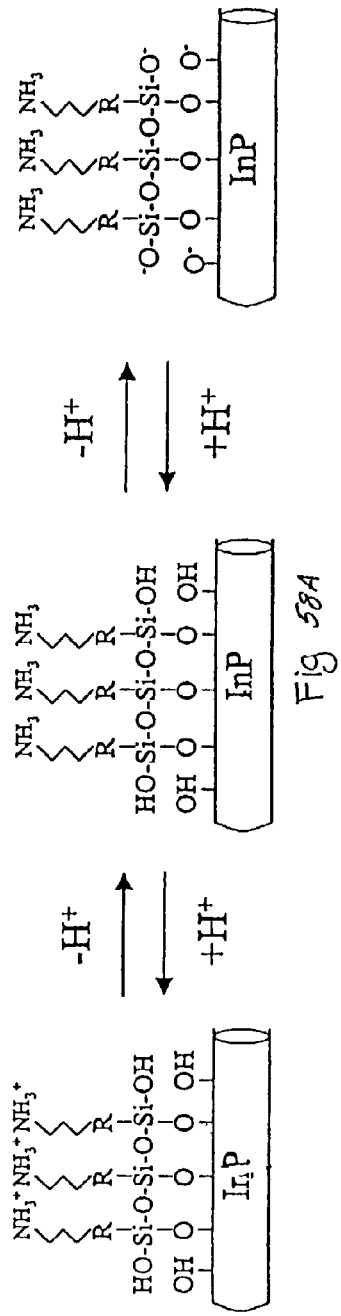
FIG. 58A is a schematic view of an InP nanoscale wire.
Figure 58B:
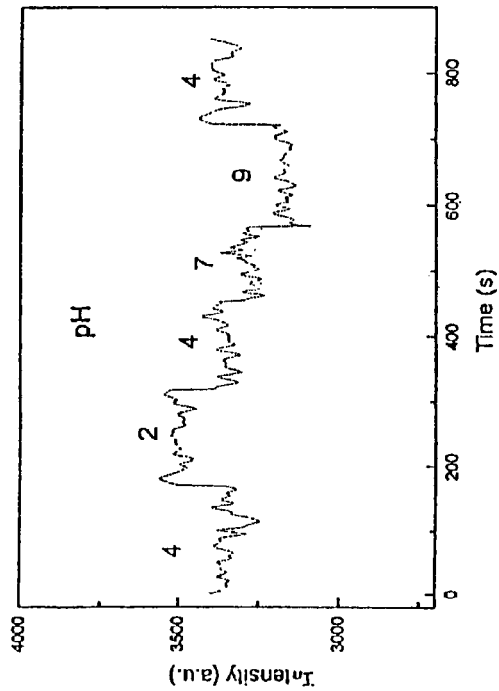
FIG. 58B shows the change in luminescence of a nanoscale wire of FIG. 58A over time as pH varies.

FIG. 58a shows a schematic view of an InP nanoscale wire. The nanoscale wire may be homogeneous, or may comprise discrete regions of dopants. FIG. 58b shows the change in luminescence of the nanoscale wire of FIG. 58a over time as pH is varied. As indicated, the intensity of the light emission of a nanoscale wire may change relative to the level of binding. As the pH increases, the light intensity may drop, and as the pH decreases, the light intensity may increase. One embodiment of the invention contemplates individually addressed light signal detection by sweeping through each electrode in a microarray. Another embodiment of the invention contemplates a two signal detector, such as an optical sensor combined with an electrical detector.

Figure 59A:
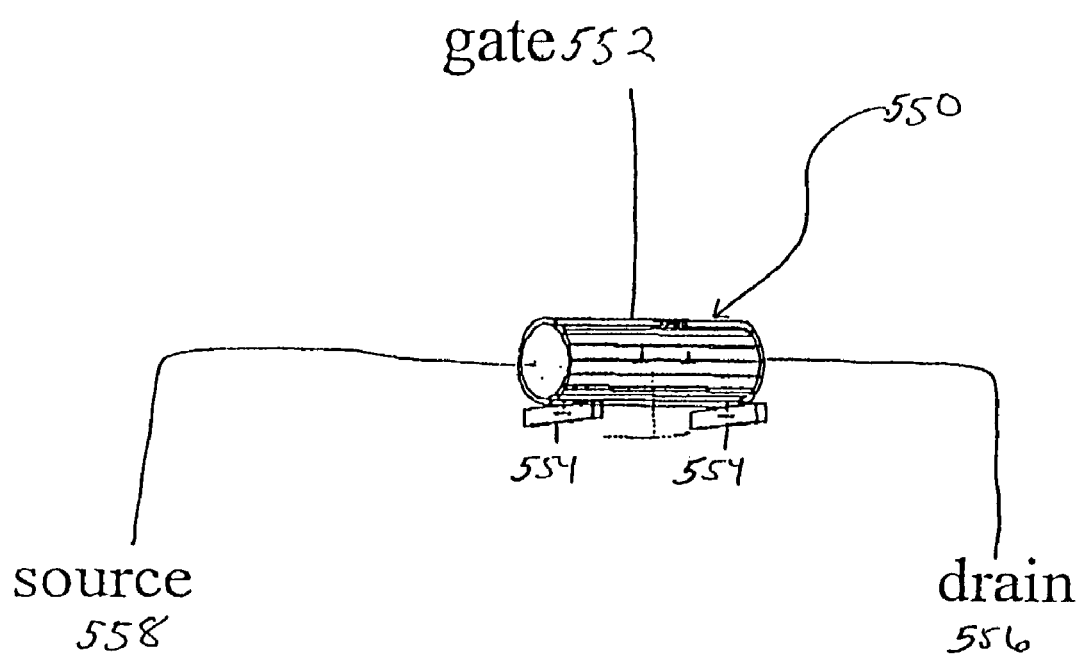
FIG. 59A depicts one embodiment of a nanoscale wire sensor, specifically a chemical or ligand-gated field effects transistor (FET)

FIG. 59a depicts one embodiment of a nanoscale wire sensor. As show in FIG. 59a, the nanoscale wire sensor of the invention comprises a single molecule of doped silicon 550. The doped silicon is shaped as a tube, and the doping may be n-doped or p-doped. Either way, the doped silicon nanoscale wire may form a high resistance semiconductor material across which a voltage may be applied. The exterior surface and the interior surface may have an oxide or other coating. The surface may act as the gate 552 of an FET device and the electrical contacts at either end may allow the nanoscale wire ends to act as a drain 556 and a source 558. In the depicted embodiment, the device is symmetric, and either end of the device may be considered the drain or the source. For purpose of illustration, the nanoscopic wire of FIG. 59a defines the left-hand side as the source and the right hand side as the drain. FIG. 59a also show that the nanoscale wire device is disposed upon and electrically connected to two conductor elements 554.

FIGS. 59a and 59b illustrate an example of a chemical/or ligand-gated field effects transistor (FET). FETs are well know in the art of electronics. Briefly, a FET is a 3-terminal device in which a conductor between 2 electrodes, one connected to the drain and one connected to the source, depends on the availability of charge carriers in a channel between the source and drain. FETs are described in more detail in, for example, *The Art of Electronics, Second Edition* by Paul Horowitz and Winfield Hill, Cambridge University Press, 1989, pp. 113-174, the entire contents of which is hereby incorporated by reference in its entirety for all purposes. This availability of charge carriers may be controlled by a voltage applied to a third "control electrode," also known as the gate electrode. The conduction in the channel is controlled by a voltage applied to the gate electrode which may produce an electric field across the channel. The device of FIGS. 59a and 59b may be considered a chemical or ligand-FET because the chemical or ligand provides the voltage at the gate which produced the electric field which changes the conductivity of the channel. This change in conductivity in the channel affects the flow of current through the channel. For this reason, a FET is often referred to as a transconductant device in which a voltage on the gate controls the current through the channel through the source and the drain. The gate of a FET is insulated from the conduction channel, for example, using a semiconductor junction such in a junction FET (JFET) or using an oxide insulator such as in a metal oxide semiconductor FET (MOSFET). Thus, in FIGS. 59a and 59b, the $SiO_2$ exterior surface of the nanoscale wire sensor may serve as the gate insulation for the gate.

In application, the nanoscale wire device illustrated in FIG. 59a may provide an FET device that may be contacted with a sample or disposed within the path of a sample flow. Elements of interest within the sample can contact the surface of the nanoscale wire device and, under certain conditions, bind or otherwise adhere to the surface.

To this end the exterior surface of the device may have reaction entities, e.g., binding partners that are specific for a moiety of interest. The binding partners may attract the moieties or bind to the moieties so that moieties of interest within the sample will adhere so and bind to the exterior surface. An example of this is shown in FIG. 59c where there is depicted a moiety of interest 560 (not drawn to scale) being bound to the surface of the nanoscale wire device.

Also shown, with reference to FIG. 59c, that as the moieties build up, a depletion region 562 is created within the nanoscale wire device that limits the current passing through the wire. The depletion region can be depleted of holes or electrons, depending upon the type of channel. This is shown schematically in FIG. 59d. The moiety has a charge that may lead to a voltage difference across the gate/drain junction.

A nanoscale sensor of the present invention may collect real time data in some embodiments. The real time data may be used, for example, to monitor the reaction rate of a specific chemical or biological reaction. Physiological conditions or drug concentrations present in vivo may also produce a real time signal that may be used to control a drug delivery system. For example, the present invention includes, in one aspect, an integrated system, comprising a nanoscale wire detector, a reader and a computer controlled response system. In this example, the nanoscale wire detector detects a change in the equilibrium of an analyte in the sample, feeding a signal to the computer controlled response system causing it to withhold or release a chemical or drug. This may be particularly useful as an implantable drug or chemical delivery system because of its small size and low energy requirements. Those of ordinary skill in the art will be aware of the parameters and requirements for constructing implantable devices, readers, and computer-controlled response systems suitable for use in connection with the present invention. That is, the knowledge of those of ordinary skill in the art, coupled with the disclosure herein of nanoscale wires as sensors, enables implantable devices, real-time measurement devices, integrated systems, and the like. Such systems may be made capable of monitoring one, or a plurality of physiological characteristics individually or simultaneously. Such physiological characteristics may include, for example, oxygen concentration, carbon dioxide concentration, glucose level, concentration of a particular drug, concentration of a particular drug by-product, or the like. Integrated physiological devices may be constructed to carry out a function depending upon a condition sensed by a sensor of the invention. For example, a nanoscale wire sensor of the invention may be constructed and arranged to detect glucose and, based upon the determined glucose level, may cause the release of insulin into a subject through an appropriate controller mechanism.

In another embodiment, the article may comprise a cassette comprising a sample exposure region and a nanoscale wire. The detection of an analyte in a sample in the sample exposure region may occur while the cassette is disconnected to a detector apparatus, allowing samples to be gathered at one site, and detected at another. The cassette may be operatively connectable to a detector apparatus able to determine a property associated with the nanoscale wire. As used herein, a device is "operatively connectable" when it has the ability to attach and interact with another apparatus.

In another embodiment, one or more nanoscale wires may be positioned in a microfluidic channel. One or more nanoscale wires may cross the same microchannel at different positions to detect different analytes, or to measure the flowrate of the same analyte. In another embodiment, one or more nanoscale wires may be positioned in a microfluidic channel, which may form one of a plurality of analytic elements in a microneedle probe or a dip-and-read probe. The microneedle probe may be implantable in some instances, and be capable of detecting several analytes simultaneously in real time. In another embodiment, one or more nanoscale wires may be positioned in a microfluidic channel, and may form one of the analytic elements in a microarray for a cassette or a lab on a chip device. Those skilled in the art will know that such a cassette or lab on a chip device will be in particular suitable for high throughout chemical analysis and combinational drug discovery. The associated method of using the nanoscale sensor may not require labeling, as in certain other sensing techniques. The ability to include multiple nanoscale wires in one nanoscale sensor, may allow for the simultaneous detection of different analytes suspected of being present in a single sample. For example, a nanoscale pH sensor may include a plurality of nanoscale wires that each detect different pH levels, or a nanoscale oligo sensor with multiple nanoscale wires may be used to detect multiple sequences, or combination of sequences.

The function and advantages of these and other embodiments of the present invention will be more fully understood from the following examples. These examples are intended to be illustrative in nature and are not considered to be limiting the scope of the invention.

EXAMPLES

Example 1

Single crystal n-type and p-type silicon nanowires (SiNWs) were prepared and characterized by electrical transport measurements. As used herein, a "single crystal" item is an item that has covalent bonding, ionic bonding, or a combination thereof throughout the item. Such a single crystal item may include defects in the crystal, but is distinguished from an item that includes one or more crystals, not ionically or covalently bonded, but merely in close proximity to one another. Laser catalytic growth was used to introduce controllably either boron or phosphorous dopants during the vapor phase growth of SiNWs. Estimates of the carrier mobility made from gate-dependent transport measurements are consistent with diffusive transport. In addition, these studies show it is possible to heavily dope SiNWs and approach a metallic regime. Temperature-dependent measurements made on heavily doped SiNWs show no evidence for coulomb blockade at temperature down to 4.2 K, and thus testify to the structural and electronic uniformity of the SiNWs.

Currently, there is intense interest in nanoscale wires ("1D" structures) due to their potential to test fundamental concepts about how dimensionality and size affect physical properties, and to serve as critical building blocks for emerging nanotechnologies. Of particular importance to 1D nanostructures is the electrical transport through these wires, since predictable and controllable conductance will be critical to many nanoscale electronics applications.

Controlled doping of SiNWs and characterization is reported of the electrical properties of these doped nanoscale wires using transport measurements. Gate-dependent, two terminal measurements demonstrate that boron-doped (B-doped) and phosphorous-doped (P-doped) SiNWs behave as p-type and n-type materials, respectively, and estimates of the carrier mobilities suggest diffusive transport in these nanoscale wires.

SiNWs were synthesized using the laser-assisted catalytic growth (LCG). Briefly, a Nd-YAG laser (532 nm; 8 ns pulse width, 300 mJ/pulse, 10 Hz) may be used to ablate a gold target, which produces gold nanocluster catalyst particles within a reactor. The SiNWs may be grown in a flow of $SiH_4$ as the reactant. Such SiNWs may be doped with boron by incorporating $B_2H_6$ in the reactant flow, and may be doped with phosphorous using a Au—P target (99.5:0.5 wt %, Alfa Aesar) and additional red phosphorous (99%, Alfa Aesar) at the reactant gas inlet. Transmission electron microscopy (TEM) measurements demonstrate that doped SiNWs grown using this technique have a single crystal silicon core that is covered by a dense $SiO_x$ or $SO_2$ sheath as previously described.

Electrical contact to individual SiNWs were made using standard electron beam lithography methods using a JEOL 6400 writer. The nanoscale wires were supported on oxidized Si substrate (1-10 Ωcm resistivity, 600 nm $SiO_2$, Silicon Sense, Inc.) with the underlying conducting Si used as a back gate. The contacts to the SiNWs were made using thermally evaporated Al (50 nm) and Au (150 nm). Electrical transport measurements were made using a homebuilt system with less than or equal to 1 pA noise under computer control. The temperature-dependent measurements were made in a Quantum Design magnetic property measurement system.

TEM studies show that the boron and phosphorous-doped SiNWs are single crystals. It is demonstrated unambiguously the presence of p-type (boron) or n-type (phosphorous) dopants and the relative doping levels using electrical transport spectroscopy. In these measurements, a gate electrode is used to vary the electrostatic potential of the SiNW while measuring current versus voltage of the nanoscale wire. The change in conductance of SiNWs as function of gate voltage can be used to distinguish whether a given nanoscale wire is p-type or n-type since the conductance will vary oppositely for increasing positive (negative) gate voltages.

Figure 8A:
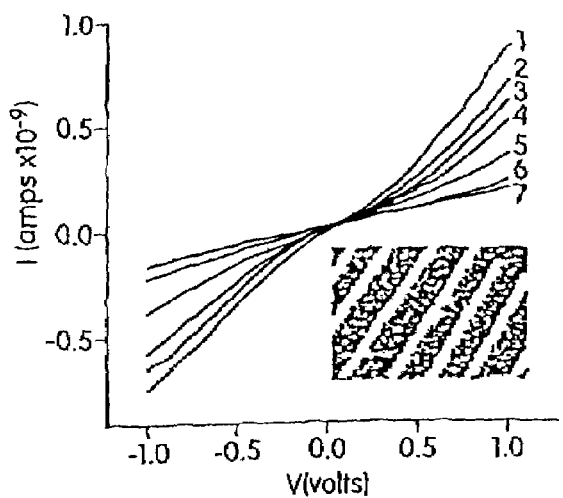
FIGS. 8A-8C show silicon nanoscale current as a function of bias voltage for different doping levels and gate voltages.
Figure 8B:
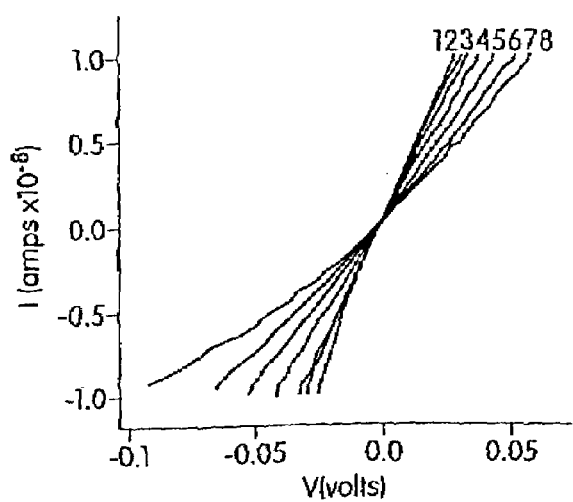
Figure 8C:
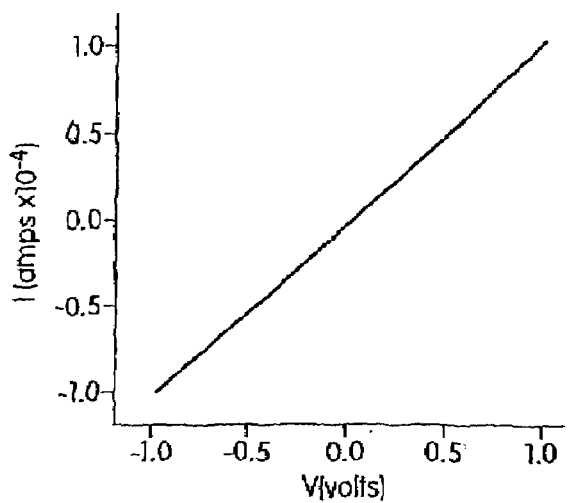

Typical gate-dependent current versus bias voltage (I-V) curves recorded on intrinsic and B-doped SiNWs are shown in FIGS. 8A-8C. The two B-doped wires shown in FIGS. 8B and 8C were synthesized using $SiH_4$:$B_2H_6$ ratios of 1000:1 and 2:1, respectively. In general, the two terminal I-V curves are linear and thus suggest that the metal electrodes make ohmic contacts to the SiNWs. The small nonlinearity observed in the intrinsic nanoscale wire indicates that this contact is slightly nonohmic. Analysis of I-V data, recorded at zero gate voltage ($V_g$=0), which accounts for contributions from the contact resistance and oxide coating on the SiNW, yield a resistivity of $3.9 \times 10^2$ Ωcm. Significantly, when $V_g$ is made increasingly negative (positive), the conductance increases (decreases). This gate dependence shows that the SiNW is a is a p-type semiconductor. Similar I-V versus $V_g$ curves were recorded for the lightly B-doped SiNW, and show that it is also p-type. Moreover, the $V_g$=0 resistivity of this B-doped SiNW (1 Ωcm) is more than two orders of magnitude smaller than the intrinsic SiNW, and demonstrates clearly this ability to chemically control conductivity. This latter point is further supported by I-V measurements on the heavily B-doped SiNWs show in FIG. 8C. This wire has a very low resistivity of $6.9 \times 10^{-3}$ Ωcm and shows no dependence on $V_g$; that is, I-V data recorded with $V_g$ of 0 V and 20 V are overlapping. These results are consistent with a high carrier concentration that is near the metallic limit.

$V_g$-dependent transport in lightly and heavily P-doped SiNWs were measured. The I-V recorded on the lightly doped nanoscale wire (FIG. 9A) is somewhat nonlinear, which indicates nonideal contact between the electrodes and nanoscale wire, and the $V_g$ dependence is opposite of that observed for the B-doped SiNWs. Significantly, this observed gate dependence is consistent with n-type material as expected for P-doping. The estimated resistivity of this wire at $V_g$=0 is $2.6 \times 10^2$ Ωcm. This relatively high resistivity is suggestive of a low doping level and/or low mobility. In addition, heavily P-doped SiNWs have also been made and studied. The I-V data recorded on a typical heavily P-doped wire are linear, have a resistivity of $2.3 \times 10^{-2}$ Ωcm, and shows no dependence on $V_g$. The low resistivity (four orders of magnitude smaller than the lightly P-doped sample) and $V_g$ independence demonstrate that high carrier concentrations can also be created via P-doping of the SiNWs.

The above results demonstrate that boron and phosphorous can be used to change the conductivity of SiNWs over many orders of magnitude and that the conductivity of the doped SiNWs respond oppositely to positive (negative) $V_g$ for boron and phosphorous dopants. Indeed, the $V_g$-dependence provides strong proof for p-type (holes) doping with boron and n-type (electrons) doping with phosphorous in the SiNWs. The observed gate dependencies can be understood by referring to the schematics shown in FIGS. 10A and 10B, which show the effect of the electrostatic potential on the SiNW bands. In these diagrams, a p-type nanoscale wire (FIG. 10A) and n-type nanoscale wire (FIG. 10B) are contacted at both ends to metal electrodes. As for a conventional metal-semiconductor interface, the SiNW bands bend (up for p-type; down for n-type) to bring the nanoscale wire Fermi level in line with that of the metal contacts. When $V_g$>0, the bands are lowered, which depletes the holes in B-doped SiNWs and suppress conductivity, but leads to an accumulation of electrons in P-doped SiNWs and enhance the conductivity. Conversely, $V_g$<0 will raise the bands and increase the conductivity of B-doped (p-type) SiNWs and decrease the conductivity of the P-doped (n-type) nanoscale wires.

In addition, it is possible to estimate the mobility of carriers from the transconductance, $dI/dV_g$=$\mu C/L^2$) V, where $\mu$ is the carrier mobility, C is the capacitance, and L is the length of the SiNW. The SiNW capacitance is given by C is approximately equal to $2\pi\epsilon\epsilon_o L/\ln(2h/r)$, where $\mu$ is the dielectric constant, h is the thickness of the silicon oxide layer, and r is the SiNW radius. Plots of $dI/dV_g$ versus V were found to be linear for the intrinsic (FIG. 8A) and lightly B-doped (FIG. 8B) SiNWs, as expected for this model. The slopes of $dI/dV_g$ for the intrinsic ($2.13 \times 10^{-11}$) and B-doped ($9.54 \times 10^{-9}$) SiNW yield mobilities of $5.9 \times 10^{-3}$ cm$^2$/V/s and 3.17 cm$^2$/V/s, respectively. The mobility for the B-doped nanoscale wire is comparable to that expected in bulk Si at a doping concentration of $10^{20}$ cm$^{-3}$.

Figure 11A:
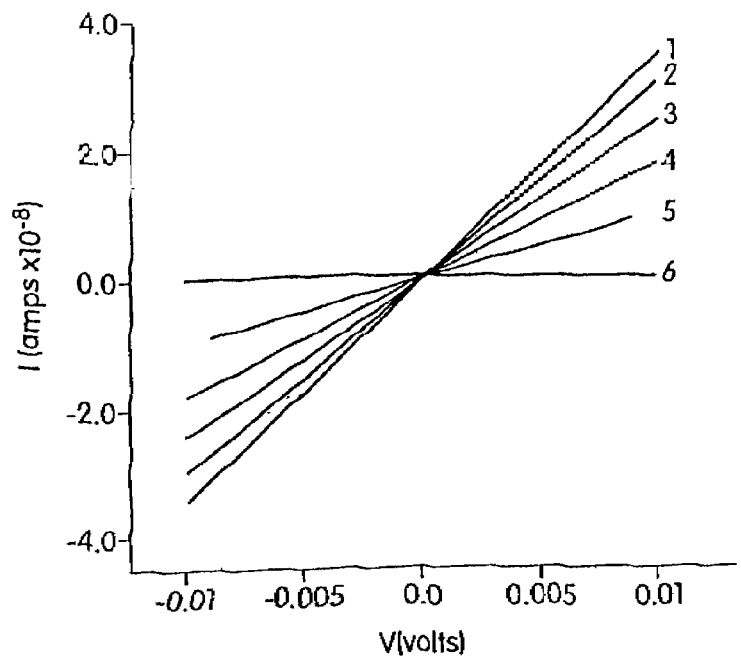
FIGS. 11A and 11B show temperature dependent current-voltage curves recorded on a heavily boron doped silicon nanoscale wire.
Figure 11B:
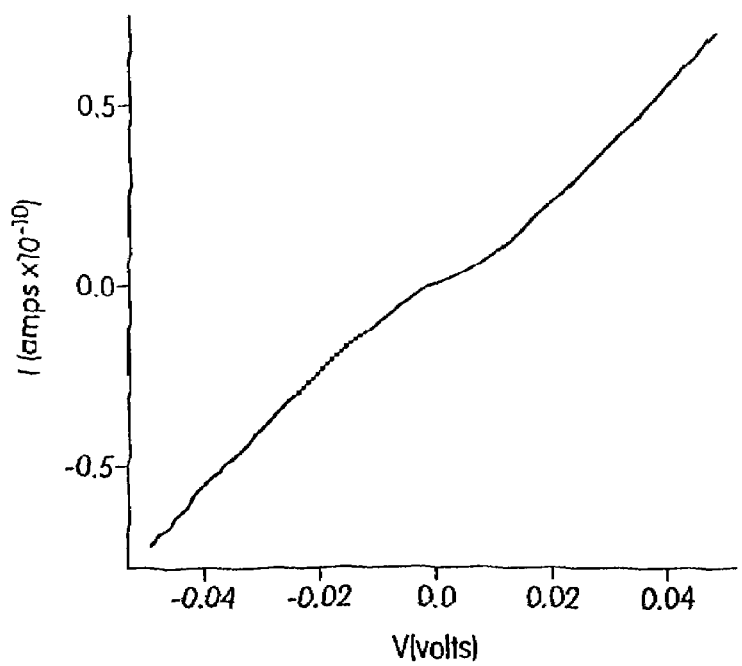

Temperature-dependent studies of heavily B-doped SiNWs were carried out. Temperature dependent I-V curves show that the conductance decreases with decreasing temperature, as expected for a doped semiconductor (FIGS. 11A and 11B). More importantly, no evidence for a coulomb blockade is down to the lowest accessible temperature (FIG. 11B). The small nonlinearity near V=0 is attributed to a contact effect since high resolution I-V versus $V_g$ measurements show no signature for coulomb blockade. Coulomb charging effect in this homogenous wire between the electrodes (a 150 nm thick, 2.3 μm long wire) would require a temperature below about 26 mK estimated from $kT=e^2/2C$. This indicates strongly that variations in SiNW diameter and defects are sufficiently small that they do not effectively "break up" the SiNW into small islands, which would exhibit coulomb blockade at these temperatures. These results contrast studies of lithographically patterned SiNWs, which show coulomb blockade, and testify to the high quality of these free standing nanoscale wires. Single crystal n-type and p-type silicon nanoscale wires (SiNWs) were prepared and characterized by electrical transport measurements. Laser catalytic growth was used to introduce controllably either boron or phosphorous dopants during the vapor phase growth of SiNWs. Two-terminal, gate-dependent measurements made on individual boron-doped and phosphorous-doped SiNWs show that these materials behave as p-type and n-type materials, respectively. Estimates of the carrier mobility made from gate-dependent transport measurements are consistent with diffusive transport, and show an indication for reduced mobility in smaller diameter wires. In addition, these studies show it is possible to incorporate high dopant concentrations in the SiNWs and approach the metallic regime. Temperature-dependent measurements made on heavily doped SiNWs show no evidence for single electron charging at temperatures down to 4.2 K, and thus suggest that the SiNWs possess a high degree of structural and doping uniformity.

Specifically, crossed SiNW p-n junctions were formed by directed assembly of p-type (n-type) SiNWs over n-type (p-type) SiNWs. Transport measurements exhibit rectification in reverse bias and a sharp current onset in forward bias. Simultaneous measurements made on the p-type and n-type SiNWs making up the junction demonstrate that the contacts to these nanoscale wires are ohmic (nonrectifying), and thus that the rectifying behavior is due to the p-n junction between the two SiNWs.

FIG. 8A shows current (I) vs bias voltage (V) curves recorded on a 70 nm diameter intrinsic SiNW at different gate voltages ($V_g$). Curves 1, 2, 3, 4, 5, 6, and 7 correspond to $V_g$=−30, −20, −10, 0V, 10, 20, and 30 V, respectively. The inset is a typical scanning electron micrograph of the SiNW with metal contacts (scale bar=10 em). FIG. 8B shows I-V data recorded on a 150 nm diameter B-doped SiNW; curves 1-8 correspond to $V_g$=−20, −10, −5, 0, 5, 10, 15 and 20 V, respectively. FIG. 8C shows I-V curves recorded on a 150 nm diameter heavily B-doped SiNW; $V_g$=20 V (solid line) and 0 V (heavy dashed line).

Figure 9B:
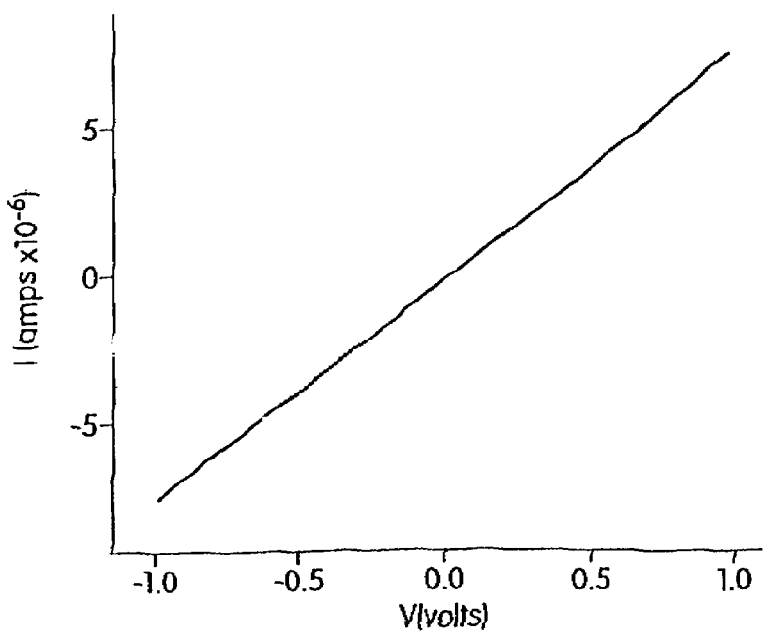

FIG. 9A shows I-V data recorded on a 60 nm diameter P-doped SiNW. Curves 1, 2, 3, 4, 5, and 6 correspond to $V_g$=20, 5, 1, 0, −20, and −30 V, respectively. FIG. 9B shows I-V curves recorded on a 90 nm diameter heavily P-doped SiNW; $V_g$=0 V (solid line) and −20 V (heavy dash line).

Figure 10A:
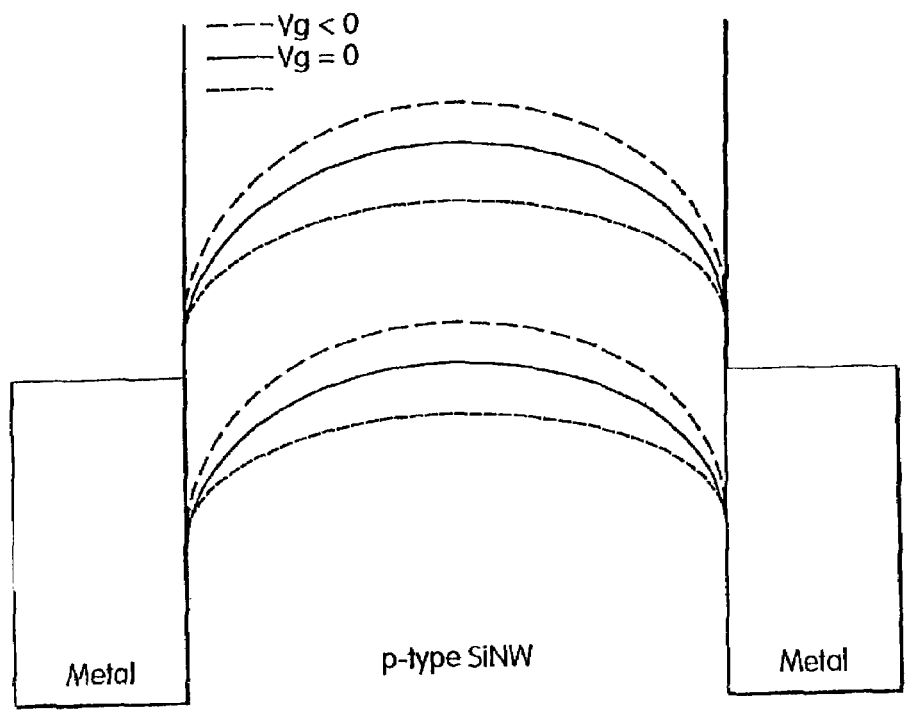
FIGS. 10A and 10B show energy band diagrams for p-type and n-type silicon nanoscale devices, respectively.
Figure 10B:
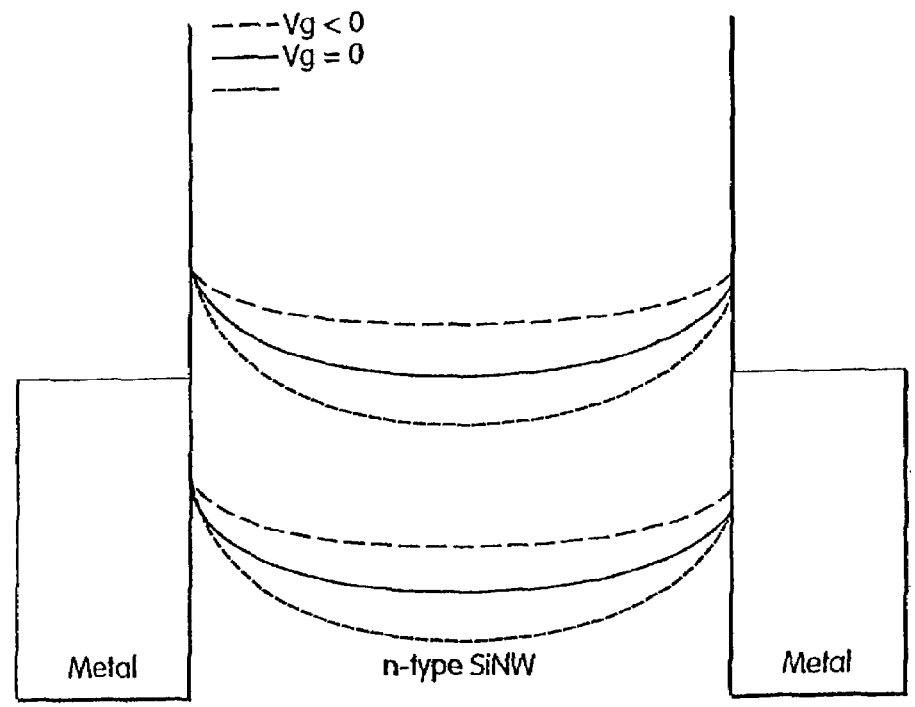

FIG. 10A shows energy band diagrams for p-type SiNW devices. FIG. 10B shows energy band diagrams for n-type SiNW devices. The diagrams show schematically the effect of $V_g$ on the electrostatic potential for both types of nanoscale wires.

FIGS. 11A and 11B show temperature dependent I-V curves recorded on a heavily B-doped SiNW. In FIG. 11A, curves 1, 2, 3, 4, 5, and 6 correspond to temperatures of 295, 250, 200, 150, 100, and 50 K, respectively. FIG. 11B shows I-V data recorded on the nanoscale wire at 4.2 K.

Example 2

Nearly monodisperse samples of single crystalline GaP nanowires were synthesized with diameters of 10, 20, and 30 nm and lengths greater than 10 μm by exploiting well-defined gold colloids as catalysts in this laser catalytic growth (LCG) process. In this method, the Ga and P reactants generated by laser ablation of solid GaP are subsequently directed into a nanowire structure by gold nanocluster catalysts. Transmission electron microscopy (TEM) studies of nanowires prepared in this way demonstrate that the distributions of nanowire diameters are defined by those of the nanocluster catalysts. High-resolution TEM shows that the wires are single crystal zinc blend with a [111] growth direction, and energy dispersive X-ray analysis confirms that the nanowire composition is stoichiometric GaP. The use of monodisperse nanocluster catalysts combined with the LCG method enablesthe growth of a wide range of semiconductor nanoscale wires with well-defined and controlled diameters, and thus provides opportunities from fundamental properties of one-dimensional (1D) systems to the assembly of functional nanodevices.

Figure 12:
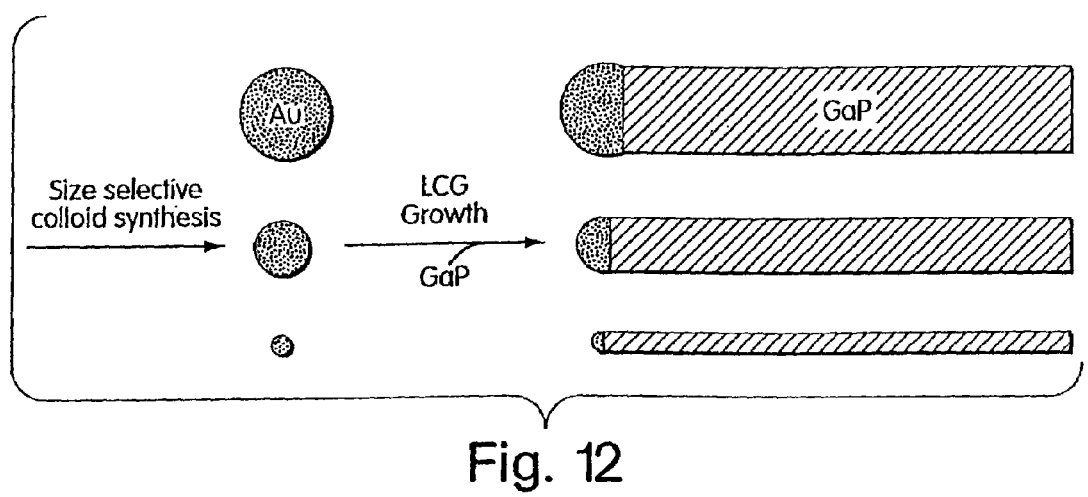
FIG. 12 is a schematic diagram that depicts the use of monodispersed gold colloids as catalysts for the growth of well-defined GaP semiconductor nanoscale wires.

This example also demonstrates the development of a general synthetic approach to free-standing single-crystal semiconductor nanoscale wires via the LCG method. In LCG, laser ablation of a solid target is used to simultaneously generate nanoscale metal catalyst clusters and reactive semiconductor atoms that produce nanoscale wires via a vapor-liquid-solid growth mechanism. This method was used to produce a wide range of groups III-IV-IV, and II-VI nanoscale wires. The size of the catalyst nanocluster determines the size of the wire during growth, and thus one can create wires with a narrow size distribution by exploiting monodisperse catalyst nanoclusters (FIG. 12). Nanometer diameter gold colloids were utilized in this technique.

Figure 13A:
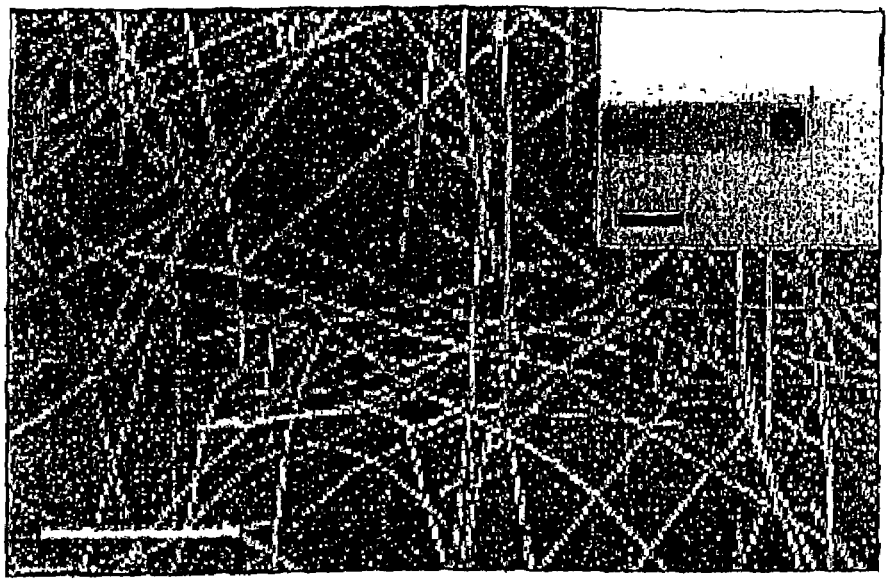
FIG. 13A shows a FE-SEM image of nanoscale wires synthesized from 28.2 nanometer colloids.

GaP nanoscale wires were grown by LCG using 8.4, 18.5, and 28.2 nm diameter gold colloids. In these experiments the catalyst nanoclusters are supported on a SiO$_2$ substrate and laser ablation is used to generate the Ga and P reactants from a solid target of GaP. Field emission scanning electron microscopy (FESEM) demonstrates that nanoscale wires with lengths exceeding 10 μm (FIG. 13A) were obtained using all three sizes of catalyst. Examination of the nanoscale wire ends also shows the presence of the nanocluster catalyst (FIG. 13A, inset). Control experiments carried out without the Au colloids did not produce nanoscale wires. The FESEM images show that the nanoscale wire diameter distributions are narrower than obtained in experiments without the colloid catalysts.

The growth apparatus used in these experiments is described as follows. Substrates were made by placing a silicon wafer with 600 nm of thermal oxide (Silicon Sense) into a solution of 95:5 EtOH:H$_2$O with 0.4% N-[3-(tri-methoxysilyl)propyl]-ethylenediamine for 5 minutes, followed by curing at 100-110° C. for 10 minutes. Solutions of Au colloids were diluted to concentrations of $10^9$-$10^{11}$ particles/mL to minimize aggregation and were deposited on the substrates. Substrates were placed in a quartz tube at the downstream end of the furnace with a solid target of GaP placed 3-4 cm outside of the furnace at the upstream end. The chamber was evacuated to less than 100 mTorr, and then maintained at 250 Torr with an airflow of 100 sccm. The furnace was heated to 700° C. and the target was ablated for 10 minutes with an ArF excimer laser (wavelength=193 nm, 100 mJ/pulse, 10 Hz). After cooling, the substrates were examined by FESEM (LEO 982). For TEM (JEOL 200CX and 2010) and EDAX analysis, nanoscale wires were deposited onto copper grids after removal from the substrates by sonication in ethanol.

TEM was used to obtain a quantitative measure of the nanoscale wire diameter distributions produced using the gold colloids, and to better characterize their structure and composition. High resolution TEM shows that the wires are single crystal (FIG. 13B), growing in the [111] direction, and EDAX confirms the composition to be stoichiometric GaP (Ga:P 1.00:0.94), within the limits of this technique. Significantly, extensive TEM analysis of nanoscale wire diameters demonstrates the extremely good correlation with the colloid catalyst diameters and dispersion (FIGS. 14A and 14B); that is, for wires grown from 28.2±2.6, 18.5±0.9, and 8.4±0.9 nm colloids were observed with mean diameters of 30.2±2.3, 20.0±1.0, and 11.4±1.9 nm, respectively. The mean nanoscale wire diameter is generally 1-2 nm larger than that of the colloids. This increase is due to alloying of the Ga and P reactants with the colloids before nucleation of the nanoscale wire occurs. For the 30 nm and 20 nm wires (FIGS. 14A and 14B, respectively) it is clear that the width of the nanoscale wire distributions mirrors those of the colloid, suggesting that the monodispersity of the wires is limited only by the dispersity of the colloids. For the 10 nm diameter wires (FIG. 14C), a small broadening (1 nm) of the wire distribution can be attributed to aggregation of the colloids. The mean diameter and distribution width increased as more concentrated solutions of the colloid were dispersed onto the substrate. The fact that the distribution has peaks separated by about 2.5 nm suggests that some of the wires grow from aggregates of two colloids. In all cases, the distribution of wire diameters is more than an order of magnitude narrower than those grown without the use of colloid catalyst (FIG. 14D): 43±24 nm.

This work demonstrates an ability to exert systematic control over the diameter of semiconductor nanoscale wires for a variety of colloids. In summary, demonstration of the controlled synthesis of semiconductor wires with monodisperse diameter distributions has been accomplished.

Specifically, FIG. 12 is a schematic depicting the use of monodisperse gold colloids as catalysts for the growth of well-defined GaP semiconductor nanoscale wires.

Figure 13B:
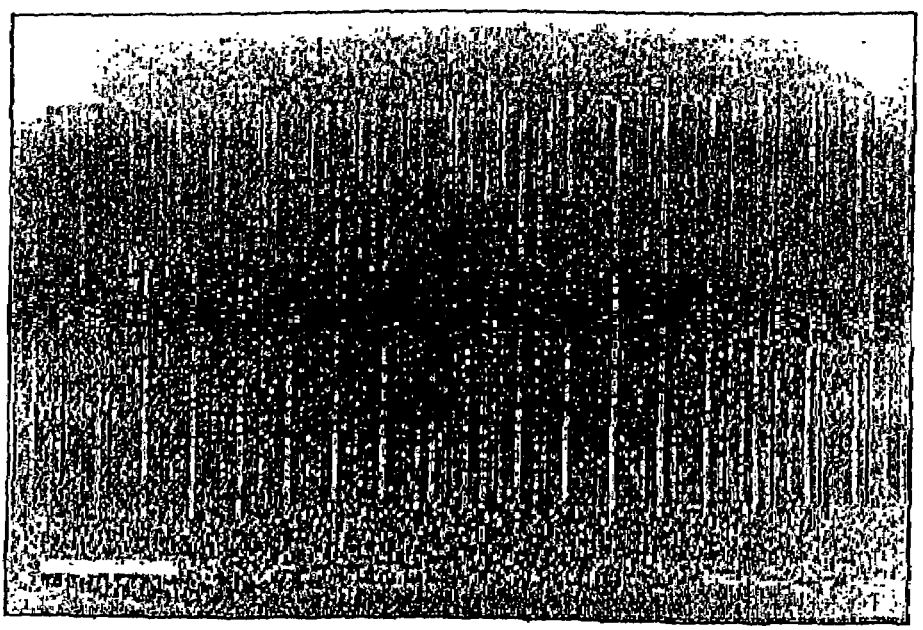
FIG. 13B shows a TEM image of another wire in the sample.

FIG. 13A shows a FESEM image of nanoscale wires synthesized from 28.2 nm colloids (scale bar is 5 μm). The inset is a TEM image of the end of one of these wires (scale bar is 50 nm). The high contrast feature corresponds to the colloid catalyst at the end of the wire. FIG. 13B shows a TEM image of another wire in this sample (scale bar is 10 nm). The [111] lattice planes are resolved, showing that wire growth occurs along this axis, in agreement with earlier work. Measurement of the inter-plane spacing gives a lattice constant of 0.54 nm (±0.05 nm) for the wire, in agreement with the bulk value for GaP, 0.5451 nm.

Figure 14A:
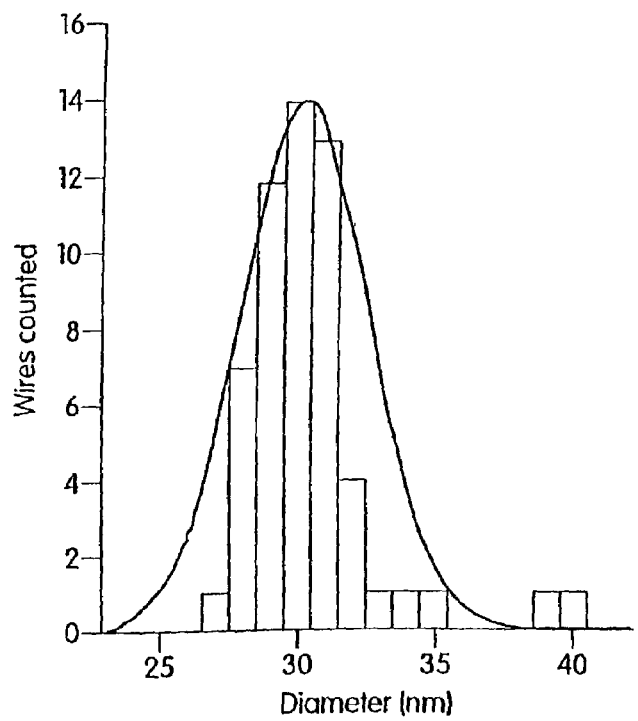
FIGS. 14A-14C show histograms of measured diameters for wires grown from different diameter colloids.
Figure 14B:
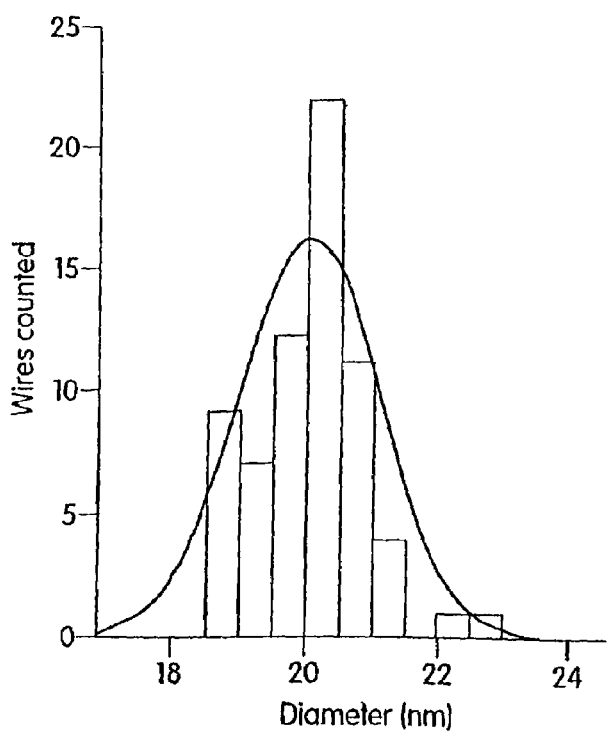
Figure 14C:
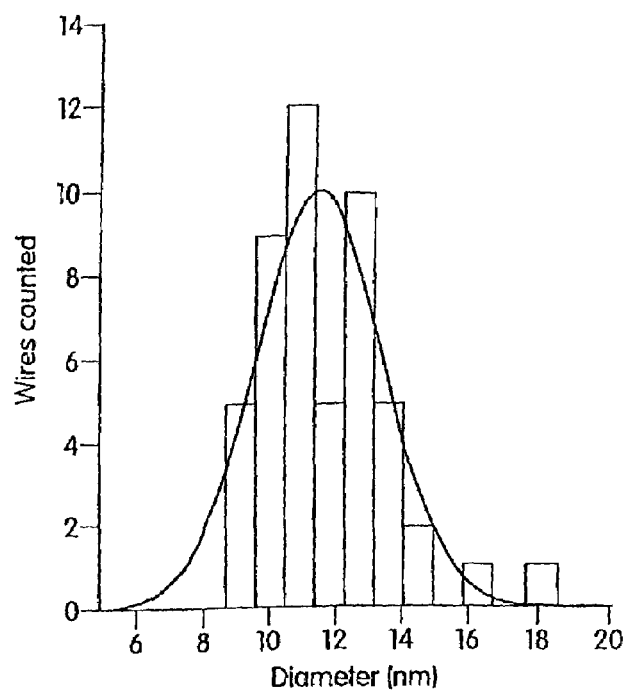
Figure 14D:
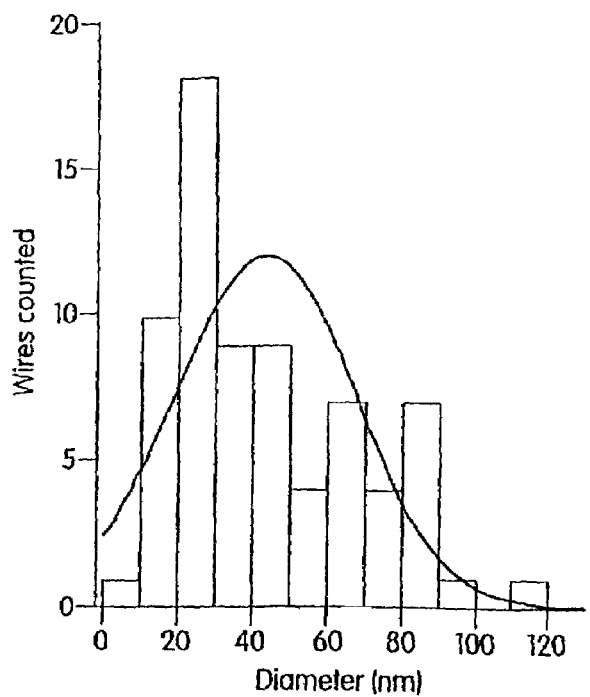
FIG. 14D shows a histogram of diameters for wires grown using the previous method without colloids, in which the laser is used to both generate the gold nanoclusters and the GaP reactants.

FIGS. 14A-14C show histograms of measured diameters for wires grown from 28.2 nm (FIG. 14A), 18.5 nm (FIG. 14B), and 8.4 nm (FIG. 14C) colloids. The solid line shows the distribution of wire. FIG. 14D shows a histogram of diameters for wires grown using the previous method without colloids, in which the laser is used to both generate the Au nanoclusters and the GaP reactants. The distribution is very broad (standard deviation=23.9 nm) and the mean diameter (42.7 nm) greater than those synthesized using the predefined colloid catalyst. In all cases, the reported nanoscale wire diameters correspond to the crystalline cores. The amorphous oxide layers on the surface of all nanoscale wires are relatively uniform from wire to wire within the same experiment, but vary from 2-6 nm in thickness between syntheses.

Example 3

The synthesis of a broad range of multicomponent semiconductor nanoscale was accomplished using laser-assisted catalytic growth. Nanoscale wires of binary group III-V materials (GaAs, GaP, InAs and InP), ternary III-V materials (GaAs/P, InAs/P), binary II-VI compounds (ZnS, ZnSe, CdS, and CdSe) and binary SiGe alloys were prepared in bulk quantities as high purity (>90%) single crystals. The nanoscale wires have diameters varying from three to tens of nanometers, and lengths extending to tens of micrometers. The synthesis of this wide range of technologically important semiconductor nanoscale wires can be extended to many other materials.

The present technique involves the growth of elemental Si and Ge nanoscale wires using the LCG method, which uses laser ablation to generate nanometer diameter catalytic clusters that define the size and direct the growth of the crystalline nanoscale wires by a vapor-liquid-solid (VLS) mechanism. A key feature of the VLS growth process and the LCG method is that equilibrium phase diagrams can be used to select catalysts and growth conditions, and thereby enable rational synthesis of new nanoscale wire materials. Significantly, the present example shows here that semiconductor nanoscale wires of the III-V materials GaAs, GaP, GaAsP, InAs, InP and InAsP, the II-VI materials ZnS, ZnSe, CdS and CdSe, and IV-IV alloys of SiGe can be synthesized in high yield and purity using this approach. Compound semiconductors, such as GaAs and CdSe, are especially intriguing targets since their direct band gaps give rise to attractive optical and electrooptical properties. The nanoscale wires were prepared as single crystals with diameters as small as 3 nm, which places them in a regime of strong radial quantum confinement, and lengths exceeding 10 μm. These studies demonstrate that LCG represents a very general and controllable approach for nanoscale wire synthesis.

Figure 15:
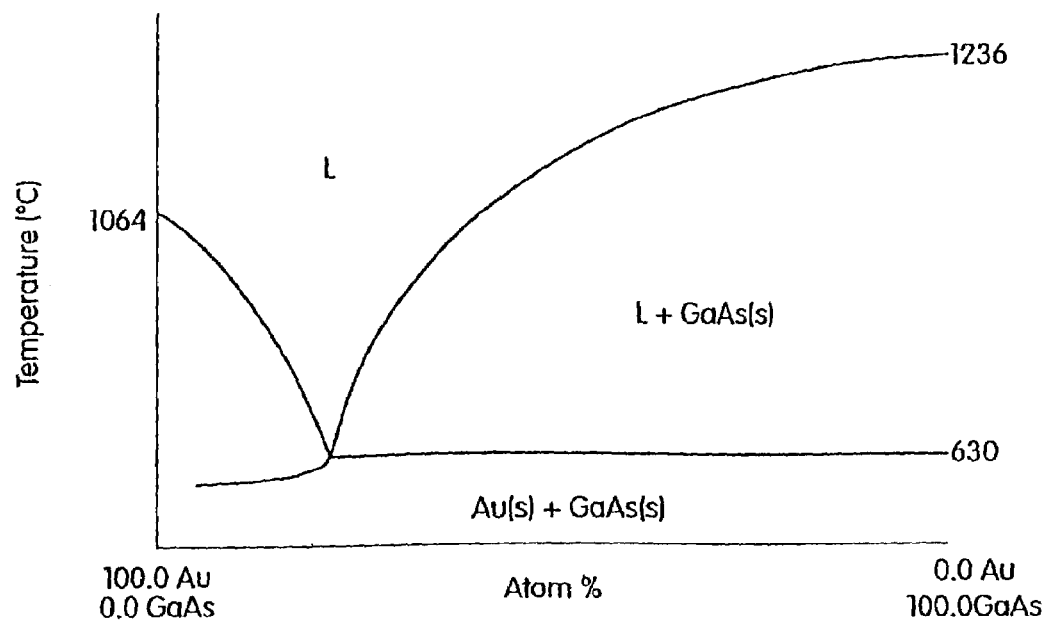
FIG. 15 shows a pseudobinary phase diagram for gold and gallium arsenide.

The selection and control of growth conditions for binary and more complex nanoscale wires using the LCG method can be enhanced by considering pseudobinary phase diagrams for the catalyst and compound semiconductor of interest. For example, the pseudobinary phase diagram of Au—GaAs shows that Au—Ga/As liquid and GaAs solid are the principle phases above 630° C. in the GaAs rich region (FIG. 15). This implies that Au can serve as a catalyst to grow GaAs nanoscale wires by the LCG method, if the target composition and growth temperature are set to this region of the phase diagram. Indeed, LCG using (GaAs)$_{0.95}$Au$_{0.05}$ targets produce samples consisting primarily of nanoscale wires. A typical field-emission scanning electron microscopy (FE-SEM) image of material prepared at 890° C. (FIG. 16A) shows that the product is wire-like with lengths extending to 10 μm or more. Analyses of these high-resolution SEM images shows that at least 90% of the product produced by the LCG method is nanoscale wire with only a small amount of particle material. X-ray diffraction data from bulk samples can be indexed to the zinc-blende (ZB) structure with a lattice constant consistent with bulk GaAs, and also show that the material is pure GaAs to the 1% level. Lastly, it is noted that high yields of GaAs nanoscale wires were also obtained using Ag and Cu catalysts. These data are consistent with the fact that these metals (M=Ag, Cu) exhibit M-Ga/As liquid and GaAs solid phase in the GaAs rich regions of the psuedobinary phase diagrams, and furthermore, demonstrate the predictability of the LCG approach to nanoscale wire growth.

The structure and composition of the GaAs nanoscale wires were characterized in detail using transmission electron microscopy (TEM), convergent beam electron diffraction (ED) and energy dispersive X-ray fluorescence (EDX). TEM studies show that the nanoscale wires have diameters ranging from about 3 nm to about 30 nm. A typical diffraction contrast image of a single 20 nm diameter wire (FIG. 17A) indicates that the wire is single crystal (uniform contrast) and uniform in diameter. The Ga:As composition of this wire determined by EDX, 51.4:48.6, is the same, within limits of instrument sensitivity, as the composition obtained from analysis of a GaAs crystal standard. Moreover, the ED pattern recorded perpendicular to the long axis of this nanoscale wire (inset, FIG. 17A) can be indexed for the <112> zone axis of the ZB GaAs structure, and thus shows that growth occurs along the [111] direction. Extensive measurements of individual GaAs nanoscale wires show that growth occurs along the <111> directions in all cases. This direction and the single crystal structure are further confirmed by lattice resolved TEM images (e.g., FIG. 17B) that show clearly the (111) lattice planes (spacing 0.32 nm+/−0.01 nm; bulk GaAs, 0.326 nm) perpendicular to the wire axis. Lastly, the TEM studies reveal that most nanoscale wires terminate at one end with a nanoparticle (inset, FIG. 16A). EDX analysis indicates that the nanoparticles are composed mainly of Au. The presence of Au nanoparticles at the ends of the nanoscale wires is consistent with the pseudobinary phase diagram, and represents strong evidence for a VLS growth mechanism proposed for LCG.

The successful synthesis of binary GaAs nanoscale wires by LCG is not an isolated case but general to a broad range of binary and more complex nanoscale wire materials (Table-1). To extend this synthetic approach to the broadest range of nanoscale wires, catalysts for LCG can be chosen in the absence of detailed phase diagrams by identifying metals in which the nanoscale wire component elements are soluble in the liquid phase but that do not form solid compounds more stable than the desired nanoscale wire phase; that is, the ideal metal catalyst should be physically active but chemically stable. From this perspective the noble metal Au is a good starting point for many materials. It is significant that this LCG method is readily extended to many different materials (e.g., Table-1) simply by producing solid targets of the material of interest and catalyst.

Work on GaAs was extended to include GaP and ternary alloys $GaAs_{1-x}P_x$. FE-SEM images of the product obtained by LCG from $(GaP)_{0.95}Au_{0.05}$ targets exhibit high purity nanoscale wires with lengths exceeding 10 μm (FIG. 16B). Extensive TEM characterization shows that these nanoscale wires: (i) are single crystal GaP, (ii) grow along the <111> directions, and (iii) terminate in Au nanoparticles (inset, FIG. 16B) as expected for the LCG mechanism. The limits of the LCG has further tested the approach through studies of ternary GaAsP alloy nanoscale wires. The synthesis of ternary III-V alloys is of particular interest for band gap engineering that is critical for electronic and optical devices. LCG of GaAsP nanoscale wires using a $GaAs_{0.6}P_{0.4}$ target with a Au catalyst yielded nearly pure nanoscale wires (FIG. 16C). TEM images, ED and EDX show that these nanoscale wires are single crystals, grow along the <111> directions, have a Ga:As:P ratio, 1.0:0.58:0.41, that is essentially the same as the starting target composition, and terminate in nanoclusters that are composed primarily of Au (inset, FIG. 16C). High-resolution TEM images recorded on nanoscale wires with diameters of about 10 and 6 nm (FIGS. 17C and 17D) show well-ordered (111) lattice planes and no evidence for compositional modulation.

Figure 18A:
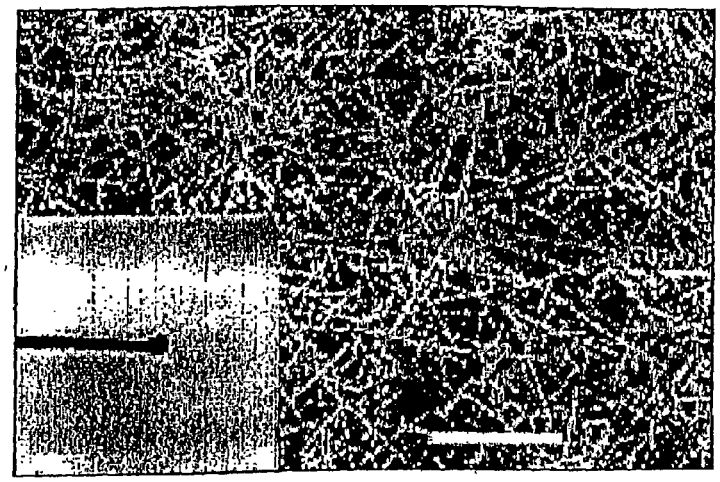
FIG. 18A shows a FE-SEM image of CdSe nanoscale wires prepared by laser assisted catalytic growth.

LCG was also used successfully to prepare III-V binary and ternary materials containing In-As-P (Table-1). This synthetic approach can also be easily extended to the preparation of many other classes of nanoscale wires, including the II-VI materials ZnS, ZnSe, CdS and CdSe (Table-l), IV-IV SiGe alloys. The cases of the II-VI nanoscale wires CdS and CdSe are especially important, because a stable structural phase of these materials, wurtzite (W), is distinct from the ZB structure of the III-V materials described above and the ZB structure of ZnS and ZnSe. Significantly, it is found that nanoscale wires of CdS and CdSe can be synthesized in high yield using the LCG approach with a Au catalyst (FIG. 18A). TEM and ED data obtained on individual CdSe nanoscale wires (for example, FIGS. 18B and 18C) demonstrate that these materials are single crystals with a W-type structure and <110> growth direction that is clearly distinguished from the <111> direction of ZB structures.

LCG also was used to prepare nanoscale wires of IV-IV binary Si—Ge alloys (Table-1). Using a Au catalyst, it was possible to synthesize single crystal nanoscale wires over the entire $Si_{1-x}Ge_x$ composition range. Unlike the case of GaAsP discussed above, the Si—Ge alloys do not exhibit the same compositions as the starting targets. Rather, the composition varies continuously within the growth reactor with Si rich materials produced in the hotter central region and Ge rich materials produced at the cooler end. Specifically, LCG growth from a $(Si_{0.70}Ge_{0.30})_{0.95}Au_{0.05}$ target at 1150° C. produced nanoscale wires with a Si:Ge ratio of 95:5, 81:19, 74:26, 34:66 and 13:87 from the furnace center to end, respectively. This composition variation arises from the fact that the optimal growth temperatures of the two individual nanoscale wire materials are quite different. Such differences can be used to prepare a range of alloy compositions in a single growth experiment.

In conclusion, a wide-range of single crystal binary and ternary compound semiconductor nanoscale wires have been synthesized using this LCG technique, demonstrating the usefulness of this approach for rational nanoscale wire synthesis. These nanoscale wires can be used to probe the confinement, dynamics and transport of excitons in 1D, and can serve as optically-active building blocks for nanostructured materials. Moreover, the LCG approach can be used to synthesize more complex nanoscale wire structures, including single wire homo- and heterojunctions and superlattices, and thus enables the synthesis of nanoscale light-emitting diodes and laser devices.

The apparatus and general procedures for LCG growth of nanoscale wires are specifically described: The targets used in syntheses consisted of $(material)_{0.95}Au_{0.05}$. Typical conditions used for synthesis were: (i) 100-500 torr Ar:H$_2$ (95:5), (ii) 50-150 sscm gas flow, and (iii) ablation with a pulsed Nd:YAG laser (wavelength=1064 nm; 10 Hz pulse rate; 2.5 W average power). Specific temperatures used for the growth of different nanoscale wire materials are given in Table-1. The nanoscale wire products were collected at the down-stream cold end of the furnace.

The nanoscale wire samples were characterized using X-ray diffraction (SCINTAG XDS 2000), FE-SEM (LEO 982), and TEM (Philips 420 and JEOL 2010). Electron diffraction and composition analysis (EDX) measurements were also made on the TEMs. Samples for TEM analysis were prepared as follows: samples were briefly sonicated in ethanol, which suspended the nanoscale wire material, and then a drop of suspension was placed on a TEM grid and allowed to dry.

Table 1 is a summary of single crystal nanoscale wires synthesized. The growth temperatures correspond to ranges explored in these studies. The minimum (Min.) and average (Ave.) nanoscale wire diameters (Diam.) were determined from TEM and FE-SEM images. Structures were determined using electron diffraction and lattice resolved TEM imaging: ZB, zinc blende; W, wurtzite; and D, diamond structure types. Compositions were determined from EDX measurements made on individual nanoscale wires. All of the nanoscale wires were synthesized using Au as the catalyst, except GaAs, for which Ag and Cu were also used. The GaAs nanoscale wires obtained with Ag and Cu catalysts have the same size, structure and composition as those obtained with the Au catalyst.

$GaAs_{0.6}P_{0.4}$ nanoscale wires. The (111) lattice planes (perpendicular to the wire axes) are clearly resolved in all three nanoscale wires. The scale bars in FIGS. 17C and 17D are 5 nm.

Figure 18B:
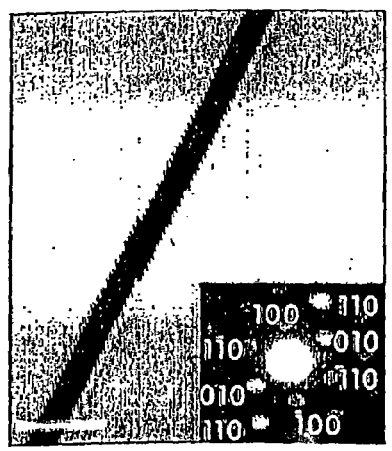
FIG. 18B shows a diffraction contrast TEM image of an 18 nanometer diameter CdSe nanoscale wire.
Figure 18C:
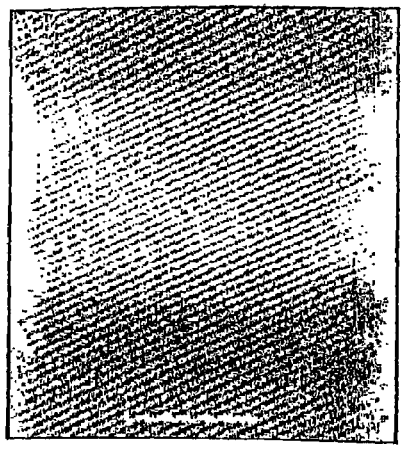
FIG. 18C shows a high resolution TEM image of an approximately 13 nanometer diameter CdSe nanoscale wire.

FIG. 18A shows a FE-SEM image of CdSe nanoscale wires prepared by LCG. The scale bar corresponds to 2 μm. The inset in FIG. 18A is a TEM image of an individual CdSe nanoscale wire exhibiting nanocluster (dark feature) at the wire end. EDX shows that the nanocluster is composed primarily of Au. The scale bar is 50 nm. FIG. 18B shows a diffraction contrast TEM image of a 18 nm diameter CdSe nanoscale wire. The uniform contrast indicates that the nanoscale wire is single crystal. The inset in FIG. 18B is an ED pattern, which has been indexed to the wurtzite structure, recorded along the <001> zone axis. The [110] direction of the ED pattern is parallel to the wire axis, and thus shows that growth occurs along the [110] direction. The scale bar is 50 nm. FIG. 18C shows a high-resolution TEM image of a about 13 nm diameter CdSe nanoscale wire exhibiting well-resolved (100) lattice planes. The experimental lattice spacing, 0.36±0.01 nm is consistent with the 0.372 nm separation in bulk crystals. The 30° orientation (100) lattice planes with respect to the nanoscale wire axis

TABLE 1

| Material | Growth Temp. (° C.) | Min. Diam. (nm) | Ave. Diam. (nm) | Structure | Growth Direction | Ratio of Components |
|---|---|---|---|---|---|---|
| GaAs | 800-1030 | 3 | 19 | ZB | <111> | 1.00:0.97 |
| GaP | 870-900 | 3-5 | 26 | ZB | <111> | 1.00:0.98 |
| $GaAs_{0.6}P_{0.4}$ | 800-900 | 4 | 18 | ZB | <111> | 1.00:0.58:0.41 |
| InP | 790-830 | 3-5 | 25 | ZB | <111> | 1.00:0.98 |
| InAs | 700-800 | 3-5 | 11 | ZB | <111> | 1.00:1.19 |
| $InAs_{0.5}P_{0.5}$ | 780-900 | 3-5 | 20 | ZB | <111> | 1.00:0.51:0.51 |
| ZnS | 990-1050 | 4-6 | 30 | ZB | <111> | 1.00:1.08 |
| ZnSe | 900-950 | 3-5 | 19 | ZB | <111> | 1.00:1.01 |
| CdS | 790-870 | 3-5 | 20 | W | <100>, <002> | 1.00:1.04 |
| CdSe | 680-1000 | 3-5 | 16 | W | <110> | 1.00:0.99 |
| $Si_{1-x}Ge_x$ | 820-1150 | 3-5 | 18 | D | <111> | $Si_{1-x}Ge_x$ |

FIG. 15 shows a pseudobinary phase diagram for Au and GaAs. The liquid Au—Ga—As component is designated by L.

Figure 16A:
FIGS. 16A-16C show FE-SEM images of different nanoscale wires prepared by laser assisted catalytic growth.
Figure 16B:
Figure 16C:

FIGS. 16A-16C show FE-SEM images of GaAs (FIG. 16A), GaP (FIG. 16B) and $GaAs_{0.6}P_{0.4}$ (FIG. 16C) nanoscale wires prepared by LCG. The scale bars in FIGS. 16A-16C are 2 μm. The insets in FIGS. 16A-16C are TEM images of GaAs, GaP and $GaAs_{0.6}P_{0.4}$ nanoscale wires, respectively. The scale bars in are all 50 nm. The high contrast (dark) features correspond to the solidified nanocluster catalysts.

Figure 17A:
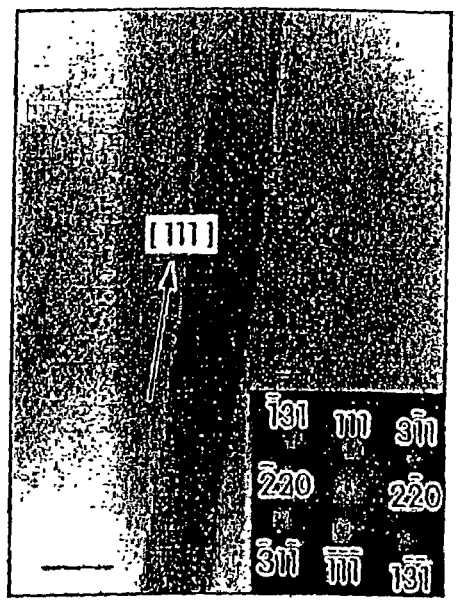
FIG. 17A shows a diffraction contrast TEM image of an approximately 20 nanometer diameter gallium arsenide nanoscale wire.
Figure 17B:
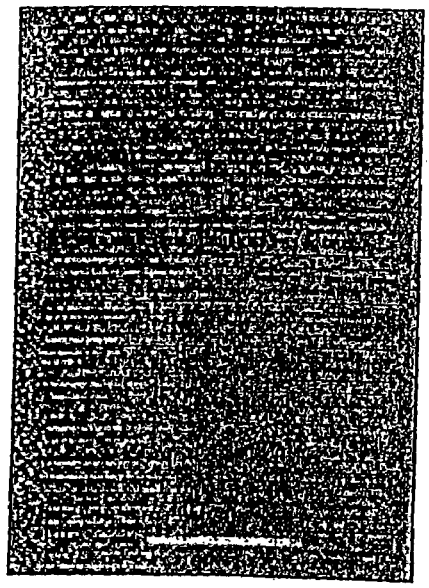
FIGS. 17B-17D show high resolution TEM images of different diameter nanoscale wires.
Figure 17C:
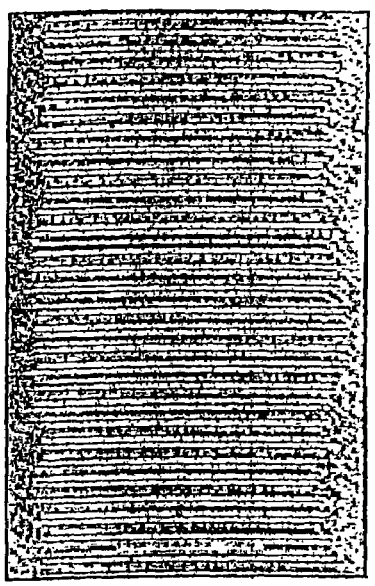
Figure 17D:
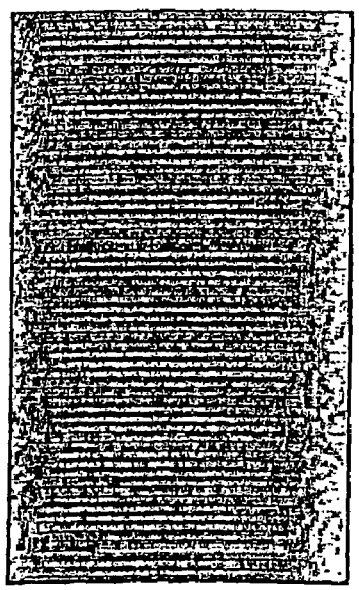

FIG. 17A shows a diffraction contrast TEM image of a about 20 nm diameter GaAs nanoscale wire. The inset shows a convergent beam electron diffraction pattern (ED) recorded along the <112> zone axis. The [111] direction of the ED pattern is parallel to the wire axis, and thus shows that growth occurs along the [111] direction. The scale bar corresponds to 20 nm. FIG. 17B shows a high-resolution TEM image of a ca. 20 nm diameter GaAs nanoscale wire. The lattice spacing perpendicular to the nanoscale wire axis, 0.32±0.01 nm, is in good agreement with the 0.326 nm spacing of (111) planes in bulk GaAs. The scale bar corresponds to 10 nm. FIGS. 17C and 17D show high-resolution TEM images of 10 and 6 nm diameter, respectively, is consistent with the [110] growth direction determined by ED. The scale bar corresponds to 5 nm.

Example 4

Single crystalline GaN nanoscale wires were synthesized in bulk quantities using laser-assisted catalytic growth (LCG). Laser ablation of a (GaN, Fe) composite target generates liquid nanoclusters that serve as catalytic sites confining and directing the growth of crystalline nanoscale wires. Field emission scanning electron microscopy shows that the product primarily consists of wire-like structures, with diameters on the order of 10 nm, and lengths greatly exceeding 1 μm. Powder X-ray diffraction analyses of bulk nanoscale wire samples can be indexed to the GaN wurtzite structure, and indicate >95% phase purity. Transmission electron microscopy, convergent beam electron diffraction, and energy dispersive X-ray fluorescence analyses of individual nanoscale wires show that they are GaN single crystals with a [100] growth direction.

Figure 19:
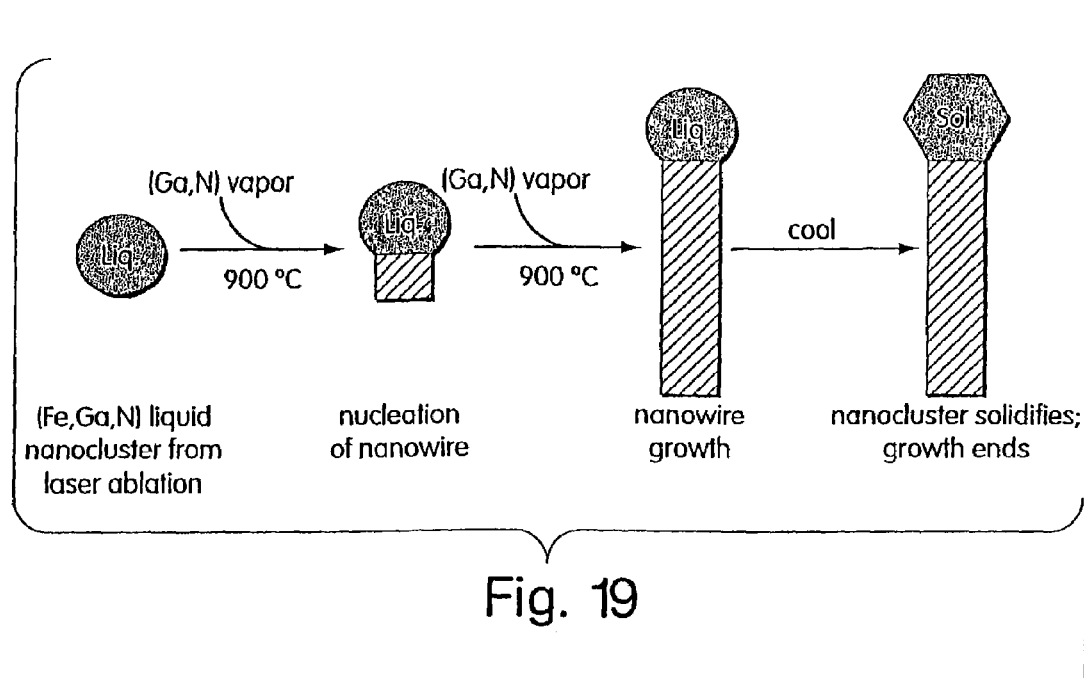
FIG. 19 is a schematic diagram showing GaN nanoscale wire growth by laser assisted catalytic growth.

Nanostructured GaN materials were formed as follows. Catalyst was selected based on the growth process. Specifically, the catalyst was selected to form a miscible liquid phase with GaN but not form a more stable solid phase under the nanoscale wire growth conditions. Fe, which dissolves both Ga and N, and does not form a more stable compound than GaN was determined to be a good catalyst for GaN nanoscale wire growth by LCG. The overall evolution of nanoscale wire growth following the generation of the catalytic nanocluster by laser ablation is illustrated in FIG. 19.

Figure 20A:
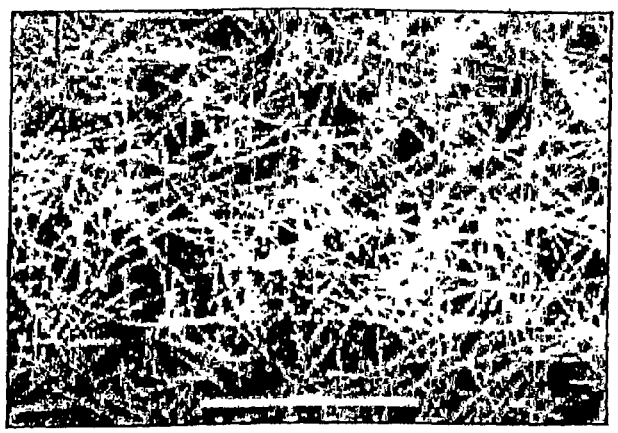
FIG. 20A shows a FE-SEM image of bulk GaN nanoscale wire synthesized by laser assisted catalytic growth.
Figure 20B:
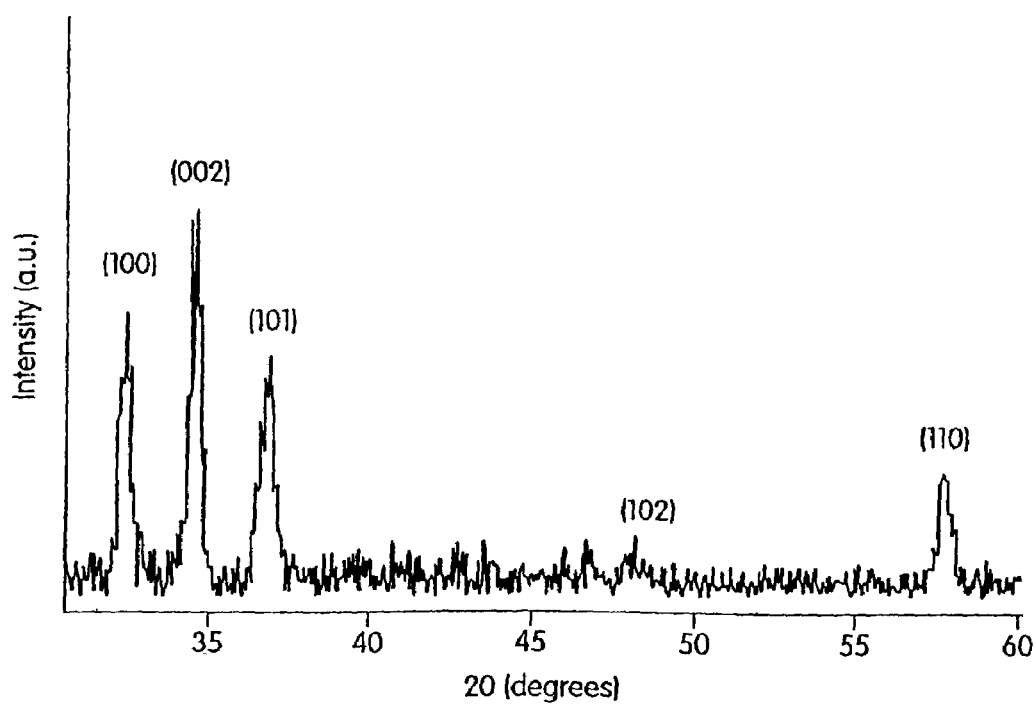
FIG. 20B shows a PXRD pattern recorded on bulk GaN nanoscale wires.

Significantly, it was found that LCG using a GaN/Fe target produces a high yield of nanometer diameter wire-like structures. A typical FE-SEM image of the product produced by LCG (FIG. 20A) shows that the product consists primarily of 1D structures with diameters on the orders of 10 nm and lengths greatly exceeding 1 µm; that is, high aspect ratio nanoscale wires. The FE-SEM data also show that the products consist of ca. 90% nanoscale wires, with the remaining being nanoparticles. Also assessed is the overall crystal structure and phase purity of the bulk nanoscale wire samples using PXRD (FIG. 20B). All the relatively sharp diffraction peaks in the PXRD pattern can be indexed to a wurtzite structure with lattice constants of a=3.187 and c=5.178 Å. These values are in good agreement with literature values for bulk GaN: a=3.189, c=5.182 Å. In addition, comparison of the background signal and observed peaks indicates that the GaN wurtzite phase represents >95% of the crystalline material produced in the syntheses.

The LCG experimental apparatus was as follows: A GaN/Fe (atomic ratio (GaN):Fe=0.95:0.05) composite target was positioned with a quartz tube at the center of a furnace. The experimental system was evacuated to 30 mtorr, and then refilled with anhydrous ammonia gas. While the pressure and flow rate were maintained at about 250 torr and 80 sccm, respectively, the furnace temperature was increased to 900° C. at 30° C./min. A pulsed Nd-YAG laser (1064 nm, 8 ns pulse width, 10 Hz repetition, 2.5 W average power) was then used to ablate the target with a typical ablation duration of 5 min. After ablation, the furnace was turned off and allowed to cool to room temperature. The system was then vented and light yellowish powders were collected from the end of inner quartz tube wall. The product was used directly for FE-SEM and PXRD studies. The product was suspended in ethanol and then transferred onto TEM grids for TEM, CBED and EDX measurements.

The morphology, structure and composition of the GaN nanoscale wires were characterized in further detail using TEM, CBED and EDX. TEM studies show that the nanoscale wires are straight with uniform diameters, and typically terminate in a nanoparticle at one end. FIG. 20A shows a representative diffraction contrast image of one nanoscale wire. The uniform contrast along the wire axis indicates that the nanoscale wire is a single crystal. The nanoparticle (dark, high contrast feature) observed at the nanoscale wire end is faceted as expected following crystallization of the liquid nanocluster (FIG. 19). Also, EDX is used to address the composition of the nanoscale wires and terminal nanoparticles. Data recorded on the nanoscale wire show only Ga and N in a ratio ca. the same as a GaN standard, while the nanoparticles contain Ga, N, and Fe. The presence of Fe (with Ga and N) only in the terminal nanoparticle confirms the catalytic nature of Fe in the synthesis.

To probe further the importance of the catalyst, GaN nanoscale wire growth using a Au catalyst was investigated. Gold has been used recently as a catalyst for growth of a number of nanoscale wires of III-V and II-VI material, and as such might be expected to also function effectively in the growth of GaN nanoscale wires. However, Au exhibits poor solubility of N and thus may not transport N efficiently to the liquid/solid growth interface. Consistent with this analysis, GaN nanoscale wire, using the Au catalyst have not been obtained. This highlights the important role of the catalyst and how it can be rationally chosen.

The structure of GaN nanoscale wires was characterized in greater detail using CBED and high resolution TEM (HRTEM). A typical CBED pattern (inset, FIG. 21A) of a nanoscale wire exhibits a sharp diffraction pattern consistent with the single crystal structure inferred from the diffraction contrast images. Indexing this pattern further demonstrates that the [100] direction is aligned along the wire axis. In addition, FIG. 21B shows a lattice resolved HRTEM image of a GaN nanoscale wire with a about 10 nm diameter. The image, which was recorded along the <001> zone axis, shows clearly the single crystal structure of the nanoscale wire and the lattice planes along the [100], [010] and [−110] directions. This image demonstrates that the [100] direction runs parallel to the wire axis, and thus confirms the [100] growth direction in GaN nanoscale wires.

In conclusion, the LCG method for the rational synthesis of GaN nanoscale wires was exploited. Highly pure GaN nanoscale wires were obtained as single crystals with a unique [100] growth direction. This approach can be readily extended to the synthesis of InN, (GaIn)N alloys and related nitride nanoscale wires.

Specifically, FIG. 19 is a schematic diagram showing GaN nanoscale wire growth by laser-assisted catalytic growth.

FIG. 20A shows a FE-SEM (LEO 982) image of bulk GaN nanoscale wires synthesized by LCG. The scale bar corresponds to 1 µm. FIG. 20B shows a PXRD (Scintag, XDS2000) pattern recorded on bulk GaN nanoscale wires. The numbers above the peaks correspond to the (hkl) values of the wurtzite structure.

Figure 21A:
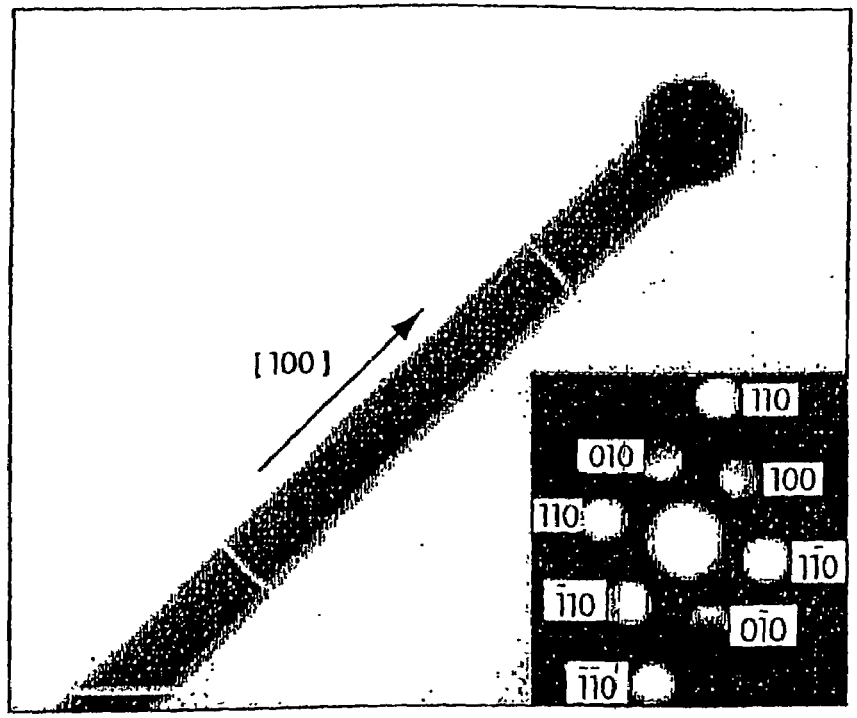
FIG. 21A shows a diffraction contrast TEM image of a GaN nanoscale wire that terminates in a faceted nanoparticle of higher contrast.
Figure 21B:
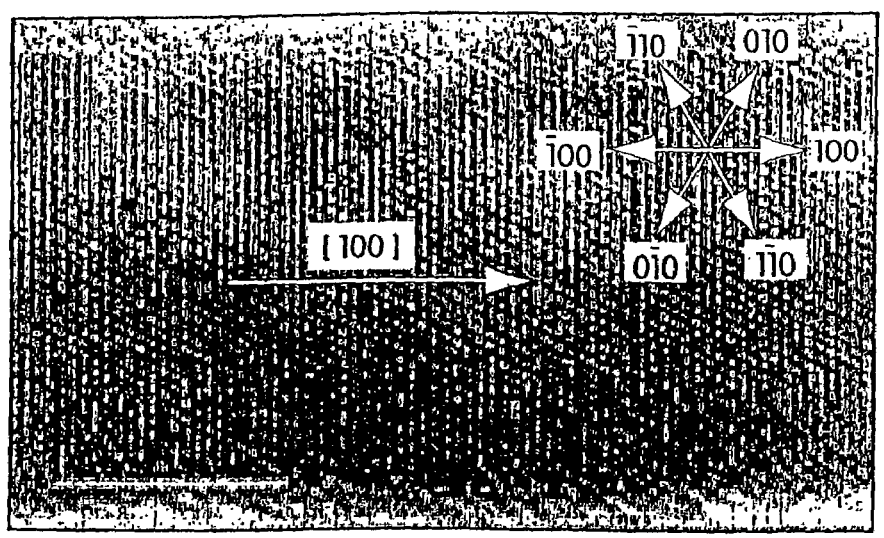
FIG. 21B shows an HRTEM image of another GaN nanoscale wire with a diameter of approximately 10 nanometers.

FIG. 21A shows a diffraction contrast TEM (Philips, EM420) image of a GaN nanoscale wire that terminates in a faceted nanoparticle of higher (darker) contrast. The inset in FIG. 21A shows a CBED pattern recorded along <001> zone axis over the region indicated by the white circle. The white scale bar corresponds to 50 nm. FIG. 21B shows a HRTEM (JEOL 2010) image of another GaN nanoscale wire with a diameter of about 10 nm. The image was taken along <001> zone axis. The [100], [010] and [−110] directions are indicated with the [100] parallel to the wire axis. The white scale bar corresponds to 5 nm.

Example 5

This example demonstrates the rational assembly of functional nanoscale devices from compound semiconductor NW building blocks in which the electrical properties were been controlled by doping. Gate-dependent transport measurements demonstrated that indium phosphide (InP) NWs can be synthesized with controlled n-type and p-type doping, and can function as nanoscale FETs. In addition, the availability of well-defined n- and p-type materials has enabled the creation of p-n junctions by forming crossed NW arrays. Transport measurements reveal that the nanoscale p-n junctions exhibit well-defined current rectification. Significantly, forward biased InP p-n junctions exhibit strong, quantum confined light emission making these structures extremely effective and extremely small light emitting diodes Electric field directed assembly is shown to be one strategy capable of creating highly integrated and functional devices from these new nanoscale building blocks.

Single crystal InP NWs were prepared by a laser-assisted catalytic growth (LCG). The n-type and p-type InP NWs were prepared using tellurium (Te) and zinc (Zn) as dopants, respectively, and found to be of similar high quality as NWs produced without the addition of dopants. Field emission scanning electron microscopy (FE-SEM) images of synthesized Zn-doped InP NWs (FIG. 22A) demonstrate that the wires extend up to tens of micrometers in length with diameters on the order of 10 nanometers. High-resolution transmission electron microscopy (TEM) images (inset, FIG. 22A) further show that the doped NWs are single crystals with <111> growth directions. Generally, a 1-2 nm amorphous over-layer on the NWs is visible in TEM images. This thin layer is attributed to oxides formed when the NWs are exposed to air after synthesis. The overall composition of individual NWs determined by energy dispersive X-ray (EDX) analysis was found to be 1:1 In:P, thus confirming the stoichiometric composition of the NWs. EDX and other elemental analytic methods are, however, insufficiently sensitive to determine the doping level in individual NWs.

To confirm the presence and type of dopants in the NWs, gate-dependent, two terminal transport measurements on individual NWs were performed. In these measurements, the NW conductance will respond in an opposite way to change in gate voltage ($V_g$) for n-and p-type NWs. Specifically, $V_g>0$ will lead to an accumulation of electrons and an increase in conductance for n-type NWs, while the same applied gate will deplete holes and reduce conductance for p-type NWs. FIGS. 22B and 22C show the typical gate-dependent I-V curves obtained from individual Te- and Zn-doped NWs, respectively. The I-V curves are nearly linear for both types of NWs at $V_g=0$, indicating the metal electrodes make ohmic contact to the NWs. The transport data (FIG. 22B) recorded on Te-doped NWs show an increase in conductance for $V_g>0$, while the conductance decreases for $V_g<0$. These data clearly show that Te-doped InP NWs are n-type. Gate-dependent transport data recorded on Zn-doped NWs show opposite changes in conductance with variation in $V_g$ compared to the n-type, Te-doped InP NWs. Specifically, for $V_g>0$, conductance decreases and for $V_g<0$ conductance increases (FIG. 22C). These results demonstrate that the Zn-doped InP NWs are p-type.

Measurements taken from twenty individual NWs, with diameters ranging from 20 nm to 100 nm, show gate effects in each case that are consistent with the dopant used during InP NW synthesis. In addition, the gate voltage can be used to completely deplete electrons and holes in n- and p-type NWs such that the conductance becomes immeasurably small. For example, the conductance of the NW in FIG. 22B can be switched from a conducting (on) to an insulating (off) state when $V_g$ is less than or equal to −20 V, and thus it functions as a FET. The conductance modulation can be as large as 4-5 orders of magnitude for some of the NWs. The relatively large switching voltage is related to the thick (600 nm) oxide barrier used in these measurements. This gate-dependent behavior is similar to that of metal-oxide-semiconductor (MOS) FETs and recent studies of semiconducting NT FETs. Taken together, these results clearly illustrate that single crystal InP NWs can be synthesized with controlled carrier type. Because these NWs are produced in bulk quantities, they represent a readily available material for assembling devices and device arrays.

Figure 23A:
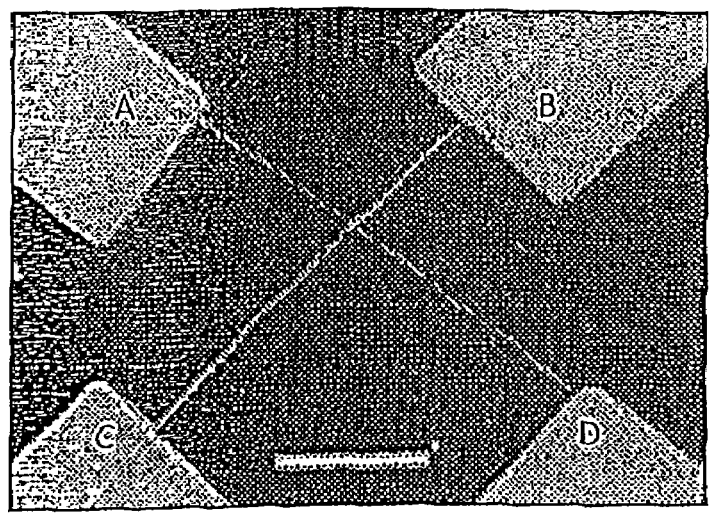
FIGS. 23A-23D illustrate crossed nanoscale wire junctions and electrical properties.

Transport behavior was studied of n-n, p-p and p-n junctions formed by crossing two n-type, two p-type, and one n-type and one p-type NW, respectively. FIG. 23A shows a representative crossed NW device formed with a 29 nm and 40 nm diameter NW. The four arms are designated as A, B, C, D for the simplicity of discussion below. Significantly, the types of junctions studied are controllable for every experiment since the types of NWs used to produce the crossed junction prior to assembly can be selected.

Figure 23B:
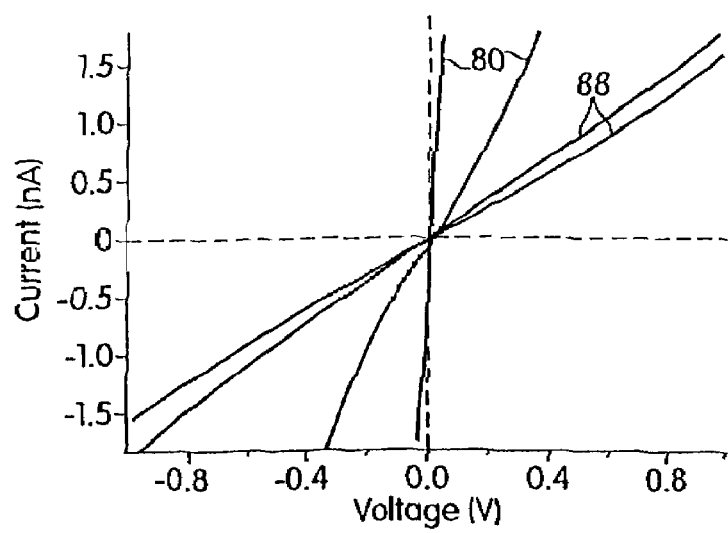
Figure 23C:
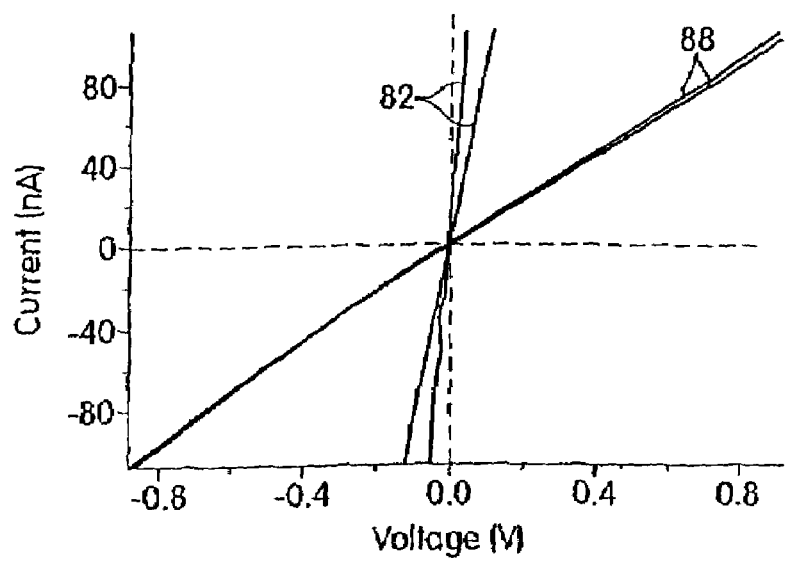

FIGS. 23B and 23C show the current-voltage (I-V) data recorded on n-n and p-p junctions, respectively. For both types of junctions, the transport data recorded on the individual NWs (AC, BD) show linear or nearly linear I-V behavior (curves 80, FIG. 23B and curve 82, FIG. 23C). These results show that the metal electrodes used in the experiments make ohmic or nearly ohmic contact to the NWs, and will not make nonlinear contributions to the I-V measurements across junctions. In general, transport measurements made across the n-n and p-p junctions show linear or nearly linear behavior, and to infer two important points about junctions made in this way. First, interface oxide between individual NWs does not produce a significant tunneling barrier, since such a barrier will lead to highly non-linear I-V behavior. Second, the I-V curves recorded through each pair (AB, AD, CB, CD) of adjacent arms shows a similar current level, which is smaller than that of the individual NWs themselves. These results demonstrate that the junction dominates the transport behavior. The data indicate that individual NWs make good electrical contact with each other, despite the small contact area ($10^{-12}$-$10^{-10}$ cm$^2$) and simple method of junction fabrication.

Figure 23D:
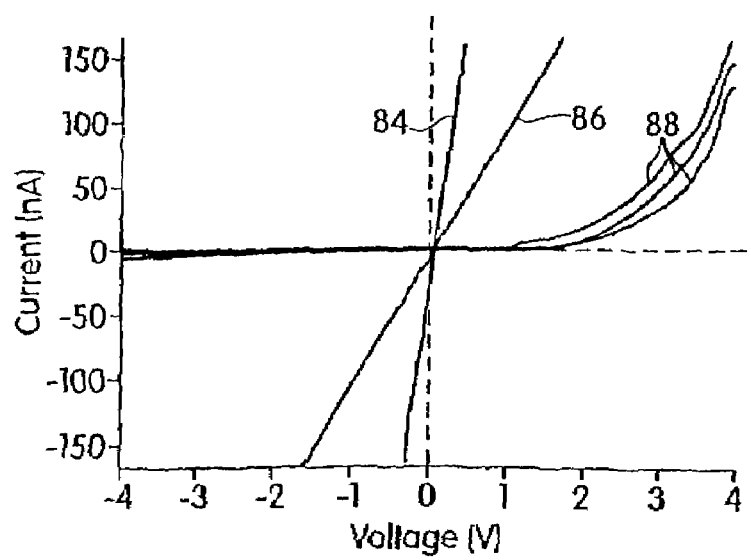

The good contact between individual NWs provides the basis for functional devices. As an example, p-n junctions were made from crossed p- and n-type NWs. These junctions can be made reproducibly by sequential deposition of dilute solutions of n- and p-type NWs with intermediate drying. FIG. 23D shows typical I-V behavior of a crossed NW p-n junction. The linear I-V of the individual n- and p-type NWs components (curves 84 and 86) indicates ohmic contact between the NWs and metal electrodes. Transport behavior across the p-n junction (curves 88) shows clear current rectification (i.e., little current flows in reverse bias, while there is a sharp current onset in forward bias). Significantly, the behavior is similar to bulk semiconductor p-n junctions, which form the basis for many critical electronic and optoelectronic devices. In a standard p-n junction, rectification arises from the potential barrier formed at the interface between p- and n-type materials. When the junction is forward biased (p-side positively biased), the barrier is reduced and a relatively large current can flow through the junction; on the other hand, only small current can flow in reverse bias since the barrier is further increased.

There are several reasons that the observed rectification is due to the p-n junction formed at the crossing point between p- and n-type InP NWs. First, the linear or nearly linear I-V behavior of individual p- and n-type NWs used to make the junction shows that ohmic contact have been made between the NWs and metal electrodes. This excludes the possibility that rectification arises from metal-semiconductor Schottky diodes. Second, the I-V behavior of the junction determined through every pair (AB, AD, CD, CD) of adjacent electrodes (curves 88 in FIG. 23D) exhibits a similar rectification effect and current level, which is also much smaller than the current level through the individual NWs. These results demonstrate that the junction dominates the I-V behavior. Third, four terminal measurements in which current is passed through two adjacent electrodes (e.g., A-B) while the junction voltage drop is measured across two independent electrodes (e.g., C-D) exhibit similar I-V and rectification with only a slightly smaller voltage drop (0.1-0.2V) compared to two terminal measurements at the same current level. Lastly, measurements made on ten independent p-n junctions showed similar rectification in the I-V data (i.e., significant current can only flow through p-n junctions when the p-type NW is positively biased).

Figure 24A:
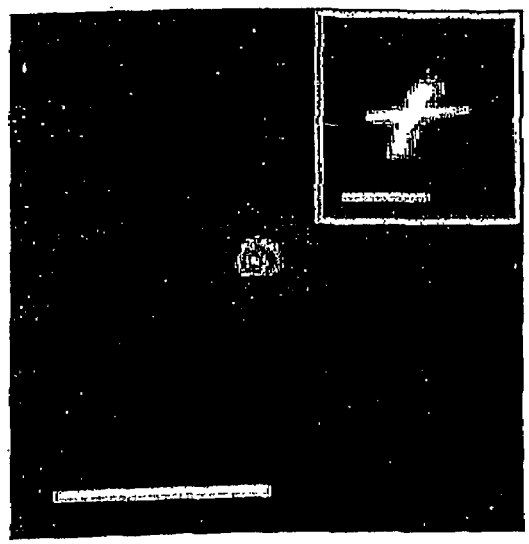
FIGS. 24A-24D illustrate optoelectrical characterization of nanoscale wire P-N junctions.

The above data show unambiguously the rational fabrication of nanoscale p-n junctions. In direct band gap semiconductors like InP, the p-n junction forms the basis for the critical optoelectronics devices, including light emitting diodes (LED) and lasers. To assess whether these nanoscale devices might behavior similarly, the photoluminescence (PL) and electroluminescence (EL) from crossed NW p-n junctions have been studied. Significantly, EL can be readily observed from these nanoscale junctions in forward bias. FIG. 24A shows an EL image taken from a typical NW p-n junction at forward bias, and the inset shows the PL image of a crossed NW junction. The PL image clearly shows two elongated wire-like structures, and the EL image shows that the light comes from a point-like source. Comparison of the EL and PL images shows that the position of the EL maximum corresponds to the crossing point in the PL image, thus demonstrating the light indeed comes out from the NW p-n junction.

The I-V characteristic of the junction (inset, FIG. 24B) shows clear rectification with a sharp current onset at about 1.5 volts. The EL intensity versus voltage curve of the junction shows significant light can be detected with the system at a voltage as low as 1.7 volts. The EL intensity increases rapidly with the bias voltage, and resembles the I-V behavior. The EL spectrum (FIG. 24C) shows a maximum intensity around 820 nm, which is significantly blue shifted relative to the bulk band gap of InP (925 nm). The blue-shift is due in part to quantum confinement of the excitons, although other factors may also contribute. The importance of quantum confinement can be seen clearly in EL results recorded from p-n junctions assembled from smaller (and larger) diameter NWs (FIG. 24D), which show larger (smaller) blue-shifts. The ability to tune color with size in these nanoLEDs can be especially useful.

GaN is a direct wide bandgap semiconductor material, which emits light in the short wavelength (UV and blue) region at room temperature. Blue LEDs are important as emitters where strong, energy efficient and reliable light source are needed. Also it is important to enable production of full color LED displays and LED white lamp, since blue is one of the three primary colors (red, green and blue). Here BLUE/UV nanoLEDs (light emitting region on the order of 10 nm's) are described, which is constructed with P-type Si and N-type (unintentionally doped) GaN nanowires.

Figure 25A:
FIG. 25A shows an EL image taken from a p-type Si and n-type GaN nanojunction.
Figure 25B:
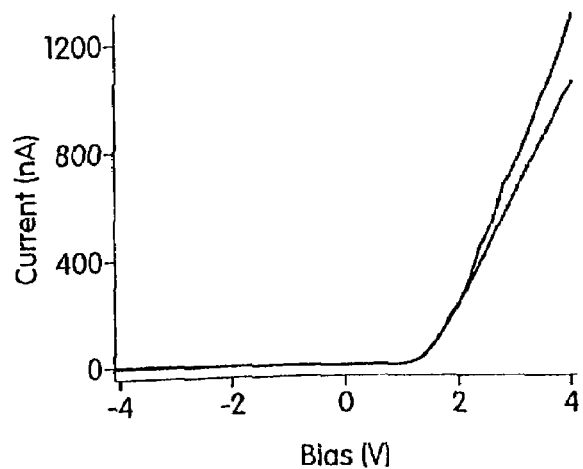
FIG. 25B shows current as a function of voltage for various gate voltages.
Figure 25C:
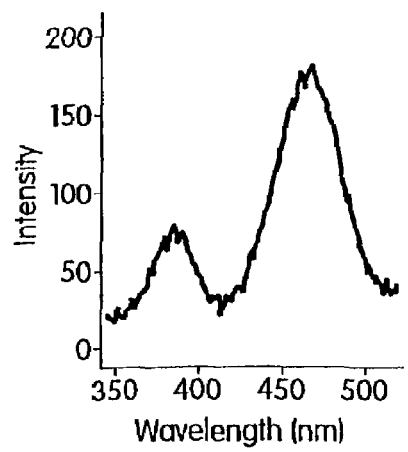
FIG. 25C shows an EL spectrum for the nanojunction of FIG. 25A.

FIG. 25A shows an EL image taken from two P-type Si and N-type GaN crossed nanojunctions. The p-Si is doped with boron. FIG. 25B illustrates current vs. voltage for various gate voltages. The nanojunction shows good rectification at different gate voltages. The El spectrum shown in FIG. 25C shows light emission is about 380 nm and 470 nm. A n-InP and p-Si nanojunction has good rectification.

To make highly integrated NW-based devices requires techniques to align and assemble these building blocks into well-defined arrays. To demonstrate this, electric fields (E-field) were used to align and position individual NWs into parallel and crossed arrays-two basic geometries for integration. The E-field directed assembly was carried out by placing a solution of NWs between electrodes (FIG. 26A), and then applying a bias of 50-100 V. The usefulness of this approach is readily seen in the case of alignment of a chlorobenzene suspended NWs between parallel electrodes (FIG. 26B). FE-SEM images show that nearly all of the NWs are aligned perpendicular to the parallel electrodes and along E-field direction. Electrode arrays were also used to position individual NWs at specific positions. For example, E-field assembly of NWs between an array of electrodes (FIG. 26C) demonstrates that individual NWs can be positioned to bridge pairs of diametrically-opposed electrodes and form a parallel array. In addition, by changing the field direction, the alignment can be done in a layer-by-layer fashion to produce crossed NW junctions (FIG. 26D). These data clearly show that E-field assembly is useful to controllably deposit individual NWs.

Specifically, InP NWs were synthesized using LCG. The LCG target typically consisted of 94% (atomic ratio) InP, 5% Au as the catalyst, and 1% of Te or Zn as the doping element. The furnace temperature (middle) was set at 800° C. during growth, and the target was placed at the upstream end rather than middle of the furnace. A pulsed (8 ns, 10 Hz) Nd-YAG laser (1064 nm) was used to vaporize the target. Typically, growth was carried out for 10 minutes with NWs collected at the downstream, cool end of the furnace.

Transport measurement on individual NWs were carried out as follows. Briefly, NWs were first dispersed in ethanol, and then deposited onto oxidized silicon substrates (600 nm oxide, 1-10 Ωcm resistivity), with the conductive silicon used as a back gate. Electrical contact to the NWs was defined using electron beam lithography (JEOL 6400). Ni/In/Au contact electrodes were thermally evaporated. Electrical transport measurements were made using home built system with <T1/pA noise under computer control.

The n-n and p-p junctions were obtained by random deposition. NWs were onto oxidized silicon substrates using relatively high concentrations, the positions of crossed NWs were determined, and then electrodes on all four arms of the cross by electron beam lithography were defined. Ni/In/Au electrodes were used to make contact to the NWs.

The p-n junctions were obtained by layer-by-layer deposition. First, a dilute solution of one type (e.g., n-type) of NW was deposited on the substrate, and the position of individual NWs was recorded. In a second step, a dilute solution of the other type (e.g., p-type) of NW was deposited, and the positions of crossed n- and p-type NWs were recorded. Metal electrodes were then defined and transport behavior was measured.

EL was studied with a home-built micro-luminescence instrument. PL or scattered light (514 nm, Ar-ion laser) was used to locate the position of the junction. When the junction was located, the excitation laser was shut off, and then the junction was forward biased. EL images were taken with a liquid nitrogen cooled CCD camera, and EL spectra were obtained by dispersing EL with a 150 line/mm grating in a 300 mm spectrometer.

Figure 22A:
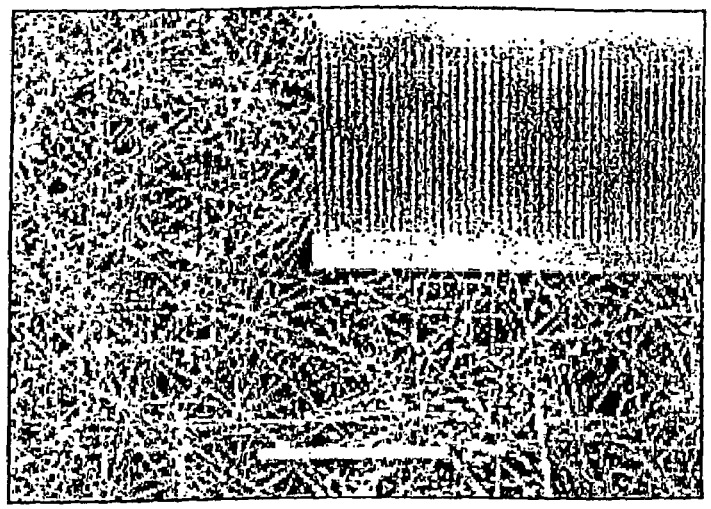
FIGS. 22A-22C illustrate doping and electrical transport of InP nanoscale wires.
Figure 22B:
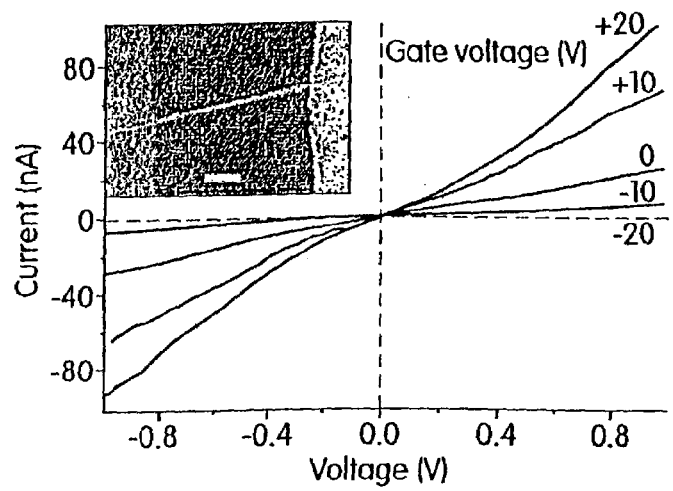
Figure 22C:
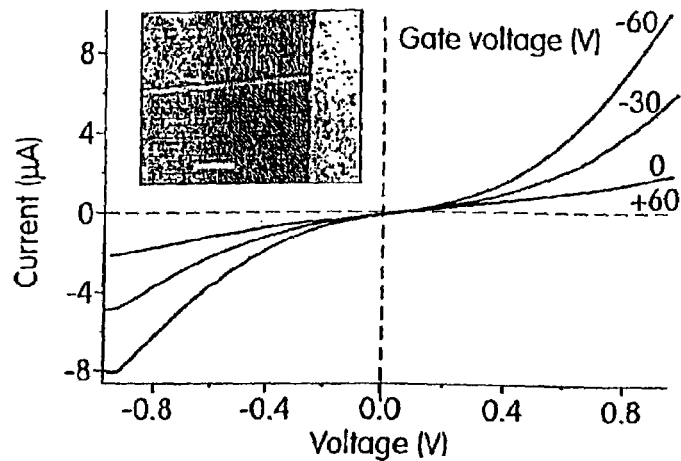

FIGS. 22A-22C illustrate doping and electrical transport of InP NWs. FIG. 22A shows a typical FE-SEM image of Zn-doped InP NWs. Scale bar is 10 μm. The (111) lattice planes are visible perpendicular to the wire axis. Scale bar is 10 nm. FIGS. 22B and 22C show gate-dependent I-V behavior for Te- and Zn-doped NWs, respectively. The insets in FIGS. 22B and 22C show the NW measured with two terminal Ni/In/Au contact electrodes. The scale bars correspond to 1 μm. The diameter of the NW in FIG. 22B is 47 nm, while that in FIG. 22C is 45 nm. Specific gate-voltages used in the measurements are indicated on the right hand sides of FIGS. 22B-22C for the corresponding I-V curves. Data were recorded at room temperature.

FIGS. 23A-23D illustrate crossed NW junctions and electrical properties. FIG. 23A shows a FE-SEM image of a typical crossed NW device with Ni/In/Au contact electrodes. The scale bar corresponds to 2 μm. The diameters of the NWs are 29 nm (A-C) and 40 nm (B-D); the diameters of the NWs used to make devices were in the range of 20-75 nm.

FIGS. 23B-23D show I-V behavior of n-n, p-p and p-n junctions, respectively. The curves 80 and 82 correspond to the I-V behavior of individual n- and p-NWs in the junctions, respectively. The curves 88 represent the I-V behavior across the junctions. The current recorded for the p- and n-type NWs in FIG. 23D is divided by a factor of 10 for better viewing. The solid lines represent transport behavior across one pair of adjacent arms, and the dashed lines represent that of the other three pairs of adjacent arms. Data were recorded at room temperature.

Figure 24B:
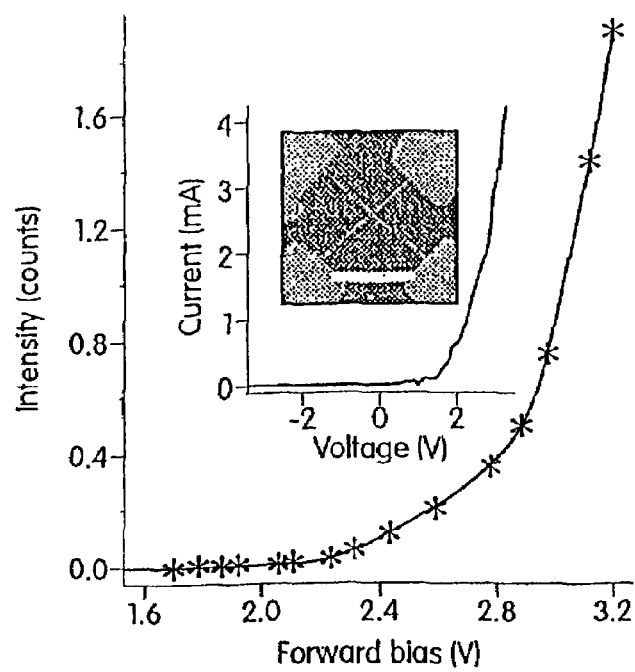
Figure 24C:
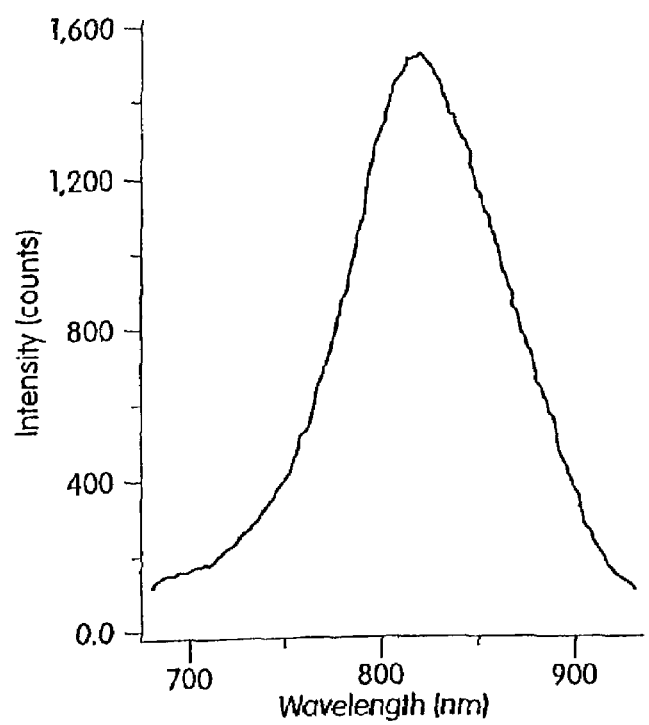
Figure 24D:
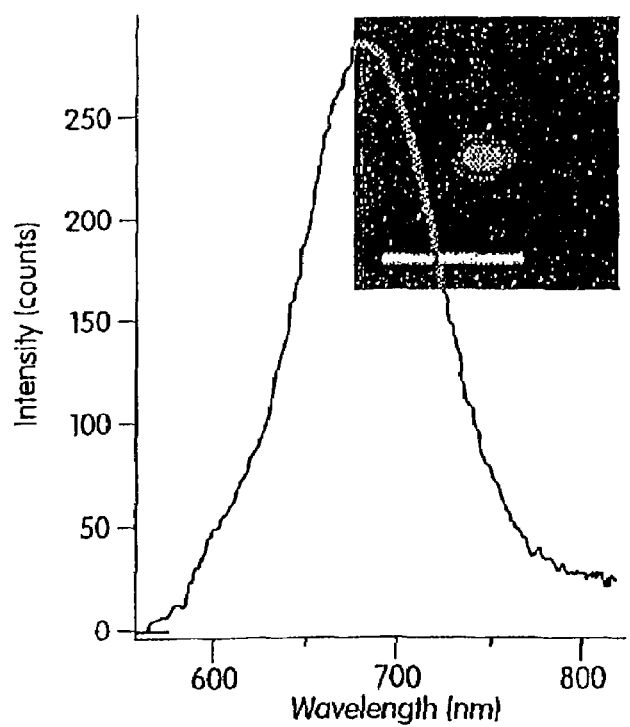

FIGS. 24A-24D illustrate optoelectrical characterization of NW p-n junctions. FIG. 24A is an EL image of the light emitted from a forward biased NW p-n junction at 2.5 V. The inset in FIG. 24A shows the PL image of the junction. Both scale bars correspond to 5 µm. FIG. 24B shows the EL intensity versus voltage. The inset in FIG. 24B shows the I-V characteristics and the inset in the inset shows the FE-SEM image of the junction itself. The scale bar corresponds to 5 µm. The n-type and p-type NWs forming this junction have diameters of 65 and 68 nm, respectively. FIG. 24C shows an EL spectrum of the junction shown in FIG. 24A. The spectrum peaks at 820 nm. FIG. 24D shows an EL spectrum recorded from a second forward biased crossed NW p-n junction. The EL maximum occurs at 680 nm. The inset in FIG. 24D shows the EL image and demonstrates that the EL originates from the junction region. The scale bar is 5 µm. The n-type and p-type NWs forming this junction have diameters of 39 and 49 nm, respectively.

Figure 26A:
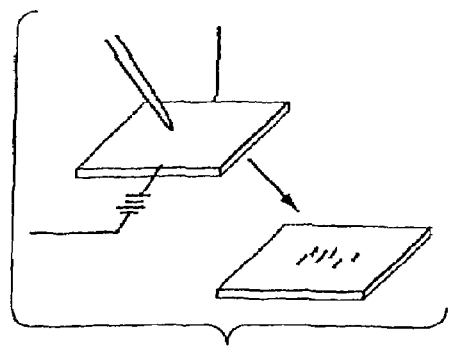
FIGS. 26A-26D illustrate parallel and orthogonal assembly of nanoscale wires with electric fields.
Figure 26B:
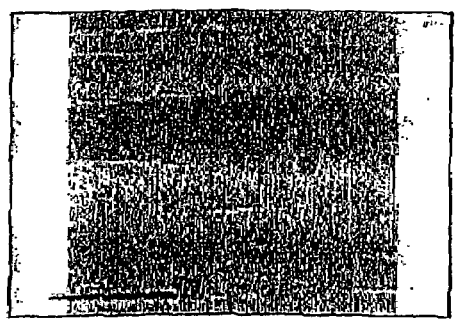
Figure 26C:
Figure 26D:
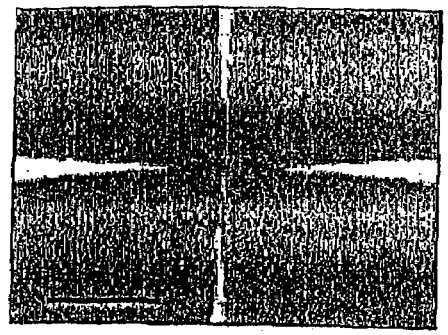

FIGS. 26A-26D illustrate parallel and orthogonal assembly of NWs with E-fields. FIG. 26A is a schematic view of E-field alignment. The electrodes (orange) are biased at 50-100 V after a drop of NW solution is deposited on the substrate (blue) FIG. 26B shows a parallel array of NWs aligned between two parallel electrodes. The NWs were suspended in chlorobenzene and aligned using an applied bias of 100 V. FIG. 26C shows a spatially positioned parallel array of NWs obtained following E-field assembly using a bias of 80 V. The top inset in FIG. 26C shows 15 pairs of parallel electrodes with individual NWs bridging each diametrically opposed electrode pair. FIG. 26D shows a crossed NW junction obtained using layer-by-layer alignment with the E-field applied in orthogonal directions in the two assembly steps. The applied bias in both steps was 80 V. The scale bars in FIGS. 26B-26D correspond to 10 µm.

Example 6

Four types of important functional nanodevices were created by rational bottom-up assembly from p and n-type silicon nanowires (SiNWs) with well controlled dopant type and level. In all these devices, electrical transport measurements on individual p and n-type SiNWs showed ohmic or nearly ohmic contact between SiNWs and leads. Significantly, four-probe measurements across pn junctions consisting of crossed p-type and n-type SiNWs showed current rectification behavior as expected for pn diode behavior. Also, $n^+pn$ crossed junctions were assembled to create bipolar transistors, in which common base/emitter current gains as large as 0.94/16 were obtained. Complementary inverters made of crossed lightly doped pn junctions showed clear output voltage inverse to input voltage with a gain of 0.13. Tunnel diodes in form of heavily doped SiNW pn crosses showed negative differential resistance (NDR) behavior in forward bias with a peak-to-valley ratio (PVR) of 5 to 1.

Figure 27A:
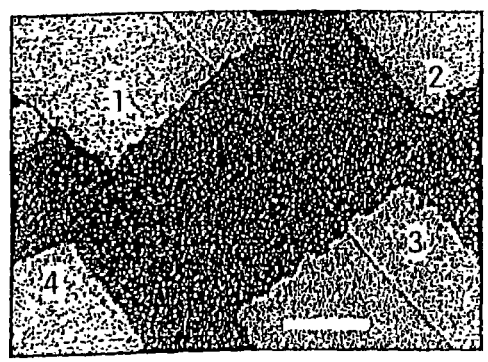
FIGS. 27A-27F illustrate crossed silicon nanoscale wire junctions.
Figure 27B:
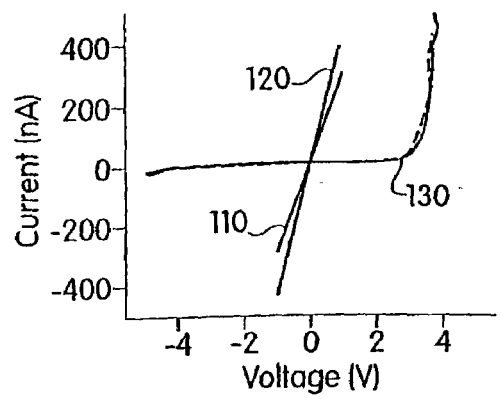

Four types of important functional structures including pn diodes, bipolar transistors, complementary inverters and tunnel diodes were created by controllably combining SiNWs of varying p and n-type doping levels. Nanoscale pn junctions were created in form of crossed SiNW junctions. Electrical transport measurements on these pn junctions showed the current rectification. The ability to exploit the construction of $n^+pn$ crossed SiNW junctions to bipolar transistors and were demonstrated to have common base/emitter current gains as large as 0.94/16. The inverters made of lightly doped pn crosses showed clearly the output voltage inverse to the input voltage with voltage gain of 0.13. The results of tunnel diodes made of heavily doped pn crossed showed NDR behavior in forward bias with a PVR of 5 to 1. The p-type and n-type SiNWs were synthesized by using diborane and phosphorus, respectively as doping source during laser-assisted catalytic growth of SiNWs. Metal leads contact with SiNWs on doped silicon substrate with 600 nm thermal oxide were defined by electron beam lithography. The pn, pp and nn junctions were formed by crossing one p-type and one n-type, two p-type and two n-type SiNWs, respectively. The types of junctions were controlled by choosing the types of SiNWs used to create a given junction. A typical field emission scanning electron microscopy (FE-SEM) image of cross junctions is shown in FIG. 27A, where the four contact leads are labeled as 1, 2, 3 and 4 for the convenience of discussion. FIG. 27B shows current versus voltage (I-V) data on a pn crossed junction with diameters of p and n-type SiNWs as small as 20.3 nm and 22.5 nm, respectively. Four-terminal measurements across junction were performed by flowing current between two adjacent leads (e.g., leads 1-2 or leads 1-4, the positive current direction is from p to n-type SiNW) and measuring the voltage drop between the other two leads (e.g., leads 3-4 or leads 3-2). The I-V curve across junction (FIG. 27B curve 130) shows little current in reverse bias (negative bias in this setup) and very sharp current onset in forward bias (positive bias). In contrast, single p (between leads 1-3) and n-type (between leads 2-4) SiNWs show linear I-V behavior (FIG. 27B curves 110 and 120, respectively), which suggests ohmic contact between SiNWs and leads. This rectifying behavior must be caused by junction itself and can be explained by the energy band diagrams of a pn junction diode. The built-in potential barrier forms at the junction interface when p and n-type SiNW contact with each other. Electrons can not tunnel through the wide space charge region forming at the junction interface but can be transported by thermal excitation. Forward bias decreases the built-in potential barrier and thus large amount of current can flow (FIG. 27E), while reverse bias increases the barrier and thus current level is low (FIG. 27F).

The p and n-type SiNWs were dispersed in to aceton separately. The p-n junctions were obtained by sequential deposition. The solution of one type of SiNWs (e.g., n-type) was first deposited onto the substrate and the positions of SiNWs were recorded with respect to alignment marks. Secondly, the solution of the other type of SiNWs (e.g., p-type) was deposited and the positions of crossed pn junctions were recorded. The pp or nn junctions were obtained by depositing only one type of SiNWs: p-type or n-type. The junction positions were then recorded.

The intrinsic oxide layer of SiNWs is thin enough that electrons can easily tunnel through the oxide layer and the reasonable strong coupling between p and n-type wire at the junction still exists and thus the built-in potential barrier can form. This is confirmed by the transport measurements on pp and nn junctions. The single wires (between leads 1-3, 2-4) in pp (FIG. 27C, curves 110) and nn junctions (FIG. 27D, curves 120) show linear or almost linear I-V behavior suggesting good contact. Two terminal measurements (between leads 1-2, 1-4, 2-3, or 3-4) on pp (FIG. 27C, curves 130) and nn (FIG. 27D, curves 130) junctions show linear and almost linear I-V. Comparing two-terminal measurement resistance across junctions to single SiNW resistance, the magnitude of junction resistance is similar to the wire resistance, suggesting that the oxide does not cause significant electron tunneling barrier. The measurements on 20 independent pn junctions showed consistent correct rectifying behavior.

Figure 28A:
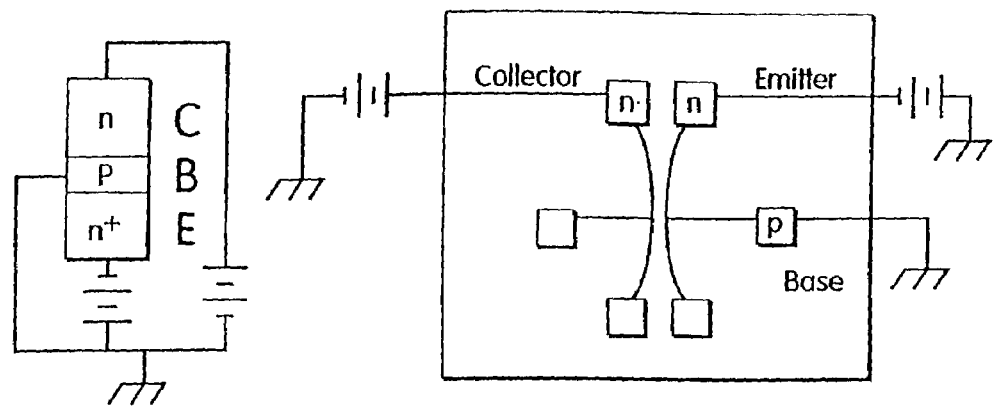
FIGS. 28A-28D illustrate n+pn crossed silicon nanoscale wire bipolar transistors.
Figure 28B:
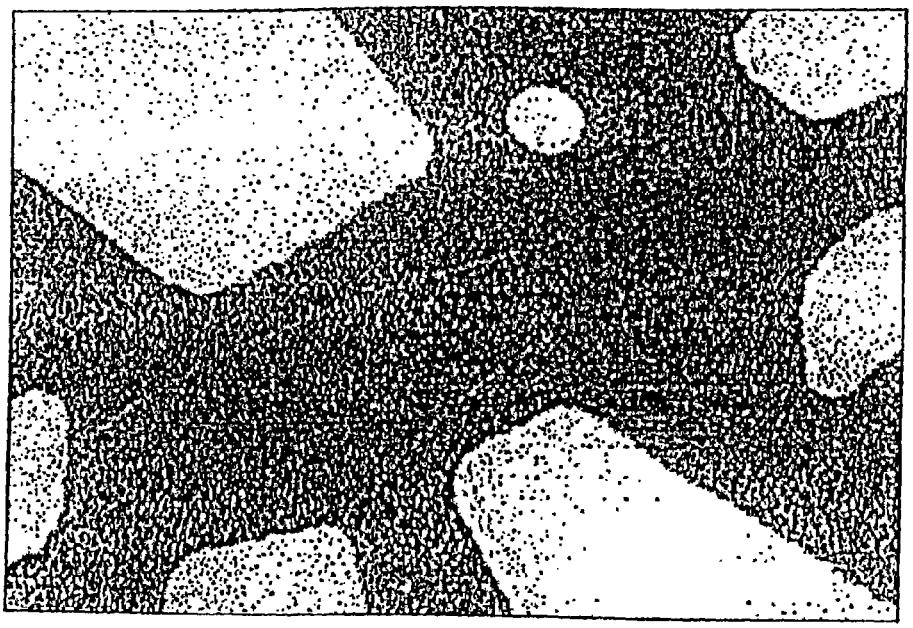
Figure 28C:
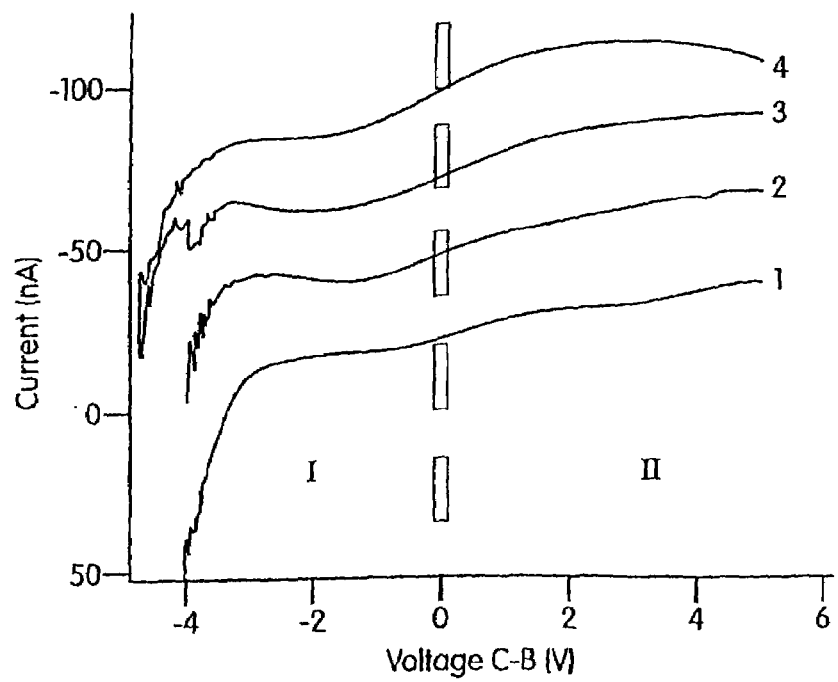

A bipolar transistor is a $n^+pn$ (FIG. 28A, left) or $p^+np$ junction device, which requires high doping level in emitter, low doping in base and collector. Good control in doping of SiNWs provided the capability to make this complex device. The $n^+pn$ bipolar transistors were constructed by mechanically manipulating two n-type SiNWs (one heavily doped, the other lightly doped) onto one lightly doped p-type wire and were operated in common base configuration (FIG. 28A, right). FIG. 28B is a typical SEM image of bipolar transistors. The SiNWs and junctions in transistors were first characterized individually. The I-V curves of three individual SiNWs are linear and the two individual junctions have correct rectifying behavior. The $n^+$-type SiNW was used as an emitter while the n-type as collector to do bipolar transistor measurements. The emitter-base (E-B) is usually forward biased to inject electrons into base region. When the collector-base (C-B) voltage is greater than zero, the transistor is operated in the active mode, in which the C-B junction is reverse biased and only a very small leakage current will flow across the junction. However, the electrons injected from emitter can diffuse through the base to reach the C-B junction space charge region and will be collected by collector. The actual collector current depends only on the injected electrons from emitter and thus depends only on the E-B voltage. This is clearly seen in FIG. 28C, regime II, where the collector current goes high with the forward E-B voltage while change slowly with C-B voltage which results from Early effect and the existence of slowly increasing leakage current with reverse bias. The transistor action is demonstrated by large current flow in a reverse biased collector junction and can result from carriers injected from a nearby emitter junction. When the (C-B) voltage is bellow zero, the bipolar transistor works in saturation mode (FIG. 28C regime I), in which both E-B and C-B junctions are forward biased. The collector current from emitter injection will be compensated by the forward biased C-B current. So the collector current goes down with forward C-B voltage. The higher the forward bias on E-B, the higher the forward bias on C-B needed to compensate the current to zero (FIG. 28C curve 1 to 4).

The $n^+pn$ bipolar transistors were fabricated by deposition and machanical manipulation. First, p-type SiNWs were deposited from solution onto the substrate. In the second step, the $n^+$ and n-type SiNWs were attached to sharp STM tips and released onto the p-type SiNWs under optical microscope.

The common base current gain of the bipolar transistor in active mode is as large as 0.94 (FIG. 28D) and the common emitter current gain is 16. Three important points are suggested from this large current gain. The efficiency of electron injection from emitter to base is quite high, resulting from the higher doping concentration in emitter than in base. Although the base region is wide (15 μm), the active interaction between emitter and collect still exists. Most of injected electrons from emitter can go through the base to reach the collector, which suggests that the mobility of electrons in base is quite high. The space charge region between base and collector has high efficiency to collect electrons and sweep them into collector, suggesting that the oxide barrier at the interface does not contribute significantly, which further confirms the analysis on single pn junctions. The bipolar transistor can be improved, for example, by reducing the base width, to approach the performance of the commercial one in which the typical common base current gain is larger than 0.99.

Figure 29A:
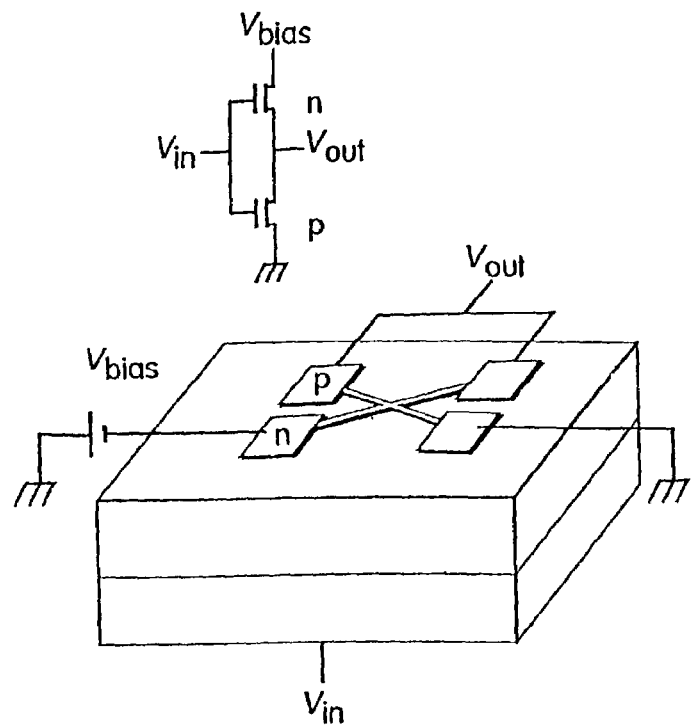
FIGS. 29A-29D illustrate complementary inverters and tunnel diodes.
Figure 29B:
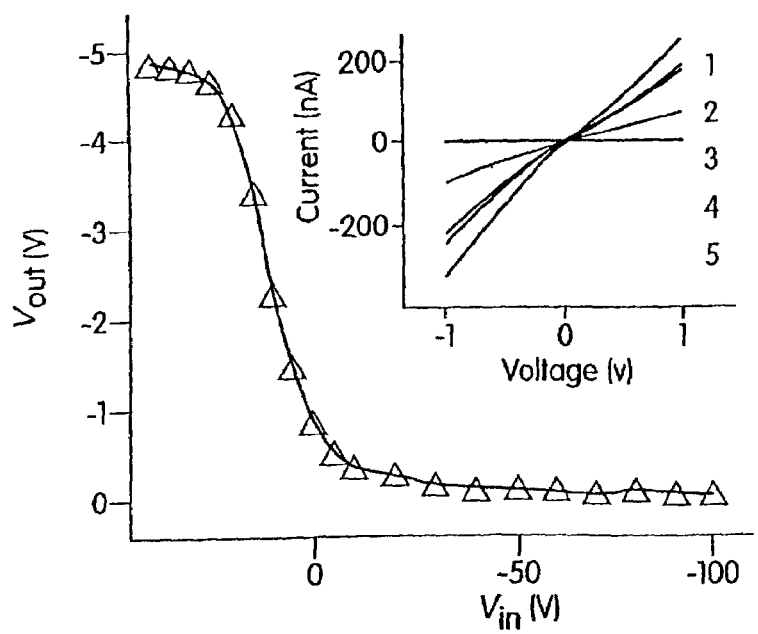

A complementary inverter in form of a lightly p and a lightly n-doped SiNW cross was used to exploit the applications of these bottom-up building blocks in logic circuit, and to further demonstrate the capability that contolled doping of SiNWs. The schematics of a crossed SiNW inverter structure is shown in FIG. 29A (bottom) while that of an inverter in semiconductor physics is shown in FIG. 29A (top). The lightly doped p and n-type SiNWs in the inverter show very large gate effect and can be completely depleted as is shown for p-type SiNW in FIG. 29B inset. As seen in FIG. 29B, the output voltage is negative (zero) with the positive(negative) input voltage, which is the typical inverter behavior. The depletion of n-type (p-type) wires by negative (positive) input makes the output equal to ground (bias). The voltage gain is calculated as 0.13, the slope of voltage inversion. The gain is lower than that in commercial inverters which is larger than 1, but can be improved by using thinner gate oxide layer instead of the 600 nm oxide, which reduces the gate response of SiNWs, and using more lightly doped SiNWs, which needs more effort to make ohmic contact with and to be further investigated.

While two crossed lightly doped p-type and n-type SiNWs make inverters, two crossed degenerately doped $p^+$-type and $n^+$-type SiNWs can form tunnel diodes. In contrast to the pn junction, the tunnel diode do not show rectifying behavior, but rather show NDR behavior in forward bias, with a PVR of 5 to 1 shown in FIG. 29C. The difference can be explained by Esaki diode mechanism. The built-in potential forms when $p^+$ and $n^+$-type contact each other, but the space charge region width is thin enough to allow electron tunneling. Electrons can tunnel through this thin space charge region under reverse bias (FIG. 29D left) and low forward bias (FIG. 29D middle) causing the current to flow. Beyond a certain point, a further increase in the forward bias results in the conduction band of the n-side moving into the band gap of the p-side (FIG. 29D right) which suppresses electron tunneling and thereby reduces current. Further increases of forward bias reduce the built-in potential barrier which allows thermal excitation mechanism to dominate conduction and the current goes high.

Figure 27C:
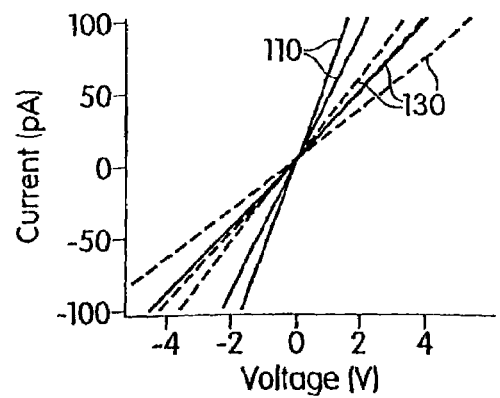
Figure 27D:
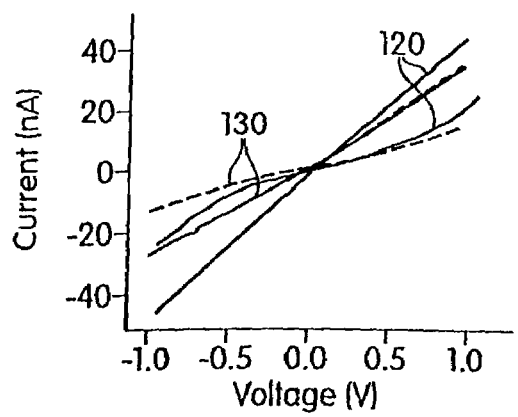
Figure 27E:
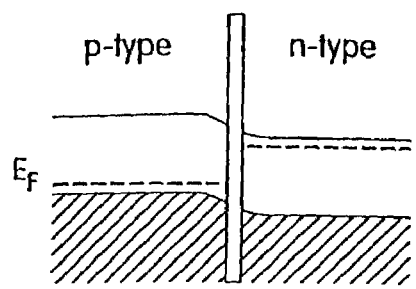
Figure 27F:
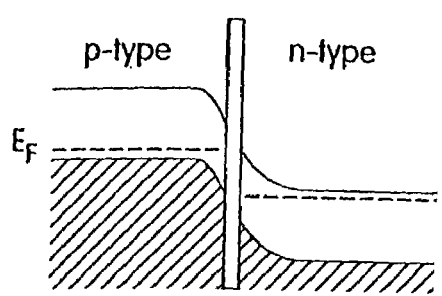

Specifically, FIGS. 27A-27F illustrate crossed SiNW junctions. FIG. 27A shows a typical FE-SEM image of crossed NW junctions with Al/Au as contact leads. The scale bar is 2 μm. The diameters of NWs are in the range of 20 to 50 nm. FIGS. 27B-27D show I-V behavior of pn, pp and nn junctions, respectively. The curves 110 and 120 correspond to the I-V behavior of individual p and n-type SiNWs injunctions, respectively. The curves 130 represent the four-terminal I-V through pn junction in FIG. 27B and two terminal I-V through pp and nn junction in FIGS. 27C and 27D, respectively. In FIG. 27B, the solid line is I-V by following current between lead 1 and 2 and simultaneouly measuring the voltage between lead 3 and 4 while the dashed line correponds to that by following current between 1 and 4 and measuring voltage between 3 and 2. In FIGS. 27C and 27D, the solid lines are I-V across one pair of adjacent leads (1-2) and the dashed lines are those across the other three pairs (1-4, 2-3, 3-4). FIGS. 27E and 27F show the energy band diagrams of a pn junction under forward bias and reverse bias, respectively.

Figure 28D:
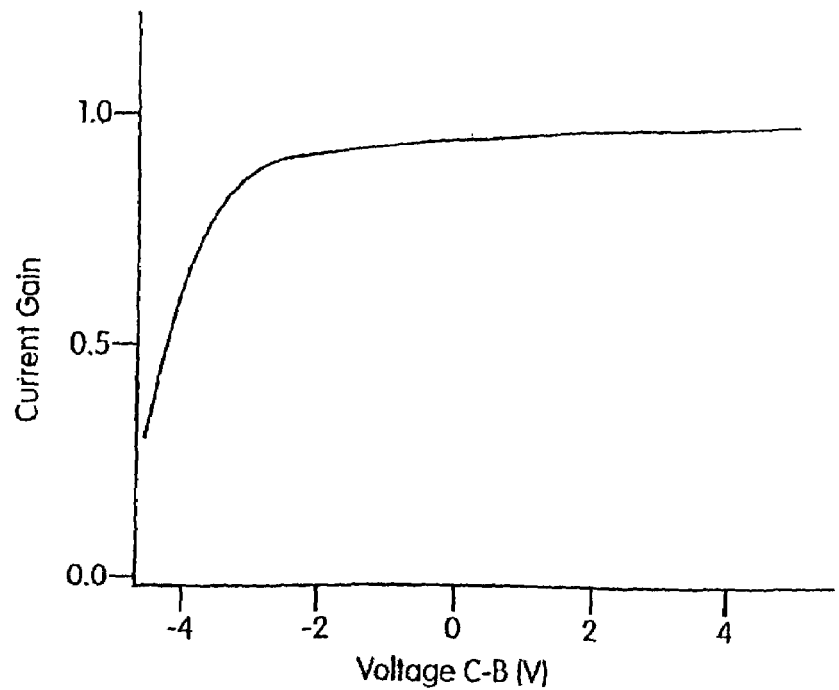

FIGS. 28A-28D illustrate n$^+$pn crossed SiNW bipolar transistors. FIG. 28A shows the common base configuration schematics of an n$^+$pn bipolar transistor in semiconductor physics (left) and in crossed SiNW structure (right). The n$^+$, p and n-type SiNWs function as emitter, base and collector, respectively. Base is grounded. Emitter is negatively biased at specific values. Collector voltage is scanned from postive to negative. FIG. 28B shows a typical FE-SEM image of SiNW bipolar transistor. The scale bar is 5 µm. FIG. 28C shows a collector current vs collector-base voltage behavior recorded on an n$^+$pn transistor with emitter and base SiNWs 15 um apart. Curve 1 to 4 correspond to the behavior at emitter-base voltages of −1, −2, −3, −4 V. Regime I and II are separated by dashed line, correponding to saturation mode and active mode, respectively. FIG. 28D shows common base current gain vs. collector-base voltage.

Figure 29C:
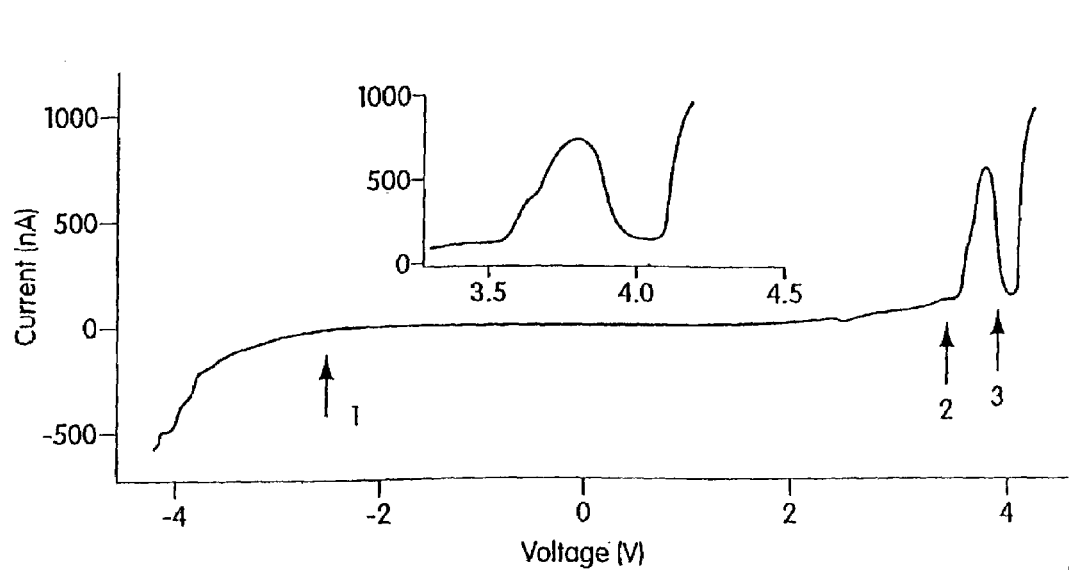
Figure 29D:
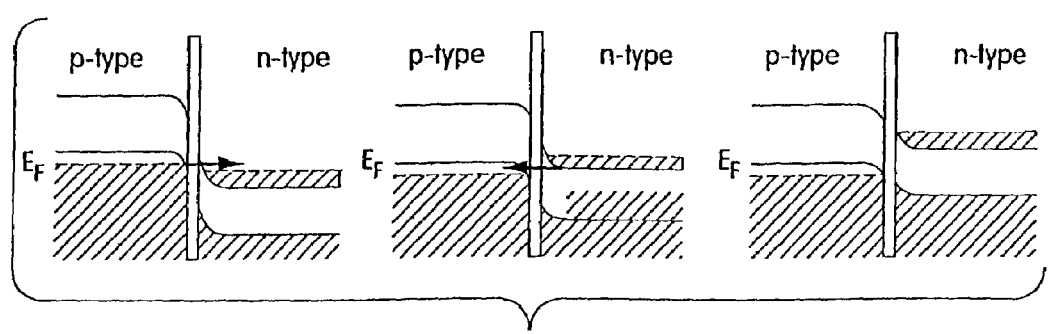

FIGS. 29A-29D illustrate complementary inverters and tunnel diodes. FIG. 29A shows schematics of a complementary inverter structure in semicondutor physics (top) and that formed by a lightly doped pn cross (bottom). In bottom schematics, one end of n-type NW is biased at −5 V and one end of p-type NW is grounded. Input voltage is back gate voltage and the other ends of p and n-type NWs are shorted as output terminal. FIG. 29B shows output voltage vs input voltage data in a pn cross inverter. The inset in FIG. 29B is the I-V curves of p-type NW in the inverter. Curve 1 to 5 correspond to I-V at back gate voltage=50, −30, −10, 0 and 10 V, respectively. The n-type NW in this inverter has similar I-V behavior and can be completely depleted at a gate voltage of −30V. FIG. 29C shows two terminal mearsurement data of a tunnel diode made from a heavily doped pn cross. The I-V behavior of individual p and n-type SiNWs have been tested to be linear. The inset in FIG. 29C spreads out the part of I-V curve showing NDR. FIG. 29D shows the energy band diagrams of a crossed SiNW tunnel diode. At reverse bias (e.g., at position 1 in FIG. 29C), electrons can tunnel through the junction (left diagram). At small forward bias (e.g., at position 2 in FIG. 29C), electron tunneling is also permitted (middle diagram). At further increased forward bias (e.g., at position 3 in FIG. 29C), electron tunneling is forbidden (right diagram).

Example 7

This example illustrates the preparation of an embodiment of the invention. A stable suspension of nanowires (NWs) in ethanol was prepared by sonicating the NWs in ethanol in a bath sonicator for around 3 minutes. The substrate (silicon wafter) was covered by a self-assembled monolayer (SAM) with —NH$_2$ termination. Microfluidic molds were then made of PDMS. A microchannel formed when the substrate came in contact with PDMS mold, with three walls of the conduit corresponding to the molded features in the mold and the fourth corresponded to the surface of the substrate, which was chemically modified as previously described.

The NW suspension was then flowed through as-made microchannel with an application of +100 volt bias on the substrate. After a flowing time around 10 min, the channel was washed with ethanol, then left to dry naturally. When the PDMS stamp was removed, NW arrays were observed aligned in the flow direction on the substrate surface.

By alteration the flow direction and applying layer-by-layer scheme, multiple cross-bars were formed out of the NW arrays.

By patterning the surface, the NWs were aligned or positioned in certain predetermined places.

The patterning process was as follow. A layer of PMMA was spin-coated on the substrate surface, then EBL (Electron Beam Lithography) was used to write a pattern, (i.e., to selectively exposed Si surface which was later chemically functionalized). The bottom of the PMMA trenches were then exposed to the Si surface covered with —NH$_2$ SAM. When the flow of NW suspensions go over these patterns, (as described above, where just the surface was patterned), the NWs were directed into PMMA trenches. The PMMA was then lifted off. The NWs were found to be stuck to the PMMA surface, allowing clean arrays of devices to be formed.

Example 8

Gallium phosphide (GaP), indium phosphide (InP) and silicon (Si) NWs used in these studies were synthesized by laser assisted catalytic growth, and subsequently suspended in ethanol solution. In general, arrays of NWs were assembled by passing suspensions of the NWs through fluidic channel structures formed between a poly(dimethylsiloxane) (PDMS) mold and a flat substrate (FIGS. 30A and 30B). Parallel and crossed arrays of NWs can be readily achieved using single (FIG. 30A) and sequential crossed (FIG. 30B) flows, respectively, for the assembly process as described below.

A typical example of parallel assembly of NWs (FIG. 31A) shows that virtually all the NWs are aligned along one direction (i.e., the flow direction). There are also some small deviations with respect to the flow direction. Examination of the assembled NWs on larger length scales (FIG. 31B) shows that the alignment readily extends over hundreds of micrometers. Indeed, alignment of the NWs has been found to extend up to millimeter length scales, and seem to be limited by the size of the fluidic channels, based on experiments carried out using channels with widths ranging from 50 to 500 µm and lengths from 6-20 mm.

Figure 31A:
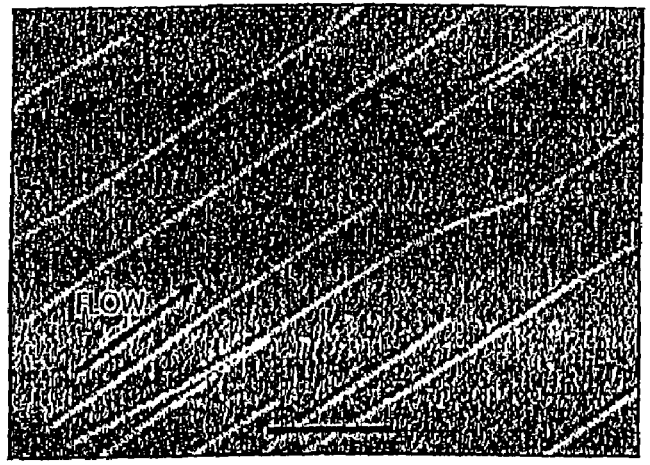
FIGS. 31A-31D illustrate parallel assembly of nanoscale wire arrays.

Several types of experiments were conducted to understand factors controlling the alignment and average separation of the NWs. First, the degree of alignment can be controlled by the flow rate. With increasing flow rates, the width of the NW angular distribution with respect to the flow direction (e.g., inset FIG. 31C) significantly narrows. Comparison of the distribution widths measured over a range of conditions shows that the width decreases quickly from the lowest flow rate, about 4 mm/s, and approaches a nearly constant value at about 10 mm/s (FIG. 31C). At the highest flow rates examined in the studies, more than 80% of the NWs are aligned within ±5 degrees of the flow direction (inset, FIG. 31C). The observed results can be explained within the framework of shear flow. Specifically, the channel flow near the substrate surface resembles a shear flow and aligns the NWs in the flow direction before they are immobilized on the substrate. Higher flow rates produce larger shear forces, and hence lead to better alignment.

Figure 31B:
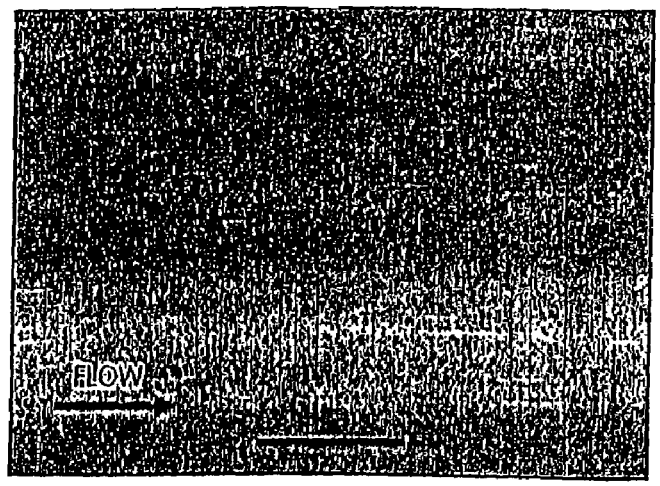
Figure 31C:
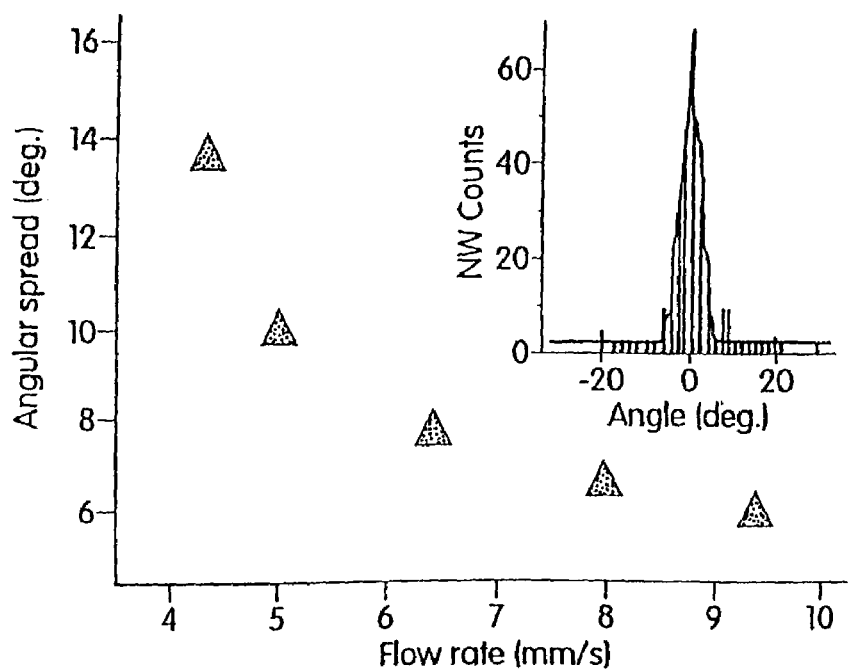
Figure 31D:
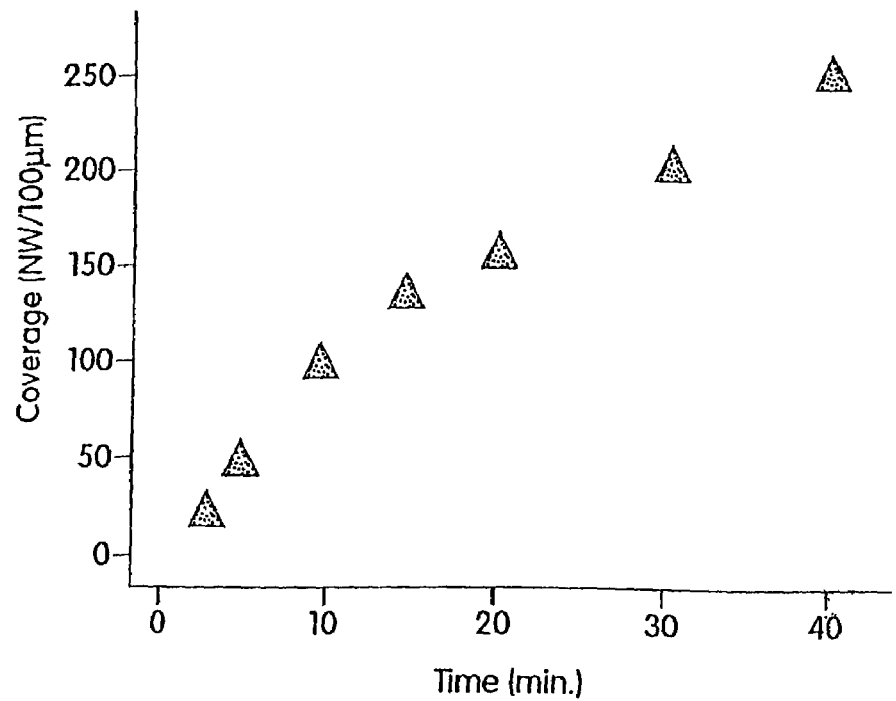

In addition, the average NW surface coverage can be controlled by the flow duration (FIG. 31D). Experiments carried out at constant flow rate show that the NW density increases systematically with flow duration. In these experiments, a flow duration of 30 min produced a density of about 250 NWs/100 µm or an average NW/NW separation of about 400 nm. Extended deposition time can produce NW arrays with spacings on the order of 100 nm or less. The deposition rate and hence average separation versus time depends strongly on the surface chemical functionality.

Specifically, the GaP, InP and Si NWs deposit more rapidly on amino-terminated monolayers, which possesses a partial positive charge, than on either methyl-terminated monolayers or bare $SiO_2$ surfaces. It is also important to recognize that the minimum separation of aligned NWs that can be achieved without NW-NW contacts will depend on the lengths of the NWs used in the assembly process. Recent progress demonstrating control of NW lengths from the 100 nanometer to tens of micrometer scale should increase the range of accessible spacings without contact.

Figure 32A:
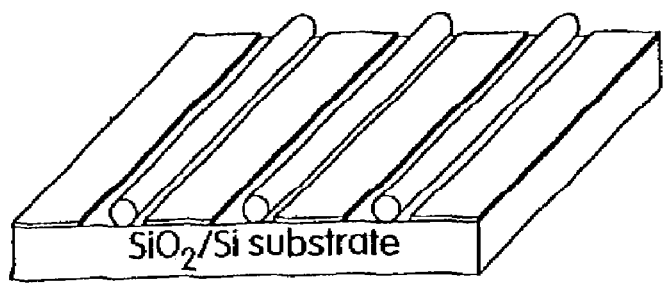
FIGS. 32A-32D illustrate assembly of periodic nanoscale wire arrays.

The results demonstrate ordering of NW structure over multiple length scales-organization of nanometer diameter wires with 100 nm to micrometer scale separations over millimeter scale areas. This hierarchical order can readily bridge the microscopic and macroscopic worlds, although to enable assembly with greatest control requires that the spatial position also be defined. This important goal is achieved by utilizing complementary chemical interactions between chemically patterned substrates and NWs (FIG. 32A). SEM images of representative experiments (FIGS. 32B-32D) show parallel NW arrays with lateral periods the same as those of the surface patterns. These data demonstrate that the NWs are preferentially assembled at positions defined by the chemical pattern, and moreover, show that the periodic patterns can organize the NWs into a regular superstructure. It is important to recognize that the patterned surface alone does not provide good control of the 1D nanostructure organization. Assembly of NTs and NWs on patterned substrates shows 1D nanostructures aligned with, bridging and looping around patterned areas with little directional control. Fluid flows are used to avoid these significant problems and enables controlled assembly in one or more directions. By combining this approach with other surface patterning methods, such as nanoscale domain formation in diblock copolymers and spontaneous ordering of molecules, it should be possible to generate well-ordered NW arrays beyond the limitations of conventional lithography.

Figure 33A:
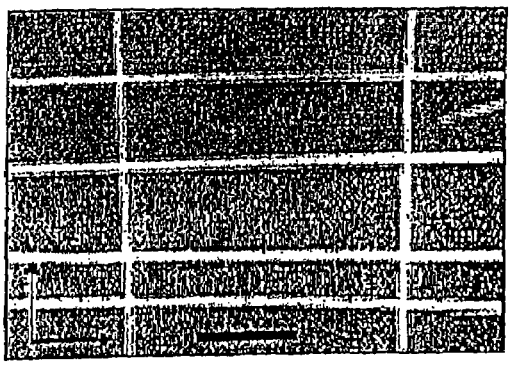
FIGS. 33A-33E illustrate layer-by-layer assembly and transport measurements of crossed nanoscale wire arrays.
Figure 33B:
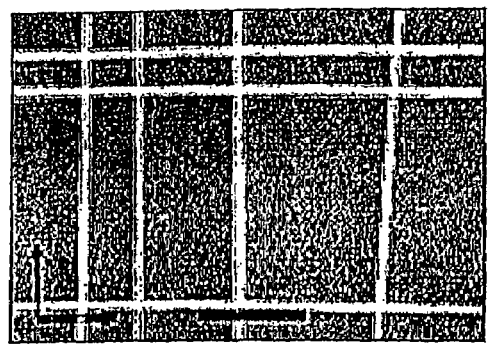

This general approach can be used to organize NWs into more complex crossed structures, which are critical for building dense nanodevice arrays, using the layer-by-layer scheme illustrated in FIG. 31B. The formation of crossed and more complex structures requires that the nanostructure-substrate interaction is sufficiently strong and that sequential flow steps do not affect preceding ones. For example, alternating the flow in orthogonal directions in a two-step assembly process yields crossbar structures (FIGS. 33A and 33B). FIGS. 33A-B show that multiple crossbars can be obtained with only hundreds of nanometer separations between individual cross points in a very straightforward, low cost, fast and scalable process. Although the separations between individual NWs are not completely uniform, a periodic array can be easily envisioned using a patterned surface as described above. Significantly, these crossbar structures can yield functional devices.

This fluidic approach is intrinsically very parallel and scalable, and moreover, allows for the directed assembly of geometrically complex structures by simply controlling the angles between flow directions in sequential assembly steps. For example, an equilateral triangle (FIG. 33C) was assembled in a three-layer deposition sequence using 60° angles between the three flow directions. The method of flow alignment thus provides a flexible way to meet the requirements of many device configurations, including those requiring assembly of multiple 'layers' of NWs.

Electric fields can be used to align suspensions of semiconductor NWs into parallel NW arrays and single NW crosses, where patterned micro-electrode arrays are used to create a field pattern. Fringing fields and charging can, however, lead to significant complications in the assembly of multiple crosses at the submicron scale.

An important feature of this layer-by-layer assembly scheme is that each layer is independent of the others, and thus a variety of homo- and hetero-junction configurations can be obtained at each crossed point by simply changing the composition of the NW suspension used for each step. For example, it is possible to directly assemble and subsequently address individual nanoscale devices using this approach with n-type and p-type NWs and NTs, in which the NWs/NTs act as both the wiring and active device elements. A typical 2×2 crossbar array made of n-type InP NWs, in which all eight ends of the NWs are connected by metal electrodes, demonstrates this point (FIG. 33D). Transport measurements (FIG. 33E) show that current can flow through any two of the eight ends, and enable the electrical characteristics of individual NWs and the NW-NW junctions to be assessed. The current-voltage (I-V) data recorded for each of the four cross points exhibit linear or nearly linear behavior (curves 200), and are consistent with expectations for n-n type junctions. Because single NW/NW p-n junctions formed by random deposition exhibit behavior characteristic of light-emitting diodes (LEDs), it is apparent that this approach can be used to assemble high-density and individually addressable nanoLEDs and electronically more complex nanodevices.

Additional studies show that suspensions of single-walled carbon nanotubes and duplex DNA can be aligned in parallel arrays using the fluidic approach.

Specifically, FIGS. 30A and 30B are schematics of fluidic channel structures for flow assembly. FIG. 30A shows a channel formed when the PDMS mold was brought in contact with a flat substrate. NW assembly was carried out by flowing a NW suspension inside the channel with a controlled flow rate for a set duration. Parallel arrays of NWs are observed in the flow direction on the substrate when the PDMS mold is removed. FIG. 30B illustrates that multiple crossed NW arrays can be obtained by changing the flow direction sequentially in a layer-by-layer assembly process.

FIGS. 31A-31D illustrate parallel assembly of NW arrays. FIGS. 31A and 31B are SEM images of parallel arrays of InP NWs aligned in channel flow. The scale bars correspond to 2 μm and 50 μm in FIGS. 31A and 31B, respectively. The silicon ($SiO_2$/Si) substrate used in flow assembly was functionalized with an amino-terminated self assembled monolayer (SAM) by immersion in a 1 mM chloroform solution of 3-aminopropyltriethoxysilane (APTES) for 30 min, followed by heating at 110° C. for 10 min. Most of the substrates used in the following experiment were functionalized in a similar way unless otherwise specified. FIG. 31C shows NW angular spread with respect to the flow direction vs. flow rate. Each data point in FIG. 31E was obtained by statistical analysis of angular distribution of about 200 NWs and shows histogram of NW angular distribution at a flow rate of 9.40 mm/s. FIG. 31D shows the average density of NW arrays vs. flow time. The average density was calculated by dividing the average number of NWs at any cross section of the channel by the width of the channel. Most of the experiments were carried out with a flow rate of 6.40 mm/s.

Figure 32B:
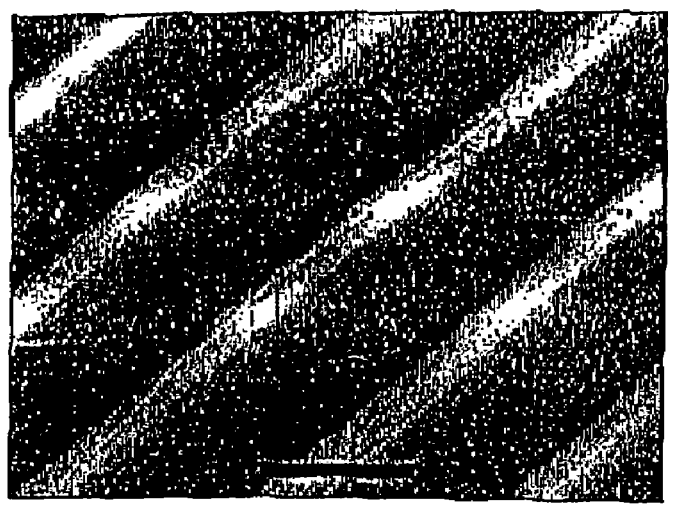
Figure 32C:
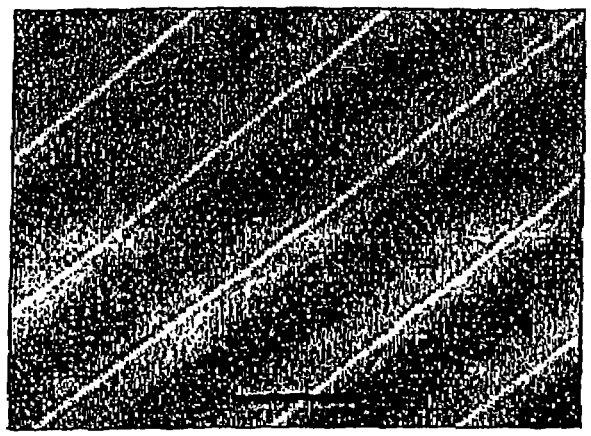
Figure 32D:
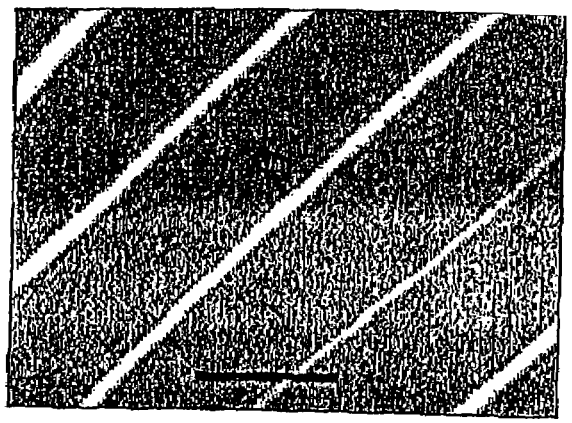

FIGS. 32A-32D illustrate assembly of periodic NW arrays. FIG. 32A is a schematic view of the assembly of NWs onto a chemically patterned substrate. The light gray areas correspond to amino-terminated surfaces, while the dark gray area corresponds to either methyl-terminated or bare surfaces. NWs are preferentially attracted to the amino-terminated regions of the surface. FIGS. 32B and 32C show parallel arrays of GaP NWs aligned on poly(methylmethacrylate) (PMMA) patterned surface with 5 µm and 2 µm separation. The dark regions in the image correspond to residual PMMA, while the bright regions correspond to the amino-terminated SiO$_2$/Si surface. The NWs are preferentially attracted to amino-terminated regions. The PMMA was patterned with standard electron beam (E-beam) lithography, and the resulting SiO$_2$ surface was functionalized by immersing in a solution of 0.5% APTES in ethanol for 10 min, followed by 10 min at 100° C. The scale bars correspond to 5 µm and 2 µm in FIGS. 32B and 32C, respectively. FIG. 32D shows parallel arrays of GaP NWs with 500 nm separation obtained using a patterned SAM surface. The SiO$_2$/Si surface was first functionalized with methyl-terminated SAM by immersing in pure hexamethyldisilazane (HMDS) for 15 min at 50° C., followed by 10 min at 110° C. This surface was patterned by E-beam lithography to form an array of parallel features with 500 nm period, followed by functionalization using APTES. The scale bar corresponds to 500 nm.

Figure 33C:
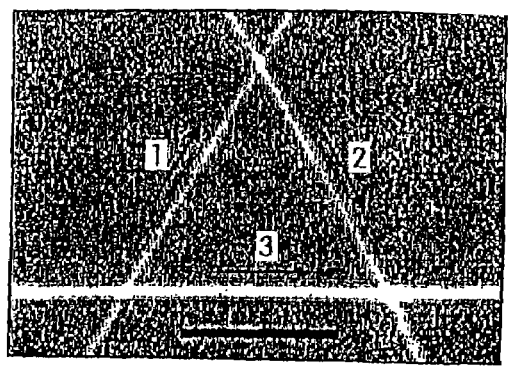
Figure 33D:
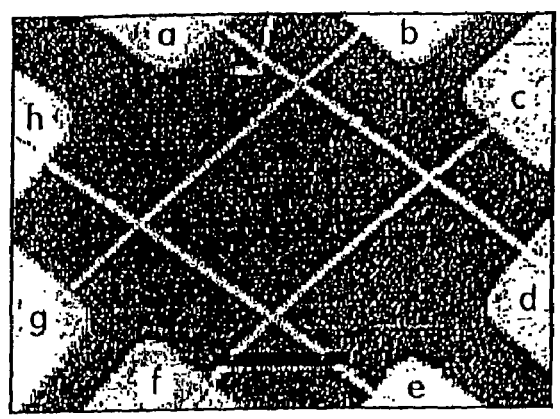
Figure 33E:
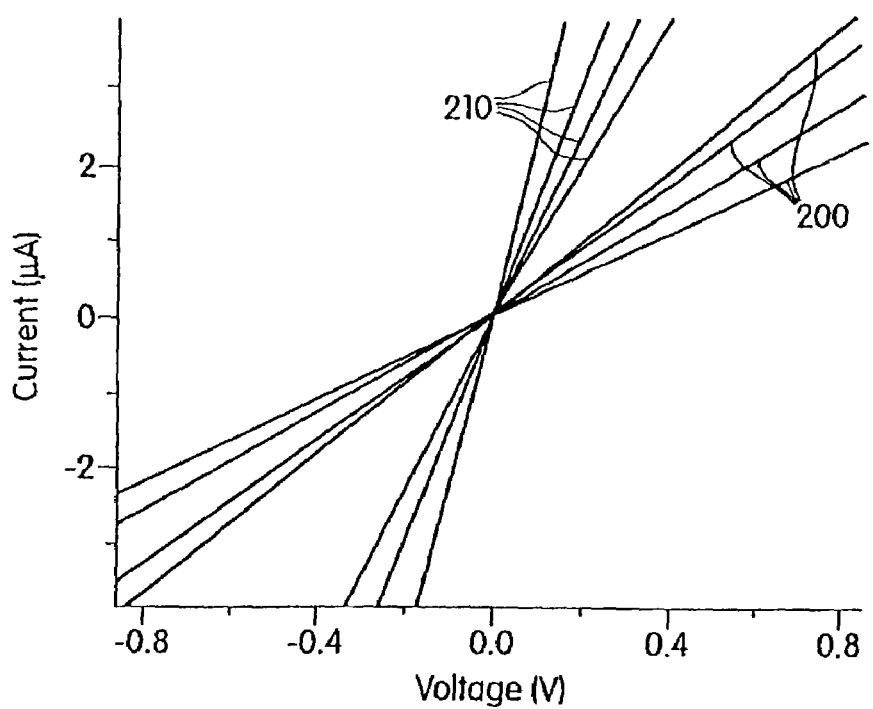

FIGS. 33A-33E illustrate layer-by-layer assembly and transport measurements of crossed NW arrays. FIGS. 33A and 33B show typical SEM images of crossed arrays of InP NWs obtained in a two-step assembly process with orthogonal flow directions for the sequential steps. Flow directions are highlighted by arrows in the images. FIG. 33C shows an equilateral triangle of GaP NWs obtained in three-step assembly process, with 60° angles between flow directions, which are indicated by numbered arrows. The scale bars correspond to 500 nm in the three images. FIG. 33D shows an SEM image of a typical 2×2 cross array made by sequential assembly of n-type InP NWs using orthogonal flows. Ni/In/Au contact electrodes, which were deposited by thermal evaporation, were patterned by E-beam lithography. The NWs were briefly (3-5 s) etched in 6% HF solution to remove the amorphous oxide outer layer prior to electrode deposition. The scale bar corresponds to 2 µm. FIG. 33E shows representative I-V curves from two-terminal measurements on a 2×2 crossed array. The curves 210 represent the I-V of four individual NWs (ad, bg, cf, eh), and the curves 200 represent I-V across the four n-n crossed junctions (ab, cd, ef, gh).

Field effect transistors, pn junctions, light emission diodes, bipolar transistors, complementary inverters, tunnel diodes have been demonstrated. The existing types of semiconductor devices can be made using nanoscale wires. The following are some examples of applications: Chemical and biological sensors; memory and computing; photodetector and polarized light detector; indicating tag using the photoluminescence properties; single electron transistors; lasers; photovoltaic solar cells; ultra-sharp tip for scanning probe microscopy and near-filed imaging; ultra-small electrodes for electrochemical and biological applications; interconnect wires for nanoelectronics and optoelectronics; temperature sensors; pressure sensors; flow sensors; mass sensors; single photon emitters and detectors; ballistic transport and coherent transport for quantum computing; spintronics devices; and assembly of nanoscale wires for 2D and 3D photonic bandgap materials.

The following is a description of alternate techniques for assembling nanoscale wires to form devices. Fluidics can be used to assemble nanoscale wires.

Nanoscale wires (or any other elongated structures) can be aligned by inducing a flow of nanoscale wire solution on surface, wherein the flow can be a channel flow or flow by any other ways. Nanoscale wire arrays with controlled position and periodicity can be produced by patterning a surface of a substrate and/or conditioning the surface of the nanoscale wires with different functionalities, where the position and periodicity control is achieved by designing specific complementary forces (chemical or biological or electrostatic or magnetic or optical) between the patterned surface and wires. For example as A wire goes to A' patterned area, B wire goes to B' patterned area, C wire goes to C' patterned area and every other wire goes to its respective patterned area. The surface of the substrate and/or nanoscale wires can be conditioned with different molecules/materials, or different charges, different magnetos or different light intensities (eg., interference/diffraction patterns from light beams) or any combination of these. As-assembled nanoscale wire arrays can also be transferred to another substrate (e.g., by stamping). Nanoscale wires can be assembled by complementary interaction. Flow can be used for assembly of nanoscale wires in the above methods, although it is not limited to flow only. Complementary chemical, biological, electrostatic, magnetic or optical interactions alone can also be exploited for nanoscale wire assembly (although with less control). Nanoscale wires can be assembled using physical patterns. Deposit nanoscale wire solution onto substrate with physical patterns, such as surface steps, trenches and others. Nanoscale wires can be aligned along the corner of the surface steps or along the trenches. Physical patterns can be formed by the natural crystal lattice steps or self-assembled diblock copolymer stripes, imprinted patterns or any other patterns. Nanoscale wires may be assembled by electrostatic or magnetic force between nanoscale wires. By introducing charge onto nanoscale wire surface, electrostatic forces between nanoscale wires can align them into certain patterns, such as parallel arrays. Nanoscale wires can be assembled using a Langmuir-Blodgett (LB) film. Nanoscale wires are first surface conditioned and dispersed to the surface of a liquid phase to form a Langmuir-Blodgett (LB) film. Nanoscale wires can then be aligned into different patterns (such as parallel arrays) by compressing the surface. Then the nanoscale wire patterns can be transferred onto desired substrate.

Nanoscale wires can be assembled by shear stretching by dispersing nanoscale wires in a flexible matrix (e.g., polymers), followed by stretching the matrix in one direction, nanoscale wires can be aligned in the stretching direction by the shear force induced. The matrix can then be removed and the aligned nanoscale wire arrays can be transferred to desired substrate. The stretching of the matrix can be induced by mechanical, electrical optical, magnetic force. The stretching direction can be either in the plane of the substrate or not.

Example 9

This example illustrates the synthesis and characterization of a compositionally modulated nanoscale wire superlattice. In this example, nanoscale wires formed from GaAs and GaP were studied. GaAs is known to be a direct band gap semiconductor, and GaP is an indirect gap semiconductor.

Figure 67:
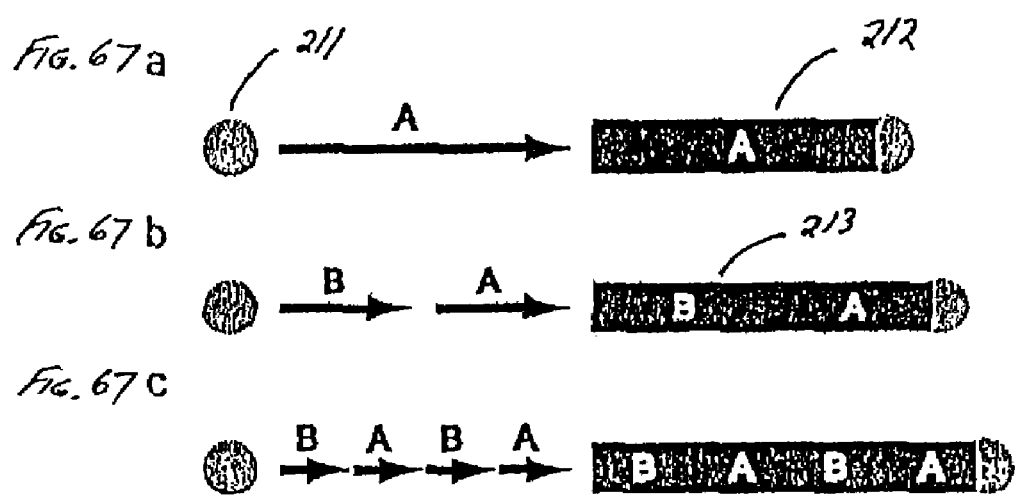
FIGS. 67A-67C are schematic diagrams of one embodiment of the invention.

Gallium arsenide (GaAs)/gallium phosphide (GaP) superlattices were grown by laser-assisted catalytic growth (LCG) using GaAs and GaP targets. A schematic of the synthesis process is illustrated in FIG. 67. A nanocluster catalyst 211 was used to nucleate and direct one-dimensional semiconductor nanoscale wire 212 growth (FIG. 67A), with the catalyst remaining at the terminus of the nanoscale wire. Upon completion of the first growth step, a different material 213 was grown from the end of the nanoscale wire (FIG. 67B). Repetition of these steps produced a compositional superlattice within a single nanoscale wire (FIG. 67C).

The nanoscale wires were synthesized either using LCG (GaAs, GaP, and InP) or CVD (Si), using gold nanoclusters to direct the growth. Gold nanoclusters were deposited onto oxidized silicon substrates and then placed in a reactor furnace. For LCG-grown nanoscale wires, solid targets of GaAs, GaP, and InP were ablated using either a pulsed ArF excimer or Nd-YAG lasers, and growth was carried out at 700-850° C. in an argon flow of 100 standard cubic centimeters per minute (scem) at 100 Torr. A pause of about 45 seconds in the ablation was made between each layer in a given superlattice. Silicon nanoscale wires were grown by CVD at 450° C. using silane (3 sccm) and either 100 ppm diborane (p-type) or phosphine (n-type) in helium (18 sccm) as dopants. The furnace was evacuated prior to switching dopants.

The resulting nanoscale wires were sonicated briefly in ethanol and deposited onto copper grids for TEM analysis. The HRTEM images and EDS spectra from nanoscale wire superlattices were collected on a JEOL 2010F microscope. The elemental mapping of the single junction was conducted on a VG HB603 STEM.

Nanoscale wires dispersed in ethanol were deposited onto silicon substrates (600 nm oxide), and electrical contacts were defined using electron beam lithography. Ti/Au contacts were used for Si nanoscale wires, and were annealed at 400° C. following deposition. InP LED contacts were fabricated by a two-step process in which the first contact (n-type) was made using Ge/Au or Ni/In/Au and the second (p-type) was made using Zn/Au. The contacts were annealed at 300-350° C. following deposition.

A Digital Instruments Nanoscope III with extender module was used for the EFM and SGM measurements. FESP tips coated with 5 nm Cr/45 nm Au were used for imaging. For EFM, the Nanoscope was operated in LiftMode with a lift height of 60 nm and a scan rate of 0.5 Hz.

Single nanoscale wire photoluminescence images and spectra were obtained using a home-built, far-field, epifluorescence microscope. Excitation light (488 nm) was focused by an objective (NA=0.7) to a ~30-µm diameter spot on a quartz substrate deposited with nanoscale wires. The typical excitation power density was ~1.0 kW/cm$^2$. A $\lambda/2$ waveplate was used to change the polarization of excitation light. The sample was mounted either in air at room temperature (i.e., about 25° C.) or on the cold finger of a cryostat and cooled to 7 K. The resulting photoluminescence images and spectra was collected by the same objective, filtered to remove excitation light, focused, and either imaged or dispersed onto a liquid nitrogen cooled charge coupled device. The emission polarization was analyzed with a Glan-Thompson polarizer placed at the front of the spectrometer.

Figure 68:
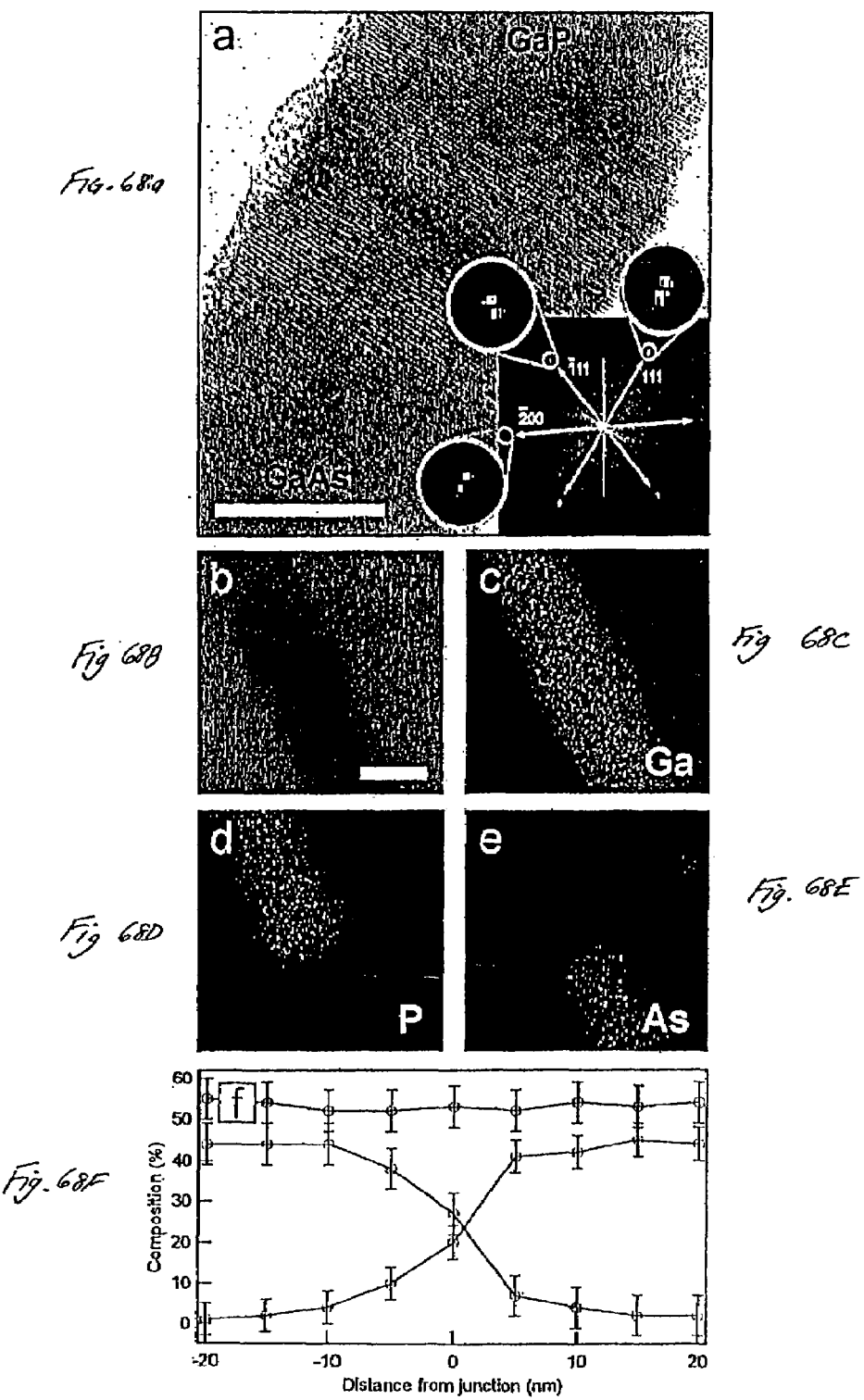
FIGS. 68A-68F illustrate data from one embodiment of the invention.

Transmission electron microscopy (TEM) images of the products of this synthesis are shown in FIG. 68. The TEM can be focused on the junction area since the nanoscale wire lengths were controlled directly by growth times. High-resolution TEM ("HRTEM") images of sample GaAs/GaP junction regions, as illustrated in FIG. 68A, exhibited a crystalline nanoscale wire core without obvious defects, and showed that the nanoscale wire axes lies along the <111> direction. The sample was grown from a 20 nm gold nanocluster catalyst. The scale bar is 10 nm. Two-dimensional Fourier transforms (2DFTs) calculated from the high-resolution images containing the junction region, shown as an inset in FIG. 68A, showed pairs of reciprocal lattice peaks along the different lattice directions, while 2DFTs calculated from the regions above and below the junction (not shown) exhibited only single reciprocal lattice peaks. Analysis of these peak data yielded lattice constants, indexed to the zinc blende structures of GaP and GaAs, of 0.5474±0.0073 nm and 0.5668±0.0085 nm, in agreement with the values for both GaP (0.5451 nm) and GaAs (0.5653 nm), respectively. 2DFT also revealed a splitting of the reciprocal lattice peaks along the <111>, <-111>, and <-200> lattice directions in the [0-22] zone axis, corresponding to the lattice constants for GaAs and GaP.

Local elemental mapping of the heterojunction by energy dispersive x-ray spectroscopy (EDS) was used to address the composition variation across the junction. Elemental maps produced from scanning TEM images showed that gallium was uniformly distributed along the length of the nanoscale wire (FIG. 68c), while phosphorous (FIG. 68d) and arsenic (FIG. 68e) appeared to be localized in the GaP and GaAs portions of the nanoscale wire heterostructure, respectively. Quantitative analysis of the phosphorous/arsenic composition variation, illustrated in FIG. 68f, indicated that the transition in this particular nanoscale wire was not atomically-abrupt, but transitioned between the GaP and GaAs phases over a length scale of 15-20 nm. The diameter of this nanoscale wire was approximately 20 nm.

Thus, this example illustrates the synthesis and characterization of a compositionally modulated nanoscale wire.

Example 10

This example illustrates the synthesis and characterization of compositionally modulated nanoscale wire superlattices in which the number of periods and repeat spacing were varied during growth.

Preparation and synthesis of gallium arsenide (GaAs)/gallium phosphide (GaP) were prepared using procedures to the ones described in Example 1. Repetition of the LCG steps was used to produce a compositional superlattice within a single nanoscale wire.

TEM images of one nanoscale wire prepared using those techniques showed a six period structure, corresponding to a (GaP/GaAs)$_3$ superlattice. These images are shown in FIG. 69a. The nanoscale wire was about 20 nm in diameter and had uniform characteristics over its 3 lm length. The background mesh in FIG. 69a is from carbon film on which the nanodeposited for imaging. The scale bar represents 300 nm.

Spatially resolved EDS measurements of the nanoscale wire (illustrated in FIG. 69b) further demonstrated that the phosphorous and arsenic regions were distinct from one another and that there was minimal cross-contamination or overlap between the two types of regions. Moreover, these data showed that each GaP and GaAs nanoscale wire segment had a length of about 500 nm, and thus was consistent with the equal growth times used for each segment. These date also showed that growth rates remained relatively constant during the entire nanoscale wire synthesis. The symbols in FIG. 69b indicate locations in the nanoscale wire shown in FIG. 69a where elemental analysis of the superlattice was performed. The P K$\alpha$ peak was found to be about 2.015 keV and the As K$\alpha$ peak was found to be about 10.543 keV. The spectra illustrate distinct, periodic modulation of the nanoscale wire composition, with three uniform periods of GaP spectra separated by three uniform periods of GaAs spectra.

Photoluminescence imaging of individual nanoscale wires from the (GaP/GaAs)$_3$ superlattice sample described above showed that these nanoscale wires exhibit an emission pattern of three spots separated by dark regions, as illustrated in FIG. 69c. This pattern was consistent with emission originating from the three GaAs regions, separated by dark GaP regions that act as optical "spacers." Control experiments on individual samples of pure GaAs and GaP nanoscale wires showed that strong luminescence was obtained from GaAs but not GaP.

The GaAs regions also exhibited a strong polarization dependence, emitting when the excitation is polarized parallel (∥) to the nanoscale wire axis and appearing dark when the polarization is perpendicular ⊥) to the nanoscale wire axis, as illustrated in FIG. 69c. The emission from the superlattice structures was also found to be highly polarized along the wire axis.

FIG. 69c illustrates a photoluminescent nanoscale wire under parallel (∥) excitation and under perpendicular (⊥) excitation (inset). The three bright regions under parallel excitation correspond to the three GaAs (direct band gap) regions, while the dark segments are from the GaP (indirect band gap) regions. No photoluminescence was observed above background for perpendicular excitation due to the dielectric contrast between the nanoscale wire and its surroundings. The scale bar is 5 µm in length.

Systematic variations in the growth time produced nanoscale wire superlattices with well-defined changes in periodicity. For example, the photoluminescence images of an 11-layer superlattice in which the length of the GaP regions was doubled each layer while maintaining a constant GaAs period showed that the separation between emitting GaAs regions doubled along the length of the nanoscale wire, as illustrated in FIG. 69d. The diameter of the nanoscale wire illustrated in FIG. 69d was about 40 nm, and the superlattice had the following structure: GaP(5 nm)/GaAs(5 nm)/GaP(5 nm)/GaAs(5 nm)/GaP(10 nm)/GaAs(5 nm)/GaP(20 nm)/GaAs(5 nm)/GaP(40 nm)/GaAs(5 nm)/GaP(5 nm). The inset illustrates this structure. The scale bar is 5 µm in length.

Additionally, photoluminescence spectra of 21-layer GaP/GaAs superlattices consisting of a short 4 period (GaP/GaAs) repeat, followed by 3 longer GaP spacer repeats, and ending in a relatively short 4 period (GaAs/GaP) repeat are illustrated in FIG. 69e, also showing well-defined separations between the two regions. The structure of the nanoscale wire shown in FIG. 69e is (GaP/GaAs)$_{10}$GaP, and the nanoscale wire has a group of four equally-spaced spots on the left, two in the middle with larger gaps, and another set of four with equal spacing on the end. The nanoscale wire is about 25 µm in length.

Thus, this example illustrates the synthesis and characterization of compositionally modulated nanoscale wire superlattices in which the number of periods and repeat spacing were varied during growth.

Example 11

This example illustrates an example of a nanoscale wire characterized as a diode.

Individual silicon nanoscale wires having p/n junctions were fabricated by gold nanocluster catalyzed chemical vapor deposition and dopant modulation. These nanoscale wire p/n junctions were characterized at the single nanoscale wire level by a variety of electrical measurement, as shown in FIG. 70, since EDS was insufficiently sensitive to characterize dopant profiles. The scale bars shown in FIG. 70 are 500 nm.

As illustrated in FIG. 70a, current (I) vs. voltage ($V_{sd}$) the silicon nanoscale wire measurements showed rectifying behavior consistent with the presence of an intra-nanoscale wire p/n junction. The insets illustrate a schematic of single nanoscale wire electrical characterization by transport and probe microscopy, and a scanning electron micrograph of the silicon nanoscale wire device with the source (S) and drain (D) electrodes as indicated.

The local nanoscale wire potential and gate response were characterized by electrostatic force microscopy (EFM) and scanned gate microscopy (SGM), respectively, to determine current rectification due to intra-nanoscale wire p/n junctions. An EFM image of a typical p/n junction (for example, as shown in FIG. 70b) in reverse bias showed that the entire voltage drop occurs at the p/n junction itself; EFM measurements showed no potential drop at the contact regions under forward or reverse bias (not shown), ruling out the contact/nanoscale wire interface as the source of rectification in the I vs. $V_{sd}$ behavior. In FIG. 70b, the EFM phase image of the nanoscale wire diode was captured under reverse bias with the tip at +3 V and the drain (right) at +2 V. The signal was proportional to the square of the tip-surface potential difference and showed an abrupt drop in the middle of the wire at the junction.

In FIG. 70c, SGM images recorded with the nanoscale wire device in forward bias and the scanned tip-gate positive showed enhanced conduction to the right of the junction, indicating an n-type region, and reduced conduction to the left of the junction, indicating depletion of a p-type region. The image shows the recorded source-drain current, as the tip of the probe (at +10 V) was scanned across the device. With the drain biased at −2 V ($V_{sd}$=+2 V), bright regions correspond to an increase in the positive quantity ISD and dark regions correspond to a decrease in ISD. Vertical dashed white lines indicate the junction also indicated in FIGS. 70b and 70c.

FIG. 70d illustrates a schematic of an InP nanoscale wire LED, and FIG. 70e illustrates polarized emission from the LED along the nanoscale wire axis. Dashed white lines indicate the edges of the electrodes in FIG. 70d, and were determined from a white light image. No electroluminescence was detected with perpendicular polarization. The scale bar in FIG. 70e indicates 3 µm.

In conclusion, the abrupt change in majority carrier type coincided with the location of the intra-nanoscale wire junction determined by EFM. Thus, this doped nanoscale wire shows diode behavior.

Example 12

In this example, a quantum confinement model that was constructed in order to explain the photoluminescence of certain embodiments of the invention is illustrated.

An effective mass model (EMM) was constructed using particle-in-a cylinder wavefunctions for electrons and holes. In this model, the energy shift, ΔE, relative to the bulk band gap as a function of the nanoscale wire radius, R, was given by $$\Delta E = \frac{\hbar}{2m^*}\left(\left(\frac{\alpha_{01}}{R}\right)^2 + \left(\frac{\pi}{L}\right)^2\right) - \left\langle \Psi(x_e)\Psi(x_h)\left|\frac{e^2}{\varepsilon|x_e - x_h|}\right|\Psi(x_h)\Psi(x_e)\right\rangle \quad (1)$$

where m* is the reduced effective exciton mass (me mh/(me+mh)), ℏ is Planck's constant, $\alpha_{o1}$, (≈2.405) the first zero of the zero order Bessel function, L is the effective nanoscale wire length, e the charge of the electron, and ε the dielectric constant of InP.

The exciton wavefunction in Equation (1) was taken as a simple product of the single-particle electron and hole wavefunctions in cylindrical coordinates:

$$\Psi(r_{e,h}, z_{e,h}) = N \cdot J_0(\alpha_{01} r_{e,h}) \sin(\pi z_{e,h}/L) \quad (2)$$

where $J_{0a(\alpha 01} r_{e,h})$ is the zero order Bessel function, L the length of the cylinder, and N the normalization constant. The first term in Equation (1) represented the size-dependent kinetic energy confinement imposed by the walls of the nanoscale wire cylinder. The second term was the attractive Coulomb interaction between electron and hole to first order in perturbation theory, which was numerically evaluated using the Green's function expansion of $1/|x_e - x_h|$ in terms of Bessel functions.

Using the reduced effective mass, m*, as the primary fitting parameter, this model fitted the experimental data indicating that the model captured the essential physics of the system. The reduced effective mass at room temperature determined from the fit, 0.052 $m_0$ ($m_0$, the free electron mass), was in agreement with previously published values of 0.065 $m_0$ for bulk InP. The smaller effective mass was attributed to the crystalline orientation of the nanoscale wires; that is, the nanoscale wire growth axis corresponded to the heavy hole direction in InP. The smaller observed effective mass was thus consistent with confinement perpendicular to the growth direction, where the hole mass was reduced. The value of reduced mass determined from the 7 K data, 0.082 $m_0$, was consistent with the observation that the effective carrier masses in InP increased with decreasing temperature.

Therefore, this example illustrates a quantum confinement model that was constructed in order to explain the photoluminescence of certain embodiments of the invention.

Example 13

This example illustrates the calculation of a theoretical polarization ratio in an indium phosphide nanoscale wire.

The of the can be naturally accounted for in terms of the large nanoscale wire/air dielectric contrast inherent in the free-standing materials The large polarization response of the nanoscale wires was modeled quantitatively by treating the nanoscale wire as an infinite dielectric cylinder in a vacuum, as the wavelength of the exciting light was much greater than the wire diameter. When the incident field was polarized parallel to the cylinder, the electric field inside the cylinder was not reduced, but when polarized perpendicular to the cylinder, the amplitude was attenuated according to the following:

$$E_1 = 2\epsilon_0 E_e/(\epsilon + \epsilon_0), \quad (3)$$

where $E_1$ is the electric field inside the cylinder, $E_e$ the excitation field, $\epsilon$ is the dielectric constant of the cylinder, and $\epsilon_0$ is the dielectric constant of a vacuum. Using the dielectric constant for bulk InP of 12.4, the theoretical polarization ratio was calculated to be 0.96.

Thus, this example illustrates the calculation of a theoretical polarization ratio in an indium phosphide nanoscale wire.

Example 14

This example illustrates the formation and characterization of nanoscale wires, in accordance with one embodiment of the invention.

Figure 63A:
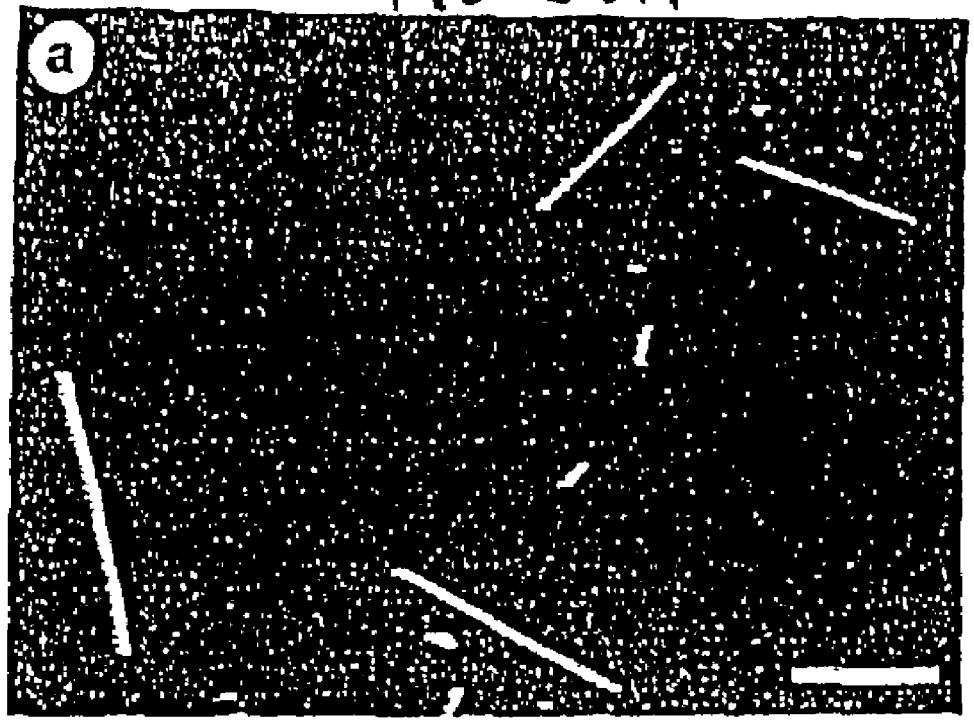
FIGS. 63A-63C illustrate data from one embodiment of the invention.

Monodisperse, single crystalline InP nanoscale wire building blocks were synthesized via a colloid mediated laser-assisted catalytic growth, and deposited from solution suspensions onto quartz substrates for photoluminescene measurements. Atomic force microscopy measurements, illustrated in FIG. 63a, showed that individual nanoscale wires deposited in this way were monodisperse and well separated, and enable intrinsic photoluminescene properties to be probed without the averaging inherent in ensemble measurements. Scale bar is 5 µm.

Figure 63B:
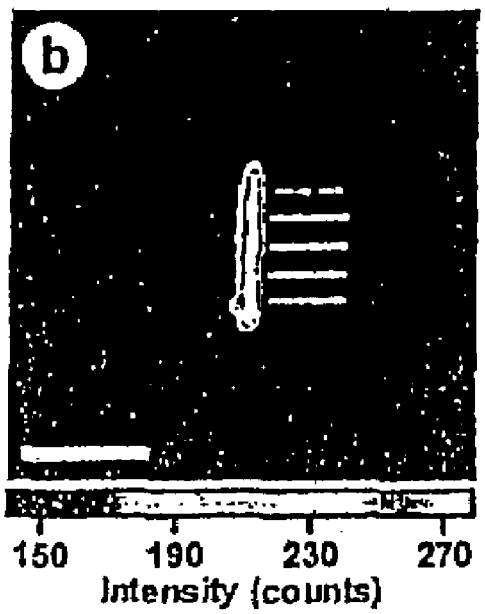

In FIG. 63b, room temperature images of the total photoluminescene intensity were recorded on individual wires exhibit uniform emission intensity over the entire nanoscale wire lengths within the approximately 1 µm spatial resolution of these experiments. The scale bar in this figure represents 5 µm. The photoluminescene image was taken at room temperature with an exposure time of about 2 s.

Figure 63C:
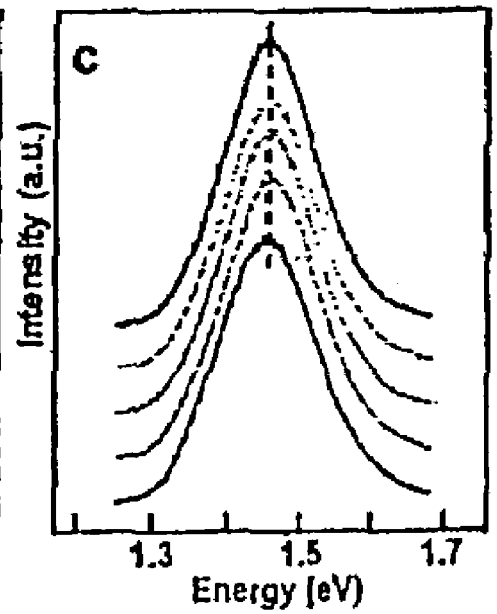

In addition, luminescence spectra recorded at different positions along the nanoscale wire axis showed nearly identical line shapes and emission energies, as illustrated in FIG. 63c. The photoluminescene spectra were collected at different positions along the nanoscale wire as is indicated in FIG. 63b. For clarity, the spectra from different locations were normalized to a common maximum and shifted upward. Uniform photoluminescene was also observed in measurements recorded at low temperatures (e.g., 7 K), and suggested that the nanoscale wires had sufficiently regular structures to prevent strong localization over this energy scale, 7-300 $k_B$. The photoluminescene image was taken at room temperature with an exposure time of about 10 s.

Figures 64A, 64B, 64C, 64D:
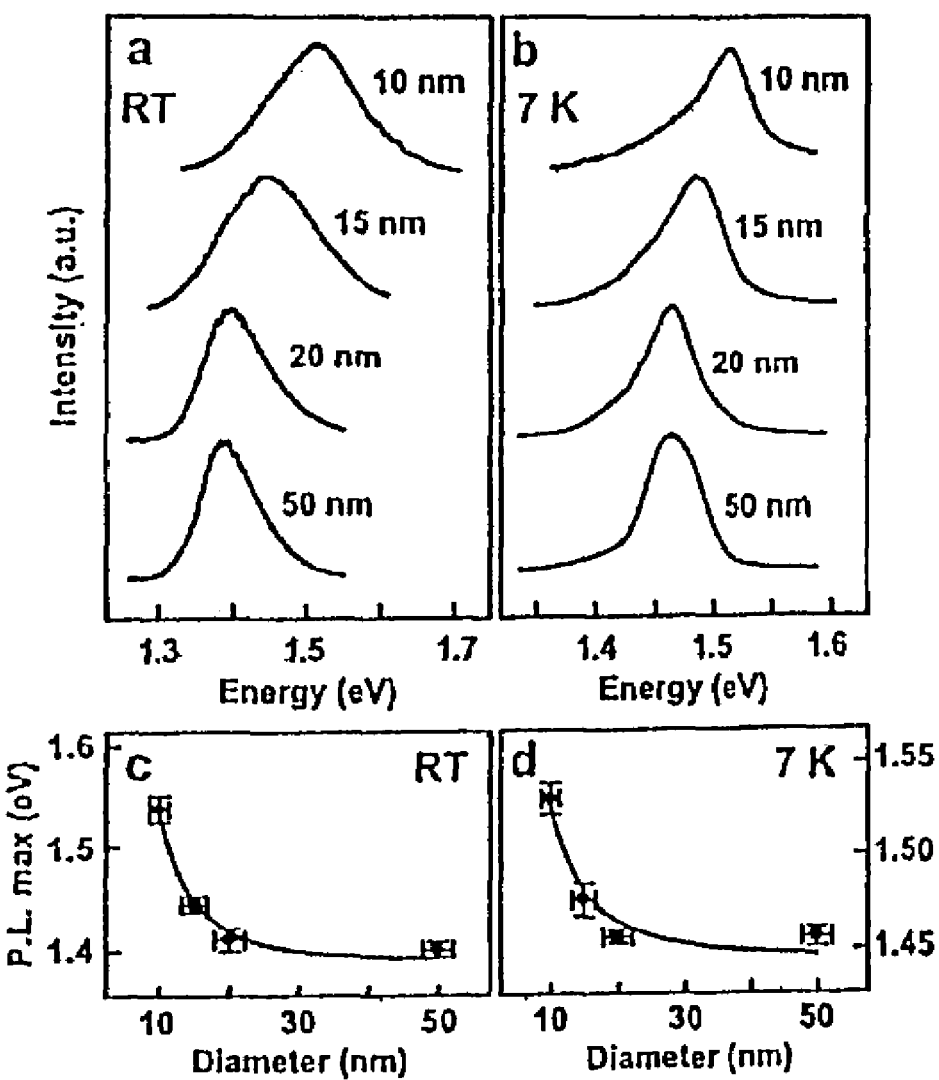
FIGS. 64A-64D illustrate data from one embodiment of the invention.

The optical and electronic properties of low-dimensional semiconductors were size-dependent due to quantum confinement effects. These effects were probed directly through photoluminescene studies of individual isolated InP nanoscale wires with diameters of 50, 20, 15, and 10 nm. Spectra recorded at room temperature (FIG. 64a) and 7 K (FIG. 64b) exhibited a systematic shift to higher energies as the nanoscale wire diameters were reduced. The typical line widths in FIGS. 64a and 64b were found to be 90-150 and 50-60 meV, respectively. In addition, these experiments showed that all of the diameter-dependent spectra recorded at 7 K shifted to higher energy, consistent with the shift of the bulk band gap from 1.35 to 1.42 eV as temperature is reduced from room temperature to 7 K.

Data recorded from a number of independent wires for each diameter, using monodisperse samples, also show virtually the same luminescence maxima and line shape for each diameter and temperature. Plots summarizing the diameter-dependent photoluminescene maxima determined at room temperature (FIG. 64c) and 7 K (FIG. 64d) demonstrate that the uncertainty in values was small compared to the size-dependent change. Wire diameters were measured using TEM, while the emission energy of maximum intensity was obtained from single nanoscale wire photoluminescene spectra. Between 20 and 50 wires were measured per sample. These results thus illustrate the uniformity of the nanoscale wires.

The data fits to the diameter-dependent photoluminescene data were relatively insensitive to the value of L, with reasonable fits obtained for L>10 nm. Values of L less than the true nanoscale wire length account phenomenologically for the slight blue shift in the PL present in 50 nm nanoscale wires, which were expected to be similar to bulk InP.

The line widths were also consistently broader in these single wire photoluminescene measurements. The broadening suggested that the widths might signify delocalization, although inhomogeneous broadening by surface states and small diameter fluctuations could also contribute. Since the spatially resolved spectra are quite uniform and evidence for localization has not yet been observed in images, these latter contributions may be less important. Thus, these data indicate a delocalized 1-dimensional system, and not strongly localized quantum dot-like emission.

Figures 65A, 65B, 65C:
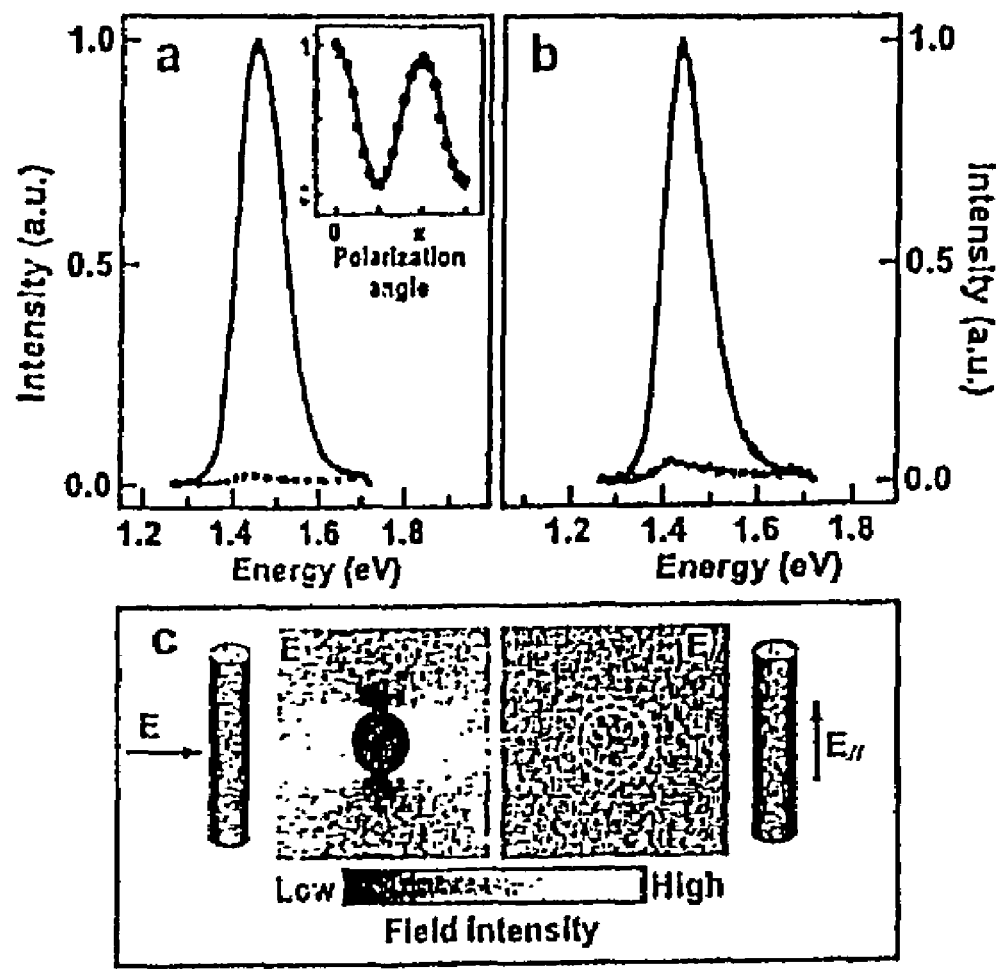
FIGS. 65A-65C illustrate one embodiment of the invention.

FIG. 65a illustrates photoluminescene polarization anisotropy of single InP nanoscale wires. These spectra were recorded with the polarization of the laser aligned parallel (solid line) and perpendicular (dashed line) to the wire axis. The polarization ratio, p (p), was found to be 0.96. The inset illustrates changes in intensity as a function of the laser polarization angle with respect to the wire axis.

In FIG. 65b, emission spectra of the wire in FIG. 65a are shown. These spectra were taken with the excitation parallel to the wire, while a polarizer was placed in the detection optics. The polarization ratio of the parallel (solid line) to perpendicular (dashed line) emission was found to be 0.92. The spectra in FIGS. 65a and 65b were taken at room temperature, although spectra recorded at 7 K displayed nearly identical behavior.

FIG. 65c illustrates a dielectric contrast model for the polarization anisotropy. The nanoscale wire was treated as an infinite dielectric cylinder in a vacuum while the laser polarizations were considered as electrostatic fields, oriented as depicted. Field intensities ($|E|^2$) calculated from Maxwell's equations showed that the field was strongly attenuated inside the nanoscale wire for the perpendicular polarization, $E_\perp$, while the field inside the nanoscale wire was unaffected for the parallel polarization, $E_\parallel$.

Figure 66A:
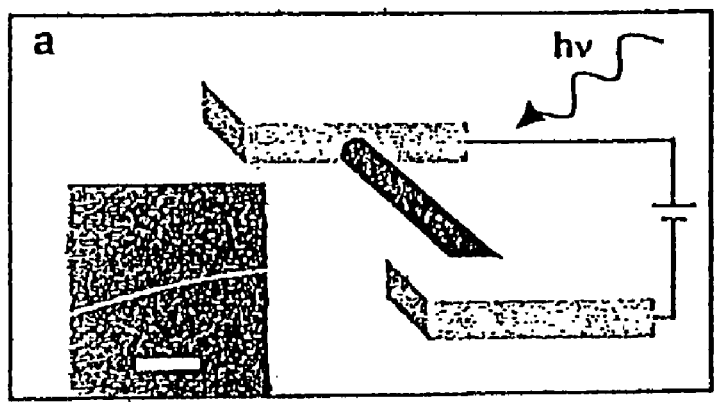
FIGS. 66A-66C illustrate data from one embodiment of the invention.

FIG. 66 illustrates various InP nanoscale wire photodectors. FIG. 66a is a schematic, depicting the use of a nanoscale wire as a photodetector by measuring the change in photoconductivity as a function of incident light intensity and polarization. The inset illustrates an FE-SEM image of a 20 nm diameter nanoscale wire having contact electrodes. The scale bar is 2 μm. Electrical contacts to the nanoscale wires were defined using electron beam lithography, and Ni/In/Au contact electrodes were thermally evaporated.

Figure 66B:
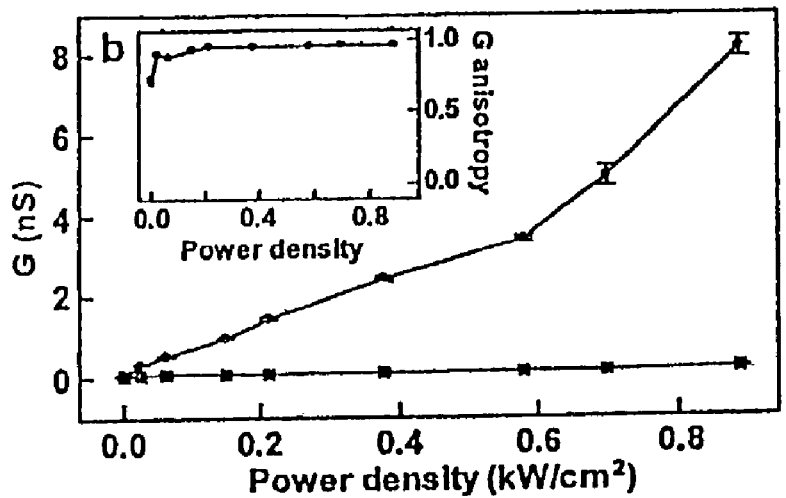

FIG. 66b is a graph of the conductance, G, vs. the excitation power density. The photoconductivity response when the illumination is polarized parallel (circles) and perpendicular (squares) to the wire is shown. The inset illustrates photoconductivity anisotropy, σ (sigma), vs. excitation power, calculated from the graph of FIG. 66b. The measured anisotropy for the shown device was determined to be 0.96.

Figure 66C:
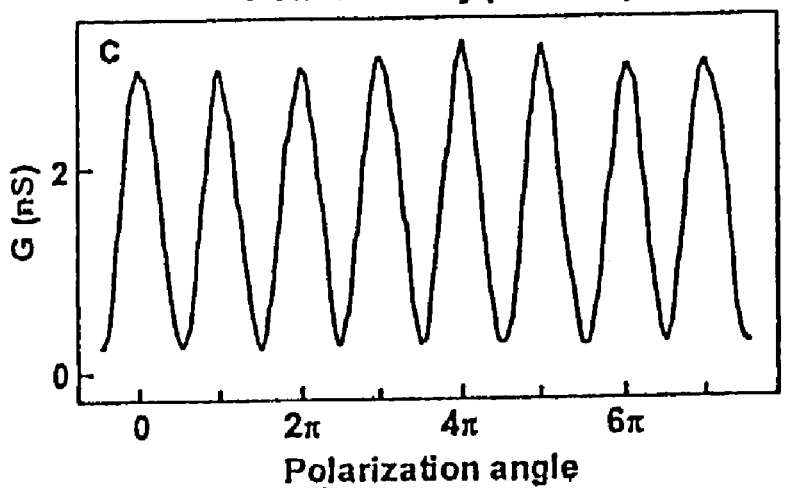

FIG. 66c is a graph of the conductance versus the polarizaton angle. All photoconductivity measurements were made at room temperature. The current collected at the drain electrode was measured using standard lock-in techniques, with an excitation voltage of 50 mV at 31 Hz. No gate voltage was applied. An excitation wavelength of 514.5 nm was used for these measurements.

Thus, this example illustrated the formation and characterization of nanoscale wires, in accordance with one embodiment of the invention.

Example 15

This example demonstrates the assembly of p-type silicon (p-Si) and n-type gallium nitride (n-GaN) NWs to form crossed nanoscale p-n junctions and junction arrays in which the electronic properties and function are controlled to provide both diode and FET elements in high yield. Significantly, nanoscale p-n junction and FET arrays were configured as OR, AND and NOR logic gates with substantial gain, and these gates were interconnected to demonstrate computation with a half-adder. This approach leads naturally through the bottom-up paradigm to integration at the nanoscale and represents a step towards the creation of sophisticated nanoelectronics.

Figure 60:
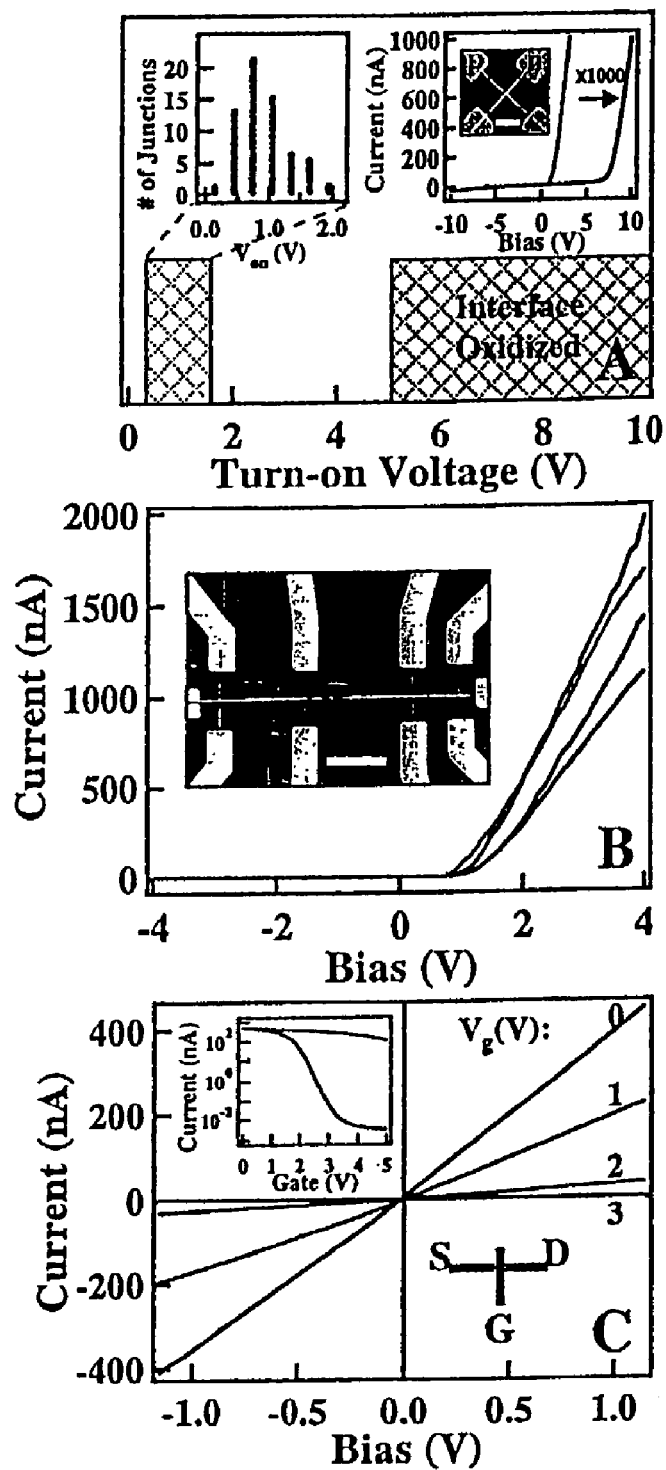
FIGS. 60A-60C illustrate various crossed nanoscale wire nanodevice elements.

The single crystal p-Si and n-GaN NWs used were synthesized by nanocluster-catalyzed methods and had diameters of 10-25 and 10-30 nm, respectively. NWs as small as 2 nm can be prepared. These NWs were chosen since the oxide coating on their surfaces can be independently varied to enable good control of junction electronic properties. To demonstrate this point, which is critical for assembly of more complex integrated devices, the electronic properties of a large number of crossed p-Si/n-GaN junctions are provided (FIG. 60). Current-voltage (I-V) measurements show that the p-Si/n-GaN crossed NW devices exhibit current rectification characteristic of p-n diodes with a typical turn-on voltage of about 1.0 V (FIG. 60a). These results are highly reproducible. Clear current rectification was observed in over 95% of the more than 70 crossed p-n NW devices studied, and moreover, 85% of the devices exhibited low turn-on voltages between 0.6-1.3 V (top-left inset, FIG. 60a). The reproducible assembly of crossed NW structures with predictable electrical properties contrasts sharply with results from NT based devices. Significantly, electrical transport measurements made on a typical 4×1 crossed p-Si/n-GaN junction array (FIG. 60b) show that the four nanoscale cross points form independently addressable p-n junctions with clear current rectification and similar turn-on voltages. These data demonstrate clearly the high yield and reproducibility of the crossed NW p-n devices, and represent an important and necessary step for the rational assembly of more complex devices such as logic gates.

In addition to these low turn-on voltage diodes, high turn-on voltage p-n junctions can be used as nanoscale FETs (FIG. 60c). Specifically, a p-channel FET with both a nanoscale conducting channel and a nanoscale gate is formed from a n-GaN/p-Si crossed NW structure and referred to as crossed NW FETs (cNW-FETs). The high turn-on voltage junctions required to assemble cNW-FETs were reproducibly formed by increasing the oxide layer thickness at the junctions by either thermal oxidation of the SiNWs or by passing a high current through the junction in the air. Transport data recorded on over 50 p-n junctions prepared in this way (FIG. 60A) show that turn-on voltages in excess of 5 volts can be achieved in nearly quantitative yield, while still maintaining good conduction through individual NWs. The corresponding I-V data recorded on a typical cNW-FET, where the n-GaN NW is used as a nano-gate, exhibits a large decrease in conductance with increasing gate voltage (FIG. 60c). Specifically, the conductance can be changed by more than $10^5$-times with only a 1-2 V variation in the nano-gate, while the conductance changes by only a factor 10 when a global back-gate is used (top-left inset, FIG. 60c). The high sensitivity of the cNW-FETs is attributed to the intrinsically thin gate dielectric between the crossed NWs. The reproducibility, large gate response and potential for nanoscale integration make the cNW-FETs attractive for assembling more complex electronic devices where FETs are critical elements. Moreover, these characteristics contrast recent work on NTs that have employed either global back gates, which are incompatible with independent device function, or lithographically defined local gates, which use and are constrained by conventional lithography to obtain nanoscale structures.

Specifically, FIG. 60 illustrates these crossed nanoscale wire nanodevice elements. FIG. 60a illustrates a turn-on voltage distribution for crossed NW junctions. The green shaded area indicates the range for low turn-on voltage junctions formed from as-assembled NW junctions, and the red shaded area indicates high turn-on voltage devices after local oxidation of the junction. The top-left inset shows histogram of turn-on voltage for over 70 as-assembled junctions showing a narrow distribution around 1 volt. The high turn-on voltage devices have a broad distribution but generally fall into the range of 5-10 V. The top-right inset shows an example I-V response for low (green) and high (red) turn-on voltage elements. Note that the red curve is multiplied by 1000 for better view. The inset in top-right inset shows a typical SEM image of a crossed NW device. Scale bar is 1 micrometer. FIG. 60$b$ illustrates I-V behavior for a 4(p)×1(n) multiple junction array. The four curves represent the I-V for each of the four junctions and highlight reproducibility of assembled device elements. The inset shows an example of a multiple crossed NW device. The scale bar represents 2 micrometers. FIG. 60$c$ illustrates gate dependent I-V characteristics of a crossed NW-FET. The NW gate voltage for each I-V curve is indicated (0, 1, 2, 3 V). The red and blue curves in the top-left inset show I vs. $V_{gate}$ for n-NW (red) and global back (blue) gates when the bias is set at 1 V. The transconductance for this device was 80 and 280 nS ($V_{sd}$=1V) using the global back gate and NW gate, respectively. The bottom-right inset shows the measurement configuration.

Figure 61:
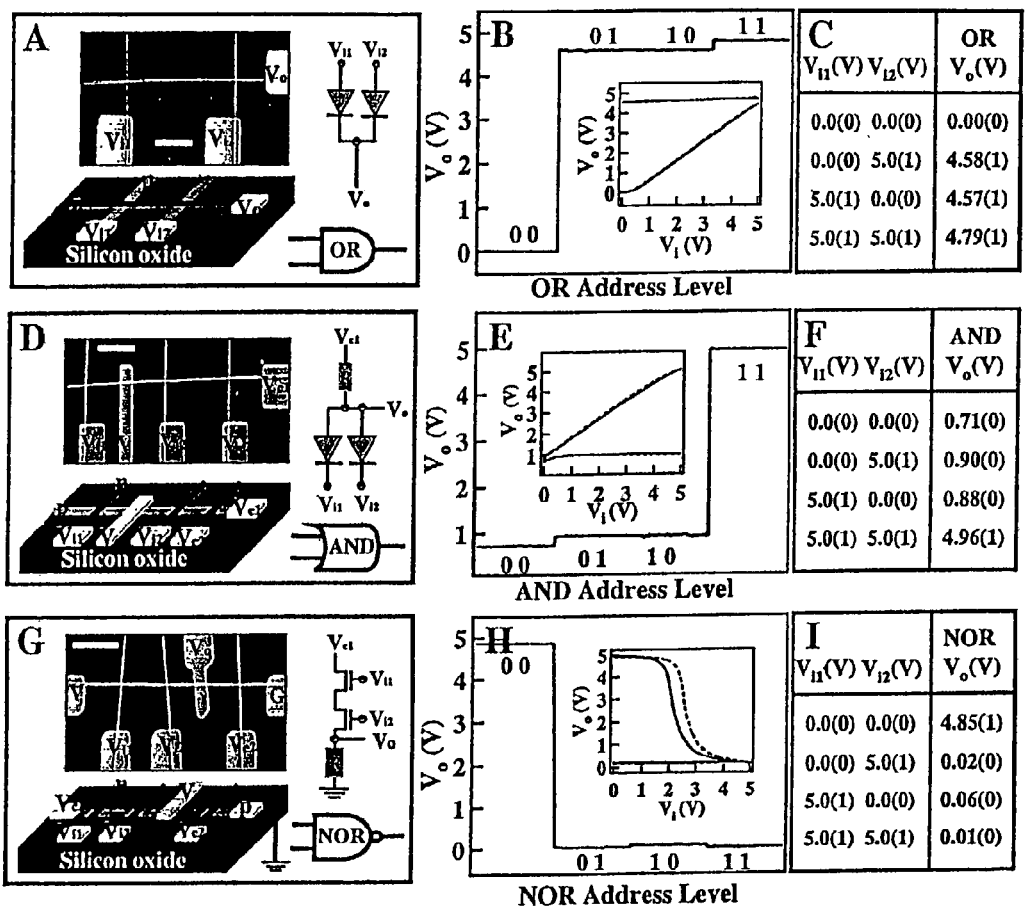
FIGS. 61A-61I illustrate various nano-logic gates.

The high-yield assembly of crossed NW p-n junctions and cNW-FETs enables the bottom-up approach to be used for formation of more complex and functional electronic devices, such as logic gates. To demonstrate the flexibility of these NW device elements, both diode- and FET-based logic was investigated. First, a two-input OR gate was realized using a 2(p) by 1(n) crossed p-n junction array with the two p-Si NWs as inputs and the n-GaN NW as the output (FIG. 61$a$). In this device, the output is low (logic 0) when both input voltages are low (0 V), and the output is high (logic 1) when either or both of the input voltages are high (5 V) (FIG. 61B), where a high input corresponds to forward bias of the corresponding p-n junction. The output-input ($V_o$-$V_i$) voltage response (inset, FIG. 61$b$) shows that $V_o$ increases linearly with $V_i$ when one input is set low (0V) except for the region near 0 V. This low response region is due to the finite turn-on voltage of the p-n junctions, and produces a logic output typically 0.4-0.2 V less than the input voltage. Small reductions in $V_o$ do not affect the operation of the logic gates because the low turn-on voltage contributions are reproducible and can be readily accounted for in defining the 0 and 1 states. The $V_o$-$V_i$ data also show a nearly constant high output when the second input is set high (e.g., 5 V). The experimental truth table for the 1×2 crossed NW device (FIG. 61$c$) summarizes the input-output response and confirms that this NW device behaves as a logic OR gate. The assembly of more p-n junctions can produce a multiple input OR gate; that is, a 1×n junction array for an n-input OR gate.

Also fabricated was an AND gate from a 1(p-Si)×3(n-GaN) multiple junction array (FIG. 61$d$). In this structure, the p-Si NW is biased at 5 V. Two of the GaN NWs are used as inputs and the third is used a gate with a constant voltage to create a resistor by depleting a portion of the p-Si NW. The logic 0 is observed from this device when either one or both of the inputs are low (FIG. 61$e$), since $V_i$=0 corresponds to a forward biased, low resistance p-n junction that pulls down the output (logic "0"). The logic 1 is observed only when both inputs are high, because this condition corresponds to reverse biased p-n diodes with resistances much larger than the constant resistor; that is, little voltage drop across the constant resistor and a high voltage is achieved at the output. The $V_o$-$V_i$ data (inset, FIG. 61$e$) shows constant low $V_o$ when the other input is low, and nearly linear behavior when the other input is set at high. The truth table for the NW device (FIG. 61$f$) summarizes the input-output response and confirms that this device functions as a logic AND gate.

In addition, a logic NOR gate was assembled using a 1(p-Si)×3(n-GaN) cNW-FET array (FIG. 61$g$). The NOR gate was configured with 2.5 V applied to one cNW-FET to create a constant resistance about 100 MOhms, and the p-SiNW channel was biased at 5 V. The two remaining n-GaN NW inputs act as gates for two cNW-FETs in series. In this way, the output depends on the resistance ratio of the two cNW-FETs and the constant resistor. The logic 0 is observed when either one or both of the inputs is high (FIG. 61$h$). In this case, the transistors are off and have resistances much higher than the constant resistor, and thus most of the voltage drops across the transistors. A logic 1 state can only be achieve when both of the transistors are on; that is, both inputs low. The $V_o$-$V_i$ relation (inset, FIG. 61$h$) shows constant low $V_o$ when the other input is high, and a nonlinear response with large change in $V_o$ when the other input is set low. Analysis of this data and that from similar structures demonstrates that these 2-input NOR gates routinely exhibit gains in excess of five, which is substantially larger than the gain reported for complementary inverters based on Si-NWs and carbon NTs. High gain is a critical characteristic of gates since it enables interconnection of arrays of logic gates without signal restoration at each stage. The truth table for this NW device (FIG. 61I) summarizes the $V_o$-$V_i$ response and demonstrates that the device behaves as a logic NOR gate. Lastly, multiple input logic NOR gates can function as NOT gates (simple inverters) by eliminating one of the inputs.

Specifically, FIG. 61 illustrates these nanoscopic nanologic gates. FIG. 61$a$ illustrates schematics of logic OR gate constructed from a 2×1 crossed NW p-n junction. The insets show an example SEM image (scale bar: 1 micrometer) of the assembled "OR" gate and symbolic electronic circuit. FIG. 61$b$ illustrates the output voltage vs. the four possible logic address level inputs: (0,0); (0,1); (1,0); (1,1), where logic 0 input is 0 V and logic 1 input is 5 V. same for the below). The inset shows output-input ($V_o$-$V_i$) relation. The solid and dashed red (blue) lines show $V_o$-$V_{i1}$ and $V_o$-$V_{i2}$ when the other input is 0 (1). FIG. 61$c$ illustrates the experimental truth table for the OR gate. FIG. 61$d$ illustrates a schematic of logic AND gate constructed from a 1×3 crossed NW junction array. The insets show a typical SEM image (bar is 1 micrometer) of the assembled AND gate and symbolic electronic circuit. FIG. 61$e$ illustrates the output voltage vs. the four possible logic address level inputs. The inset shows the $V_o$-$V_i$, where the solid and dashed red (blue) lines correspond to $V_o$-$V_{i1}$ and $V_o$-$V_{i2}$ when the other input is 0 (1). FIG. 61$f$ illustrates the experimental truth table for the AND gate. FIG. 61$g$ illustrates a schematic of logic NOR gate constructed from a 1×3 crossed NW junction array. The insets show an example SEM image (bar is 1 micrometer) and symbolic electronic circuit. FIG. 61$g$ illustrates the output voltage vs. the four possible logic address level inputs. The inset shows $V_o$-$V_i$ relation, where the solid and dashed red (blue) lines correspond to $V_o$-$V_{i1}$ and $V_o$-$V_{i2}$ when the other input is 0 (1). The slope of the data shows that device voltage gain is larger than 5. FIG. 61$i$ illustrates the measured truth table for the NOR gate.

The controllable assembly of logic OR, AND and NOR (NOT) gates enables the organization of virtually any logic circuit, and represents a substantial advance.

Interconnected multiple AND and NOR gates implement basic computation in the form of an XOR gate (FIG. 62a), which corresponds to the binary logic function SUM, and a half adder (FIG. 62b), which corresponds to the addition of two binary bits. The XOR gate is configured by using the output from AND and NOR gates as the input to a second NOR gate, while the logic half adder uses an additional logic AND gate as the CARRY. The truth table for the proposed logic XOR is summarized in FIG. 62c. Significantly, the experimental $V_o$-$V_i$ transport data for the XOR device (FIGS. 62d and 62e) show: (1) that the output is logic state 0 or low when the inputs are both low or high, and logic state 1 or high when one input is low and the other is high, and moreover (2) that the response is highly nonlinear. The linear response region corresponds to a voltage gain of in excess of five and is typical of the devices measured to date. This large gain is achieved in an XOR configured from a low gain diode AND gate, and is due to the high gain of the cNT-FET NOR gate. Further improvements in device performance could be obtained by using cNT-FET elements for all of the logic elements. Significantly, the data summarized in the experimental truth table (FIG. 62f) demonstrate that the response is that of the binary logic SUM operation, and thus implements a basic computation with the NW logic devices.

Figure 62:
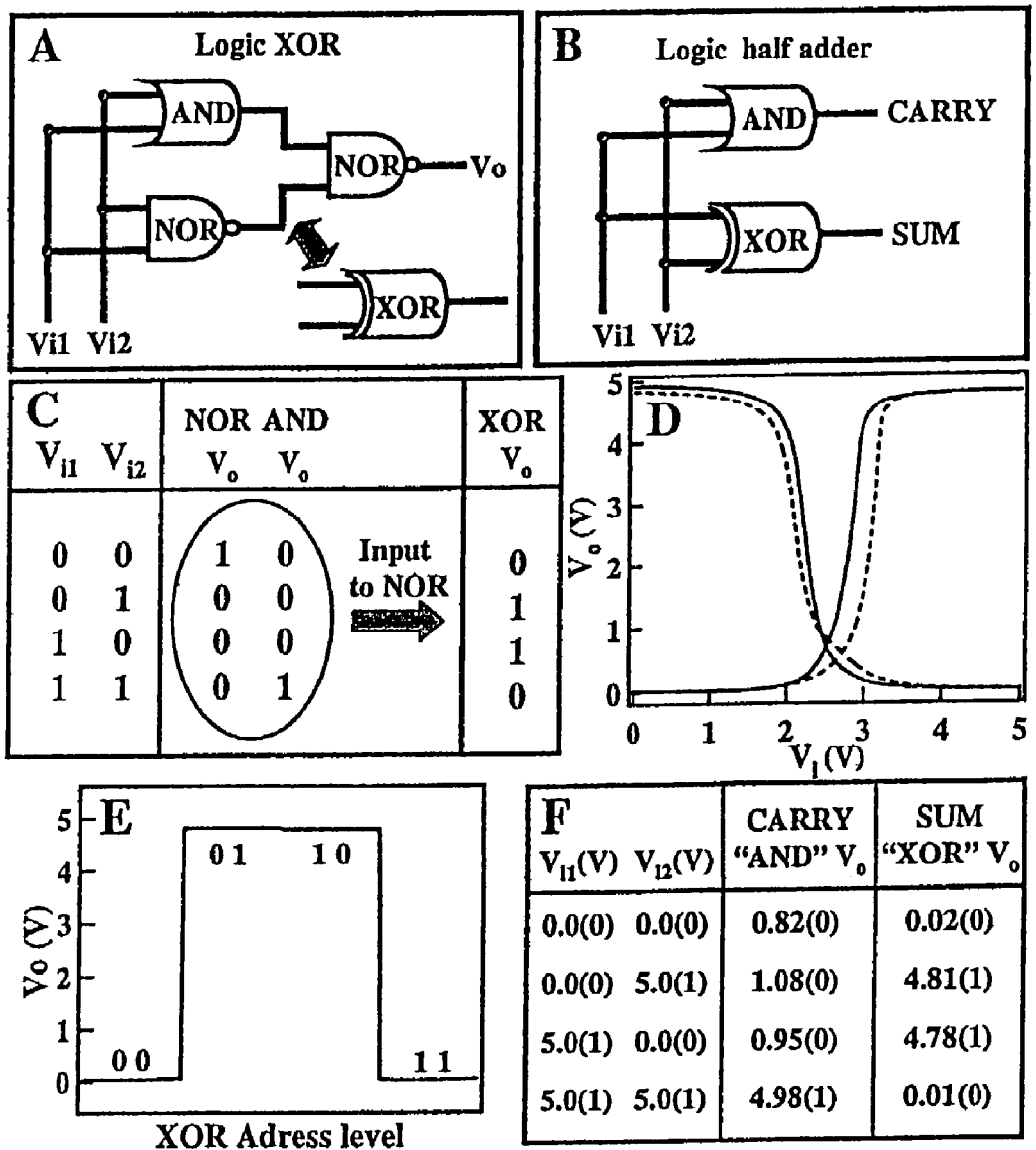
FIGS. 62A-62F illustrate various nanocomputation devices.

Specifically, FIG. 62 illustrates these computational devices. FIG. 62a illustrates a schematic of logic XOR gate constructed using the output from an AND and a NOR as the input to a second NOR gate. FIG. 62b illustrates a schematic for logic half adder. FIG. 62c illustrates a truth table for logic XOR gate. FIG. 62d illustrates XOR output voltage vs. input voltages. The solid and dashed red (blue) lines show $V_o$-$V_{i1}$ and $V_o$-$V_{i2}$ when the other input is 0 (1). The slope of the $V_o$-$V_i$ data shows that the gain exceeds 10. The XOR gate was achieved by connecting the output electrodes of an AND and NOR gate to two inputs of another NOR gate. FIG. 62e illustrates the output voltage vs. the four possible logic address level inputs for the XOR gate. FIG. 62f illustrates an experimental truth table for the logic half adder. The logic half adder was obtained by using the XOR gate as the SUM, and an AND gate as the CARRY.

Overall, the controllable and reproducible bench-top assembly of nanoscale crossed p-n diode and cNW-FET elements and arrays, which have enabled the demonstration of all critical logic gates and basic computation, represents a significant step towards integrated nanoelectronics built from primarily bottom-up vs. top-down approaches. Further steps can involve assembling NWs directly onto predefined metal electrode arrays and creating more highly integrated circuit elements by feeding the output from NW to NW. Implementing these approaches can eliminate the conventional lithography used to wire-up devices in this study. Moreover, in a crossbar array using 5 nm diameter NWs, it can be possible to achieve device densities approaching $10^{12}/cm^2$, which is off the present semiconductor roadmap for top-down manufacturing.

Example 16

This example illustrates one approach to the synthesis of core-shell nanoscale wire structures based upon control of axial and radial growth in chemical vapor deposition (FIG. 74). FIG. 74a illustrates a flexible method for the synthesis of main-group semiconductor nanoscale wires using nanocluster catalysts to preferentially direct axial growth via a vapor-liquid-solid growth process, as discussed above. In FIG. 74a, gaseous reactants catalytically decompose on the surface of a gold nanocluster, which may lead to nucleation and directed nanowire growth.

One-dimensional axial growth may be achieved when reactant activation and addition occurs at the catalyst site and not on the surface (FIG. 74b). In FIG. 74b, one-dimensional growth may be maintained as reactant decomposition on the gold catalyst occurs.

Thus, conformal shell growth may be driven by altering the synthetic conditions to favor homogeneous vapor phase deposition on the surface (FIG. 74c). In FIG. 74c synthetic conditions may be altered to induce homogeneous reactant decomposition on the surface, leading to a shell structure. Subsequent introduction of different reactants or dopants may produce multiple shell structures having arbitrary composition, although epitaxial growth of these shells requires consideration of lattice structures. This approach to core-shell nanoscale wire heterostructures is further discussed below in reference to examples of silicon (Si) and germanium (Ge). In FIG. 74d, multiple shells may be grown by repeated modulation of reactants.

Homoepitaxial Si—Si core shell nanoscale wires were grown by chemical vapor deposition (CVD) using silane as the silicon reactant (FIG. 75). In this example, intrinsic silicon (i-Si) nanoscale wires cores were prepared by gold nanocluster directed axial growth, which yielded single crystal structures having diameters controlled by the nanocluster catalyst diameter, then boron-doped (p-type) silicon (p-Si) shells were grown by homogeneous CVD, where the shell thickness was found to be directly proportional to the growth time. Radial shell growth was activated by the addition of diborane, which may serve to, for example, lower the decomposition temperature of silane, act as a p-type dopant, or increase the reaction temperature.

FIGS. 75a,b illustrate diffraction contrast and high-resolution TEM images, respectively, of an unannealed intrinsic silicon core and p-type silicon shell nanowire grown at 450° C. Crystal facets in the HRTEM image designated by arrows indicate initially epitaxial shell growth at low temperature. The scale bars represent 50 nm and 5 nm, respectively. Transmission electron microscopy (TEM) images of the i-Si/p-Si product obtained from constant temperature growth at 450° C. showed a uniform core-shell structure consisting of a crystalline Si core and amorphous Si shell (FIG. 75a), where the core diameter, 19 nanometers, was consistent with the 20 nanometers nanocluster used in the initial axial growth step. High-resolution TEM images showed reproducible crystalline faceting at the core-shell interface (FIG. 75b). This faceting may indicate that the nanoscale wire surfaces may be sufficiently clean following axial growth to nucleate epitaxial growth within the shell.

Example 17

To illustrate control of the Si on Si homoepitaxy in the core-shell nanowire structure, several experiments were performed, as described in this example. First, i-Si/p-Si core-shell nanoscale wires obtained from constant temperature growth at 450° C. were annealed in situ at 600° C.

FIGS. 75c,d illustrate TEM images (analogous to FIGS. 75a and b) of an i-Si/p-Si core shell nanowire annealed at 600° C. for 30 minutes after core-shell growth at 450° C. The inset shows two-dimensional Fourier transforms of the image depicting the [111] zone axis of the single crystal nanowire. The ⅓[422] reflections, although forbidden in bulk silicon, arise due to the finite thickness of the nanoscale wire. The TEM images recorded on these samples exhibited no apparent diffraction contrast between the core and shell (FIG. 75c). Lattice resolved images and electron diffraction data showed that the shell crystallized substantially uniformly to yield a single crystal structure (FIG. 75d). Second, the importance of the initial nucleation and crystalline faceting for achieving epitaxy in the shell was probed using a brief in situ oxidation of the silicon core prior to silicon shell growth. This oxidation step produced a thin amorphous silicon oxide layer at the surface of the crystalline Si core.

FIGS. 75e,f illustrate TEM images of an i-Si/SiO$_x$/p-Si nanowire. The oxide layer is too thin (<1 nm) to discern in this particular high-resolution image, but the sharp interface (dashed line) between the crystalline core and amorphous overcoat differs from the faceting seen in FIG. 75b, which may illustrate the disruption of epitaxy. The inset shows a TEM image of p-Si coating the nanowire and the Au nanocluster tip. The scale bar is 50 nm. The TEM images of i-Si/SiO$_x$/p-Si core-shell-shell structures showed a smooth and abrupt interface between the crystalline core and amorphous shell (FIGS. 75e and 75f). The low roughness of the interface may be comparable to that observed in nanoscale wires after only axial growth, and contrasts sharply with the faceted interface of the low-temperature homoepitaxy (FIG. 75b). These results illustrate that the thin oxide layer may disrupt homoepitaxy and inhibit crystallization of the shell, for example, under conditions that may lead to complete crystallization in samples without the oxide layer.

FIG. 75g illustrates two-terminal current (I) versus voltage (V) measurements of the nanoscale wires described above. Curves are labeled according to the representative TEM image from the same sample of wires. Curve f has been multiplied by a factor of $10^4$. The insets illustrate current versus backgate voltage to determine field-effect mobilities. The electrical transport properties of the core-shell structures to define the impact of the observed structural differences were also characterized. Two terminal measurements made on the three distinct types of i-Si/p-Si core-shell structures showed linear current (I) versus voltage (V) characteristics, although the transport properties exhibited certain interesting differences (FIG. 75g). First, the i-Si/SiO$_x$/p-Si nanoscale wires (FIG. 75f), which have an amorphous p-Si shell, showed relatively high resistivities, ~$10^3$ Ohm cm, and low effective hole mobilities, ~0.001 cm$^2$V$^{-1}$s$^{-1}$. These resistivity and mobility values may be comparable to those of heavily doped amorphous silicon deposited by plasma-enhanced CVD, and may suggest that conduction can be dominated by amorphous p-Si shell. In contrast, the i-Si/p-Si structures, which have partly or fully crystalline p-Si shells, exhibited lower resistivities, ca. 0.5-5×10$^{-3}$ Ohm cm. The similarity in these values may be consistent with observations of crystalline faceting (FIG. 75b), which may suggest that a continuous epitaxial layer of p-Si, which dominates transport, may have existed prior to the complete crystallization achieved by annealing. In addition to the resistivity values, the hole mobility of the crystalline p-Si shell nanowires was found to be 25 cm$^2$V$^{-1}$s$^{-1}$, which may be comparable to that of single crystal silicon at similar high doping levels.

The carrier mobility may be an important figure of merit for many semiconductor devices, affecting various properties such as device speed. Potential limitations to the mobility in our core-shell nanoscale wires may include, for example, interfacial scattering at the core-shell boundary, or ionized impurity scattering in the doped shell. Scattering at the i-Si/p-Si interface may be minimized by the achievement of epitaxial shell growth on regular nanowire cores (e.g., FIG. 75d). Some improvements may be observed if the holes created by ionized boron atoms are driven into an intrinsic core, which spatially separates dopants and carriers, minimizing ionized impurity scattering. This situation may be achieved in, for example, Si—Ge heterostructures, since the energy band offsets may produce internal fields that can drive charge carrier redistribution.

Example 18

In this example, radial heteroepitaxy of Si on Ge was pursued to illustrate an embodiment having core-shell structures in materials systems of scientific and technological importance. Single crystal Ge nanoscale wires were defined using gold nanocluster directed axial growth, and boron-doped p-Si shells were grown by homogeneous CVD as discussed elsewhere. FIG. 76a illustrates bright field image of an unannealed Ge—Si core-shell nanoscale wire with an amorphous p-Si shell. The scale bar represents 50 nm. The bright field TEM images revealed a core-shell structure consistent with Ge-core (dark) and Si-shell (light) structure, which was further verified using elemental mapping (FIGS. 76b and 76c), which show a localized Ge core and Si shell. These figures show scanning TEM elemental maps of Ge and Si concentrations, respectively, in the nanoscale wire of FIG. 76a.

FIG. 76d illustrates high-resolution TEM image of a representative nanowire from the same synthesis as the wire in FIGS. 76a-c. The scale bar represents 5 nm. He high-resolution TEM images of i-Ge/p-Si core-shell nanowires in which the p-Si shell was deposited at low temperature without annealing showed a crystalline Ge core and predominantly amorphous Si shell (FIG. 76d).

FIG. 76e illustrates an elemental mapping cross-section showing the Ge and Si concentrations. The solid lines show the theoretical cross-section for a 26 nm diameter core, 15 nm thick shell and <1 nm interface, according to the model described elsewhere. Analysis of the cross-sectional elemental mapping data in FIG. 76e showed that the Ge core is approximately 26 nm, the Si shell is approximately 15 nm, and the Ge—Si interface width is less than about 1 nm, where the resolution estimate is limited by the electron beam width.

It was found that the amorphous Si shell may be completely crystallized following in-situ thermal annealing at 600° C. FIG. 76f is a high-resolution TEM image of an annealed Ge—Si core-shell nanoscale wire exhibiting a crystalline p-Si shell. The scale bar represents 5 nm. Lattice-resolved TEM images of Ge—Si core-shell structures following this thermal treatment exhibited a substantially uniform crystalline Si shell (FIG. 76f), which may suggest that thin regions of epitaxially grown Si are present in the unannealed wires. In FIG. 76g elemental mapping cross-section of this nanoscale wire gives a 5 nm shell thickness with a sharp interface in agreement with the TEM image. This may indicate that the Ge and Si may not interdiffuse during the annealing process. The elemental mapping illustrates that the contrast in high-resolution TEM images is due to an abrupt (<1 nm) Si—Ge interface. Higher silicon deposition temperatures may render the annealing step optional by improving surface mobility of adsorbed silicon. In addition, electrical transport studies of the i-Ge/p-Si core-shell nanoscale wires were also performed. Data recorded on the annealed samples containing crystalline Si shells illustrate linear I-V characteristics with resistances, about 10 kiloOhms, approximately four times lower than those measured in i-Si/p-Si crystalline core-shell structures. Thus, conduction may be occurring, at least in part, through the Ge-core.

Figure 77:
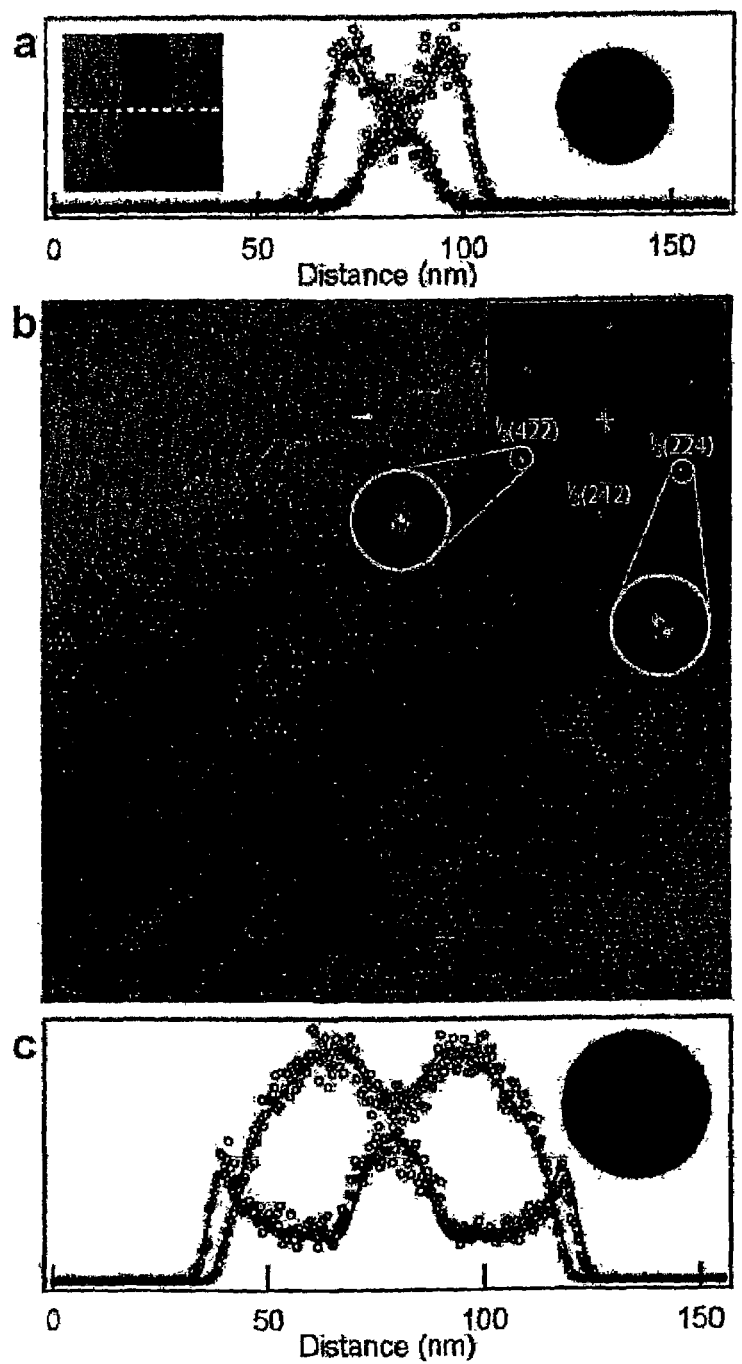
FIGS. 77A-77C illustrates certain core-shell nanoscale wires.

FIG. 77 illustrates Si—Ge and Si—Ge—Si core-shell nanoscale wires. Bright-field TEM images and composition mapping (FIG. 77a) showed Si—Ge core-shell structures having sharp (<1 nm) interfaces. In FIG. 77a, an elemental mapping cross-section indicates a 21 nm diameter Si core, 10 nm Ge shell and a <1 nm interface. The inset shows a TEM image of the corresponding Si—Ge core-shell nanoscale wire. The dashed line indicates the mapping cross-section. FIG. 77b shows a high-resolution TEM image of a representative crystalline core and shell from the same synthesis as FIG. 77a. The scale bar represents 5 nm. The insert illustrates two-dimensional Fourier transform of the real space image showing the [111] zone axis. The split lattice reflections perpendicular to the interface may be indexed to the Ge and Si lattice constants (5.657 Angstroms and 5.431 Angstroms, respectively). The high-resolution TEM image demonstrated that the Ge shell may be fully crystallized under certain low-temperature growth conditions (FIG. 77b), presumably due to the high surface mobility of Ge atoms. In addition, diffraction data may illustrate coherently strained epitaxial overgrowth (inset FIG. 77b); that is, a single diffraction peak may be observed along the axial direction, which may be indicative of compressively strained Ge and tensily strained Si. Two peaks, which may be indexed to the Ge (5.657 Å) and Si 5.431 Å) lattice constants, may also be observed in the radial direction and indicate relaxation normal to the interface. Additionally, the growth of more complex multi-shell structures has been studied, including composition mapping of a Si—Ge—Si core-double-shell structure (FIG. 77b). FIG. 77c illustrates cross-sectional elemental mapping of a double shell structure with an intrinsic silicon core (diameter, 20 nm), intrinsic germanium inner shell (thickness, 30 nm), and p-type silicon outer shell (4 nm).

Example 19

In this example of device structures, coaxially-gated nanowire FETs were prepared (FIG. 78). The coaxial geometry may be advantageous for certain nanoFETs, such as a capacitance enhancement compared to standard planar gates used in nanowire and nanotube FETs, or double-gated structures used in certain planar devices. The nanoscale building blocks used to fabricate coaxial FETs had a core-multi-shell structure: p-Si/i-Ge/SiO$_x$/p-Ge, where the active channel is the i-Ge shell. The source, drain, and gate contacts in this embodiment were made by selective etching and metal deposition onto the inner i-Ge shell and outer p-Ge shell, respectively. The continuity of the SiO$_x$ gate dielectric was confirmed by the low, <5 pA, gate to source/drain leakage currents. Transport measurements made on these initial devices show good performance characteristics (FIG. 78c) with transconductance values, ranging up to about 1500 nA/V for a 1 V source-drain bias. Minimizing SiO$_x$ trap states (which can compensate the applied gate voltage), reducing the gate dielectric thickness, or substituting a high-K dielectric may lead to improvements in the transistor performance in certain cases. These changes may be implemented during the initial synthesis stage, in some embodiments, and thus integration of this device structure may be readily achieved in semiconducting nanowire or nanotube devices.

Example 20

This example illustrates an example method of preparing a nanoscale wire having a core-shell structure.

Gold nanoclusters were deposited on oxidized silicon wafers and placed in a quartz tube furnace. Silicon nanowire cores were grown at 450° C. using silane (5 cm$^3$ STP) at 5 torr producing a one-dimensional (axial) growth rate of ~1 micron/min. P-type silicon shells were deposited using silane (1 cm$^3$ STP) and 100 ppm diborane in helium (20 cm$^3$ STP) and 20 torr, yielding a radial growth rate of ~10 nm/minute; stoichiometric incorporation of boron would yield a bulk doping level of about $2\times10^{20}$ cm$^{-3}$. Ge nanowires were grown at 380° C. using 10% germane in argon (30 cm$^3$ STP) at 30 torr (axial growth rate ~0.7 micron/min) while Ge shells were deposited at 5 cm$^3$ STP and 4 torr (radial growth rate ~10 nm/min). The ratio of axial to radical growth depended on the sample position within the furnace.

The substrate-bound nanowires were sonicated in ethanol and deposited on oxidized degenerately-doped silicon wafers or copper grids for electrical transport and TEM measurements, respectively. E-beam lithography was employed to define contact regions with subsequent deposition of Ti/Au electrodes, as described previously. Effective mobilities were then calculated.

The HRTEM images were collected on a JEOL 2010F microscope, and elemental imaging and cross-sectional mapping was conducted on a VG HB603 STEM. The elemental mapping data were modeled by calculating the cross-sectional thicknesses for concentric cylinders of different composition with abrupt interfaces, taking the electron beam profile into account by convoluting with a gaussian profile of 1.6±0.5 nm full-width, consistent with the known value for the instrument.

Example 21

In this example, a coaxially-gated nanowire transistor is characterized. FIG. 78a illustrates a device schematic showing the formed transistor structure. The inset shows the cross-section of the as grown nanowire, starting with a p-doped Si core with subsequent layers of i-Ge, SiO$_x$, and p-Ge. The source (S) and drain (D) electrodes may be contacted to the inner i-Ge core, while the gate electrode (G) may be in contact with the outer p-Ge shell and electrically isolated from the core by the SiO$_x$ layer. FIG. 78g illustrates a scanning electron micrograph (SEM) of a coaxial transistor. The source and drain electrodes were deposited after etching the Ge (30% H$_2$O$_2$, 20 sec) and SiO$_x$ layers (buffered HF, 10 sec) to expose the core layers. The etching of these outer layers is shown in the inset and is indicated by the arrow. The gate electrodes may be defined in subsequent steps without any etching prior to contact deposition. The scale bar represents 500 nm. FIG. 78c illustrates the gate response of the coaxial transistor at V$_{SD}$=1 V, showing a maximum transconductance of 1255 nA/V.

While several embodiments of the invention have been described and illustrated herein, those of ordinary skill in the art will readily envision a variety of other means and structures for performing the functions and/or obtaining the results or advantages described herein, and each of such variations or modifications is deemed to be within the scope of the present invention. More generally, those skilled in the art would readily appreciate that all parameters, dimensions, materials, and configurations described herein are meant to be exemplary and that actual parameters, dimensions, materials, and configurations will depend upon specific applications for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described. The present invention is directed to each individual feature, system, material and/or method described herein. In addition, any combination of two or more such features, systems, materials and/or methods, if such features, systems, materials and/or methods are not mutually inconsistent, is included within the scope of the present invention. In the claims, all transitional phrases or phrases of inclusion, such as "comprising," "including," "carrying," "having," "containing," and the like are to be understood to be open-ended, i.e. to mean "including but not limited to." Only the transitional phrases or phrases of inclusion "consisting of" and "consisting essentially of" are to be interpreted as closed or semi-closed phrases, respectively.

What is claimed is:

1. An electrical component comprising a plurality of field-effect transistors each comprising first and second electrodes and a non-nanotube semiconductor nanoscale wire electrically coupling the first and second electrodes, wherein each of the nanoscale wires of the component comprises at least one portion having a smallest width of less than 500 nanometers, and wherein each of the nanoscale wires of the component is taken from a population of nanoscale wires having a variation in average diameter of less than 20% relative to each other, the population of nanoscale wires being grown catalytically from a population of catalyst particles having a variation in diameter of less than 20%, wherein the diameter of each of the nanoscale wires is determined by the diameter of the catalyst particle from which the nanoscale wire is grown, and wherein each of the nanoscale wires is doped during growth of the nanoscale wire from the catalyst particle.

2. The electrical component of claim 1, wherein each of the nanoscale wires of the component comprises at least one portion having a smallest width of less than 20 nanometers.

3. The electrical component of claim 1, wherein each of the nanoscale wires of the component comprises at least one portion having a smallest width of less than 10 nanometers.

4. The electrical component of claim 1, wherein each of the nanoscale wires of the component has an aspect ratio of length to thickness of at least about 10:1.

5. The electrical component of claim 1, wherein each of the nanoscale wires of the component has an aspect ratio of length to thickness of at least about 10:1.

6. A device, comprising:
a plurality of field effect transistors, each comprising first and second electrodes and at least one non-nanotube semiconductor nanoscale wire disposed between the first and second electrodes and having a smallest dimension that is less than about 500 rim, wherein each of the semiconductor nanoscale wires of the device is taken from a population of semiconductor nanoscale wires grown catalytically from a population of catalyst particles having a variation in diameter of less than 20%, wherein the diameter of each of the semiconductor nanoscale wires is determined by the diameter of the catalyst particle from which the nanoscale wire is grown, and wherein each of the semiconductor nanoscale wires is doped during growth of the semiconductor nanoscale wire from the catalyst particle.

7. The device of claim 6, wherein the smallest dimension is less than about 20 nm.

8. The device of claim 6, wherein the smallest dimension is less than is about 10 nm.

9. The device of claim 6, wherein the nanoscale wire comprises at least one shell.

10. The device of claim 6, wherein the nanoscale wire disposed between the first and second electrodes comprises a longitudinal axis and two regions differing in composition along the longitudinal axis.

11. The device of claim 6, wherein at least one semiconductor nanoscale wire of the plurality of transistors has an aspect ratio of length to thickness of at least about 100:1.

12. The device of claim 6, wherein at least one of the transistors comprises a pair of crossed wires.

13. The device of claim 6, wherein at least one semiconductor nanoscale wire of the plurality of transistors has an aspect ratio of length to thickness of at least about 10:1.

14. A device comprising a plurality of doped semiconductors, wherein each of the doped semiconductors of the device is at least one of the following: an elongated semiconductor that, at any point along its longitudinal axis, has a largest cross-sectional dimension less than 500 nanometers, and a semiconductor with at least one portion having a smallest width of less than 500 nanometers, wherein the device comprises a field effect transistor comprising at least one of the plurality of doped semiconductors, and wherein each of the doped semiconductors of the device is non-nanotube a nanoscale wire taken from a population of nanoscale wires having a variation in average diameter of less than 20% relative to each other, the population of nanoscale wires being grown catalytically from a population of catalyst particles having a variation in diameter of less than 20%, wherein the diameter of each of the nanoscale wires is determined by the diameter of the catalyst particle from which the nanoscale wire is grown, and wherein each of the nanoscale wires is doped during growth of the nanoscale wire from the catalyst particle.

15. An electrical device comprising a plurality of field effect transistors, each field effect transistor comprising:
a substrate, and a conducting channel associated with the substrate, the conducting channel comprising a doped non-nanotube semiconductor nanoscale wire having at least one portion having a smallest width of less ten 500 nanometers; and
a gate electrode comprising an elongated material having at least one portion having a smallest width of less then 500 nanometers;
wherein each of the doped non-nanotube semiconductor nanoscale wires of the field effect transistors is taken from a population of semiconductor nanoscale wires having a variation in average diameter of less than 20% relative to each other, the population of semiconductor nanoscale wires being grown catalytically from a population of catalyst particles having a variation in diameter of less than 20%, wherein the diameter of each of the semiconductor nanoscale wires is determined by the diameter of the catalyst particle from which the semiconductor nanoscale wires is grown, and wherein each of the semiconductor nanoscale wires is doped during growth of the semiconductor nanoscale wires from the catalyst particle.

16. The electrical device of claim 15, wherein each of the doped semiconductor nanoscale wires of at least some of the plurality of the field effect transistors is a single crystal.

17. The electrical device of claim 15, wherein the doped semiconductor nanoscale wires and the elongated material of at least some of the plurality of the field effect transistors intersect.

18. The electrical device of claim 15, wherein a width of at least one of the field effect transistors of at least some of the plurality of the field effect transistors is equal to the width of the doped semiconductor nanoscale wires.

19. The electrical device of claim 15, wherein each of the doped semiconductor nanoscale wires of at least some of the plurality of the field effect transistors includes an oxide layer that functions as a gate dielectric for the field effect transistor.

20. The electrical device of claim 15, wherein each of the doped non-nanotube semiconductor nanoscale wires of the field effect transistors comprises at least one portion having a smallest width of less than 20 nanometers.

21. The electrical device of claim 15, wherein each of the doped non-nanotube semiconductor nanoscale wires of the field effect transistors comprises at least one portion having a smallest width of less than 10 nanometers.

22. The electrical device of claim 15, wherein each of the doped non-nanotube semiconductor nanoscale wires of the field effect transistors has an aspect ratio of length to thickness of at least about 10:1.

23. The electrical device of claim 15, wherein each of the doped non-nanotube semiconductor nanoscale wires of the field effect transistors has an aspect ratio of length to thickness of at least about 100:1.

* * * * *

UNITED STATES PATENT AND TRADEMARK OFFICE
CERTIFICATE OF CORRECTION

PATENT NO. : 7,301,199 B2 Page 1 of 1
APPLICATION NO. : 10/196337
DATED : November 27, 2007
INVENTOR(S) : Charles M. Lieber et al.

It is certified that error appears in the above-identified patent and that said Letters Patent is hereby corrected as shown below:

Please replace the paragraph beginning at column 1, line 38 with the following:

FEDERALLY SPONSORED RESEARCH

This invention was made with government support under N00014-01-1-0651, N00014-00-1-0476, N00014-99-1-0495, N00014-98-1-0499, and N00014-94-1-0302 awarded by Office of Naval Research and DBI-98346603 awarded by the National Science Foundation. The government has certain rights in the invention.

Signed and Sealed this

Twenty-third Day of December, 2008

JON W. DUDAS
*Director of the United States Patent and Trademark Office*